(12) United States Patent
Bonutti et al.

(10) Patent No.: US 11,134,995 B2
(45) Date of Patent: Oct. 5, 2021

(54) METHOD AND DEVICES FOR INTRACORPOREAL BONDING OF IMPLANTS WITH THERMAL ENERGY

(71) Applicant: P Tech, LLC, Effingham, IL (US)

(72) Inventors: Peter M. Bonutti, Manalapan, FL (US); Matthew J. Cremens, Effingham, IL (US); Justin E. Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 0 days.

(21) Appl. No.: 15/208,939

(22) Filed: Jul. 13, 2016

(65) Prior Publication Data

US 2017/0027625 A1    Feb. 2, 2017

Related U.S. Application Data

(63) Continuation of application No. 11/671,556, filed on Feb. 6, 2007, now Pat. No. 9,421,005.
(Continued)

(51) Int. Cl.
*A61B 17/72*    (2006.01)
*A61B 17/70*    (2006.01)
(Continued)

(52) U.S. Cl.
CPC ...... *A61B 17/7233* (2013.01); *A61B 17/0401* (2013.01); *A61B 17/686* (2013.01);
(Continued)

(58) Field of Classification Search
None
See application file for complete search history.

(56) References Cited

U.S. PATENT DOCUMENTS

| 319,296 A | 6/1885 | Molesworth |
| 668,878 A | 2/1901 | Jensen |

(Continued)

FOREIGN PATENT DOCUMENTS

| CA | 2641580 | 8/2007 |
| CA | 2680827 | 9/2008 |

(Continued)

OTHER PUBLICATIONS

Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 (February), 2010: pp. 286-290.

(Continued)

*Primary Examiner* — Eduardo C Robert
*Assistant Examiner* — Steven J Cotroneo
(74) *Attorney, Agent, or Firm* — Stinson LLP

(57) ABSTRACT

The present invention provides a method for stabilizing a fractured bone. The method includes positioning an elongate rod in the medullary canal of the fractured bone and forming a passageway through the cortex of the bone. The passageway extends from the exterior surface of the bone to the medullary canal of the bone. The method also includes creating a bonding region on the elongate rod. The bonding region is generally aligned with the passageway of the cortex. Furthermore, the method includes positioning a fastener in the passageway of the cortex and on the bonding region of the elongate rod and thermally bonding the fastener to the bonding region of the elongate rod while the fastener is positioned in the passageway of the cortex.

20 Claims, 82 Drawing Sheets

Related U.S. Application Data

(60) Provisional application No. 60/810,080, filed on Jun. 1, 2006, provisional application No. 60/784,186, filed on Mar. 21, 2006, provisional application No. 60/765,857, filed on Feb. 7, 2006.

(51) Int. Cl.

| | | |
|---|---|---|
| *A61B 17/80* | (2006.01) | |
| *A61B 17/82* | (2006.01) | |
| *G06F 21/10* | (2013.01) | |
| *A61B 17/68* | (2006.01) | |
| *A61B 17/86* | (2006.01) | |
| *A61B 17/88* | (2006.01) | |
| *A61F 2/40* | (2006.01) | |
| *A61B 17/04* | (2006.01) | |
| *A61B 17/17* | (2006.01) | |
| *A61B 17/11* | (2006.01) | |
| *A61B 17/00* | (2006.01) | |
| *A61F 2/30* | (2006.01) | |
| *A61F 2/32* | (2006.01) | |
| *A61F 2/36* | (2006.01) | |
| *A61F 2/38* | (2006.01) | |
| *A61F 2/42* | (2006.01) | |
| *A61F 2/44* | (2006.01) | |
| *A61F 2/46* | (2006.01) | |
| *A61F 2/28* | (2006.01) | |
| *A61F 2/34* | (2006.01) | |
| *A61F 2/82* | (2013.01) | |
| *A61B 17/32* | (2006.01) | |

(52) U.S. Cl.
CPC ...... *A61B 17/7032* (2013.01); *A61B 17/7058* (2013.01); *A61B 17/7059* (2013.01); *A61B 17/7062* (2013.01); *A61B 17/72* (2013.01); *A61B 17/725* (2013.01); *A61B 17/80* (2013.01); *A61B 17/8033* (2013.01); *A61B 17/82* (2013.01); *A61B 17/866* (2013.01); *A61B 17/88* (2013.01); *A61B 17/8863* (2013.01); *A61F 2/4081* (2013.01); *G06F 21/10* (2013.01); *A61B 17/11* (2013.01); *A61B 17/1128* (2013.01); *A61B 17/1146* (2013.01); *A61B 17/1721* (2013.01); *A61B 17/1742* (2013.01); *A61B 17/320068* (2013.01); *A61B 17/8038* (2013.01); *A61B 17/8685* (2013.01); *A61B 2017/00004* (2013.01); *A61B 2017/00504* (2013.01); *A61B 2017/044* (2013.01); *A61B 2017/0409* (2013.01); *A61B 2017/8655* (2013.01); *A61F 2/30756* (2013.01); *A61F 2/32* (2013.01); *A61F 2/3603* (2013.01); *A61F 2/38* (2013.01); *A61F 2/3804* (2013.01); *A61F 2/389* (2013.01); *A61F 2/3859* (2013.01); *A61F 2/40* (2013.01); *A61F 2/4202* (2013.01); *A61F 2/4455* (2013.01); *A61F 2/468* (2013.01); *A61F 2002/2817* (2013.01); *A61F 2002/30062* (2013.01); *A61F 2002/30065* (2013.01); *A61F 2002/3068* (2013.01); *A61F 2002/30133* (2013.01); *A61F 2002/30451* (2013.01); *A61F 2002/30604* (2013.01); *A61F 2002/30677* (2013.01); *A61F 2002/30785* (2013.01); *A61F 2002/30787* (2013.01); *A61F 2002/30878* (2013.01); *A61F 2002/30892* (2013.01); *A61F 2002/30894* (2013.01); *A61F 2002/30971* (2013.01); *A61F 2002/30973* (2013.01); *A61F 2002/3401* (2013.01); *A61F 2002/3403* (2013.01); *A61F 2002/444* (2013.01); *A61F 2002/828* (2013.01); *A61F 2210/0004* (2013.01); *A61F 2210/0071* (2013.01); *A61F 2220/0058* (2013.01); *A61F 2230/0015* (2013.01); *A61F 2250/0068* (2013.01); *A61F 2310/00011* (2013.01); *A61F 2310/00365* (2013.01); *A61F 2310/00383* (2013.01); *G06F 2221/0773* (2013.01); *G06F 2221/2137* (2013.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1936 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,367,809 A | 2/1968 | Soloff |
| 3,391,690 A | 7/1968 | Armao |
| 3,400,805 A | 9/1968 | Thompson |
| 3,477,429 A | 11/1969 | Sampson |
| 3,513,848 A | 5/1970 | Winston |
| 3,518,993 A | 7/1970 | Blake |
| 3,577,991 A | 5/1971 | Wilkinson |
| 3,596,292 A | 8/1971 | Erb |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston |
| 3,678,980 A | 7/1972 | Gutshall |
| 3,709,218 A | 1/1973 | Halloran |
| 3,711,347 A | 1/1973 | Wagner |
| 3,760,808 A | 9/1973 | Bleuer |
| 3,788,318 A | 1/1974 | Kim |
| 3,789,852 A | 2/1974 | Kim |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,888,405 A | 6/1975 | Jones et al. |
| 3,898,992 A | 8/1975 | Balamuth |
| 3,918,442 A | 11/1975 | Nikolaev |
| 3,968,800 A | 7/1976 | Vilasi |
| 4,023,559 A | 5/1977 | Gaskell |
| 4,064,566 A | 12/1977 | Fletcher |
| 4,089,071 A | 5/1978 | Kainberz |
| 4,102,421 A | 7/1978 | Ozaki et al. |
| 4,156,574 A | 5/1979 | Boben |
| 4,164,794 A | 8/1979 | Spector |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |

(56) References Cited

U.S. PATENT DOCUMENTS

| | | |
|---|---|---|
| 4,235,238 A | 11/1980 | Ogiu |
| 4,257,411 A | 3/1981 | Cho |
| 4,265,231 A | 5/1981 | Scheller |
| 4,281,649 A | 8/1981 | Derweduwen |
| 4,291,698 A | 9/1981 | Fuchs |
| 4,309,488 A | 1/1982 | Heide |
| 4,320,762 A | 3/1982 | Bentov |
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | CHarlson |
| 4,437,191 A | 3/1984 | Van der Zat |
| 4,437,362 A | 3/1984 | Hurst |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,493,317 A | 1/1985 | Klaue |
| 4,495,664 A | 1/1985 | Bianquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins |
| 4,556,350 A | 12/1985 | Bernhardt |
| 4,566,138 A | 1/1986 | Lewis |
| 4,589,868 A | 5/1986 | Dretler |
| 4,590,928 A | 5/1986 | Hunt |
| 4,597,379 A | 7/1986 | Kihn |
| 4,599,085 A | 7/1986 | Riess |
| 4,601,893 A | 7/1986 | Cardinal |
| 4,606,335 A | 8/1986 | Wedeen |
| 4,621,640 A | 11/1986 | Mulhollan |
| 4,630,609 A | 12/1986 | Chin |
| 4,632,101 A | 12/1986 | Freedland |
| 4,645,503 A | 2/1987 | Lin |
| 4,653,487 A * | 3/1987 | Maale ............... A61B 17/7098 606/62 |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,685,458 A | 8/1987 | Leckrone |
| 4,691,741 A | 10/1987 | Hayhurst |
| 4,705,040 A | 11/1987 | Mueller |
| 4,706,670 A | 11/1987 | Andersen |
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,749,585 A | 6/1988 | Greco |
| 4,750,492 A | 6/1988 | Jacobs |
| 4,768,507 A | 9/1988 | Fischell |
| 4,772,286 A | 9/1988 | Goble |
| 4,773,406 A | 9/1988 | Spector et al. |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steffee |
| 4,792,336 A | 12/1988 | Hlavacek |
| 4,817,591 A | 4/1989 | Klaue |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gattuma |
| 4,899,729 A | 2/1990 | Gill et al. |
| 4,899,744 A | 2/1990 | Fujitsuka |
| 4,901,721 A | 2/1990 | Hakki |
| 4,911,718 A | 3/1990 | Lee et al. |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green |
| 4,935,026 A | 6/1990 | Drews |
| 4,935,028 A | 6/1990 | Drews |
| 4,945,625 A | 8/1990 | Winston |
| 4,946,468 A | 8/1990 | Libarid |
| 4,954,126 A | 9/1990 | Wallsten |
| 4,955,910 A | 9/1990 | Bolesky |
| 4,957,498 A | 9/1990 | Caspari |
| 4,961,741 A | 10/1990 | Hayhurst |
| 4,962,882 A | 10/1990 | Sarazen, Jr. et al. |
| 4,963,151 A | 10/1990 | Ducheyne |
| 4,966,583 A | 10/1990 | Debbas |
| 4,968,315 A | 11/1990 | Gattuma |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,035,713 A | 7/1991 | Friis |
| 5,037,404 A | 8/1991 | Golds |
| 5,037,422 A | 8/1991 | Hayhurst |
| 5,041,093 A | 8/1991 | Chu |
| 5,041,114 A | 8/1991 | Chapman |
| 5,041,129 A | 8/1991 | Hayhurst |
| 5,046,513 A | 9/1991 | Gattuma |
| 5,047,055 A | 9/1991 | Bao |
| 5,051,049 A | 9/1991 | Wills |
| 5,053,046 A | 10/1991 | Janese |
| 5,053,047 A | 10/1991 | Kuslich |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,108,399 A | 4/1992 | Eitenmuller |

(56) References Cited

U.S. PATENT DOCUMENTS

| | | |
|---|---|---|
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,388 A | 1/1993 | DiCarlo |
| 5,258,007 A | 1/1993 | Spetzler |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,493 A | 6/1993 | Raad |
| 5,219,359 A | 6/1993 | McQuilkin |
| 5,226,899 A | 7/1993 | Lee |
| 5,234,006 A | 8/1993 | Eaton |
| 5,234,425 A | 8/1993 | Fogarty |
| 5,236,438 A | 8/1993 | Wilk |
| 5,236,445 A | 8/1993 | Hayhurst |
| 5,242,902 A | 9/1993 | Murphy |
| 5,254,113 A | 10/1993 | Wilk |
| 5,258,015 A | 11/1993 | Li |
| 5,258,016 A | 11/1993 | DiPoto |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Habermyer |
| 5,282,832 A | 2/1994 | Toso |
| 5,290,281 A * | 3/1994 | Tschakaloff ....... A61B 17/8085 606/229 |
| 5,304,119 A | 4/1994 | Balaban |
| 5,306,280 A | 4/1994 | Bregen |
| 5,306,301 A | 4/1994 | Graf |
| 5,306,309 A | 4/1994 | Wagner et al. |
| 5,315,741 A | 5/1994 | Dubberke |
| 5,318,570 A | 6/1994 | Hood |
| 5,318,588 A | 6/1994 | Horzewski |
| 5,320,611 A | 6/1994 | Bonutti |
| 5,329,846 A | 7/1994 | Bonutti |
| 5,329,924 A | 7/1994 | Bonutti |
| 5,330,446 A | 7/1994 | Weldon et al. |
| 5,330,468 A | 7/1994 | Burkhart |
| 5,330,476 A | 7/1994 | Hiot |
| 5,330,486 A | 7/1994 | Wilkinson |
| 5,336,231 A | 8/1994 | Adair |
| 5,336,240 A | 8/1994 | Metzler |
| 5,339,799 A | 8/1994 | Kami |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,365,784 A | 11/1994 | Morrissey |
| 5,366,480 A | 11/1994 | Corriveau |
| 5,370,646 A | 12/1994 | Reese |
| 5,370,660 A | 12/1994 | Weinstein |
| 5,372,146 A | 12/1994 | Branch |
| 5,374,235 A * | 12/1994 | Ahrens ................ A61B 17/72 606/101 |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,173 A | 2/1995 | Wilk |
| 5,395,308 A | 3/1995 | Fox |
| 5,397,311 A | 3/1995 | Walker |
| 5,403,312 A | 4/1995 | Yates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Skikhman |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr |
| 5,447,503 A | 9/1995 | Miller |
| 5,449,372 A | 9/1995 | Schmaltz |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donnell |
| 5,464,426 A | 11/1995 | Bonutti |
| 5,464,427 A | 11/1995 | Curtis |
| 5,470,337 A | 11/1995 | Moss |
| 5,472,444 A | 12/1995 | Huebner |
| 5,474,554 A | 12/1995 | Ku |
| 5,478,351 A | 12/1995 | Meade |
| 5,478,353 A | 12/1995 | Yoon |
| 5,480,403 A | 1/1996 | Lee |
| 5,486,197 A | 1/1996 | Le |
| 5,487,844 A | 1/1996 | Fujita |
| 5,488,958 A | 2/1996 | Topel |
| 5,496,292 A | 3/1996 | Burnham |
| 5,496,335 A | 3/1996 | Thomason |
| 5,496,348 A | 3/1996 | Bonutti |
| 5,499,382 A | 3/1996 | Nusinov et al. |
| 5,500,000 A | 3/1996 | Feagin |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,522,844 A | 6/1996 | Johnson |
| 5,522,845 A | 6/1996 | Wenstrom |
| 5,522,846 A | 6/1996 | Bonutti |
| 5,527,341 A | 6/1996 | Gogolewski |
| 5,527,342 A | 6/1996 | Pietrzak |
| 5,527,343 A | 6/1996 | Bonutti |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,718 A | 7/1996 | Bartlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin |
| 5,569,305 A | 10/1996 | Bonutti |
| 5,569,306 A | 10/1996 | Thal |
| 5,571,190 A | 11/1996 | Ulrich et al. |
| 5,573,517 A | 11/1996 | Bonutti |
| 5,573,538 A | 11/1996 | Laboureau |
| 5,573,542 A | 11/1996 | Stevens |
| 5,575,801 A | 11/1996 | Habermyer |
| 5,580,344 A | 12/1996 | Hasson |
| 5,584,835 A | 12/1996 | Greenfield |
| 5,584,860 A | 12/1996 | Goble |
| 5,584,862 A | 12/1996 | Bonutti |

(56) References Cited

U.S. PATENT DOCUMENTS

| | | | |
|---|---|---|---|
| 5,591,206 | A | 1/1997 | Moufarrege |
| 5,593,422 | A | 1/1997 | Muijs Van De Moer |
| 5,593,425 | A | 1/1997 | Bonutti |
| 5,593,625 | A | 1/1997 | Rieble |
| 5,601,557 | A | 2/1997 | Hayhurst |
| 5,601,558 | A | 2/1997 | Torrie |
| 5,601,595 | A | 2/1997 | Schwartz |
| 5,607,427 | A | 3/1997 | Tschakaloff |
| 5,609,595 | A | 3/1997 | Pennig |
| 5,618,314 | A | 4/1997 | Harwin |
| 5,620,461 | A | 4/1997 | Muijs Van De Moer |
| 5,626,612 | A | 5/1997 | Bartlett |
| 5,626,614 | A | 5/1997 | Hart |
| 5,626,718 | A | 5/1997 | Philippe |
| 5,628,751 | A | 5/1997 | Sander |
| 5,630,824 | A | 5/1997 | Hart |
| 5,634,926 | A | 6/1997 | Jobe |
| 5,643,274 | A | 7/1997 | Sander |
| 5,643,293 | A | 7/1997 | Kogasaka |
| 5,643,295 | A | 7/1997 | Yoon |
| 5,643,321 | A | 7/1997 | McDevitt |
| 5,645,553 | A | 7/1997 | Kolesa |
| 5,645,597 | A | 7/1997 | Krapiva |
| 5,645,599 | A | 7/1997 | Samani |
| 5,649,955 | A | 7/1997 | Hashimoto |
| 5,649,963 | A | 7/1997 | McDevitt |
| 5,651,377 | A | 7/1997 | O'Donnell |
| 5,658,313 | A | 8/1997 | Thal |
| 5,660,225 | A | 8/1997 | Saffran |
| 5,662,658 | A | 9/1997 | Wenstrom |
| 5,665,089 | A | 9/1997 | Dall |
| 5,665,109 | A | 9/1997 | Yoon |
| 5,667,513 | A | 9/1997 | Torrie |
| 5,669,917 | A | 9/1997 | Sauer |
| 5,674,240 | A | 10/1997 | Bonutti |
| 5,681,310 | A | 10/1997 | Yuan |
| 5,681,333 | A | 10/1997 | Burkhart |
| 5,681,351 | A | 10/1997 | Jamiolkowski |
| 5,681,352 | A | 10/1997 | Clancy |
| 5,685,820 | A | 11/1997 | Riek |
| 5,688,283 | A | 11/1997 | Knapp |
| 5,690,654 | A | 11/1997 | Ovil |
| 5,690,655 | A | 11/1997 | Hart |
| 5,690,676 | A | 11/1997 | DiPoto |
| 5,693,055 | A | 12/1997 | Zahiri |
| 5,697,950 | A | 12/1997 | Fucci |
| 5,702,397 | A | 12/1997 | Gonie |
| 5,702,462 | A | 12/1997 | Oberlander |
| 5,707,395 | A | 1/1998 | Li |
| 5,713,903 | A | 2/1998 | Sander |
| 5,713,921 | A | 2/1998 | Bonutti |
| 5,718,717 | A | 2/1998 | Bonutti |
| 5,720,747 | A | 2/1998 | Burke |
| 5,720,753 | A | 2/1998 | Sander |
| 5,725,541 | A | 3/1998 | Anspach |
| 5,725,556 | A | 3/1998 | Moser |
| 5,725,582 | A | 3/1998 | Bevan |
| 5,730,747 | A | 3/1998 | Ek |
| 5,733,306 | A | 3/1998 | Bonutti |
| 5,735,875 | A | 4/1998 | Bonutti |
| 5,735,877 | A | 4/1998 | Pagedas |
| 5,735,899 | A | 4/1998 | Schwartz |
| 5,741,282 | A | 4/1998 | Anspach |
| 5,752,952 | A | 5/1998 | Adamson |
| 5,752,974 | A | 5/1998 | Rhee |
| 5,755,809 | A | 5/1998 | Cohen |
| 5,762,458 | A | 6/1998 | Wang |
| 5,766,221 | A | 6/1998 | Benderev |
| 5,769,894 | A | 6/1998 | Ferragamo |
| 5,772,672 | A | 6/1998 | Toy |
| 5,776,151 | A | 7/1998 | Chan |
| 5,779,706 | A * | 7/1998 | Tschakaloff ....... A61B 17/8085 219/229 |
| 5,782,862 | A | 7/1998 | Bonutti |
| 5,785,713 | A | 7/1998 | Jobe |
| 5,792,096 | A | 8/1998 | Rentmeester |
| 5,797,931 | A | 8/1998 | Bito |
| 5,800,537 | A | 9/1998 | Bell |
| 5,807,403 | A | 9/1998 | Beyar |
| 5,810,849 | A | 9/1998 | Slavros |
| 5,810,853 | A | 9/1998 | Yoon |
| 5,810,884 | A | 9/1998 | Kim |
| 5,814,072 | A | 9/1998 | Bonutti |
| 5,814,073 | A | 9/1998 | Bonutti |
| 5,817,107 | A | 10/1998 | Schaller |
| 5,823,994 | A | 10/1998 | Sharkey |
| 5,824,009 | A | 10/1998 | Fukuda |
| 5,830,125 | A | 11/1998 | Scribner |
| 5,836,897 | A | 11/1998 | Sakural |
| 5,839,899 | A | 11/1998 | Robinson |
| 5,843,178 | A | 12/1998 | Vanney |
| 5,845,645 | A | 12/1998 | Bonutti |
| 5,851,185 | A | 12/1998 | Berns |
| 5,865,834 | A | 2/1999 | McGuire |
| 5,866,634 | A | 2/1999 | Tokushige |
| 5,868,749 | A | 2/1999 | Reed |
| 5,874,235 | A | 2/1999 | Chan |
| 5,879,372 | A | 3/1999 | Bartlett |
| 5,891,166 | A | 4/1999 | Schervinsky |
| 5,891,168 | A | 4/1999 | Thal |
| 5,893,880 | A | 4/1999 | Egan |
| 5,897,574 | A | 4/1999 | Bonutti |
| 5,899,911 | A | 5/1999 | Carter |
| 5,899,921 | A | 5/1999 | Caspari |
| 5,906,579 | A | 5/1999 | Vander Salm |
| 5,906,625 | A | 5/1999 | Bito |
| 5,908,429 | A | 6/1999 | Yoon |
| 5,911,721 | A | 6/1999 | Nicholson |
| 5,918,604 | A | 7/1999 | Whelan |
| 5,919,193 | A | 7/1999 | Slavitt |
| 5,919,194 | A | 7/1999 | Anderson |
| 5,919,208 | A | 7/1999 | Valenti |
| 5,919,215 | A | 7/1999 | Wiklund |
| 5,921,986 | A | 7/1999 | BOnutti |
| 5,925,064 | A | 7/1999 | Meyers |
| 5,928,244 | A | 7/1999 | Tovey |
| 5,928,267 | A | 7/1999 | Bonutti |
| 5,931,838 | A | 8/1999 | Vito |
| 5,931,869 | A | 8/1999 | Boucher |
| 5,940,942 | A | 8/1999 | Fong |
| 5,941,900 | A | 8/1999 | Bonutti |
| 5,941,901 | A | 8/1999 | Egan |
| 5,945,002 | A | 9/1999 | Bonutti |
| 5,947,982 | A | 9/1999 | Duran |
| 5,948,000 | A | 9/1999 | Larsen |
| 5,948,001 | A | 9/1999 | Larsen |
| 5,951,590 | A | 9/1999 | Goldfarb |
| 5,957,953 | A | 9/1999 | DiPoto |
| 5,961,499 | A | 10/1999 | Bonutti |
| 5,961,521 | A | 10/1999 | Roger |
| 5,961,554 | A | 10/1999 | Janson |
| 5,964,765 | A | 10/1999 | Fenton |
| 5,964,769 | A | 10/1999 | Wagner |
| 5,968,046 | A | 10/1999 | Castleman |
| 5,968,047 | A | 10/1999 | Reed |
| 5,948,002 | A | 11/1999 | Bonutti |
| 5,980,520 | A | 11/1999 | Vancaillie |
| 5,980,559 | A | 11/1999 | Bonutti |
| 5,984,929 | A | 11/1999 | Bashiri |
| 5,989,282 | A | 11/1999 | Bonutti |
| 5,993,458 | A | 11/1999 | Vaitekunas |
| 5,993,477 | A | 11/1999 | Vaitekunas |
| 6,007,567 | A | 12/1999 | Bonutti |
| 6,007,580 | A | 12/1999 | Lehto |
| 6,010,525 | A | 1/2000 | Bonutti |
| 6,010,526 | A | 1/2000 | Sandstrom |
| 6,017,321 | A | 1/2000 | Boone |
| 6,033,429 | A | 3/2000 | Magovern |
| 6,033,430 | A | 3/2000 | Bonutti |
| 6,045,551 | A | 4/2000 | Bonutti |
| 6,050,998 | A | 4/2000 | Fletcher |
| 6,056,751 | A * | 5/2000 | Fenton, Jr. ......... A61B 17/0401 606/151 |
| 6,056,772 | A | 5/2000 | Bonutti |

(56) References Cited

U.S. PATENT DOCUMENTS

| | | | |
|---|---|---|---|
| 6,056,773 A | 5/2000 | Bonutti | |
| 6,059,797 A | 5/2000 | Mears | |
| 6,059,817 A | 5/2000 | Bonutti | |
| 6,059,827 A | 5/2000 | Fenton | |
| 6,063,095 A | 5/2000 | Wang | |
| 6,066,151 A | 5/2000 | Miyawaki | |
| 6,066,160 A | 5/2000 | Colvin | |
| 6,066,166 A | 5/2000 | Bischoff | |
| 6,068,637 A | 5/2000 | Popov | |
| 6,077,277 A | 6/2000 | Mollenauer | |
| 6,077,292 A | 6/2000 | Bonutti | |
| 6,080,161 A * | 6/2000 | Eaves, III | A61B 17/68 606/329 |
| 6,083,522 A | 7/2000 | Chu | |
| 6,086,593 A | 7/2000 | Bonutti | |
| 6,086,608 A | 7/2000 | Ek | |
| 6,090,072 A | 7/2000 | Kratoska | |
| 6,099,531 A | 8/2000 | Bonutti | |
| 6,099,537 A | 8/2000 | Sugai | |
| 6,099,550 A | 8/2000 | Yoon | |
| 6,099,552 A | 8/2000 | Adams | |
| 6,102,850 A | 8/2000 | Wang | |
| 6,106,545 A | 8/2000 | Egan | |
| 6,117,160 A | 9/2000 | Bonutti | |
| 6,120,536 A | 9/2000 | Ding | |
| 6,125,574 A | 10/2000 | Ganaja | |
| 6,126,677 A | 10/2000 | Ganaja | |
| 6,139,320 A | 10/2000 | Hahn | |
| RE36,974 E | 11/2000 | Bonutti | |
| 6,149,669 A | 11/2000 | Li | |
| 6,152,949 A | 11/2000 | Bonutti | |
| 6,155,756 A | 12/2000 | Mericle | |
| 6,159,224 A | 12/2000 | Yoon | |
| 6,159,234 A | 12/2000 | Bonutti | |
| 6,171,307 B1 | 1/2001 | Orlich | |
| 6,174,324 B1 | 1/2001 | Egan | |
| 6,179,840 B1 | 1/2001 | Bowman | |
| 6,179,850 B1 | 1/2001 | Goradia | |
| 6,187,008 B1 | 2/2001 | Hamman | |
| 6,190,400 B1 | 2/2001 | Van de Moer | |
| 6,190,401 B1 | 2/2001 | Green | |
| 6,200,322 B1 | 3/2001 | Branch | |
| 6,214,049 B1 | 4/2001 | Gayer et al. | |
| 6,217,591 B1 | 4/2001 | Egan | |
| 6,224,593 B1 | 5/2001 | Ryan | |
| 6,224,630 B1 | 5/2001 | Bao | |
| 6,228,086 B1 | 5/2001 | Wahl | |
| 6,231,592 B1 | 5/2001 | Bonutti | |
| 6,238,395 B1 | 5/2001 | Bonutti | |
| 6,238,396 B1 | 5/2001 | Bonutti | |
| 6,258,091 B1 | 7/2001 | Sevrain | |
| 6,264,675 B1 | 7/2001 | Brotz | |
| 6,267,761 B1 | 7/2001 | Ryan | |
| 6,273,717 B1 | 8/2001 | Hahn | |
| 6,280,474 B1 | 8/2001 | Cassidy | |
| 6,286,746 B1 | 9/2001 | Egan | |
| 6,287,325 B1 | 9/2001 | Bonutti | |
| 6,293,961 B2 | 9/2001 | Schwartz | |
| 6,306,159 B1 | 10/2001 | Schwartz | |
| 6,309,405 B1 | 10/2001 | Bonutti | |
| 6,312,448 B1 | 11/2001 | Bonutti | |
| 6,324,308 B1 | 11/2001 | Chen et al. | |
| 6,328,480 B1 | 12/2001 | Strike | |
| 6,338,730 B1 | 1/2002 | Bonutti | |
| 6,340,365 B2 | 1/2002 | Dittrich | |
| 6,348,056 B1 | 2/2002 | Bates | |
| 6,358,271 B1 | 3/2002 | Egan | |
| 6,364,897 B1 | 4/2002 | Bonutti | |
| 6,368,325 B1 | 4/2002 | McKinley | |
| 6,368,343 B1 | 4/2002 | Bonutti | |
| 6,371,957 B1 | 4/2002 | Amrein | |
| 6,409,716 B1 | 6/2002 | Sahatjian et al. | |
| 6,409,742 B1 | 6/2002 | Fulton | |
| 6,409,743 B1 | 6/2002 | Fenton | |
| 6,409,768 B1 * | 6/2002 | Tepic | A61B 17/725 623/23.27 |
| 6,419,704 B1 | 7/2002 | Ferree | |
| 6,423,088 B1 | 7/2002 | Fenton | |
| 6,425,919 B1 | 7/2002 | Lambrecht | |
| 6,428,562 B2 | 8/2002 | Bonutti | |
| 6,432,115 B1 | 8/2002 | Mollenauer | |
| 6,447,516 B1 | 9/2002 | Bonutti | |
| 6,450,985 B1 | 9/2002 | Schoelling | |
| 6,461,360 B1 | 10/2002 | Adams | |
| 6,468,293 B2 | 10/2002 | Bonutti | |
| 6,475,230 B1 | 11/2002 | Bonutti | |
| 6,488,196 B1 | 12/2002 | Fenton | |
| 6,500,195 B2 | 12/2002 | Bonutti | |
| 6,503,259 B2 | 1/2003 | Huxel | |
| 6,530,933 B1 | 3/2003 | Yeung | |
| 6,535,764 B2 | 3/2003 | Imran | |
| 6,544,267 B1 | 4/2003 | Cole | |
| 6,545,390 B1 | 4/2003 | Hahn | |
| 6,547,792 B1 | 4/2003 | Tsuji | |
| 6,551,304 B1 | 4/2003 | Whalen | |
| 6,554,852 B1 | 4/2003 | Oberlander | |
| 6,527,774 B2 | 5/2003 | Lieberman | |
| 6,558,390 B2 | 5/2003 | Cragg | |
| 6,568,313 B2 | 5/2003 | Fukui | |
| 6,569,187 B1 | 5/2003 | Bonutti | |
| 6,572,635 B1 | 6/2003 | Bonutti | |
| D477,776 S | 7/2003 | Pontaoe | |
| 6,557,426 B2 | 7/2003 | Reinermann | |
| 6,585,750 B2 | 7/2003 | Bonutti | |
| 6,592,609 B1 | 7/2003 | Bonutti | |
| 6,594,517 B1 | 7/2003 | Nevo | |
| 6,585,764 B2 | 8/2003 | Wright | |
| 6,605,090 B1 * | 8/2003 | Trieu | A61B 17/8042 606/281 |
| 6,610,080 B2 | 8/2003 | Morgan | |
| 6,618,910 B1 | 9/2003 | Pontaoe | |
| 6,623,487 B1 * | 9/2003 | Goshert | A61B 17/68 606/329 |
| 6,626,944 B1 | 9/2003 | Taylor | |
| 6,623,486 B1 | 10/2003 | Weaver | |
| 6,632,245 B2 | 10/2003 | Kim | |
| 6,635,073 B2 | 10/2003 | Bonutti | |
| 6,638,279 B2 | 10/2003 | Bonutti | |
| 6,641,592 B1 | 11/2003 | Sauer | |
| 6,645,227 B2 | 11/2003 | Fallin | |
| 6,652,585 B2 | 11/2003 | Lange | |
| 6,666,877 B2 | 12/2003 | Morgan | |
| 6,669,705 B2 | 12/2003 | Westhaver | |
| 6,679,888 B2 | 1/2004 | Green | |
| 6,685,750 B1 | 2/2004 | Plos | |
| 6,699,240 B2 | 3/2004 | Fracischelli | |
| 6,702,821 B2 | 3/2004 | Bonutti | |
| 6,705,179 B1 | 3/2004 | Mohtasham | |
| 6,709,436 B1 | 3/2004 | Hover et al. | |
| 6,709,457 B1 | 3/2004 | Otte | |
| 6,719,765 B2 | 4/2004 | Bonutti | |
| 6,719,797 B1 | 4/2004 | Ferree | |
| 6,722,552 B2 | 4/2004 | Fenton | |
| 6,733,531 B1 | 5/2004 | Trieu | |
| 6,764,514 B1 | 7/2004 | Li | |
| 6,770,078 B2 | 8/2004 | Bonutti | |
| 6,780,198 B1 | 8/2004 | Gregoire | |
| 6,786,989 B2 | 9/2004 | Torriani | |
| 6,796,003 B1 | 9/2004 | Marvel | |
| 6,818,010 B2 | 11/2004 | Eichhorn | |
| 6,823,871 B2 | 11/2004 | Schmieding | |
| 6,860,885 B2 | 3/2005 | Bonutti | |
| 6,878,167 B2 | 4/2005 | Ferree | |
| 6,893,434 B2 | 5/2005 | Fenton | |
| 6,899,722 B2 | 5/2005 | Bonutti | |
| 6,890,334 B2 | 7/2005 | Brace | |
| 6,913,666 B1 | 7/2005 | Aeschlimann | |
| 6,916,321 B2 | 7/2005 | TenHuisen | |
| 6,921,264 B2 | 7/2005 | Mayer | |
| 6,923,824 B2 | 8/2005 | Morgan | |
| 6,932,835 B2 | 8/2005 | Bonutti | |
| 6,942,684 B2 | 9/2005 | Bonutti | |
| 6,944,111 B2 | 9/2005 | Nakamura | |

(56) References Cited

U.S. PATENT DOCUMENTS

| | | |
|---|---|---|
| 6,955,540 B2 | 10/2005 | Mayer |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan |
| 7,094,251 B2 | 8/2006 | Bonutti |
| 7,104,996 B2 | 9/2006 | Bonutti |
| 7,128,761 B2 | 10/2006 | Kuras et al. |
| 7,128,763 B1 | 10/2006 | Blatt |
| 7,018,380 B2 | 12/2006 | Cole |
| 7,147,652 B2 | 12/2006 | Bonutti |
| 7,160,405 B2 | 1/2007 | Aeschlimann |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian |
| 7,250,051 B2 | 7/2007 | Francischelli |
| 7,252,685 B2 | 8/2007 | Bindseil |
| 7,273,497 B2 | 9/2007 | Ferree |
| 7,329,263 B2 | 2/2008 | Bonutti |
| 7,335,205 B2 | 2/2008 | Aeschlimann |
| 7,429,266 B2 | 9/2008 | Bonutti |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 * | 3/2009 | Raterman ............ B05C 11/1042 438/17 |
| 7,632,272 B2 * | 12/2009 | Munro .................. A61B 17/744 606/67 |
| 7,854,750 B2 | 12/2010 | Bonutti |
| 7,879,072 B2 | 2/2011 | Bonutti |
| 7,891,691 B2 | 2/2011 | Bearey |
| 7,967,820 B2 | 6/2011 | Bonutti |
| 8,128,669 B2 | 3/2012 | Bonutti |
| 8,140,982 B2 | 3/2012 | Hamilton |
| 8,147,514 B2 | 4/2012 | Bonutti |
| 8,162,977 B2 | 4/2012 | Bonutti |
| 2001/0002440 A1 | 5/2001 | Bonutti |
| 2001/0009250 A1 | 7/2001 | Herman |
| 2001/0041916 A1 | 11/2001 | Bonutti |
| 2002/0016593 A1 | 2/2002 | Hearn |
| 2002/0016633 A1 | 2/2002 | Lin |
| 2002/0019649 A1 | 2/2002 | Sikora |
| 2002/0026244 A1 | 2/2002 | Trieu |
| 2002/0029083 A1 | 3/2002 | Zucherman |
| 2002/0029084 A1 | 3/2002 | Paul |
| 2002/0045902 A1 | 4/2002 | Bonutti |
| 2002/0062153 A1 | 5/2002 | Paul |
| 2002/0082529 A1 | 6/2002 | Suorsa |
| 2002/0099379 A1 * | 7/2002 | Adam .................... A61B 17/72 606/67 |
| 2002/0103495 A1 | 8/2002 | Cole |
| 2002/0120336 A1 | 8/2002 | Santilli |
| 2002/0123750 A1 | 9/2002 | Eisermann |
| 2002/0183762 A1 | 12/2002 | Anderson |
| 2002/0188301 A1 | 12/2002 | Dallara |
| 2003/0009224 A1 | 1/2003 | Kuras |
| 2003/0039196 A1 | 2/2003 | Nakamura |
| 2003/0040758 A1 | 2/2003 | Wang |
| 2003/0065361 A1 | 4/2003 | Dreyfuss |
| 2003/0105474 A1 | 6/2003 | Bonutti |
| 2003/0167072 A1 | 8/2003 | Oberlander |
| 2003/0181800 A1 | 9/2003 | Bonutti |
| 2003/0187506 A1 | 10/2003 | Ross et al. |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler |
| 2003/0225438 A1 | 12/2003 | Bonutti |
| 2003/0229361 A1 | 12/2003 | Jackson |
| 2004/0010287 A1 | 1/2004 | Bonutti |
| 2004/0030341 A1 * | 2/2004 | Aeschlimann ... A61B 17/00491 606/232 |
| 2004/0034357 A1 | 2/2004 | Beane |
| 2004/0068320 A1 | 4/2004 | Robie et al. |
| 2004/0087902 A1 | 5/2004 | Richter |
| 2004/0097939 A1 | 5/2004 | Bonutti |
| 2004/0098050 A1 | 5/2004 | Foerster |
| 2004/0138703 A1 | 7/2004 | Alleyne |
| 2004/0143334 A1 | 7/2004 | Ferree |
| 2004/0167548 A1 | 8/2004 | Bonutti |
| 2004/0215111 A1 | 10/2004 | Bonutti et al. |
| 2004/0220616 A1 | 11/2004 | Bonutti |
| 2004/0225325 A1 | 11/2004 | Bonutti |
| 2004/0225371 A1 * | 11/2004 | Roger ....................... A61F 2/34 623/22.28 |
| 2004/0230223 A1 | 11/2004 | Bonutti |
| 2004/0236374 A1 | 11/2004 | Bonutti |
| 2004/0243241 A1 | 12/2004 | Istephanous et al. |
| 2005/0033366 A1 | 2/2005 | Cole |
| 2005/0038514 A1 | 2/2005 | Helm |
| 2005/0043796 A1 | 2/2005 | Grant |
| 2005/0071012 A1 | 3/2005 | Serhan |
| 2005/0085817 A1 | 4/2005 | Ringeisen |
| 2005/0090827 A1 | 4/2005 | Gedebou |
| 2005/0096699 A1 | 5/2005 | Wixey |
| 2005/0113928 A1 | 5/2005 | Cragg |
| 2005/0126680 A1 | 6/2005 | Aeschlimann |
| 2005/0143826 A1 | 6/2005 | Zucherman |
| 2005/0240227 A1 | 6/2005 | Bonutti |
| 2005/0149024 A1 | 7/2005 | Ferrante |
| 2005/0149029 A1 | 7/2005 | Bonutti |
| 2005/0177162 A1 | 8/2005 | McLeod et al. |
| 2005/0203521 A1 | 9/2005 | Bonutti |
| 2005/0216008 A1 | 9/2005 | Zwirnmann et al. |
| 2005/0216059 A1 | 9/2005 | Bonutti |
| 2005/0216087 A1 | 9/2005 | Zucherman |
| 2005/0222620 A1 | 10/2005 | Bonutti |
| 2005/0240190 A1 | 10/2005 | Gall |
| 2005/0246021 A1 | 11/2005 | Rigeisen |
| 2005/0261684 A1 | 11/2005 | Shaolian |
| 2005/0267481 A1 | 12/2005 | Carl |
| 2005/0267534 A1 | 12/2005 | Bonutti |
| 2006/0009855 A1 | 1/2006 | Goble |
| 2006/0015101 A1 | 1/2006 | Warburton |
| 2006/0015108 A1 | 1/2006 | Bonutti |
| 2006/0026244 A1 | 2/2006 | Watson |
| 2006/0036203 A1 | 2/2006 | Ouchene et al. |
| 2006/0142799 A1 | 2/2006 | Bonutti |
| 2006/0200199 A1 | 2/2006 | Bonutti |
| 2006/0224357 A1 | 2/2006 | Carpenter |
| 2006/0064095 A1 | 3/2006 | Senn |
| 2006/0089646 A1 | 4/2006 | Bonutti |
| 2006/0122600 A1 | 6/2006 | Cole |
| 2006/0122704 A1 | 6/2006 | Vresilovic |
| 2006/0167495 A1 | 7/2006 | Bonutti |
| 2006/0265009 A1 | 7/2006 | Bonutti |
| 2006/0265011 A1 | 7/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti |
| 2006/0229715 A1 | 10/2006 | Istephanous et al. |
| 2006/0235470 A1 | 10/2006 | Bonutti |
| 2006/0241695 A1 | 10/2006 | Bonutti |
| 2006/0264950 A1 | 11/2006 | Nelson |
| 2007/0032825 A1 | 2/2007 | Bonutti |
| 2007/0088362 A1 | 4/2007 | Bonutti |
| 2007/0118129 A1 * | 5/2007 | Fraser .................. A61F 2/0811 606/71 |
| 2007/0123878 A1 | 5/2007 | Shaver |
| 2007/0198555 A1 | 8/2007 | Friedman |
| 2007/0265561 A1 | 11/2007 | Yeung |
| 2007/0270833 A1 | 11/2007 | Bonutti |
| 2008/0021474 A1 | 1/2008 | Bonutti |
| 2008/0039845 A1 | 2/2008 | Bonutti |

(56) References Cited

U.S. PATENT DOCUMENTS

| | | | |
|---|---|---|---|
| 2008/0039873 A1 | 2/2008 | Bonutti | |
| 2008/0046090 A1 | 2/2008 | Paul | |
| 2008/0195145 A1 | 2/2008 | Bonutti | |
| 2008/0097448 A1 | 4/2008 | Binder | |
| 2008/0108897 A1 | 5/2008 | Bonutti | |
| 2008/0108916 A1 | 5/2008 | Bonutti | |
| 2008/0114399 A1 | 5/2008 | Bonutti | |
| 2008/0132950 A1* | 6/2008 | Lange | A61B 17/7059 606/246 |
| 2008/0140116 A1 | 6/2008 | Bonutti | |
| 2008/0140117 A1 | 6/2008 | Bonutti | |
| 2008/0269753 A1* | 10/2008 | Cannestra | A61B 17/7059 606/70 |
| 2008/0269808 A1* | 10/2008 | Gall | A61B 17/7225 606/299 |
| 2009/0024161 A1 | 1/2009 | Bonutti | |
| 2009/0138014 A1 | 1/2009 | Bonutti | |
| 2009/0093684 A1 | 4/2009 | Schorer | |
| 2009/0194969 A1 | 8/2009 | Bearey | |
| 2010/0211120 A1 | 2/2010 | Bonutti | |
| 2011/0060375 A1 | 3/2011 | Bonutti | |
| 2011/0295253 A1 | 12/2011 | Bonutti | |
| 2012/0165841 A1 | 6/2012 | Bonutti | |
| 2012/0191140 A1 | 7/2012 | Bonutti | |
| 2012/0197316 A1* | 8/2012 | Mayer | A61B 17/0401 606/328 |
| 2012/0215233 A1 | 8/2012 | Bonutti | |

FOREIGN PATENT DOCUMENTS

| | | |
|---|---|---|
| CA | 2698057 | 3/2009 |
| DE | 1903316 B2 | 10/1964 |
| DE | 3517204 | 11/1986 |
| DE | 3722538 | 1/1989 |
| DE | 3002844 U1 | 1/1991 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2696338 | 4/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| SU | 184396 | 7/1966 |
| WO | 199112779 | 9/1991 |
| WO | 199323094 | 4/1994 |
| WO | 1994008642 | 4/1994 |
| WO | 199516398 | 6/1995 |
| WO | 199531941 | 11/1995 |
| WO | 1996014802 | 5/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2010099222 | 2/2010 |

OTHER PUBLICATIONS

Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al, Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.
Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic Flatfoot and Skewfoot, J Bone Joint Surg 1195- p. 499-512.
Murphy et al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.
Intl Prelim Rep on Patentability and Written Opinion for PCT/US10/25263 dated Aug. 30, 2011.
Petition for Inter Partes Review of U.S. Pat. No. 5,980,559, IPR 2013-00603, Filing Date Sep. 24, 2013.
Declaration of David Kaplan, Ph.D. regarding U.S. Pat. No. 5,980,559, IPR 2013-00603, Sep. 24, 2013.
Petition for Inter Partes Review of U.S. Pat. No. 4,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013,Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8, 147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).

(56) References Cited

OTHER PUBLICATIONS

Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arcioscopic and Related Surgery, 1994.
Problem Solving Report Question No. 1014984.066, Ultrasonic Welding, (c) 1999.
Dukane Guide to Ultrasound Plastic Assembly, Ultrasonic Division Publication, (c) 1995.
Textured Surface Technology, Branson Technolog, Branson Ultrasonics Copr., (c) 1992.
Enabling Local Drug Delivery—Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford projection, compact oxford english dicitionary: projection, Mar. 30, 2013.
Ask Oxford projection, compact oxford english dicitionary: slit, Mar. 30, 2013.
Non-Final Office Action dated Jun. 25, 2015 relating to U.S. Appl. No. 11/671,556, 11 pages.
Final Office Action dated Aug. 22, 2014 relating to U.S. Appl. No. 11/671,556, 11 pages.
Non-Final Office Action dated Oct. 4, 2013 relating to U.S. Appl. No. 11/671,556, 15 pages.
Final Office Action dated Nov. 12, 2010 relating to U.S. Appl. No. 11/671,556, 11 pages.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy 2 vol. 11 No. 2 p. 245-51.

Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either A Cannulated Screw or Suture-Anchors, Acta Orthopcedica Belgica, vol. 64-2-1998.
Packer et al, Repair of Acute Scapho-Lunate Dissociation Facilitated by the "Tag"* Suture Anchor, Journal of Hand Surgery (British and European Volume, 1994) 19B: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1(Jan.-Feb.),1998: pp. 118-122.
Tfix, Acufexjust tied the knot . . . , Am. J. Sports Med., vol. 22, No. 3, May-Jun. 1994.
Non-Final Office Action dated Feb. 22, 2010 relating to U.S. Appl. No. 11/671,556, 9 pages.
Non-Final Office action for U.S. Appl. No. 15/436,168, dated Jun. 4, 2018, 12 pages.
Branson, Polymers: Characteristics and Compatibility for Ultrasonic Assembly, Applied Technologies Group, Publication unknown.

* cited by examiner

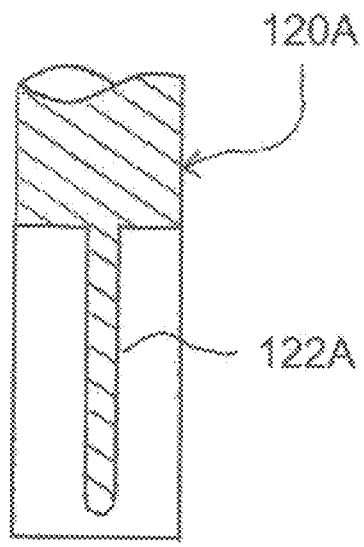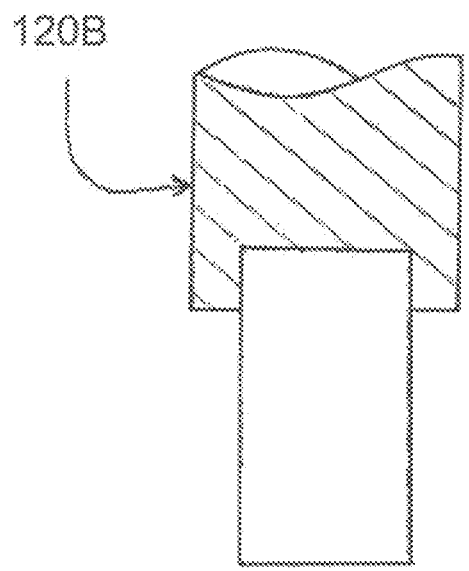
FIG. 3A　　　　　　　　　FIG. 3B
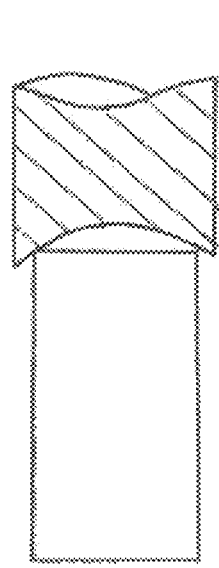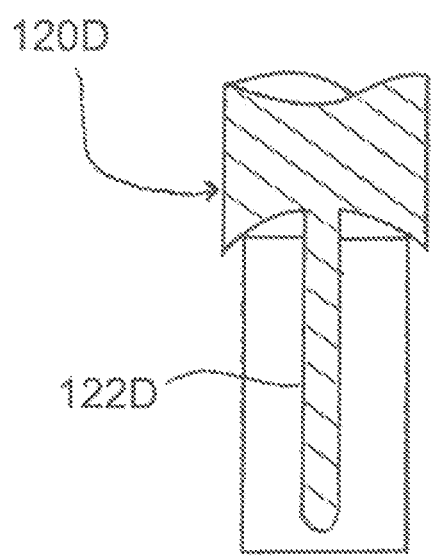
FIG. 3C　　　　　　　　　FIG. 3D

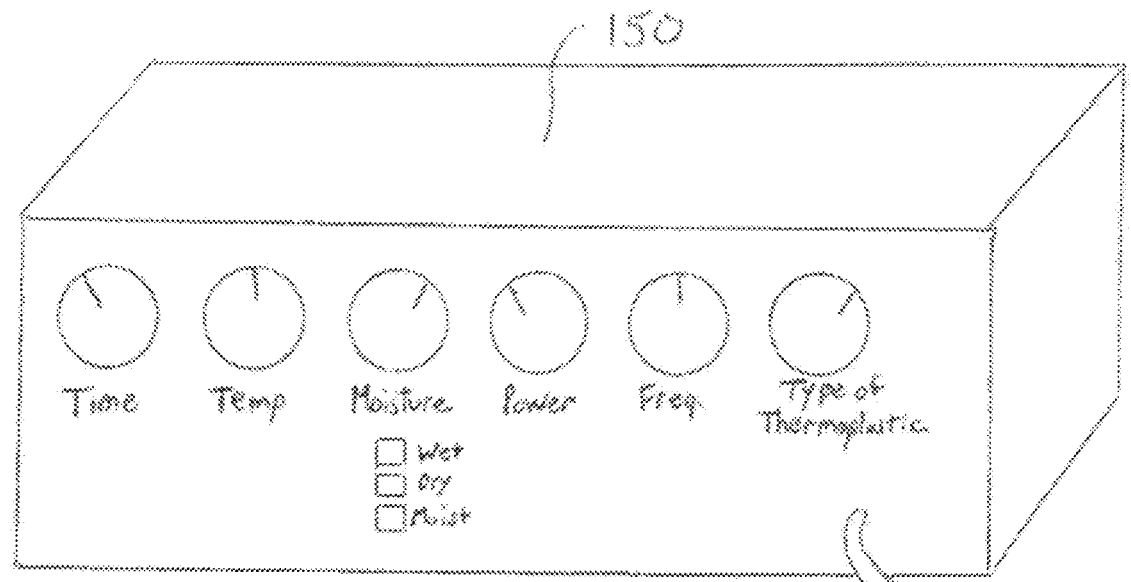
FIG. 6
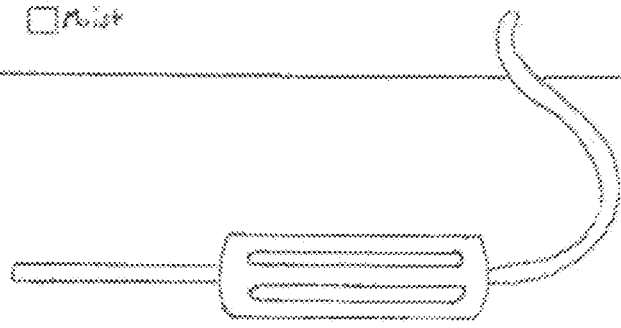
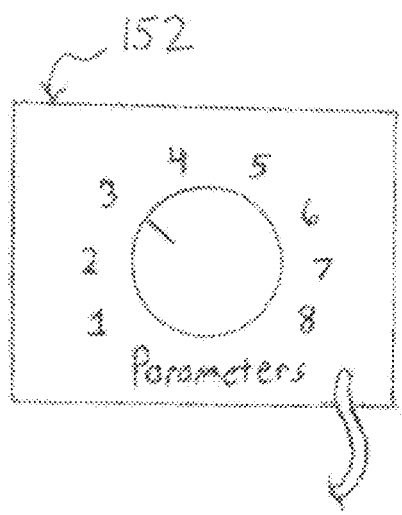
FIG. 7
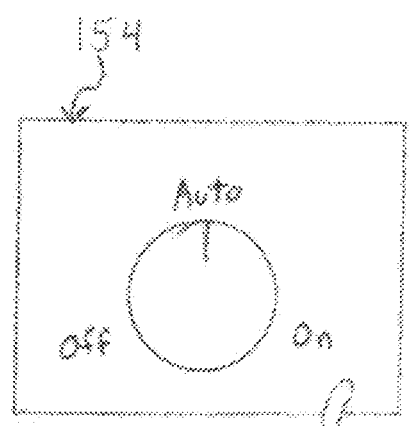
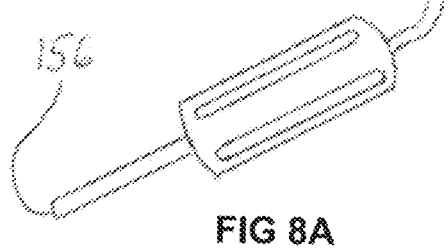
FIG 8A

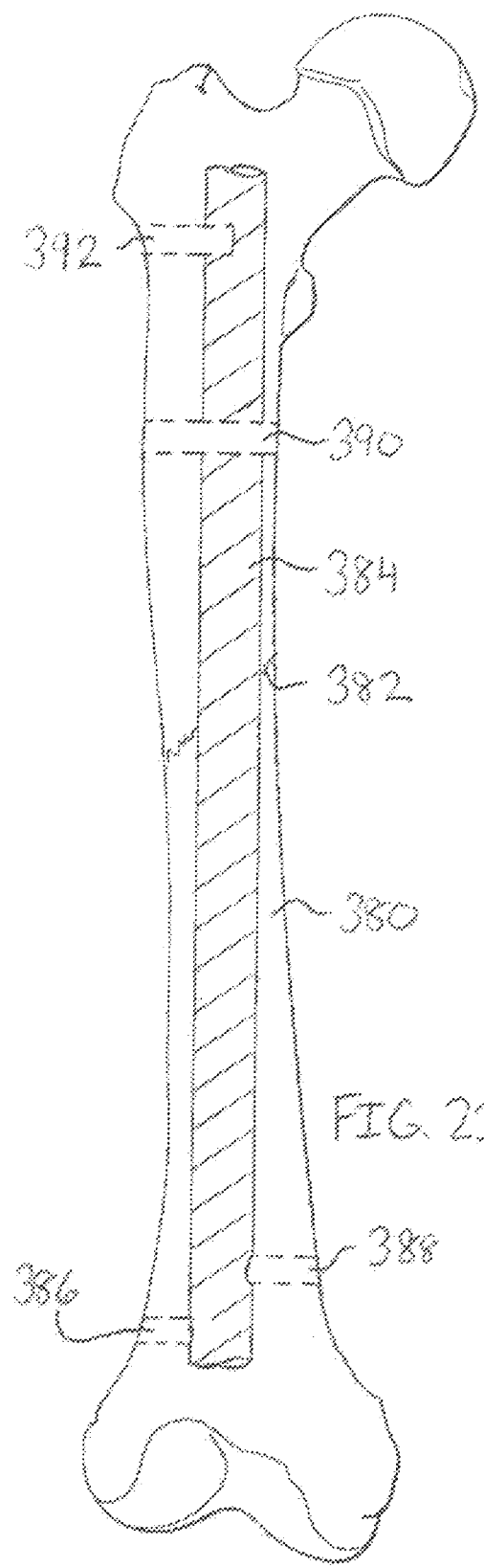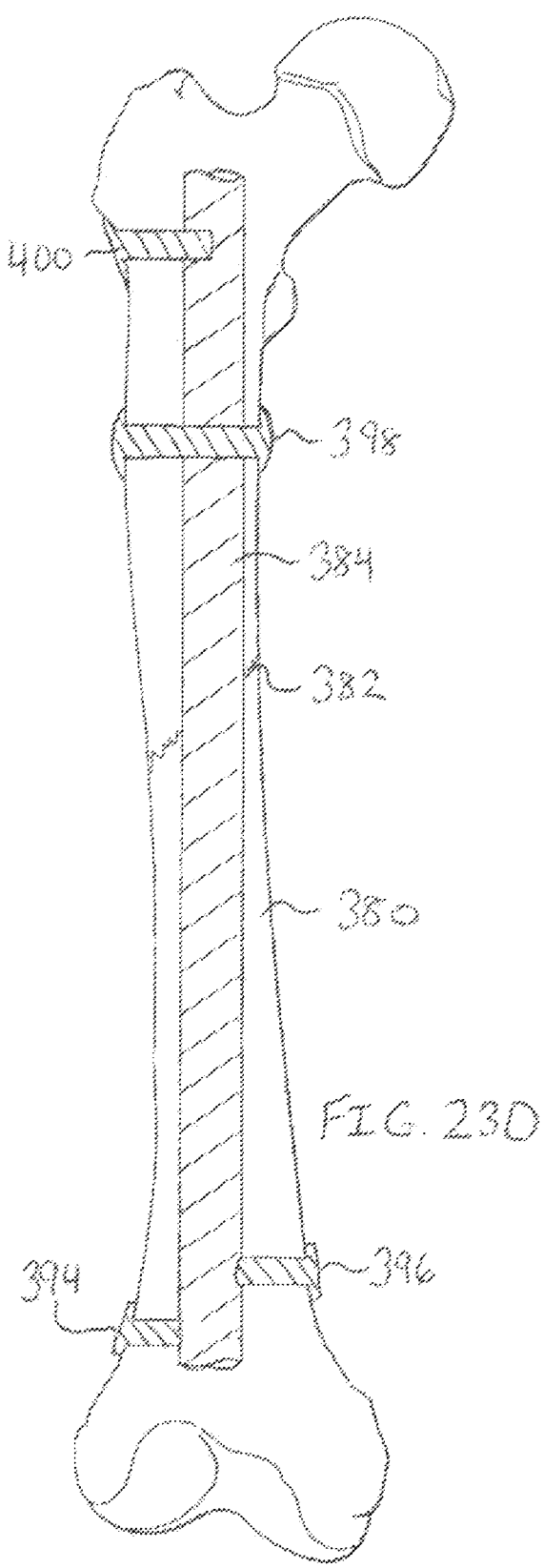

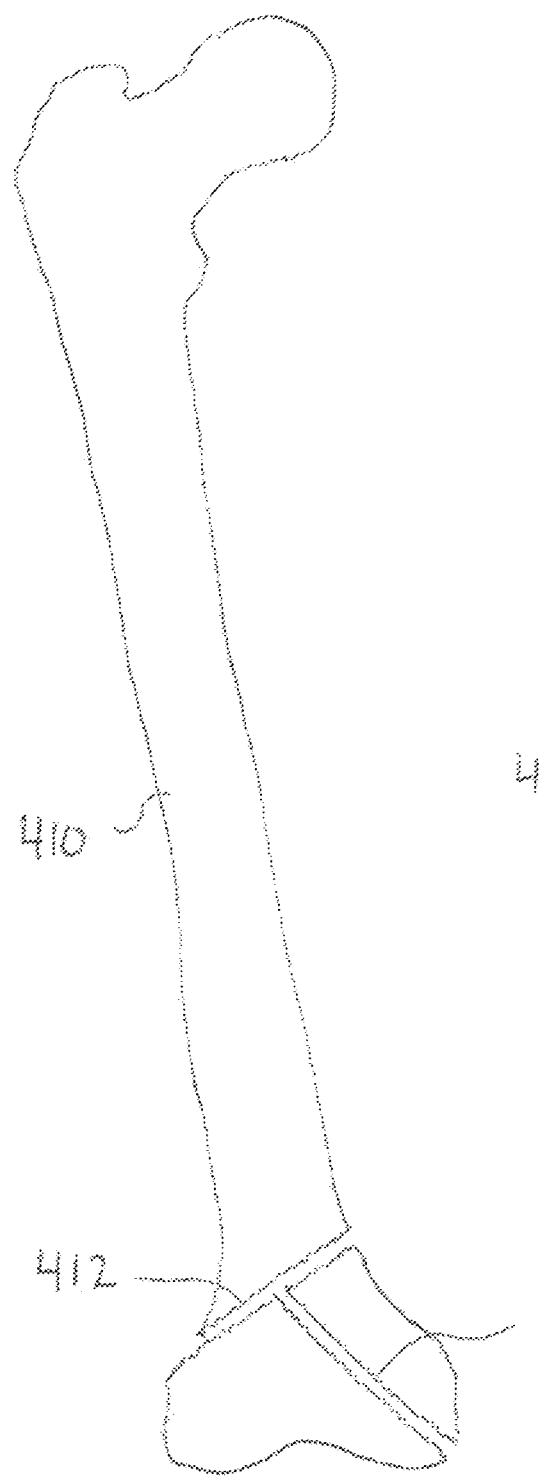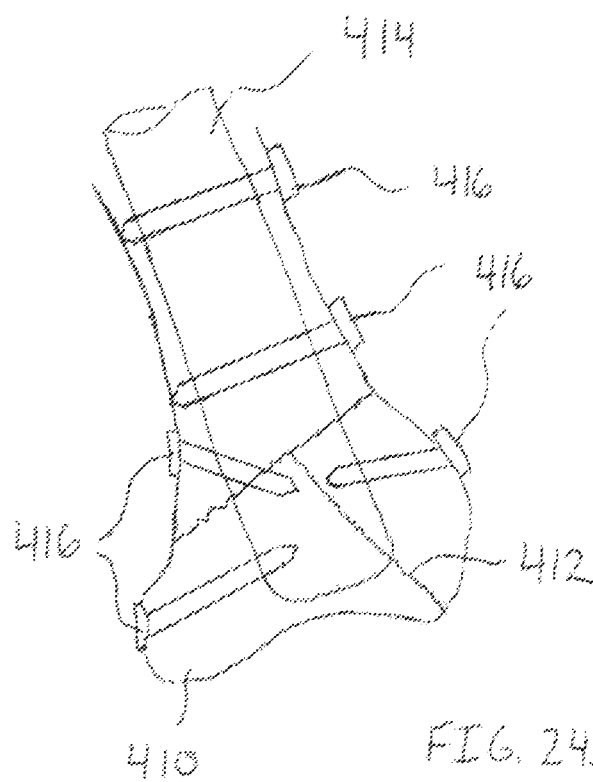
FIG. 24A
FIG. 24B

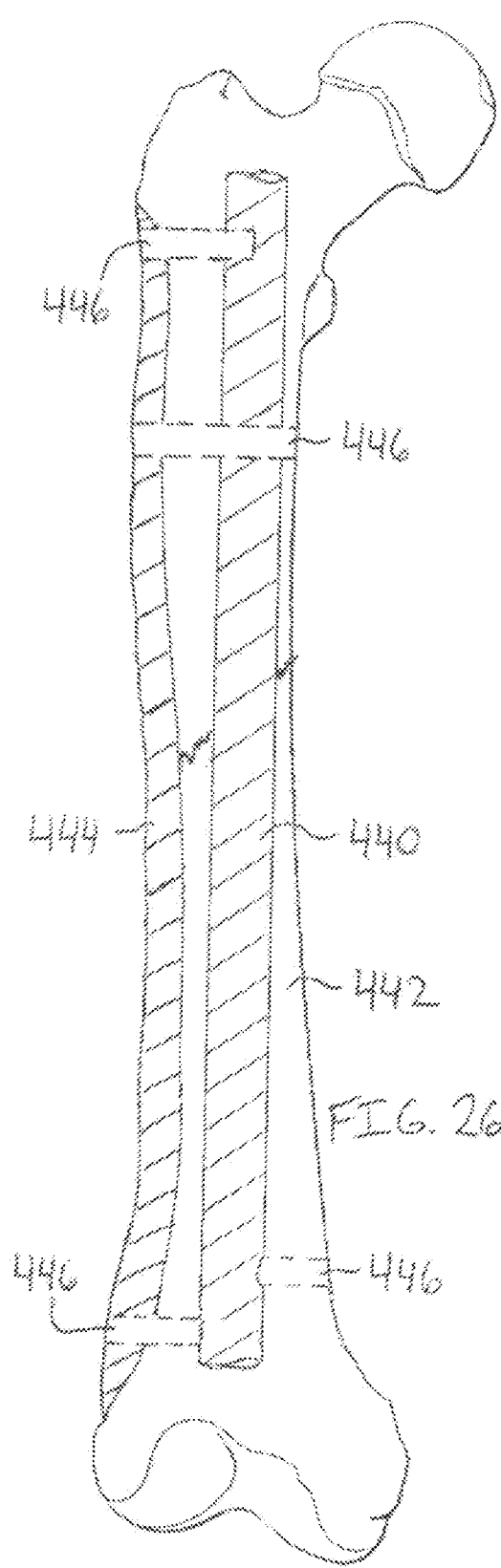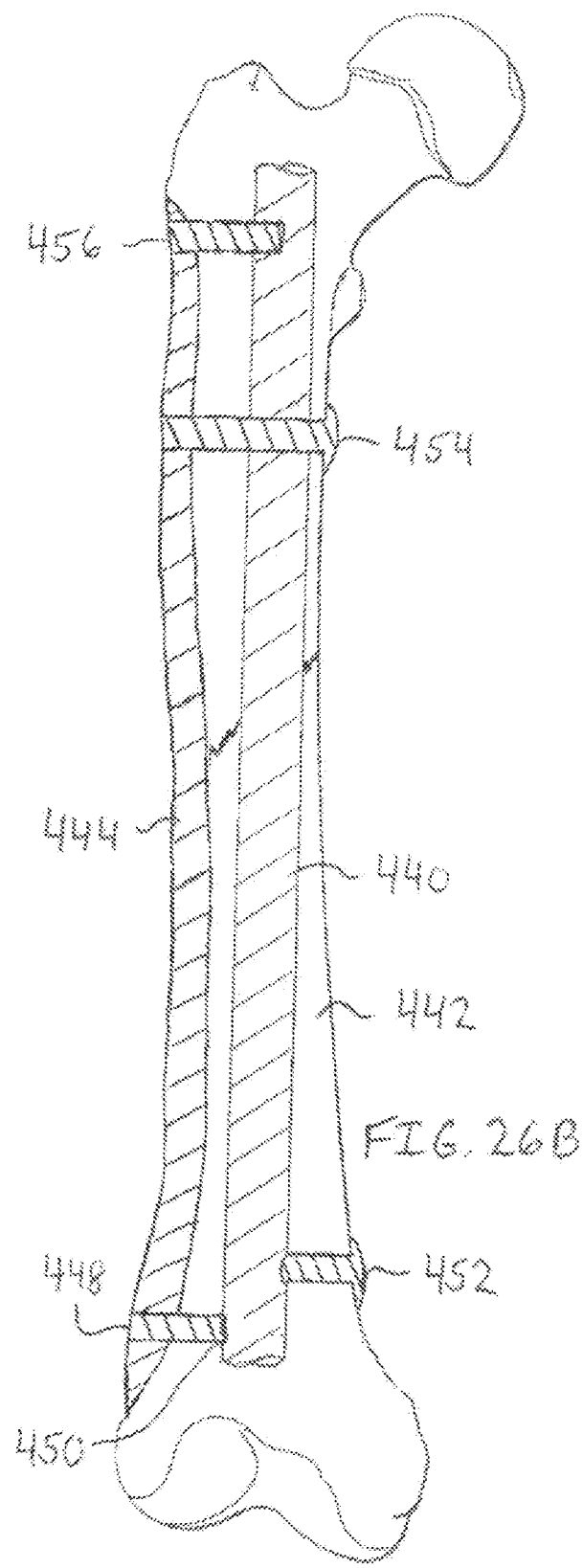

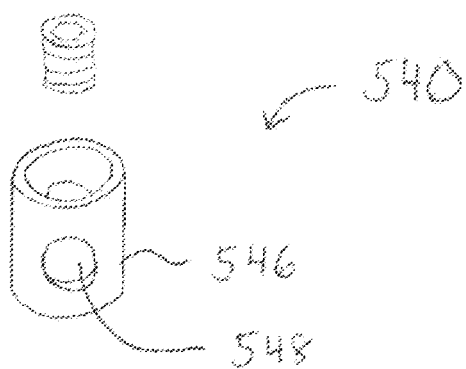
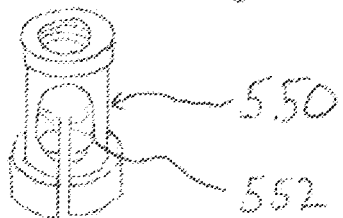
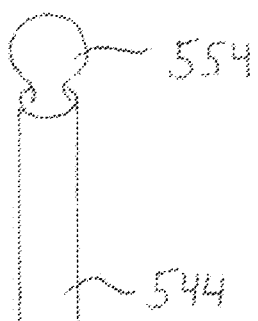
FIG. 34A
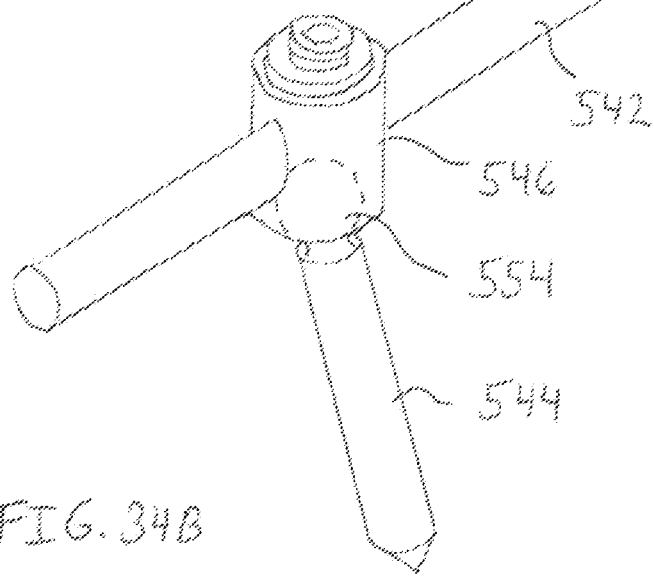
FIG. 34B

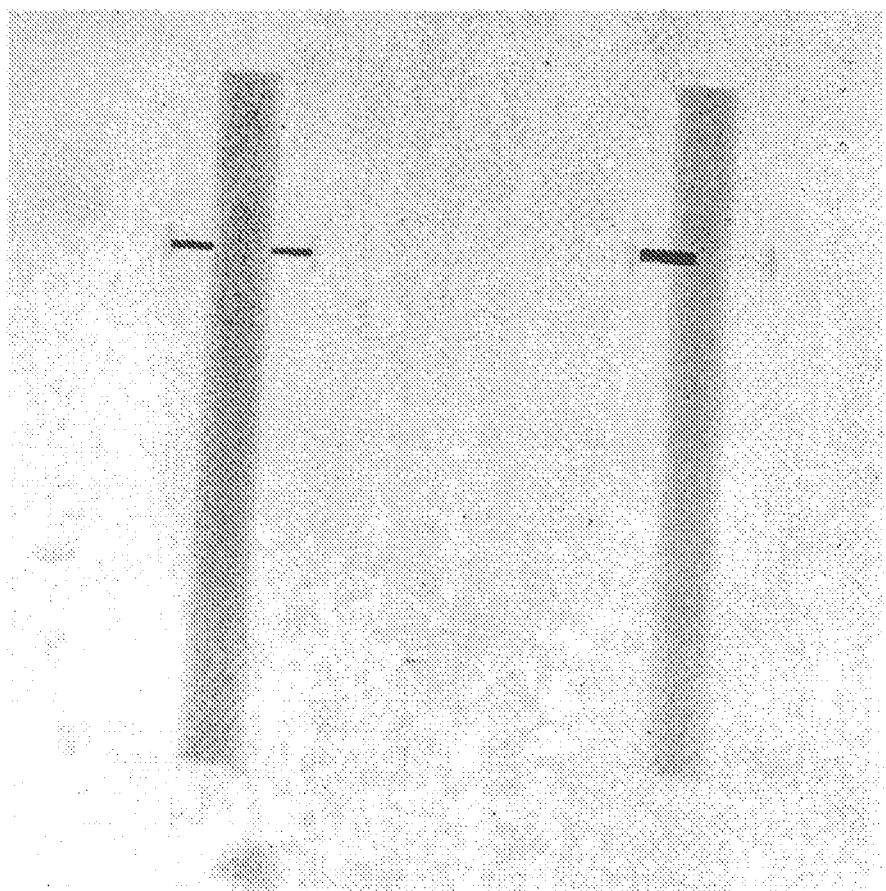
FIG. 91
FIG. 92A

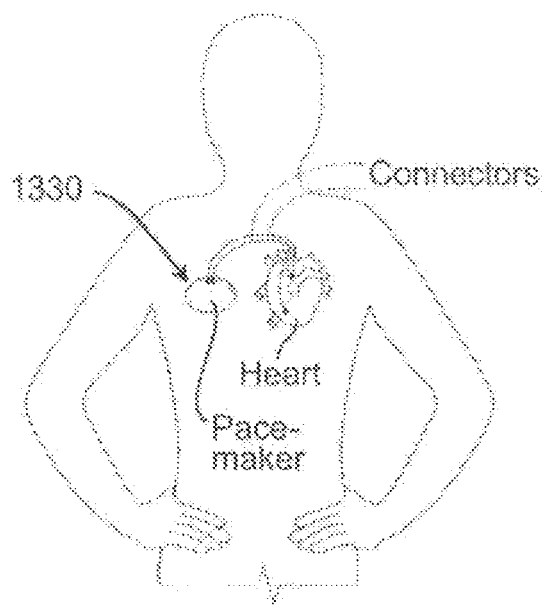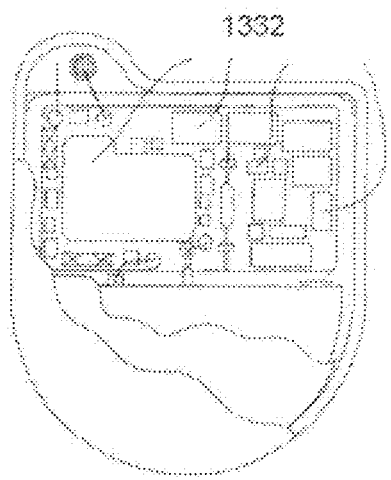
FIG. 111A  FIG. 111B
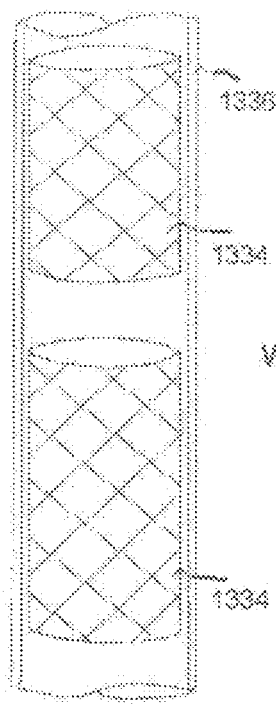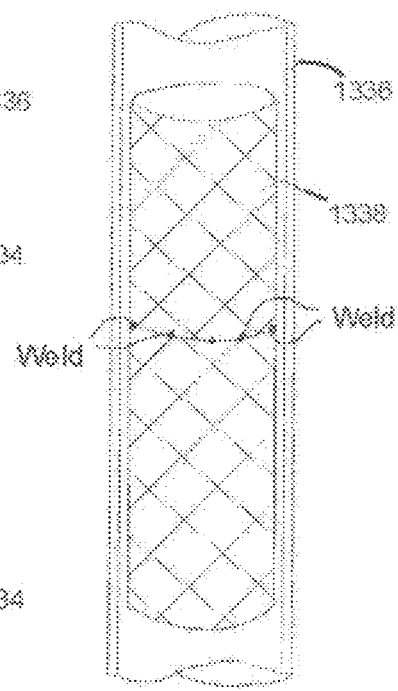
FIG. 112A  FIG. 112B

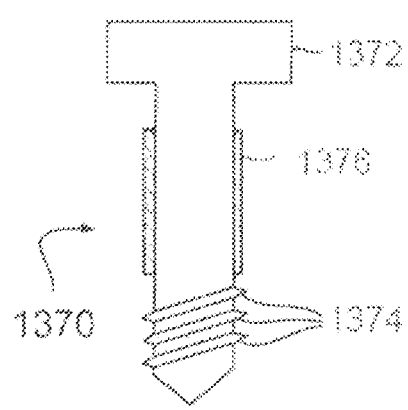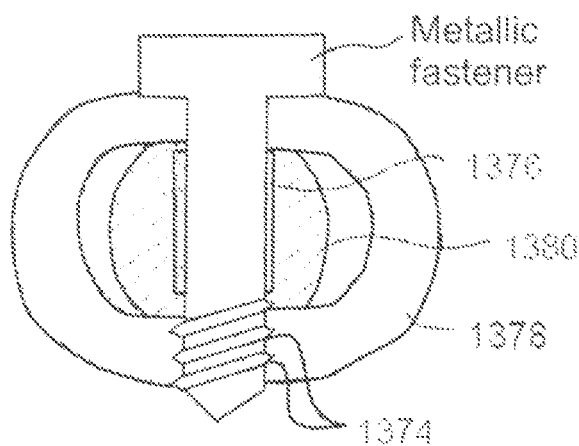
FIG. 119A  FIG. 119B
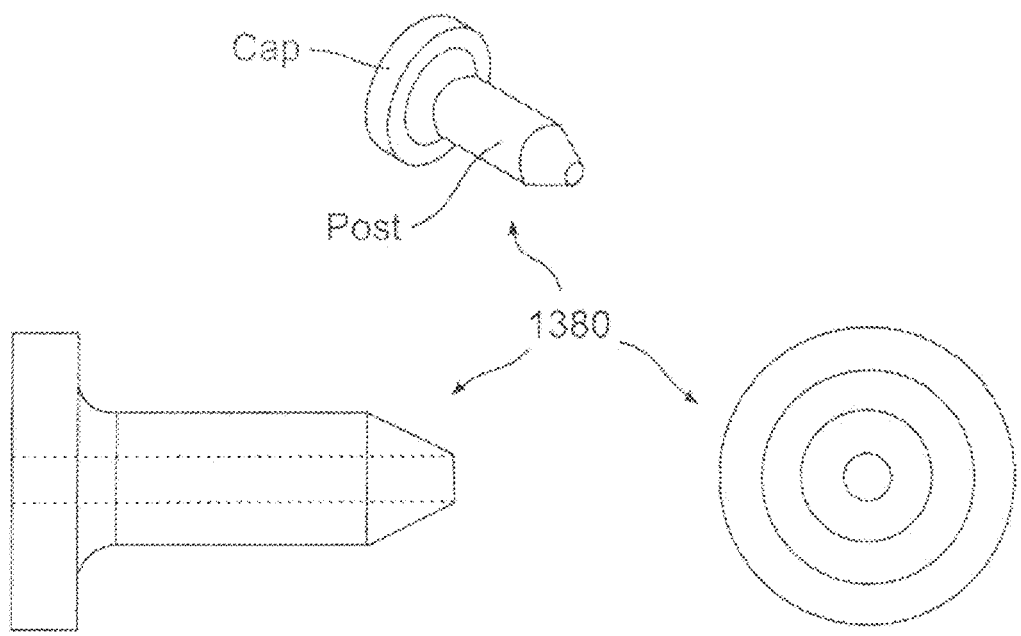
FIG. 120

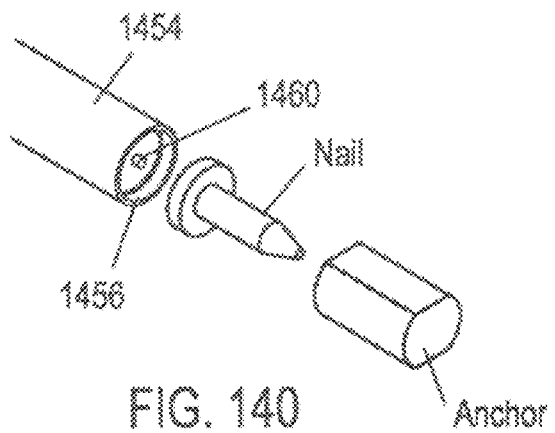
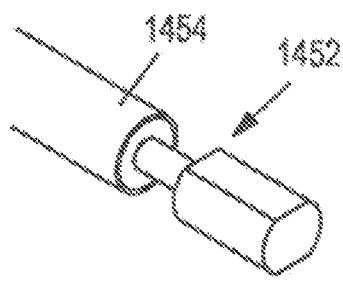
FIG. 140          FIG. 141
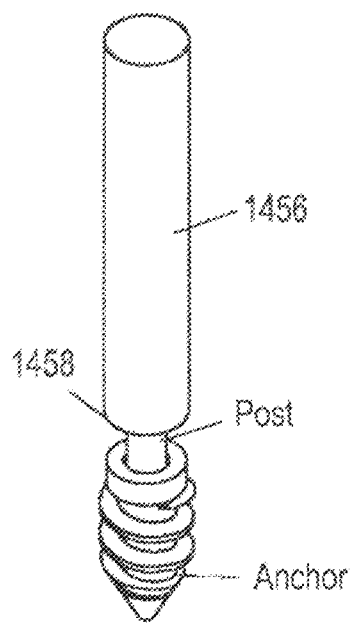
FIG. 142
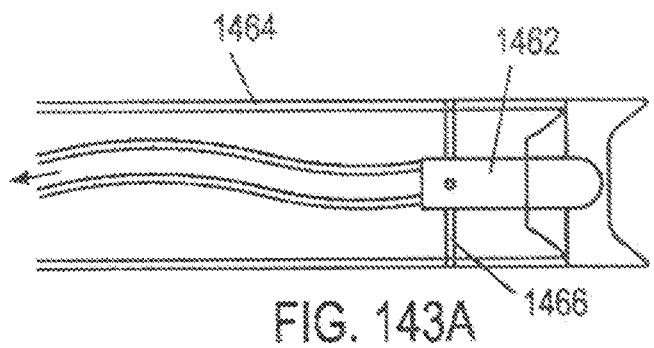
FIG. 143A
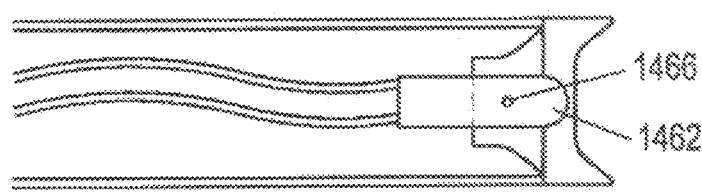
FIG. 143B

 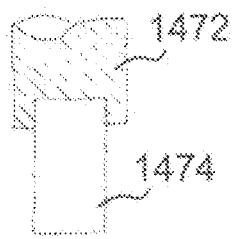 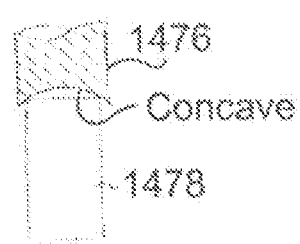 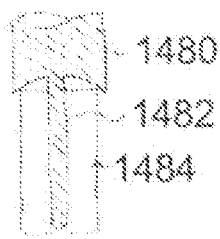
FIG. 144A   FIG. 144B   FIG. 144C   FIG. 144D
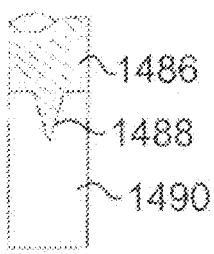 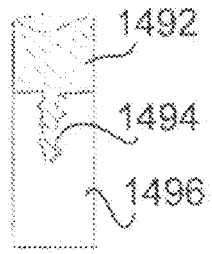 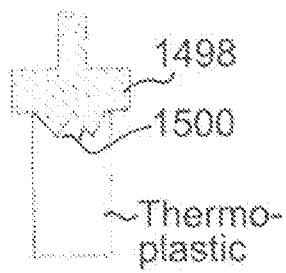 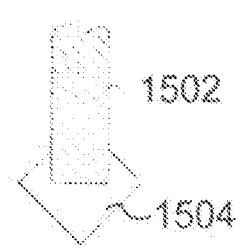
FIG. 144E   FIG. 144F   FIG. 144G   FIG. 144H
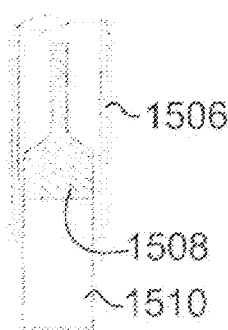 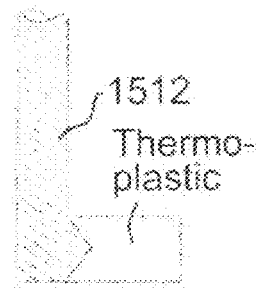 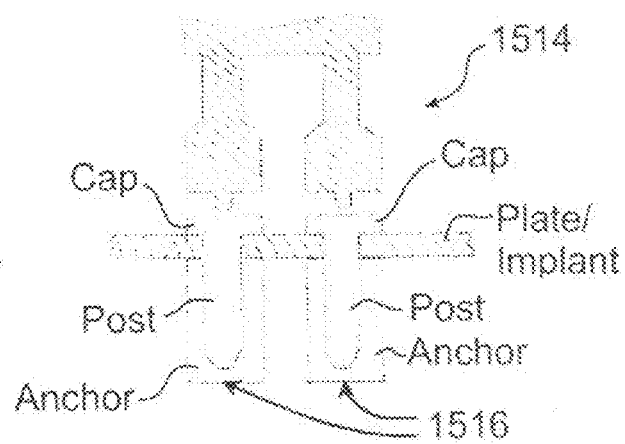
FIG. 144I   FIG. 144J   FIG. 144K

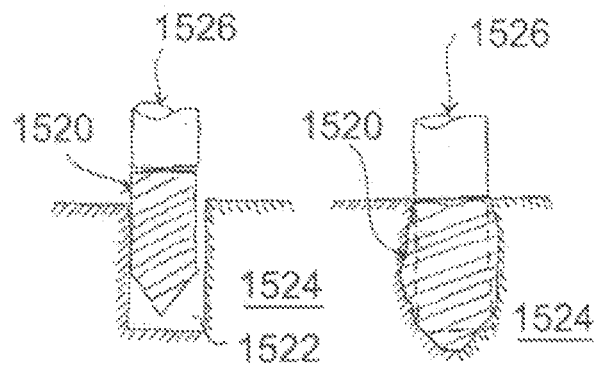
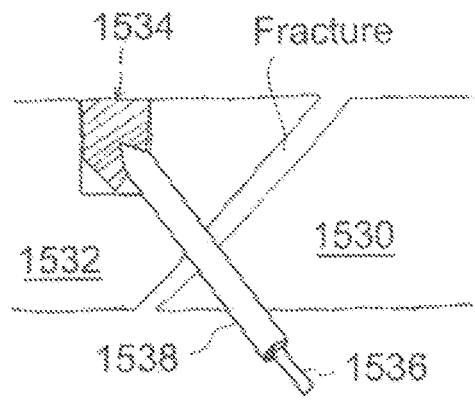
FIG. 145A  FIG. 145B  FIG. 146
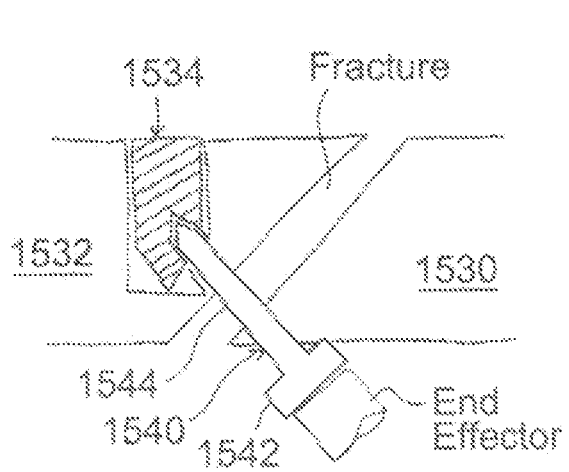
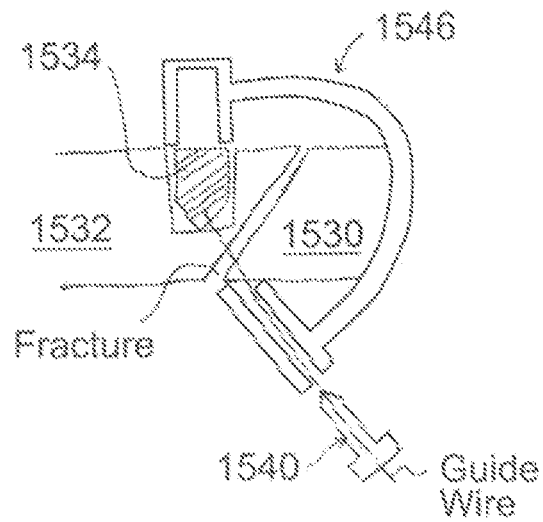
FIG. 147  FIG. 148
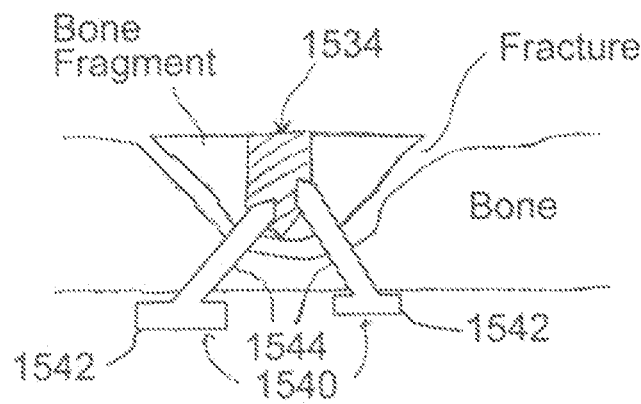
FIG. 149

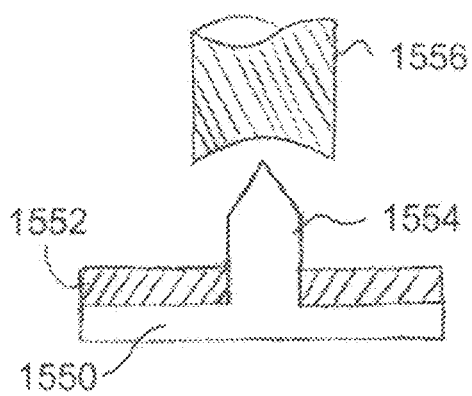
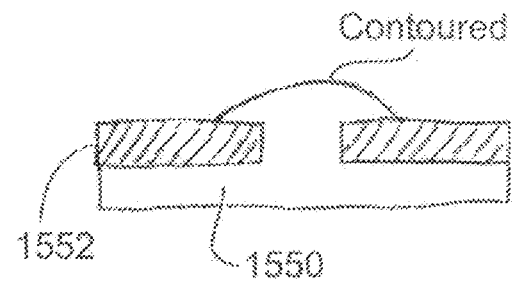
FIG. 150A
FIG. 150B
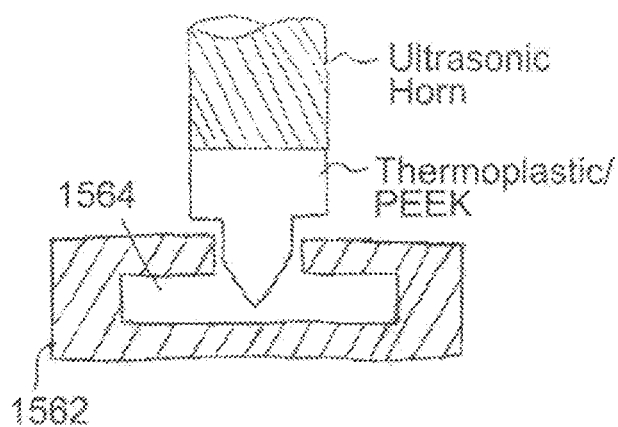
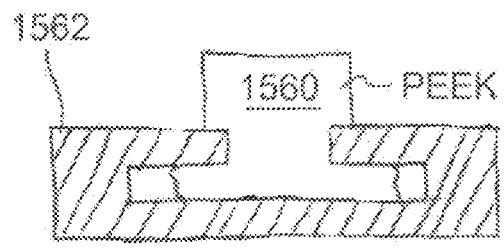
FIG. 151A
FIG. 151B

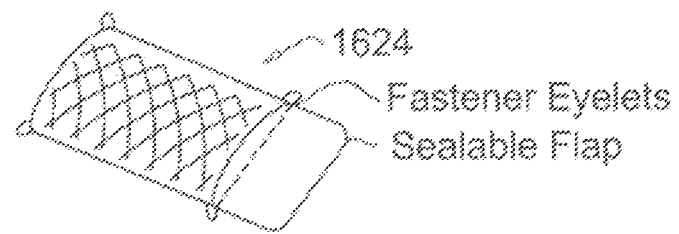
FIG. 160A
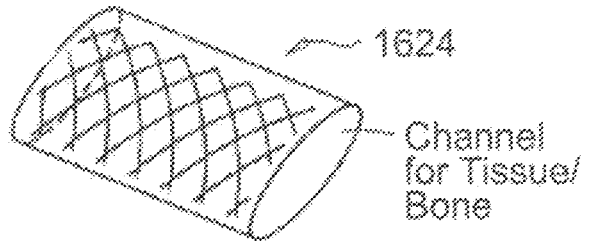 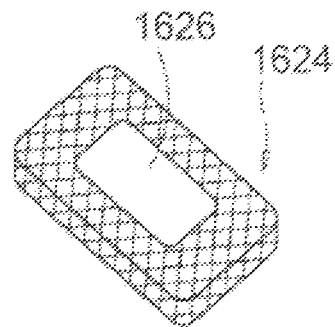
FIG. 160B  FIG. 160C
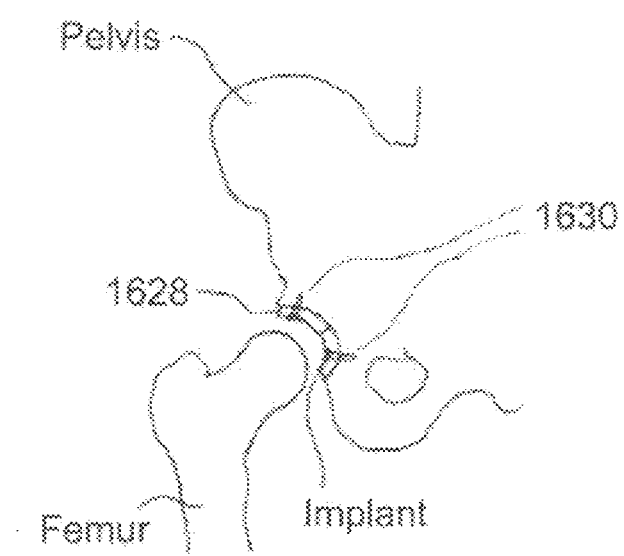
FIG. 161

METHOD AND DEVICES FOR INTRACORPOREAL BONDING OF IMPLANTS WITH THERMAL ENERGY

CROSS REFERENCE TO RELATED APPLICATIONS

This application claims the benefit of the following U.S. Provisional Applications 60/765,857 filed Feb. 7, 2006; 60/784,186 filed Mar. 21, 2006; and 60/810,080 filed Jun. 1, 2006. This application also claims priority to co-pending application U.S. patent application Ser. No. 11/416,618 filed May 3, 2006. The entirety of these related applications are incorporated by reference.

FIELD OF THE INVENTION

The invention relates to fixation of tissues and implants within the body, such as the fixation of two different tissue types, the fixation of an implant to tissue, or the fixation of an implant to another implant. This may involve using an energy source to weld biocompatible materials intracorporeally to stabilize tissue within a patient's body, such as a fractured bone.

BACKGROUND OF THE INVENTION

Body tissue often requires repair and stabilization following trauma such as a fractured bone, torn ligament or tendon, ripped muscle, or the separation of soft tissue from bone. For example, trauma to the rotator cuff usually results in a portion, if not all, of the ligament being torn away from bone. To repair such an injury, the rotator cuff must be repositioned to its anatomically correct location and secured to the bone.

One method of repairing a damaged rotator cuff is through the use of a bone anchor and a suture. A hole is drilled in the bone near where the rotator cuff will be reattached to the bone. Then, an instrument is used to place a mattress stitch with a suture in the detached portion of the rotator cuff. The suture is slideably positioned through the anchor, and the anchor is placed in the bone hole using an insertion instrument. This instrument includes an anvil and mandrel placed in contact with the anchor so that when the anvil and mandrel are moved in opposite directions relative to each other, the anchor is deformed. The deformation locks the anchor within the bone. Thereafter, the suture is tensioned drawing the rotator cuff toward the anchor. A suture lock is then activated by the insertion instrument to thereby pinch the suture between the anchor and suture lock.

In another example, fractured bones are a common injury seen in trauma centers. Sports activities, vehicle accidents, industrial-type incidents, and slip and fall cases are just a few examples of how bones may become fractured. Surgeons in trauma centers frequently encounter many different types of fractures with a variety of different bones. Each bone and each fracture type may require unique procedures and devices for repairing the bone. Currently, a one-solution-fixes-all device is not available to repair fractured bones. Instead, surgeons may use a combination of bone screws, bone plates, and intramedullary rods.

Bone plates may be positioned internal to the skin, i.e. positioned against the fractured bone, or may be positioned external to the skin with rods connecting the bone and plate. Conventional bone plates are particularly well-suited to promote healing of the fracture by compressing the fracture ends together and drawing the bone into close apposition with other fragments and the bone plate. However, one drawback with plates and screws is that with the dynamic loading placed on the plate, loosening of the screws and loss of stored compression can result.

To reduce the potential of loosening, locking screws and a locking bone plate may be used. U.S. Pat. No. 5,085,660 to Lin discloses a locking plate system. The system has multiple locking pins, each with one end formed as a screw to lock in the pending fixation bones or vertebral tubercles, with another end defining rectangular or similarly shaped locking post having a threaded locking end. Near the locking post end, there is formed a stopping protrusion. A plate defines multiple locking bores disposed at one side to be placed over the locking post end until the plate reaches the stopping protrusion on the locking pin. The plate defines multiple threaded screwing bores near the other side to receive locking pin screw. Multiple locking devices fix the side of the plate having locking bores to the locking post end or its locking pins. Multiple screwing pins each have one end formed as a pin to be used for penetrating the threaded screwing bore to lock into the hone or the vertebral tubercle. Another end which forms a head is for holding against the threaded screwing bore of the plate. Threads are provided near the head for the screwing pins to be screwed within the threaded screwing bore of the plate.

An example of an external bone plate system is disclosed in U.S. Pat. No. 6,171,307 to Orlich. Orlich teaches an apparatus and procedure for the external unilateral fracture fixation, fracture compression or enlargement of osseous tissue with a metal or equivalent material slotted forked stick to hold and position the threaded pins in its length, inserted in the bone with multiple fastening slidable screws and their bolts to attach the pins to the slotted forked stick, a solid slidable cube to hold and position the slotted forked stick, a supporting axial bar, and an axial threaded bar. A preferred embodiment includes at least three slotted forked sticks that hold and fix, with the use of compression screws and their bolts, threaded pins that penetrate the proximal and distal fragments of the bone through both corticals. Another preferred embodiment includes slotted forked sticks that adapt to the threaded pins, introduced in the bone, at any degree of inclination or orientation that these pins might have with respect to the bone.

In addition to internal or external bone plates, surgeons sometimes use intramedullary rods to repair long bone fractures, such as fractures of the femur, radius, ulna, humerus, fibula, and tibia. The rod or nail is inserted into the medullary canal of the bone and affixed therein by screws or bolts. After complete healing of the bone at the fracture site, the rod may be removed through a hole drilled in the end of the bone. One problem associated with the use of today's intramedullary rods is that it is often difficult to treat fractures at the end of the long bone. Fastener members, such as bolts, are positioned through the cortical bone and into threaded openings in the rod. However, the number and positioning of the bolt/screw openings are limited at the tip of the rod because of the decreased surface area of the rod and the reduced strength at the tip of the rod. Therefore, fractured bone sections at the distal end of a femur, for example, may not be properly fastened to the intramedullary rod.

Various inventions have been disclosed to repair tissue and fasten implants to tissue. U.S. Pat. No. 5,120,175 to Arbegast et al. discloses a fastener having an elongated shank formed of a shape memory alloy, a head at the upper end of the shank, and an annular segment al the lower end of said shank having a deformed cross-sectional shape suitable for insertion into an opening extending through adjacent workpieces. The annular segment has a frusto-conical trained shape that is larger than this opening. The annular segment radially flares from the deformed shape to an approximation of the trained shape when heated above a critical transformation temperature, thereby securing the fastener in place with respect to the workpieces. Alternatively, a sleeve made of a different material (e.g. aluminum) extending over a portion or the entire length of the fastener can be added for improved deformational characteristics, by providing the same frusto-conical shape through axial contraction of the shank.

U.S. Pat. No. 5,290,281 to Tschakaloff teaches a surgical system including a thermoplastic, body absorbable, bodily tissue fixation plate having a plurality of formations and a plurality of through-bores arranged in alternating relation along with plate. The body absorbable fasteners are adapted for insertion into the through-bores to secure the plate to underlying bodily tissue. The heating apparatus includes a wand having a heating tip of a configuration adapted to substantially matingly cooperate with the formations to facilitate heating and bending of the plate into conformance with the underlying bodily tissue.

U.S. Pat. No. 5,941,901 to Egan discloses an expandable soft tissue fixation assembly for use in anchoring soft tissue to bone. The assembly includes a tab connected to an anchor, a sleeve adapted to surround the anchor, and a flange adapted to hold a soft tissue segment next to a bone. The sleeve is inserted into a blind hole in a bone, and a section of soft tissue is placed over the bole next to the bone. Energy is applied to the flange while a predetermined axial tension is applied to the tab to compress a flared portion of the anchor against the sleeve. An upper tube portion of the anchor and the flange are bonded together, and the applied axial force on the tab separates it from the anchor, leaving the assembly anchored in the bone and the soft tissue section anchored in place between the flange and the bone.

U.S. Pat. No. 7,018,380 to Cole discloses a femoral intramedullary rod system. The rod system is capable of treating a variety of femoral bone fractures using a uniform intramedullary rod design. The system generally comprises an intramedullary rod defining an opening having an upper surface and a transverse member including a bone engaging portion and a connection portion defining a thru-hole with the nail sized to pass therethrough. A pin is selectively coupled to the transverse member to rigidly assemble the transverse member to the nail when the nail is passed through the thru-hole and the pin is received within the opening. In an alternative design, an epiphyseal stabilizer is joined to the nail by a locking member.

Also, U.S. Pat. No. 6,228,086 to Wahl et al. discloses a modular intramedullary nail. The intramedullary nail apparatus comprises a nail having a proximal portion, a middle port ion and a distal portion. The proximal portion has a longitudinal slot adapted to receive at least one fixing clement and the distal portion has at least one transverse bore. The proximal portion has a longitudinal axial bore. The apparatus further includes a set of inserts, each of which is adapted to be inserted in the longitudinal bore. Each insert has at least one guiding bore, the orientation and position of which is different for each of the inserts.

Another assembly and method to fasten tissue is disclosed in U.S. Pat. No. 6,056,751 to Fenton et al. Fenton teaches a soft tissue fixation assembly comprising an anchor element which is installed in a bone or other tissue, and a joiner element which mates with the anchor element to define a tissue capture region between them. A section of soft tissue is held within the tissue capture region, and energy is transmitted into the joiner element to cause relative vibratory motion between the respective components and localized melting of the contacting positions of the respective components to establish a welded joint. The son tissue segment is thus fixed to the bone without sutures or other fasteners.

U.S. Pat. No. 6,080,161 to Eaves, III et al. teaches a fastener for securing an osteosynthesis plate to a plurality of bone segments is provided. The fastener in the form of a fastener blank includes an elongated shank adapted for insertion through an opening in the plate and into a hole formed in the bone. The upper end of the shank forms a head that serves to secure the plate to the bone. The elongated shank is constructed of a material which when heated will deform to form a tight fit within the hole drilled in the bone. The fastener is preferably made of a resorbable material. The invention also provides a method for securing a plate to a bone using the fasteners of the invention. A fastener blank is positioned into the hole so that a portion of the blank extends into the hole provided in the bone and another portion overlies the plate. The blank is heated to raise the temperature of the blank above the transition temperature of the material from which it is made and deform the blank into a tight fit within the hole.

U.S. Pat. No. 6,605,090 to Trieu et al. discloses orthopedic implants and methods of treating bone defects. More specifically, but not exclusively, the present invention is directed to non-metallic implants and to methods for intra-operative assembly and fixation of orthopedic implants to facilitate medical treatment. The non-metallic implant assembly can be secured to underlying tissue by a fastener, such as a bone screw, that is capable of swelling on contact with fluid in the underlying tissue. Alternatively, the non-metallic implant assembly can be assembled intra-operatively using a fastener that is adhesively bonded to a bone plate or the bone plate can be deformed using heat, force or solvents to in inhibit withdrawal of the fastener. In preferred embodiments, both the fastener and the bone plate are formed of biodegradable material.

Also, U.S. Patent Publication No. 2004/0030341 to Aeschlimann et al. teaches implants at least partially consist of a material that can be liquefied by means of mechanical energy. Particularly suitable materials of this type arc thermoplastics (e.g. resorbable thermoplastics) or thixotropic materials. The implants arc brought into contact with the tissue part, are subjected to the action of ultrasonic energy and arc simultaneously pressed against the tissue part. The liquefiable material then liquefies and is pressed into openings or surface asperities of the tissue part so that, once solidified, it is positively joined thereto. The implantation involves the use of an implantation device comprising a generator, an oscillating element and a resonator, whereby the generator causes the oscillating element to mechanically oscillate, and the element transmits the oscillations to the resonator. The resonator is used to press the implant against the tissue part whereby causing oscillations to be transmitted to the implant. The implants are, for example, pin-shaped or dowel-shaped and are used in lieu of screws for forming connections with bone tissue, whereby the bone tissue is optionally pre-bored for positioning the implant. By virtue of the fact that it is unnecessary to transmit any torsional forces to the implants, these implants can be provided with a design that is weaker, i.e. slimmer than that of known screws made of the same material, and they can be implanted more quickly.

Existing systems and techniques for repairing tissue, like the ones previously described, can be complex, time consuming, lack the characteristic of being employed with precision, be damaging to tissue, and/or fail to provide a robust fixation of tissue. Therefore, there is a need for an apparatus and method for the fixation of tissue that involves reduced technical ability, fewer medical instruments, less time to complete, greater strength and precision, and preservation of living tissue. There is a need for a system that involves the precise application of energy to thermoplastic material to affix tissue and implants within the body.

SUMMARY OF THE INVENTION

The present invention provides devices and methods for the fixation of tissue or implants during a surgical procedure. The system includes devices and methods for intracorporeal bonding of thermoplastic material. An energy source welds the thermoplastics to polymers, metals, ceramics composites, and tissue. The energy source may be resistive heating, radiofrequency, ultrasound (vibratory), microwave, laser, electromagnetic, electro shockwave therapy, plasma energy (hot or cold), and other suitable sources.

In one embodiment of the invention, a fixation device includes a tissue-piercing cap positionable in the anchor. Hard and soft tissue may be fastened so that tissue-function may be at least partially restored and the operation region may be stabilized for enhanced healing. This could be ligament repair, tendon repair, muscle repair, bone repair, cartilage repair, and repair of any other tissue type. Ligaments may be fastened to ligaments; ligaments to bones; bones to bones; ligaments to muscles; muscles to muscles; tissue grafts to bone; tissue grafts to ligaments; grafts to grafts; and any other combination of tissue and implants.

Another embodiment of the invention is directed to a trauma welding system that helps stabilize tissue or implants. In some embodiments, the system may include devices and methods for intracorporeal bonding of thermoplastic material. An energy source welds the thermoplastics to polymers, metals, ceramics, composites, and tissue. The energy source may be resistive heating, radiofrequency, ultrasound (vibratory), microwave, laser, electromagnetic, electro shockwave therapy, plasma energy (hot or cold), and other suitable sources. The energy source also may enable at least part of the implanted material to be foamed.

Several embodiments of the invention involve a trauma welding system that utilizes material that can be welded within the human body. This material has requires the characteristic of becoming soft and tacky with the application of energy. The energy and techniques used to weld the material within the body are preferably selected to avoid or minimize the likelihood of tissue necrosis. Such material may include polymers and some ceramics, composites, and metals. The present invention contemplates the use of any of these materials; however, based on testing, it is believed that polymeric material, such as PEEK and PLLA, are preferred weldable materials. PEEK and PLLA are advantageous because of their desirable characteristics of being softened, reheated, molded and remolded. These characteristics are believed to exist even with the use of ultrasonic energy as the energy source to weld the material. The use of solder and ultrasonic energy are preferred when welding electrical or electronic wires and components intracorporeally.

In accordance with one aspect of the present invention, there is provided a method for stabilizing a fractured bone. The method includes the steps of positioning an elongate rod in the medullary canal of the fractured bone and forming a passageway through the cortex of the bone. The passageway extends from the exterior surface of the bone to the medullary canal of the bone. The method also includes creating a bonding region on the elongate rod where the bonding region is generally aligned with the passageway of the cortex, positioning a fastener in the passageway of the cortex and on the bonding region of the elongate rod, and thermally bonding the fastener to the bonding region of the elongate rod while the fastener is positioned in the passageway of the cortex.

In accordance with another aspect of the present invention, another method for stabilizing a fractured bone includes positioning an elongate plate on the exterior surface or a fractured bone, forming a passageway extending through the elongate plate and into the bone, positioning a fastener in the passageway, and thermally bonding the fastener to the bone while the fastener is positioned in the passageway.

Yet another embodiment of the invention involves stabilizing a fractured bone by positioning an elongate rod in the medullary canal of the fractured bone and positioning an elongate plate on the exterior surface of the bone such that the cortex of the bone is positioned between the elongate rod and plate. This method may also include forming a passageway through the elongate plate and the cortex of the bone. The passageway extends from the exterior surface or the elongate plate to the medullary canal of the bone. The method may further include creating a bonding region on the elongate rod where the bonding region is generally aligned with the passageway, positioning a fastener in the passageway and on the bonding region or the elongate rod, and thermally bonding the fastener to the bonding region or the elongate rod while the fastener is positioned in the passageway.

The elongate rod, elongate plate, and fastener may include thermoplastic material such as PEEK. Ultrasonic energy may be used to thermally bond fasteners to the bonding region of the elongate rod and/or elongate plate. The bonding region may be a roughened surface, an indentation, a channel (blind hole), or a thru-hole in the plate/rod.

When bonding the fastener to the plate/rod, the fastener may also be thermally welded to one or more cortex areas (cortical bone portions) of the bone whereby the fastener resists movement between the bone and plate/rod. Also, the fastener and implants such as bone plates and IM rods may be thermally contoured to conform to an adjacent surface or configuration.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 3A-3K show exemplary embodiments of a welding horn;

FIG. 6 illustrates a manual welding control box;

FIG. 7 shows a control box having pre-set welding parameters;

FIG. 8A illustrates an automatic welding control unit;

FIGS. 23A-23D show the repair of a fractured bone with a thermoplastic rod;

FIGS. 24A and 24B illustrate the repair of a fractured head of a bone;

FIGS. 26A and 26B illustrate the repair of a fractured bone with a combination of a thermoplastic rod and plate;

FIGS. 34A and 348 illustrate a pedicle fastener apparatus;

FIG. 91 is an x-ray image of the fasteners and rods of FIG. 90;

FIGS. 92A and 92B are photographs of thermoplastic fasteners disposed in bone;

FIGS. 111A and 111B show implantation and repair of electrical components intracorporeally;

FIGS. 112A and 112B illustrate modular metallic stents;

FIGS. 113A and 113B show modular bifurcated metallic stents;

FIG. 114 illustrates welded bone filler and an implant;

FIGS. 115A and 115B show a thermally bonded suture knot;

FIG. 116 illustrates a shrinkable suture;

FIGS. 117A and 117B show thermally scaled implantable sacs;

FIGS. 118A and 118B illustrate tissue bonded with thermoplastic material;

FIGS. 119A and 119B show a composite fastener of the present invention;

FIG. 120 illustrates an exemplary thermoplastic fastener used for testing weld parameters;

FIG. 121 is a photograph showing the apparatus used for determining the fail strength of thermoplastics;

FIG. 122 is a photograph of thermoplastic fastener of the present invention:

FIG. 123 is a photograph of neoprene (used as a tissue model) held by the fastener of FIG. 122;

FIG. 124 is a photograph or another fastener of the present invention;

Figure 124:
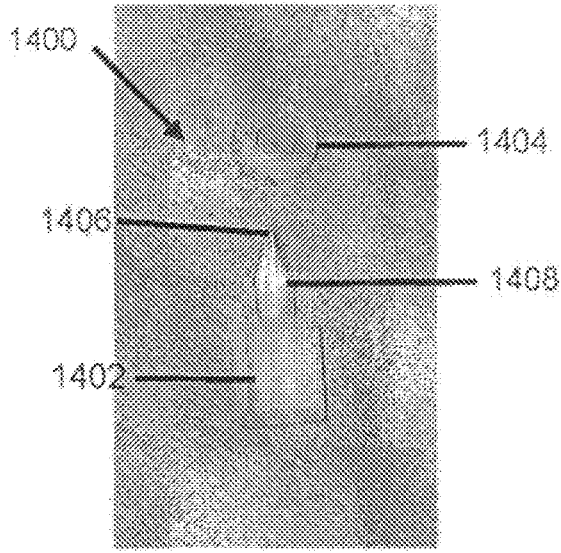
Figure 125:
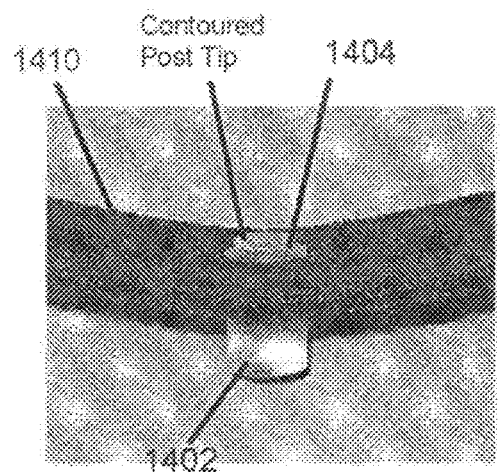
Figure 126:
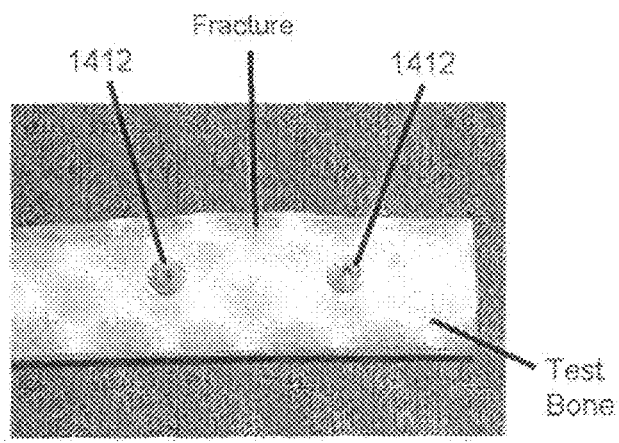
Figure 127:
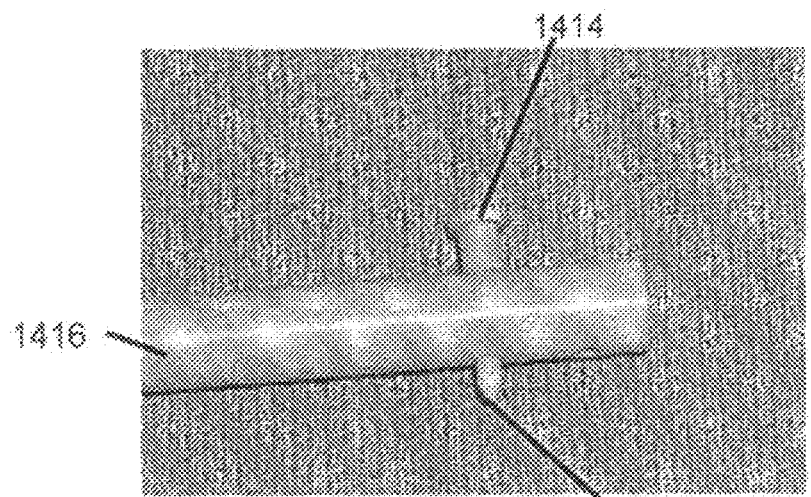
Figure 128:
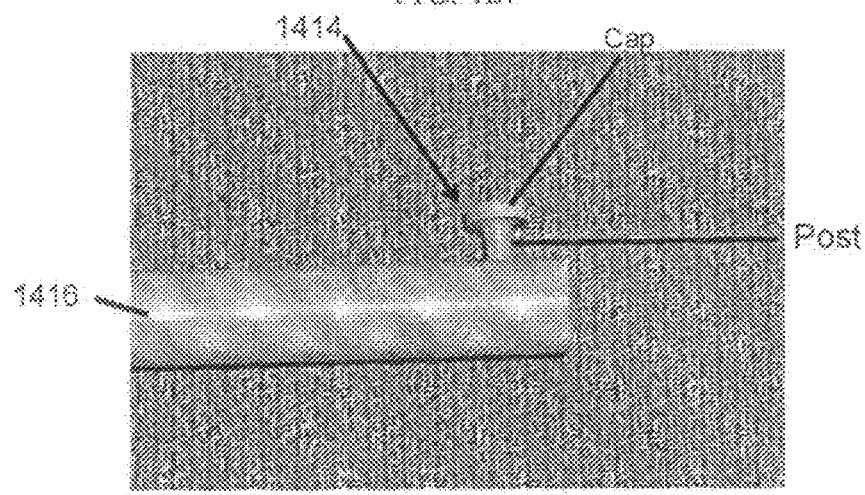
Figure 129:
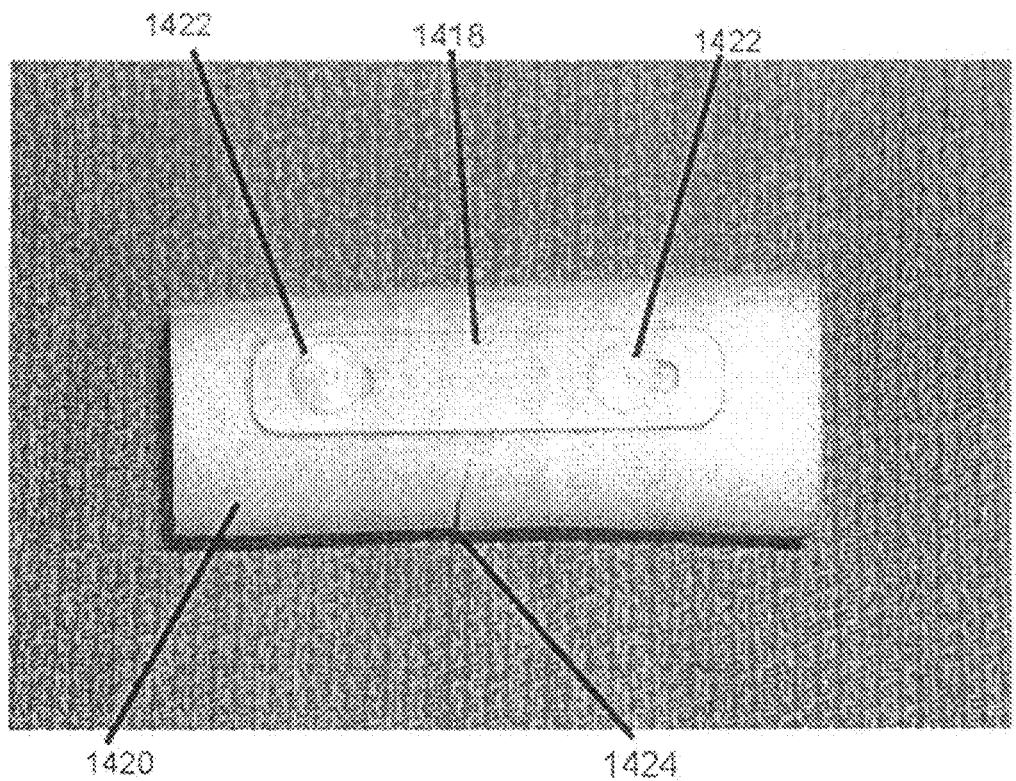
Figure 130:
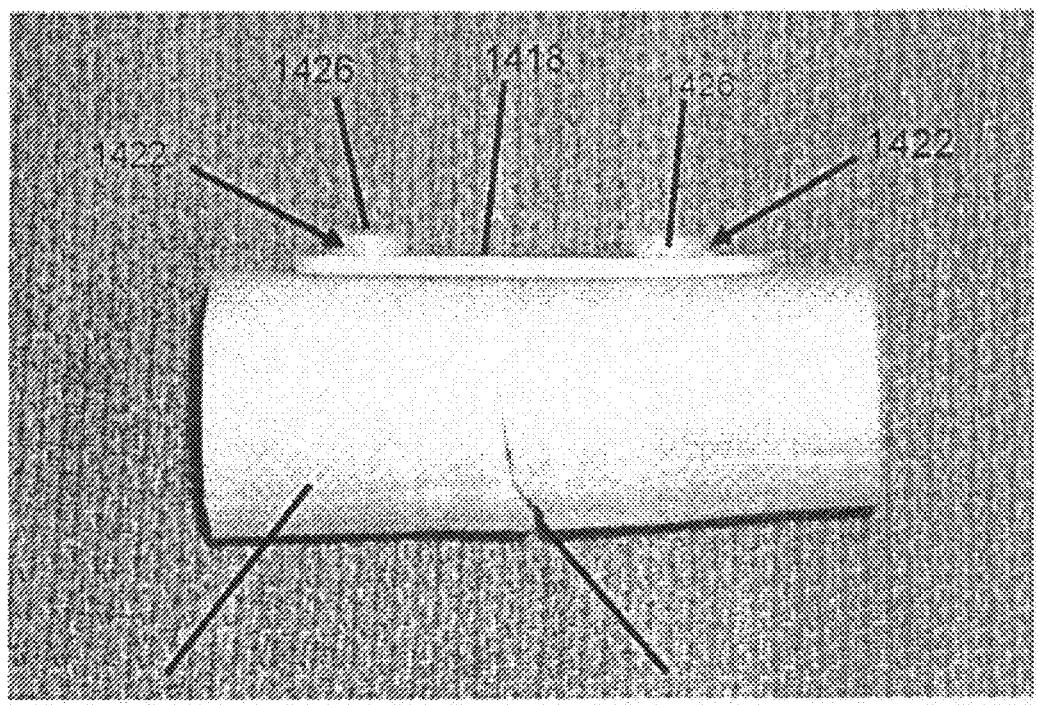
Figure 131:
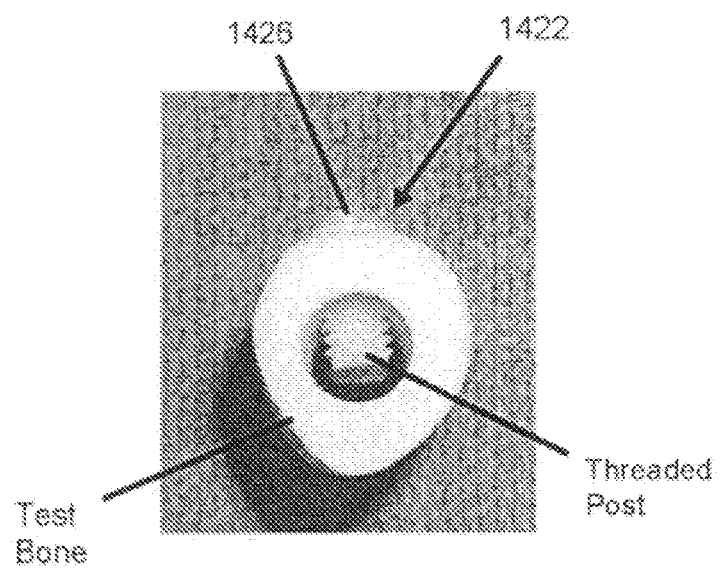
Figure 132:
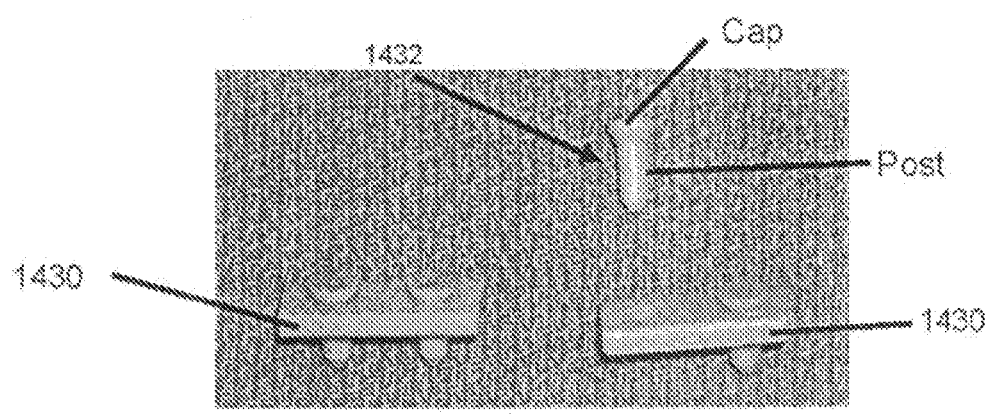
Figure 133:
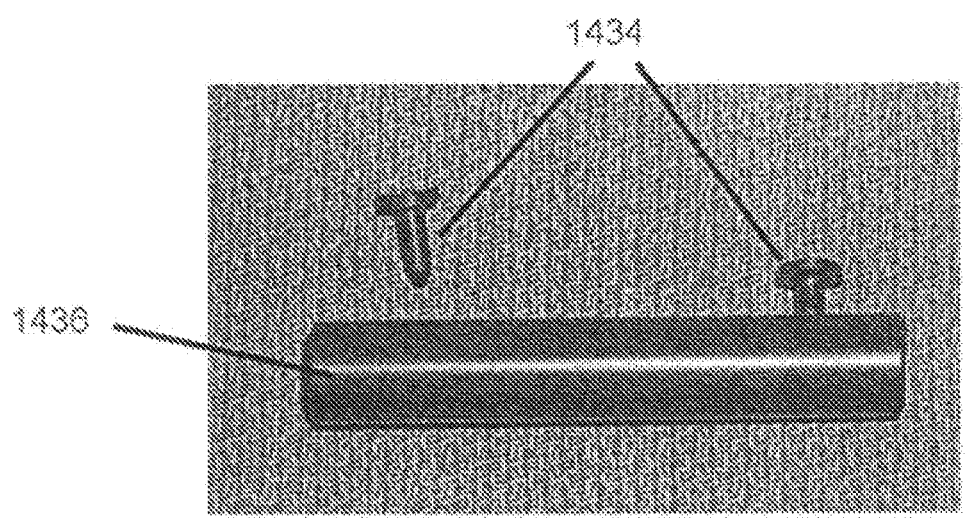
Figure 134:
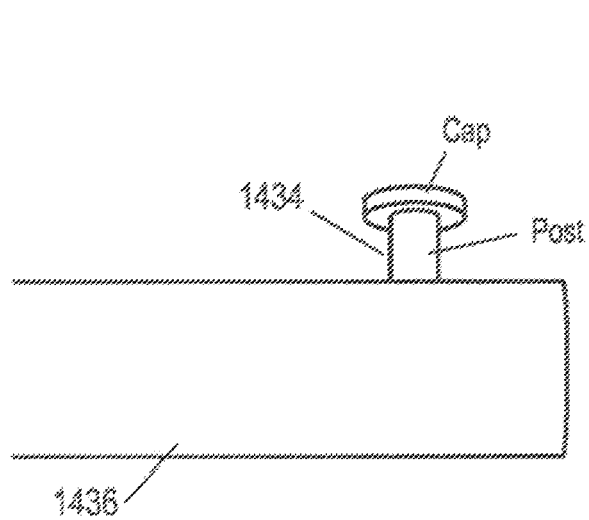
Figure 135:
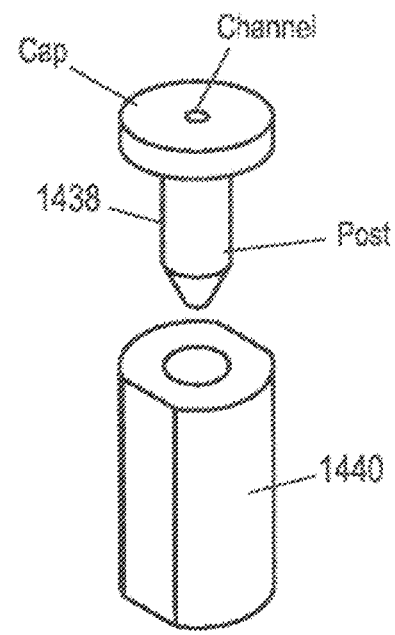
Figure 136:
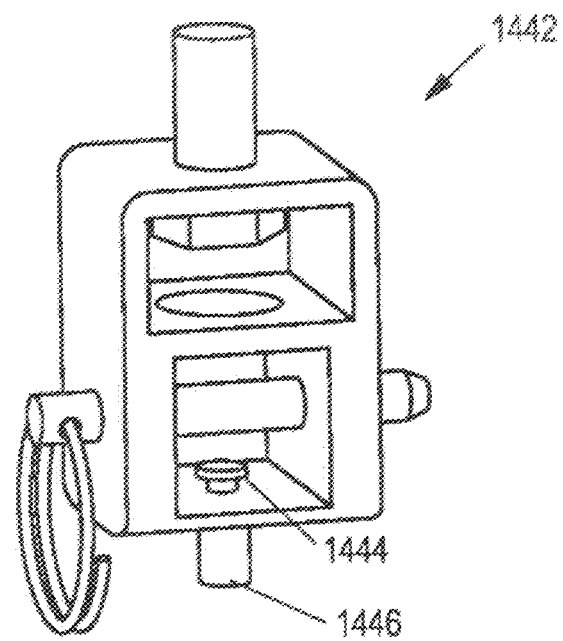
Figure 137:
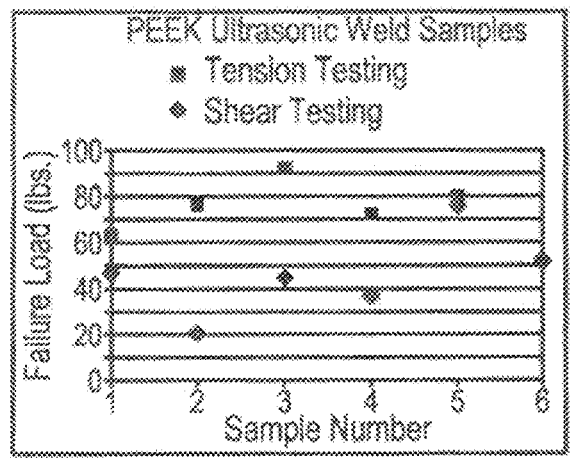
Figure 138:
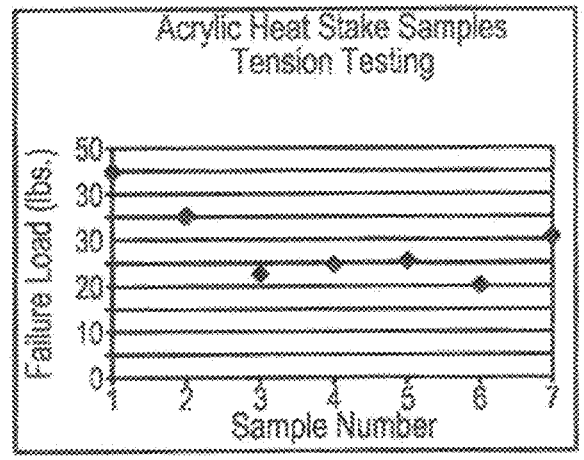
Figure 139:
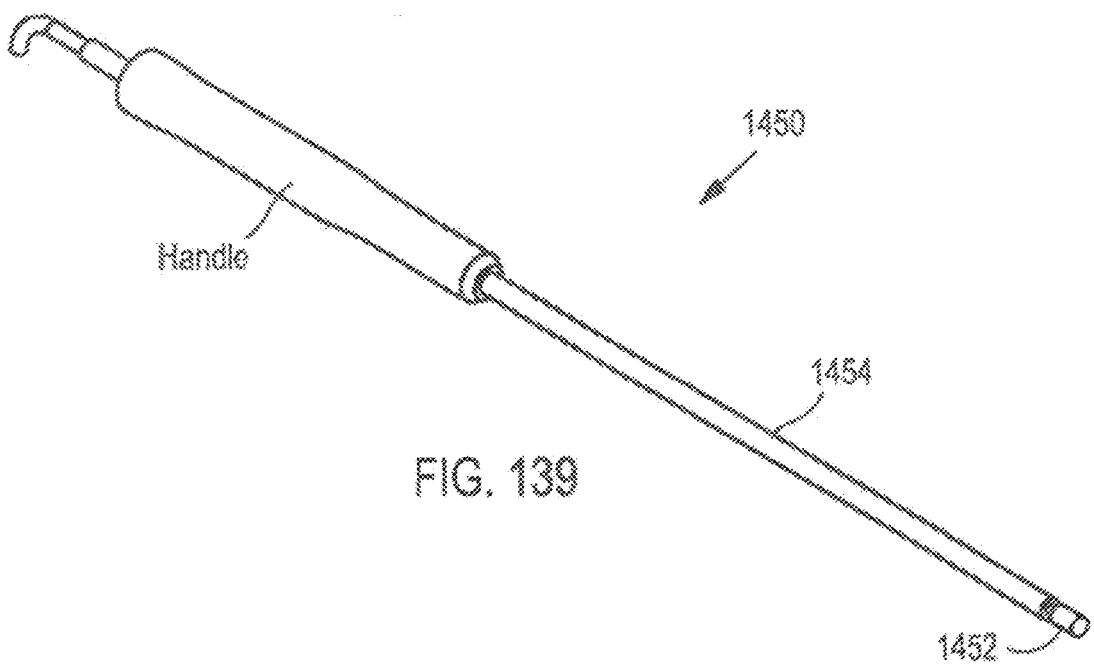

FIG. 125 is a photograph of neoprene held by the fastener of FIG. 124;

FIG. 126 is a photograph of a test specimen with PEEK fasteners welded therein;

FIG. 127 is a photograph showing a PEEK fastener extending through a test specimen;

FIG. 128 is a photograph of a PEEK fastener welded into a blind hole;

FIG. 129 is a photograph showing a PEEK bone plate and PEEK fasteners used to repair a fractured bone test specimen;

FIG. 130 is a side view photograph of FIG. 129;

FIG. 131 is a photograph of a PEEK anchor which is mechanically locked and thermally locked into a test specimen;

FIG. 132 is a photograph showing various PEEK fasteners and stabilization plates;

FIG. 133 is a photograph of a carbon reinforced PEEK specimen and fasteners;

FIG. 134 is a partial close-up photograph of FIG. 133;

FIG. 135 is a perspective view of an exemplary fastener and anchor;

FIG. 136 is a perspective view of an apparatus used during thermoplastic weld testing;

FIG. 137 is a table showing test results for PEEK ultrasonic weld samples;

FIG. 138 is a table showing test results for Acrylic heat stake samples;

FIG. 139 is a perspective view of an exemplary ultrasound welding device;

FIG. 140 is perspective view of a fastener and an end effector of the device of FIG. 139;

FIG. 141 is a perspective view of the fastener disposed against the end effector of FIG. 140

Figure 152:
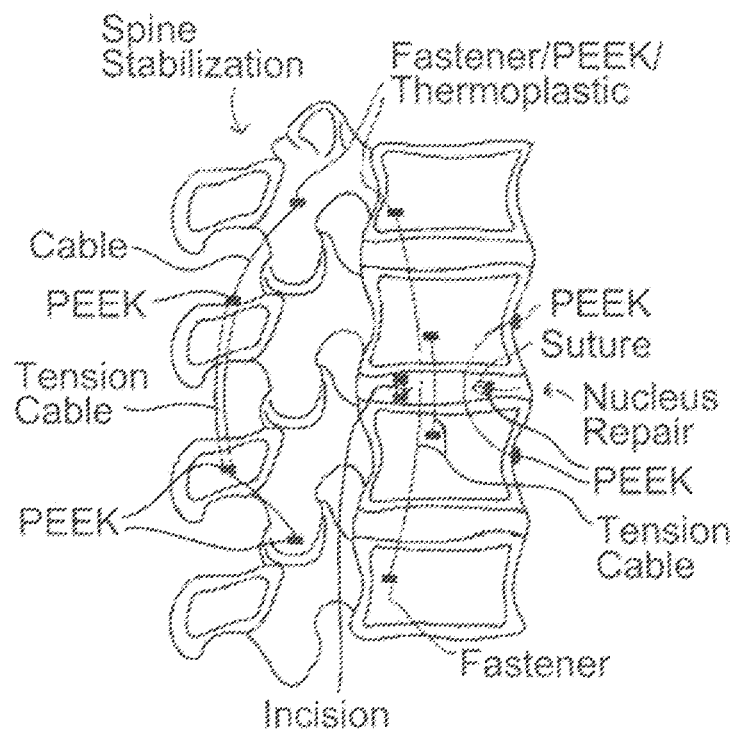
Figure 153:
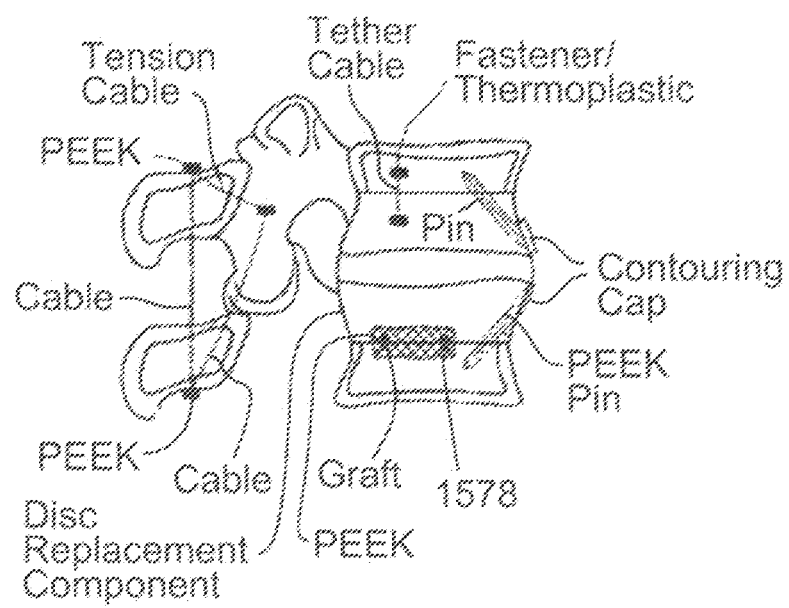
Figure 154:
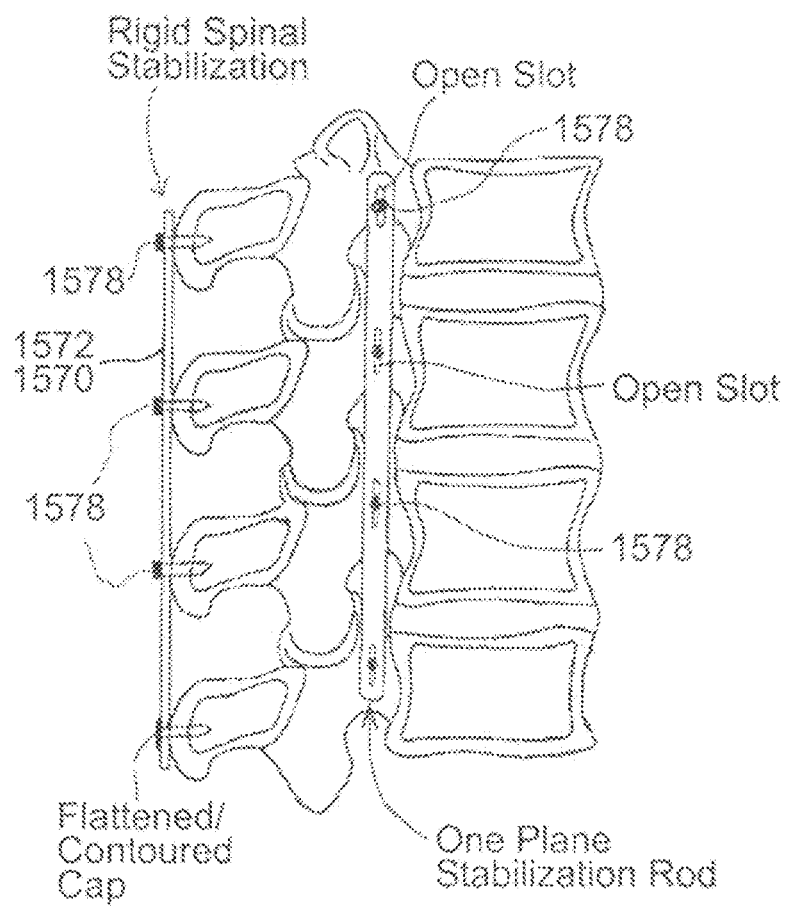
Figure 155:
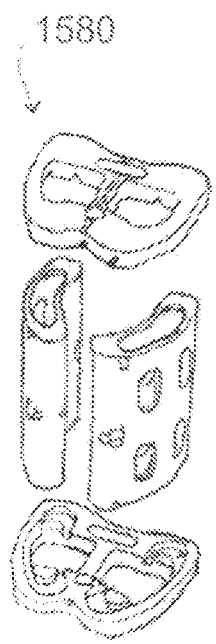
Figure 157:
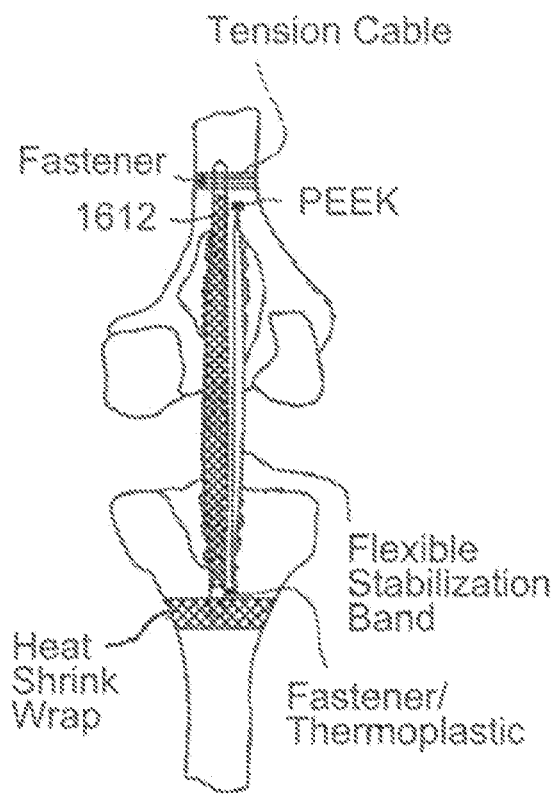
Figure 158:
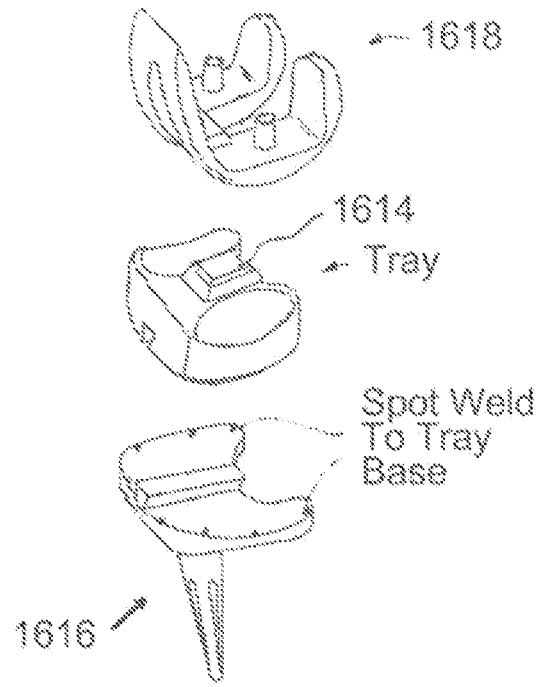
Figure 159:
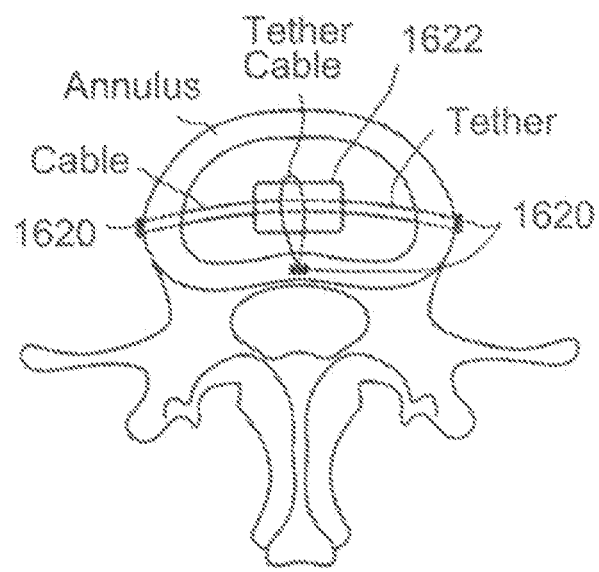
Figure 162:
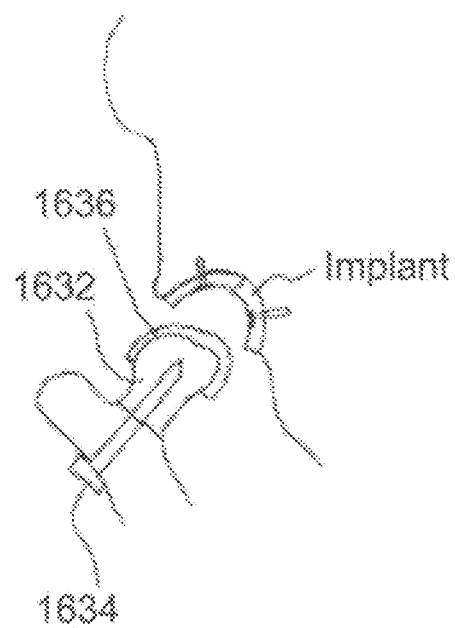

FIG. 142 is a perspective view showing an energy source horn in contact with a thermoplastic fastener which is disposed in a tissue anchor;

FIGS. 143A and 143B illustrate an exemplary cartridge heater of the present invention;

FIGS. 144A-144K show exemplary embodiments of a welding horn;

FIGS. 145A and 145B show a thermoplastic anchor welded in tissue;

FIG. 146 illustrates the repair of a fractured bone with thermoplastics and energy;

FIG. 147 shows a thermoplastic fastener and anchor used to repair a fracture in a bone;

FIG. 148 illustrates a triangulation device used to repair a fractured bone;

FIG. 149 shows multiple thermoplastic fasteners and an anchor used to fix a broken bone;

FIGS. 150A and 150B illustrate the welding of a thermoplastic component to a non-thermoplastic component;

FIGS. 151A and 151B show a thermoplastic component welded into a cavity of a non-thermoplastic component;

FIG. 152 shows dynamic spinal stabilization using thermoplastics and cables;

FIG. 153 illustrates thermal welding of a disc replacement component;

FIG. 154 shows rigid and one-plane stabilization of the spine;

FIG. 155 is a perspective view of a vertebral body replacement implant that may be assembled using thermal bonding;

FIGS. 156A-156F illustrate various embodiments of thermoplastic fasteners;

FIG. 157 shows knee repair and stabilization using the surgical welding system of the present invention;

FIG. 158 is a perspective view of a total knee replacement implant having thermoplastic stabilizers welded thereon;

FIG. 159 illustrates implant tethering using thermoplastics;

FIGS. 160A-160C show various embodiments of heat shrinkable implant pouches;

FIG. 161 illustrates thermal bonding of acetabulum implants;

FIG. 162 shows thermoplastic material functioning as a bearing surface; and

Figure 163:
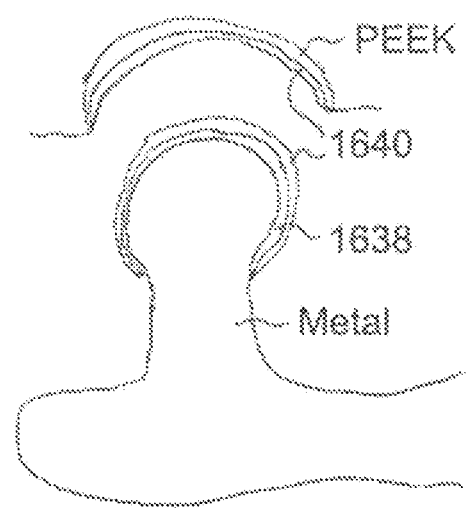

FIG. 163 illustrates thermoplastic material used to bond bearing surface material in a hip replacement implant.

DETAILED DESCRIPTION OF THE INVENTION

As indicated above, the invention relates to devices and methods that help stabilize tissue or implanted materials in a patient's body. As will be explained in greater detail below, the invention can be utilized in several ways to achieve different desired results, including the fixation of two different tissue types, the fixation of an implant to tissue, or the fixation of an implant to another implant.

The methods and devices disclosed herein may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

Also, an implant may be inserted within the body and fastened to tissue with the present invention. Such implant insertion procedures include, but are not limited to, partial or total knee replacement surgery, hip replacement surgery, shoulder replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonic cells, enzymes, and proteins.

Thus, the invention may be utilized as a trauma welding system for the stabilization of damaged tissue, such as fractured bones. In this application, the system may include devices and methods for intracorporeal bonding of thermoplastic material. An energy source can be used to weld the material in place. The energy source may be resistive heating, radiofrequency, ultrasound (vibratory), microwave, laser, electromagnetic, electro shockwave therapy, plasma energy (hot or cold), and other suitable sources. Likewise, the energy source may enable a portion of material to be foamed or expanded such that two components of the welding system are secured together. Other energy sources, surgical procedures, and medical instruments which may be used with the present invention are disclosed in U.S. Provisional Patent Applications No. 60/765,857 filed Feb. 7, 2006; 60/784,186 filed Mar. 21, 2006; and 60/810,080 filed Jun. 1, 2006, as well as U.S. patent application Ser. No. 11/416,618 filed May 3, 2006. The contents of these documents are incorporated by reference herein in their entirety.

The trauma welding system and other embodiments of the present invention contemplates the use of any biocompatible material weldable within the human body. The materials used may include, but are not limited to, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, heat bendable material, and combinations thereof.

Preferably, this material can become gel-like, tacky, or soft with the application of energy. The energy source and the technique used to weld the material within the body can be selected to minimize or avoid damage to surrounding body tissue. Exemplary materials that may be used may include polymers, ceramics, composites, and metals, although other materials may also be suitable for use with the invention. While the present invention contemplates the use of any of these materials in any of the following embodiments, polymeric material is used in the following examples and description simply to illustrate how the invention may be used.

Generally, there are two types of polymers: thermoset and thermoplastic. Thermoplastics may be used with the present invention because they can be softened, reheated, molded and remolded. Thermoplastics are generally classified as either amorphous or semi crystalline. Some semi crystalline polymers have some amorphous structure while other semi crystalline polymers may be more crystalline than others. Examples of amorphous polymers are poly carbonate (LEXAN), polystyrene, polysulfone (ULDALL), and acrylics polycarbonate (ABS and styrenes). Examples of semi crystalline polymers include acetyl (DELRIN), nylon, polyester, polyethylene, polyether ether ketone, poly propylene, polyvinylchloride (PVC), and Caprolactam. Biodegradable semi crystalline polymers may include polylactic acid and polyglycolic acid. Copolymers of PGA and PLA may also be used. These copolymers may ultrasonically bond better than pure PGA and PLA. Other polymers which may be used with the present invention, either as a thermoplastic or non-thermoplastic, are polyethylene glycol (PEG)-copolymers and D,L-lactide-co-glycolide polyesters.

Some semi crystalline materials have an amorphous structure or an amorphous region within them. These materials are particularly suitable for surgical welding, especially ultrasonic welding. Examples of such materials include PEEK and PEAK. With these special semi crystalline materials, the amorphous content of the polymer makes the material more conducive to ultrasonic welding, and therefore a better bond is achieved. Also, a lower amount of energy is needed to bond these materials.

The semi crystalline materials without an amorphous structure or region have a rigid or fixed melting point. A high level of energy it required to breakdown the crystalline structure before the melting occurs. Once the melting starts, the material very rapidly moves through the transition area from a solid to a flowable substance, i.e. a liquid. Also, the molecular structure of semi crystalline materials absorbs vibrational energy making it more difficult to transmit the vibrational energy from an energy-producing instrument to the interface of the parts being welded. For example, polylactic acid reaches its melting point and goes through its transition region rapidly which causes it to flow in the tissue. This rapid heating and complete, or nearly complete, melting of the material weakens the overall structure and causes tissue necrosis. When this material is used in surgical screws, plates, rods, etc., care must be taken to avoid over melting and weakening of the implant. The temperature, time, and pressure must be closely monitored and controlled with semi crystalline materials or the implant will fail.

The polymers used in the present invention, such as PEEK and PLLA, have randomly arranged molecules allowing vibrational energy to pass through the material with little attenuation. As such, the material requires relatively little ultrasonic energy to make the material soften and become tacky. This small amount of energy or heat needed to bond PEEK and PLLA helps avoid or minimize the likelihood of tissue necrosis. The transition period is longer in duration and therefore, when applying energy, the material gradually softens, passing from a rigid state through a transition state to a rubbery state and then to a flowable gel-like state. The amorphous features of these materials make them ultrasonically weldable with lower temperature and better welding points. To bond these materials, the true melting point does not need to be reached or exceeded, so there is less risk to surrounding body tissue. PEEK and PLLA are also useful with the welding system of the present invention because it has a modulus of elasticity very close to bone. Also, some grades of PEEK and PLLA have a hydrophilic component which permits hydrophilic interlocking when placed in the body.

The temperature, time, pressure, and other parameters of the welding process may be closely monitored and controlled to achieve an effective weld. Also, because the material does not substantially melt (only the welding region softens and becomes tacky) the holding strength of the thermoplastic during and after welding is not jeopardized. That is, a fastener made of a thermoplastic which melts, like those in the prior art, cannot maintain a compressive force against a component or implant during the welding process. This is because the material of the fastener becomes liquefied, and a fastener in liquid form cannot maintain a compressive or tension force. The present invention contemplates implants made of PEEK or PLLA which bond by softening or making tacky the polymer material at the bonding region. The remaining PEEK or PLLA material does not flow and therefore retains its ability to maintain a compression or tension force.

When bonding two thermoplastic components together, it is optimal that the components be chemically compatible to create a molecular bond. Similar thermoplastics may be compatible if their melt temperature is within about 6 degrees Celsius or if they have similar molecular structures. Generally, amorphous polymers may be welded to each other. In the present invention, PEEK may be bonded to PEEK. Biodegradable polymers may be bonded to biodegradable polymers. Biostable polymers may be bonded to biostable polymers. Biodegradable polymers may be bonded to biostable polymers.

When two dissimilar materials need to be bonded together, the welding may be performed outside the body, such as during the manufacturing process or within the operating room. This is done to avoid damage to surrounding tissue caused by the heat required to weld the dissimilar materials to each other. Then, once implanted, further welding may be done within the body to bond like thermoplastics creating the desired implant configuration. For example, a spacer made of PEEK may be bonded to a metallic implant outside the body. The spacer and implant may be placed in the body, and the PEEK may be welded with another PEEK element inside the body so that there is a PEEK to PEEK bond. The metal implant may be the load bearing surface or the bearing point, while the PEEK to PEEK weld provides for the fastening and stabilization of the implant.

There are several factors that effect welding of thermoplastic materials. One is hydroscopicity, the tendency of a material to absorb moisture. If too much fluid gets between the welded parts it can decrease the bond or create a foam which prevents proper bonding of the materials. Therefore, the welding of thermoplastics may be performed under vacuum/suction, or a hermetic seal may be placed around the thermoplastic during the welding process. Also, the welding may be performed using a cannula which prevents fluid from entering the welding area. Furthermore, pressure, such as air pressure or compression force may be applied during welding to prevent entry of moisture or liquid.

In addition to or in place of reducing moisture from the welding area, certain agents can be used to aid in the bonding process. Such agents may include filler material, glass filler, glass fiber, talc, and carbon. The agents may be placed at the bond site as a temporary welding enhancement means or may be a permanent agent to enhance the bonding. For example, the agent may be placed within the bonding region of PEEK or PLLA. The agent may be left in place to bond or could be removed. It is contemplated that any amount of agent may be used to enhance the bond strength of the thermoplastics. In an exemplary embodiment, the amount of agent may be about 10 to 20 percent.

Moisture may further be eliminated or prevented from entering the thermoplastic material through the use of desiccants. Desiccants may be added prior to or during the welding process. Also, the thermoplastic material may be stored using desiccant material to prevent change in thermal properties. It is contemplated that this moisture reducing means may be applied to any polymeric material.

Another factor effecting the welding of thermoplastic material is pigments, especially white and black coloring. In many materials used in medical applications, white pigment is added to the polymer to make it appear sterile. Some pigments negatively affect the welding characteristics of the material. In the present invention, pigment-free thermoplastics, such as PEEK, are thermally welded for proper bonding of the material.

Mold release agents also affect the welding properties of thermoplastics. Polymeric components are usually formed in a mold to create a desired configuration. The component is easily removed from the mold because a release agent is placed between the mold and polymer. These agents, lubricants, plasticizers, and flame retardants can negatively affect the bonding ability of the polymer. Thus, it is preferred in the present invention that PEEK, PLLA, and other thermoplastics used for welding are substantially free of these substances.

In addition to avoiding release agents, pigments, and moisture, the bonding of thermoplastic materials may be further enhanced by adding minute metallic material to the polymer. The metallic material may be metal flakes or metal dust. Examples of such metal include iron particles, chromium, cobalt, or other suitable metals. The metal may be embedded within the polymeric material to enhance the thermal properties. Alternatively, or in addition, the metal may be applied to the bonding surfaces of the polymeric material. Energy applied to the polymer would heat both the polymeric and metallic material providing a faster and more uniform weld. It is contemplated that glass fillers, carbon fillers, talc, or combination thereof may also be used in addition to or in lieu of the metallic material.

Other factors affecting the welding of thermoplastics include size, thickness, surface geometry, material properties of the thermoplastic, and the type of host tissue involved in the weld, i.e. soft, hard, dry, wet, or moist tissue. These and other factors are explained in more detail with reference to FIG. 5.

Furthermore, how the thermoplastic is welded is an important characteristic of obtaining a robust thermal bond. The type of energy used is one way to control the welding process. As previously mentioned, various energy sources may be used to weld polymers. In an exemplary embodiment and as used primarily throughout the invention, ultrasound energy is used to create vibrations within the polymeric material thereby exciting and heating the molecules to transition to a tacky state. Two or more different types of energy may also be used. For example, ultrasound may be used to weld a polymeric component to another component, while resistive heating may be used to contour the surface or change the geometry of the materials. The surface of the component may be smoothed out or sculpted using resistive heating.

The intensity and duration of the energy source impacts the quality of the weld. For instance, the amount of power or watts used affects the weld. Therefore, the watts may be controlled by the operator depending on the component to be welded. A switch, dial, or other control may be placed in connection with the energy source to vary the intensity of the energy applied to the weld. For example, the amount of current supplied to the instrument may be varied or controlled. In an exemplary embodiment, the ultrasound power may be varied, for example, between 80 and 100 watts. The amount of time the energy is applied affects the weld as well. The time may be varied from milliseconds to hundredths of seconds to actual seconds depending on the desired weld. Thus, controlling the time of exposure to the energy source can be used to limit the amount and the degree of thermoplastic material which softens and becomes tacky. In an exemplary embodiment, energy may be applied from 0.1 seconds to 3 seconds, such as approximately 0.3 seconds. In case of RF and ultrasonic energy, the wavelength or the energy may be varied to affect the softening or melting of the thermoplastic. It is also contemplated that the amount of time that energy is applied may be controlled not only by the operator but also via radiofrequency, optical, radiowave, etc. A computer or other microprocessor may send signals to the energy emitter to turn the energy on and off.

Pulsing of the energy source may likewise be used to intermittently apply energy to the weld site or to vary characteristics of the energy source over time, such as the power, frequency, or pressure, to enhance bonding and avoid tissue necrosis. That is, the energy may be emitted, then relaxed, then emitted, etc.

Controlling the pressure applied to the thermoplastic material also may be used to affect the welding process. During welding, a handpiece, an anvil, a horn, end effector, or combinations thereof may be used to apply controlled force against the welded component. After welding, while the welded material is cooling, the force may continue to be applied to ensure proper bonding of the materials. The handpiece, anvil, horn, and end effector may be made of aluminum, titanium, or other suitable material. Also, the pressure may be varied, increased or decreased, during the welding process. In an exemplary embodiment, the pressure may be applied by the operator or may be applied with a spring. A sensor, spring, and/or piezoelectric device may be used to monitor and control the amount of pressure applied. In another exemplary embodiment, the welding horn may apply ultrasound energy and pressure to a polymeric implant being attached to bone. The bone may act as the anvil eliminating the need for an anvil instrument. Also, a hard implant or another polymeric material may function as the anvil.

Furthermore, the placement of the energy source on the thermoplastic affects the weld. The energy may be applied to one side of the polymer, through the center of the polymer, to two or more sides of the polymer, or to generally the outer surface of the polymer.

Controlling collapse is another factor in achieving an effective thermoplastic weld. For instance, the weld time and material collapse may be monitored to ensure a proper weld. A measurement of the change of the material being welded may be made to determine when bonding is complete. This may be accomplished by using micro-switches to provide precise binary control of the mold. Also, by using a linear variable displacement transducer (LVDT), the control system can monitor the weld more precisely. Because a LVDT translates position to voltage, the weld profile can be dynamically controlled. For example, the initial energy delivered can be a higher wattage, then when the material starts co collapse the amplitude of the wave can be decreased.

By being able to monitor the position of the collapse, different weld profiles can be programmed into the system. In addition, to control how far the material collapses on the anchor during a weld, a combination of weld current and time preset in the generator control system could be used. This can also be coupled with a defined force applied during the weld. Furthermore, collapse may be controlled or monitored through the use of a mechanical stop on the fixation device itself or on the welding instrumentation. The mechanical stop would prevent collapse after a predetermined point. It is also contemplated that the collapse could be monitored by other methods such as optics, laser, or even a hall-effect sensor.

All of the above-mentioned welding parameters may be monitored and controlled by a computer. The discussion relating to FIGS. 5-8, among others, illustrate instruments that may be used for controlling weld parameters. Feedback may be provided by the computer to vary, start, and stop the various parameters of welding. The feedback and control of the computer may be programmed based on the type of polymer being welded and the type of material the polymer is being welded to. For example, for PEEK to PEEK welds, the computer may apply a set of parameters (time, power, pressure, frequency, wavelength, etc.) to achieve a desired or effective weld. Other parameters may be established or preset for other polymers, other weld materials, or for welding dissimilar materials.

Figure 1:
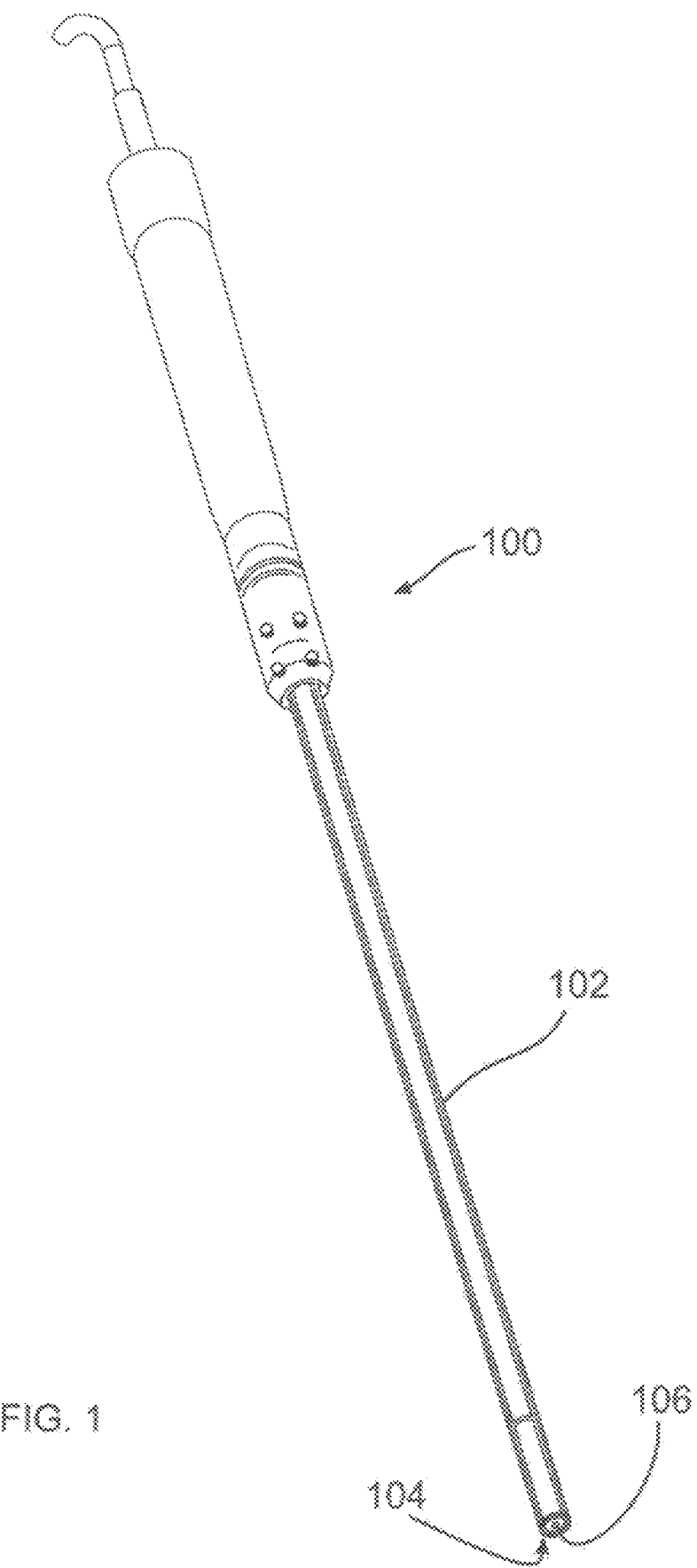
FIG. 1 is a perspective view of an exemplary ultrasound welding device.

Any known energy emitting instrument may be used with the surgical welding system of the present invention. The instrument may produce energy such as resistive heating, radiofrequency, ultrasound (vibratory), microwave, laser, electromagnetic, electro shockwave therapy, plasma energy (hot or cold), and other suitable energy. FIG. 1 illustrates an exemplary welding instrument 100 that may be used with the present invention. The welding instrument 100 may be an ultrasonic handpiece with a sheath 102 to cover and protect the end effector 104 and hold a fastener. As will be discussed in greater detail below, the welding instrument may be used to weld a cap of an implanted device to an anchor, or likewise may be used to weld other components together.

The sheath 102 may have a small counter bore at its tip to cover a portion of the cap. There also may be a bushing at a nodal point of the ultrasonic signal to prevent the end effector 104 from contacting the sheath 102. The tip of the end effector 104 has a small post 106 sticking out of the welding face which presses into a bore in the cap of the fastener. This can help align the fastener post into the anchor bore and keep the cap tight against the end effector face. The end effector 104 may be removable to allow it to be replaced or cleaned after welding.

The post 106 on the end effector 104 may be threaded or have a Morse taper to mate with the cap. Alternatively, the end effector 104 has a bore that the top of the cap mates into. The mating of the components could also be by threads or a Morse taper along with a straight post. Furthermore, the post could be roughened on the outside surface for better adhesion.

Figure 2A:
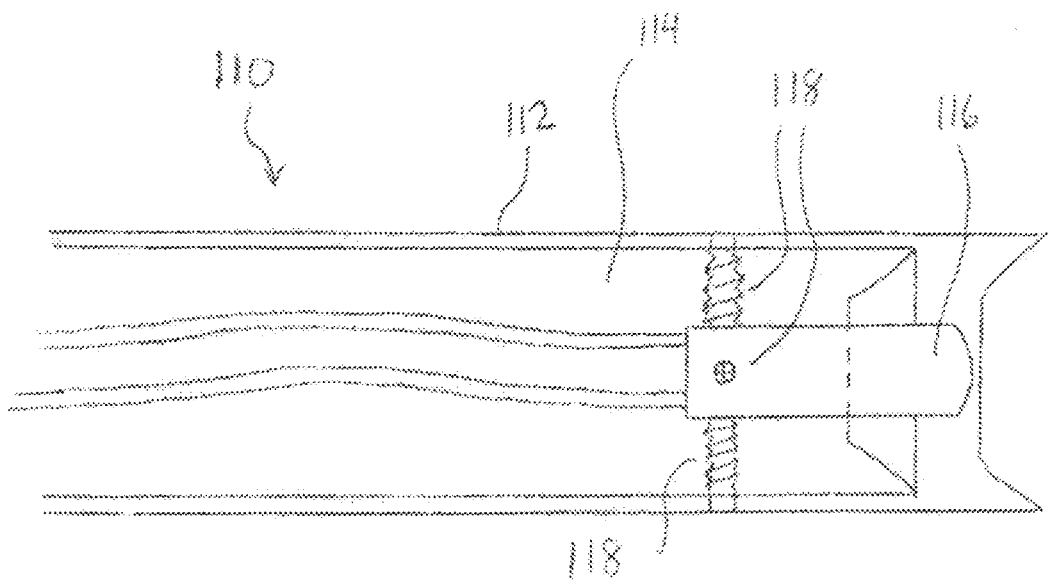
FIGS. 2A and 2B illustrate exemplary cartridge heaters of the present invention.
Figure 2B:
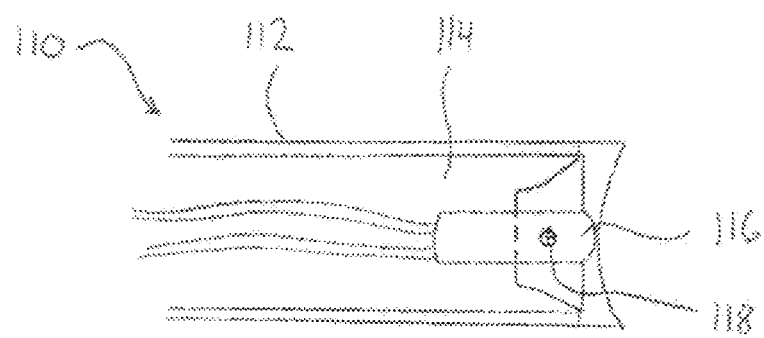

Another exemplary instrument is illustrated in FIGS. 2A and 2B. A small cartridge heater 110 may be used to deliver thermal energy. The heater 110 may be a SUNROD ⅛ inch cartridge heater. To prevent heat buildup of the outside shaft 112, an insulating region 114 may be formed between the welding horn 116 and the shaft 112. In FIG. 2A, four set screws 118 are used to create the insulating region 114, which in this example is an air barrier, while in FIG. 2B, a single set screw 118 is used.

Figure 3E:
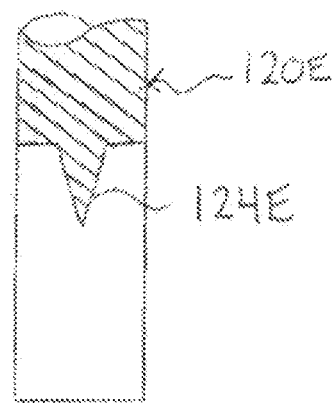
Figure 3F:
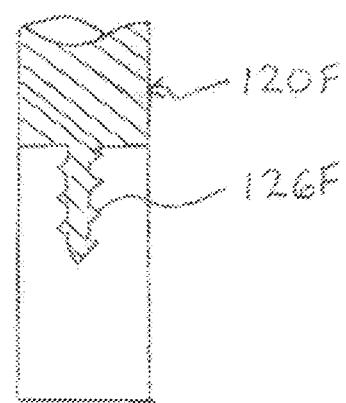
Figure 3G:
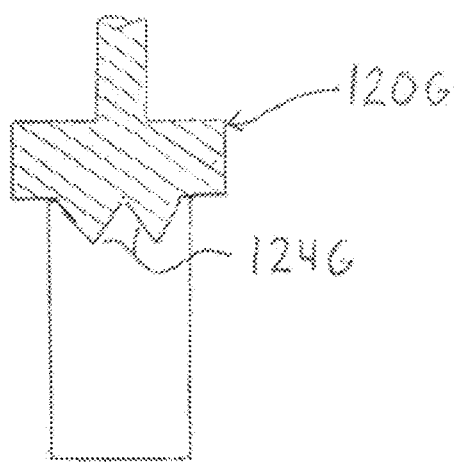
Figure 3H:
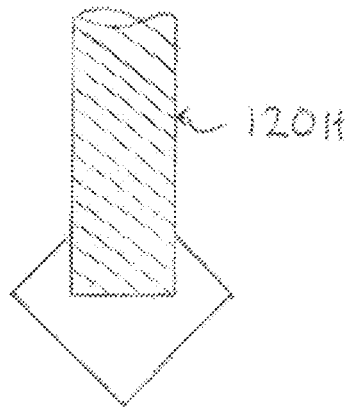
Figure 3I:
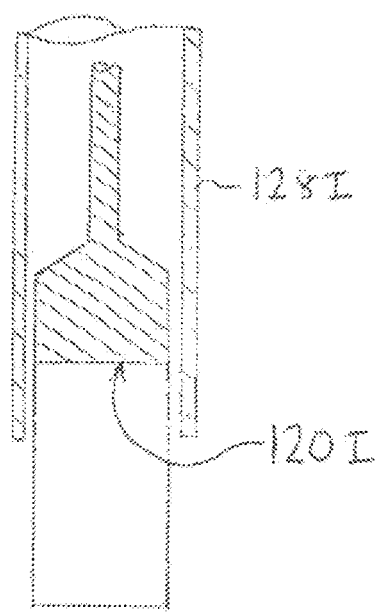
Figure 3J:
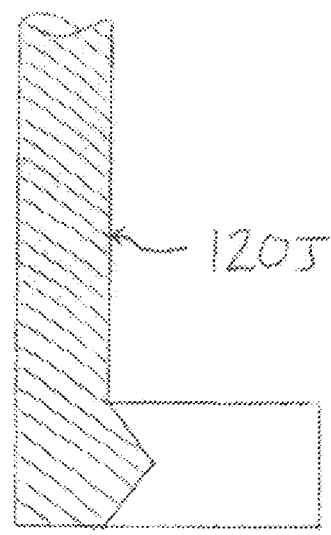
Figure 3K:
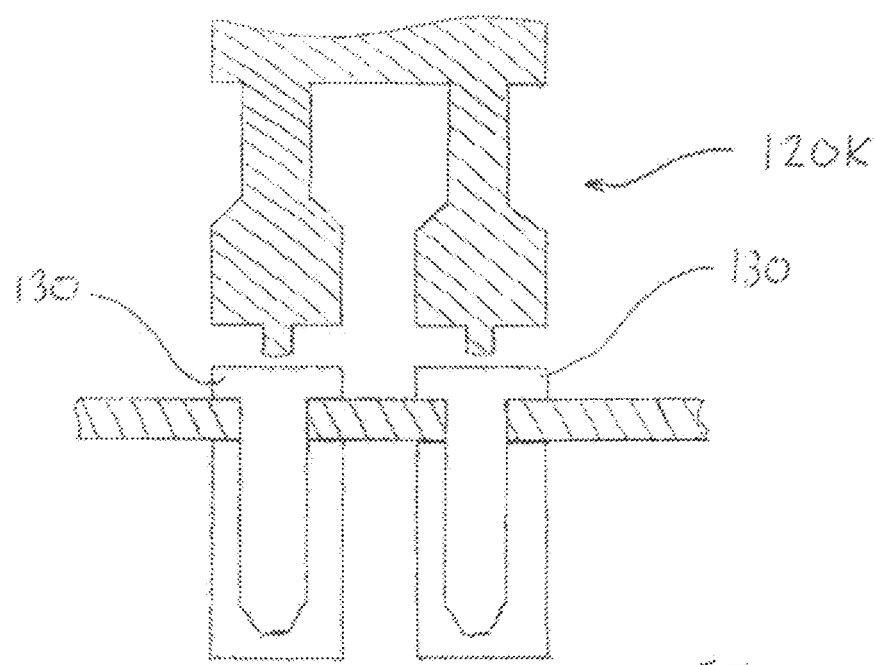

Referring to FIGS. 3A-3K, energy emitting instruments may include various horn or end effector configurations. In FIG. 3A, the horn 120A emits energy to the top surface of the implant as well as the central core via an elongate extension 122A. The horn 120B of FIG. 3B is recessed to hold the thermoplastic implant during welding. In FIG. 3C, the horn 120C is concave to provide a rounded surface to the implant after welding. The horn 120D of FIG. 3D is concave and includes a central extension 122D to deliver energy throughout the implant. In FIG. 3E, the horn 120E includes a spike 124E which may be disposed within an implant. The horn 120F of FIG. 3F includes a threaded pin 126F which may be received by a bore in the implant. In FIG. 3G, the horn 120G includes dual spikes 124G. The distal portion of the horn 120H of FIG. 3H may be dimensioned to fit within the thermoplastic implant. In FIG. 3I, a sleeve 128I is disposed about the horn 120I and implant. A side-weld horn 120J is shown in FIG. 3J. In FIG. 3K, a dual horn welder 120K is used to simultaneously weld two fasteners 130.

Figure 4C:
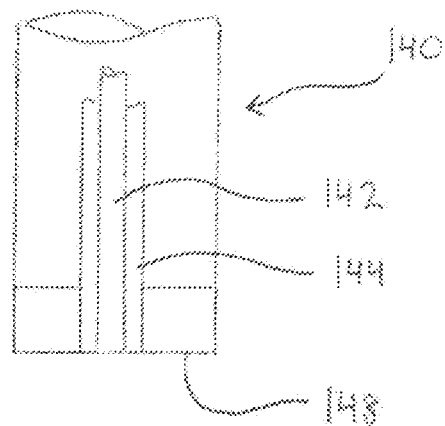
FIGS. 4A-4C illustrate a three-function welding horn.
Figure 4B:
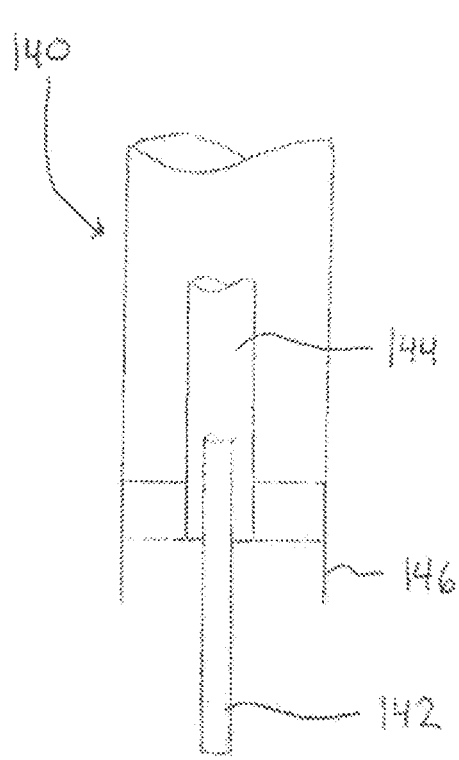
Figure 4A:
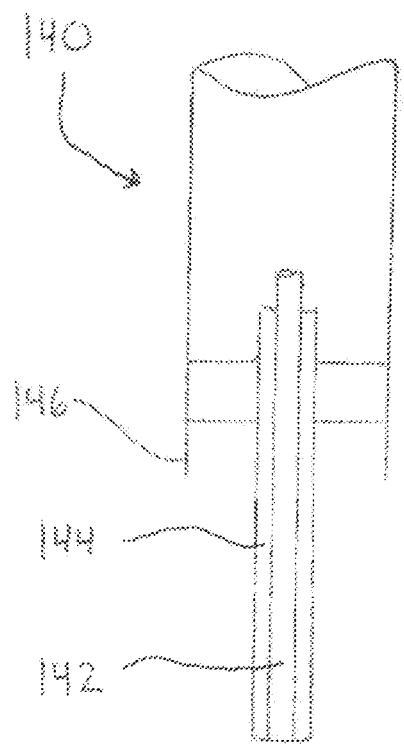

In FIGS. 4A-4C, a welding instrument 140 is shown which includes three different horn or end effector configurations in one design. The instrument 140 can be configured to have a bonding-surface horn (FIG. 4A), a welding horn (FIG. 4B), and a contouring horn (FIG. 4C). FIG. 4A shows the instrument 140 in the bonding-surface horn configuration. The center shaft 142 is extended distally from the instrument 140, and the outer shaft 144 which slides over the center shaft 142 is also extended distally. In FIG. 4B the outer shaft 144 has been retracted into the welding instrument, leaving only the center shaft 142 extended. In this position, the instrument 140 is in the welding horn configuration. Finally, FIG. 4C shows both the center and outer shafts 142 and 144 retracted into the instrument. The sheath 146 which surrounds the instrument 140 has also been retracted. In this position, the instrument 140 is in the contouring horn configuration. The distal surface 148 of the contouring horn may be used to reshape a thermoplastic implant, such as the head of a fastener.

In use, the instrument of FIGS. 4A-4C may be reconfigured quickly by the operator during a welding operation. In the bonding-surface configuration, the instrument is positioned such that the distal portion of the extended center and outer shafts 142, 144 come in contact with a thermoplastic component or implant. Energy, such as ultrasonic energy, may be emitted from the center and outer shafts to create a roughened surface on the implant, to create an indentation or blind hole in the implant, or to create a through hole in the implant. The type of fixation desired and the intended fastener to be used will determine how deep the bonding-surface horn should be moved into the implant. With the bonding surface formed, the outer shaft 144 is retracted into the instrument (FIG. 4B).

The distal portion of a fastener may be placed in or on the bonding surface of the implant, and the end effector may be placed on the fastener with the center shaft extending into a bore in the fastener. Using the desired welding parameters, the operator emits ultrasonic energy from the end effector to bond the fastener to the implant. Once welded, the fastener may be contoured or reshaped or resized with the contouring-horn of the instrument by retracting the center shaft and optionally retracting the sheath around the instrument (FIG. 4C).

Figure 5:
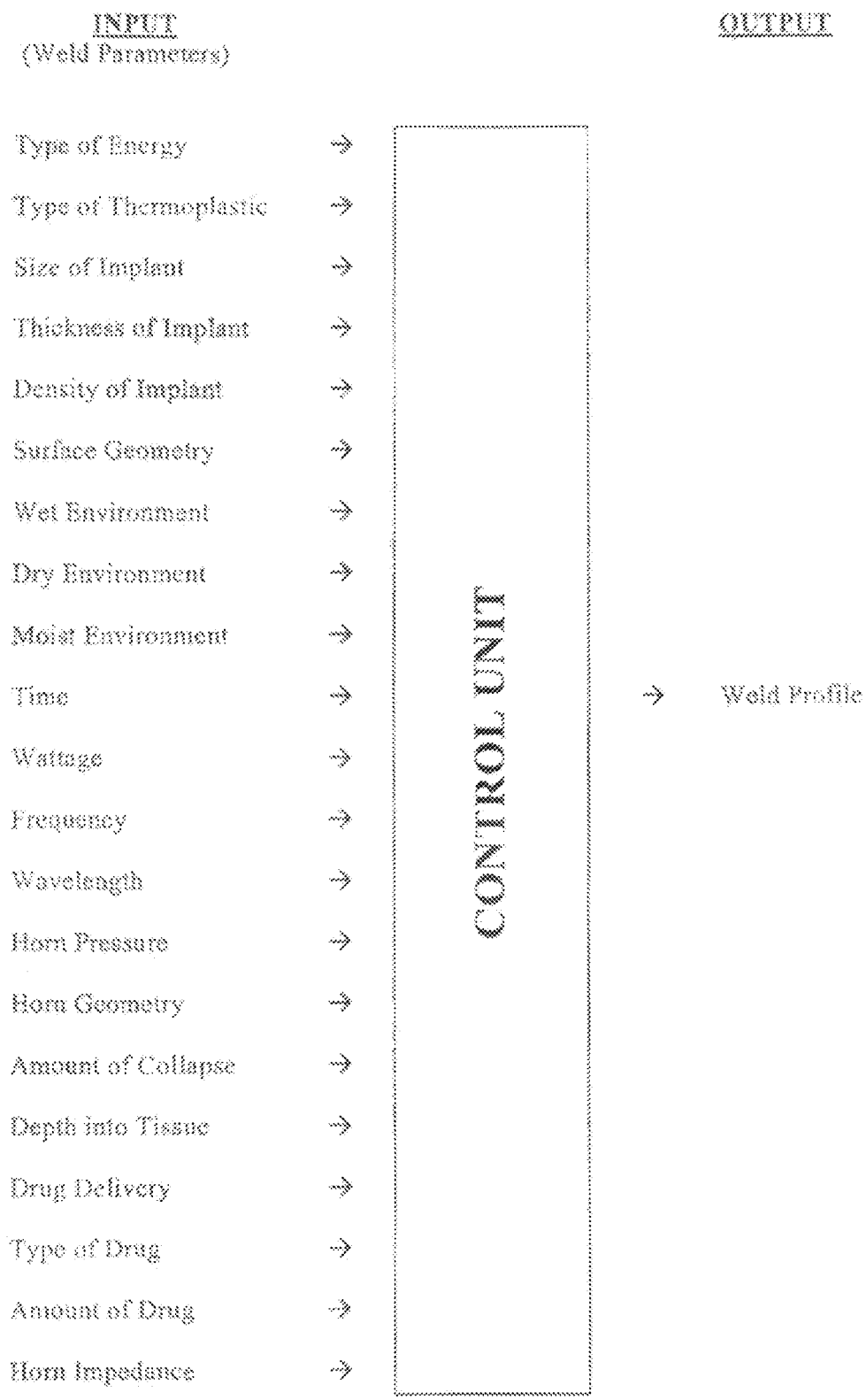
FIG. 5 shows the input parameters of a welding control unit.

As previously mentioned, monitoring and controlling the welding parameters ensures proper bonding of thermoplastics. FIG. 5 illustrates the various parameters that may be monitored and controlled for the trauma welding system of the present invention. The parameters include, but are not limited to, the type of energy to emit, type of thermoplastic material, the size and configuration of the implant, the thickness of the implant, implant surface geometry, the aqueous environment, weld time, weld power, frequency and wavelength or the energy, amount of pressure applied to the implant during and after welding, the geometry of the weld horn, the impedance of the welding horn, the density of the implant, the amount of collapse of the thermoplastic material, the depth into tissue the implant is to be inserted, and the type and amount of any therapeutic agent that may be delivered.

FIG. 6 shows a manual welding control box 150. A surgeon determines the optimum or desired welding parameters and may then enter them into the control box 150 prior to or during welding. In FIG. 7, an automatic control box 152 may be provided with pre-set weld parameters. For example, preset 1 may be for implant A which has a known material, size, etc. to be welded in a dry environment. Preset 2 may be for implant A in a moist environment. Preset 3 may be for implant A in a wet environment. Preset 4 may be for implant B using energy source X. Preset 5 may be for implant C using energy source Y. Preset 6 may be implant D using energy source Z. It is contemplated that any combination of weld parameters may be preset into the control box.

Figure 8B:
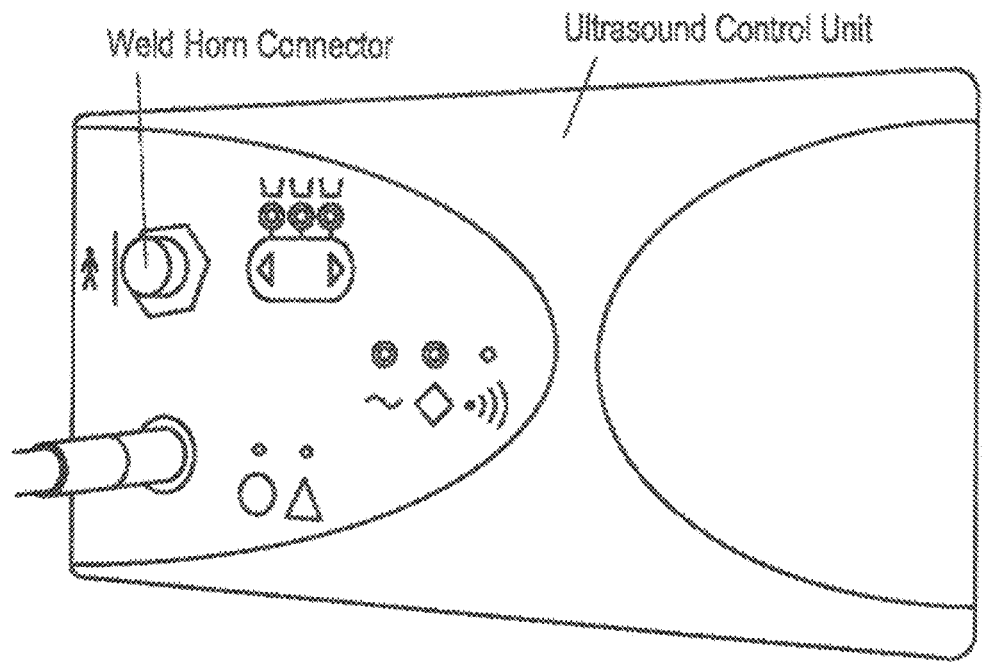
FIG. 8B is a photograph of an ultrasonic welding control unit.

The control box 154 of FIG. 8A is automatic. A sensor on the end effecter 156 determines the weld parameters when the horn is placed adjacent the thermoplastic material. The sensor 156 picks up material type, humidity of the environment, and any other parameter, then sends the data to the control box. The control box 154 automatically selects the energy source, time, wattage, and any other parameters. FIG. 8B illustrates an ultrasonic energy control box which may be used with the surgical welding systems of the present invention.

Figure 8C:
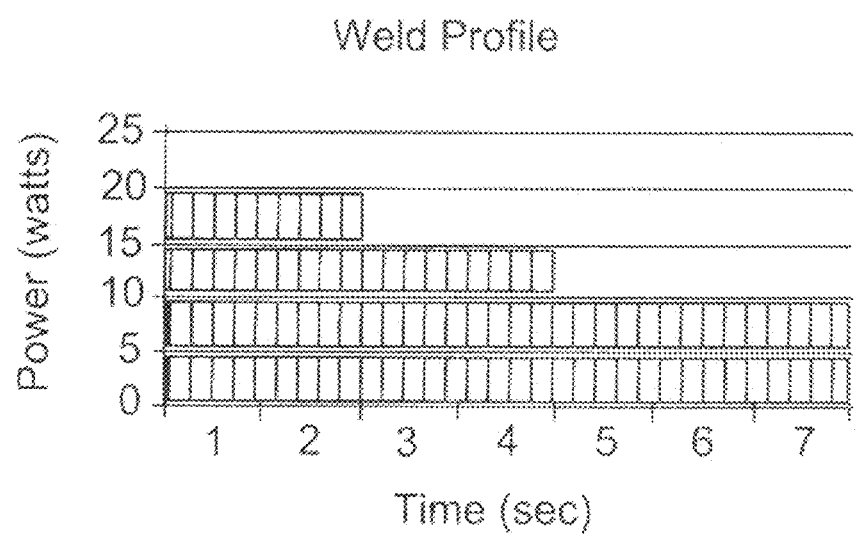
FIG. 8C is a graph showing a welding profile having varying wattage.

The exemplary energy control units described herein may be used to select and vary any of the welding parameters. In FIG. 8C for example, the power or wattage of the welding horn is varied over time. During a first period of welding, a large amount of energy is delivered to overcome heat sink. In the second period, the energy is reduced. In a subsequent period, the energy is maintained at an appropriate level to thermal weld an implant.

Other variations of the use of a control box may likewise be used. For instance, a computer may be used to query or receive data about the surgical procedure. The physician may enter an implant manufacturer, for instance, and then select or enter an implant model, size, etc. Based on the entered information, the computer may assist the physician by instructing which energy source(s), weld horns, or other parameters may be recommended for the procedure. While the control box or computer may automatically select and apply a weld profile based on expected input weld parameters, the control box or computer may also allow a physician to alter or override the expected input or otherwise select a different weld profile. The ability to allow varying degrees of manual control of the welding instrument may also be provided.

The exemplary energy control units previously described may be used to select and vary any of the welding parameters. For example, the power or wattage of the welding horn may be varied over time. During a first period of welding, a large amount of energy may be delivered to overcome heat sink. In the second period, the energy may be reduced. In a subsequent period, the energy may be maintained at an appropriate level to thermal weld an implant.

To help ensure a properly executed weld, the welding instrument of the present invention may provide a positive feedback system. One way to provide user feedback is by measuring and controlling the impedance (resistance) of the end effector or weld horn. This feedback system is based on the fact that the load placed on the end effector affects the impedance of the system. That is, the pressure put on the end effector by the object to be welded changes the resistance of the end effector. To determine the handpiece or end effector impedance, the drive voltage and current through the end effector may be monitored during the weld. By using Ohm's Law V=IR, the impedance, R, may be calculated from the voltage, V, and current, I.

Figure 9:
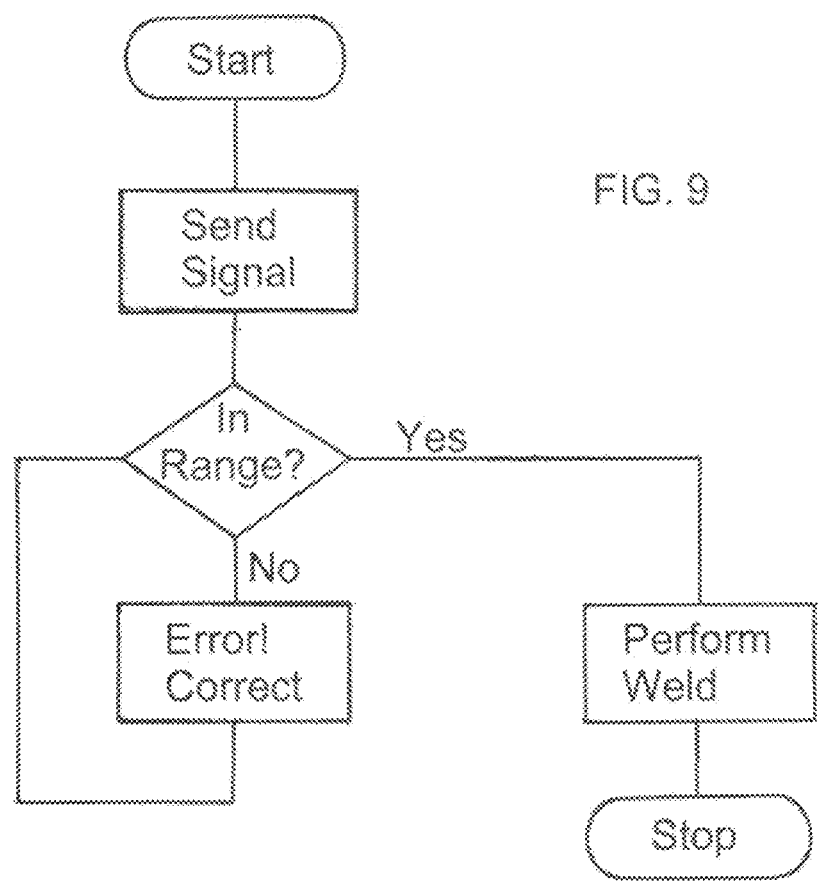
FIG. 9 is a flowchart showing the steps for adjusting the welding device.

FIG. 9 illustrates one method of ensuring a consistent or desired weld. By first transmitting a low power ultrasonic signal through the end effector, the impedance of the handpiece can be measured with no pressure. This establishes a baseline impedance for the end effector. Then, the end effector may be subjected to known pressures, and the voltage and current may be measured to calculate the impedance for each pressure. Therefore, when a surgeon or other operator applies pressure from the end effector to a thermoplastic implant to be welded, the actual amount of pressure can be fed back to the operator because the pressure can be correlated to a known impedance. The surgeon may increase or decrease the pressure on the end effector until the desired pressure is achieved. In one embodiment, the welding instrument may provide audible and/or visual signals that indicate when a surgeon is applying too much, too little, or an adequate amount of pressure. With the correct pressure applied, the surgeon may activate the handpiece and emit ultrasonic energy in accordance with the calculated weld profile.

In another exemplary embodiment for providing positive feedback, the pressure and impedance of the end effector may be monitored throughout the weld profile. In the previously described method, the proper pressure based on impedance was achieved by the surgeon using a low power signal, and then the ultrasonic energy was emitted from welding. In this method, the pressure and impedance is measured during the weld. When pressure on the end effector is applied and the weld is started, for example by a hand control or footswitch, the current may be measured and the impedance calculated by a microprocessor. When the impedance is too high or too low or outside an acceptable range indicating an incorrect applied pressure, the microprocessor may send an audible or visual signal to the surgeon.

Alternatively, or in addition to the signal, the microprocessor can stop energy emission until the correct pressure and impedance is achieved, then the welding may be resumed either automatically by the microprocessor or manually by the surgeon. If inadequate pressure is being exerted, the welding instrument may operate in a pulse mode to maintain material in a near-weld state. This may allow the welding to more rapidly continue when adequate pressure is once again being applied.

Figure 10:
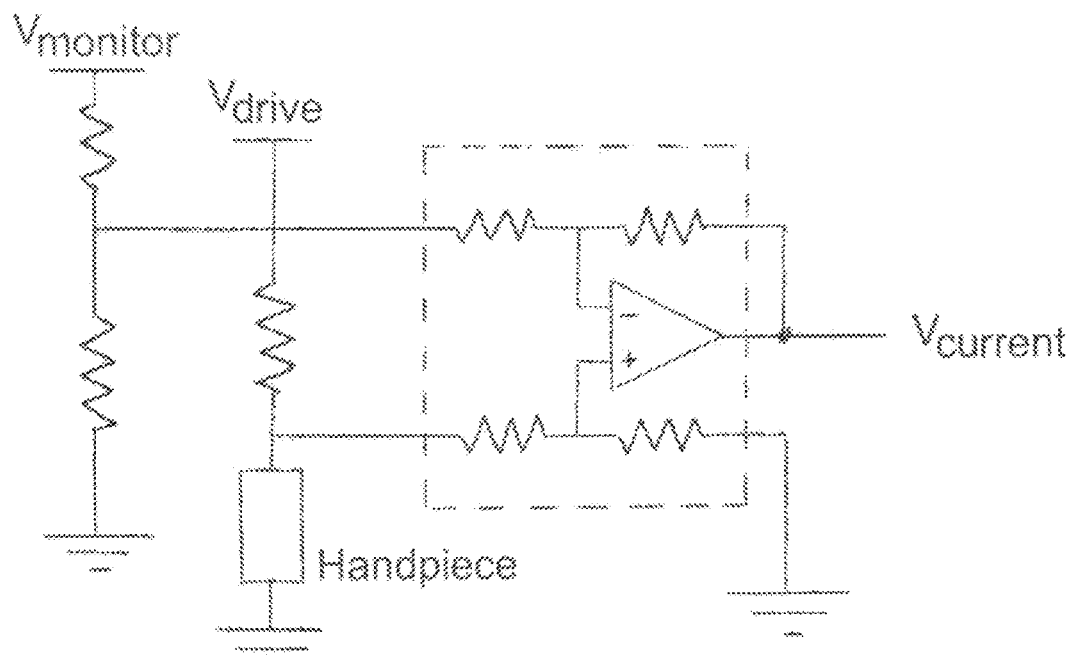
FIG. 10 is a diagram showing an electrical circuit for checking the welding device.

Referring FIG. 10, because the drive signal is sinusoidal, $V_{monitor}$ $V_{current}$ must be sampled at a rate that is at least twice the frequency of the ultrasonic waveform. For example, if the waveform is a 41 kHz sinusoid, then samples may be taken at 328 kHz, or one sample every 3 μs. In this example, solving for the impedance, the handpiece would be soon.

Also, by monitoring handpiece impedance, changes to the weld environment, such as moisture, ambient temperature, aqueous conditions, etc., may be automatically compensated for by adjusting the drive waveform of the ultrasonic energy. For example, if for a certain material it is determined that 80 W of power is required for a 400 ms period to achieve a consistent weld, then the waveform can be adjusted do ensure that this amount of energy is constantly delivered. Power is calculated using P=IV, but because the signal from the waveform is sinusoidal, the root mean square (RMS) voltage as $V=(1/\sqrt{2})A$ must be used.

As the impedance, R, of the handpiece changes, the total power delivered also changes. By increasing or decreasing the drive voltage to compensate for the change in the impedance, a constant power can be delivered.

In another exemplary method, seat collapse may be monitored, such as by the use of SONAR. Seal collapse is the distance a thermoplastic fastener or implant shrinks in height when ultrasonic energy is applied. Generally, thermoplastic fasteners may shrink about 20 percent in height and increase 30 percent in width when welded. For fasteners having two pieces, such as a cap and an anchor, the attenuation of the reflected ultrasonic waves changes as the two piece fastener becomes one piece. This change in attenuation may be monitored to alert the surgeon or operator when the weld is complete. Furthermore, an ultrasonic transducer could be used in conjunction with the end effector to detect the change in acoustic impedance/attenuation of the weld site. This signal may be monitored by a microprocessor/controller or data signal processor (DSP) and data may be automatically interpreted to indicate whether the weld was successful.

Another way of providing feedback of an effective weld is to monitor the Eddy currents created by the movement of the end effector. As the end effector vibrates, the linear motion creates a change in the magnetic field. By monitoring the travel of the end effector, the amount of collapse can be determined.

It is also contemplated that the material being welded may be translucent or transparent, and a visual indicator within the material could indicate when the weld is complete. For example, a pigment, dye, or other substance may be impregnated into the thermoplastic which when subjected to ultrasonic energy the pigment or dye would be released indicating that the weld is complete. Alternatively, the material of the thermoplastic may have the characteristic of changing color as heat, vibrations, or ultrasonic energy is applied for a predetermined time and a predetermined frequency and wattage.

The previously described methods for providing positive feedback to the weld operator included the use of measurements and/or computers. Another positive feedback system is provided which relies on physical force. When two objects are fastened to each other, it is common for the technician or mechanic to pull or tug on the assembly to ensure the parts are securely fastened. This common technique may apply to the thermoplastic welding system of the present invention. Once a fastener or other implant is ultrasonically welded, the surgeon can apply a quick tug on the assembly to verify the weld was completed as intended.

Figure 11A:
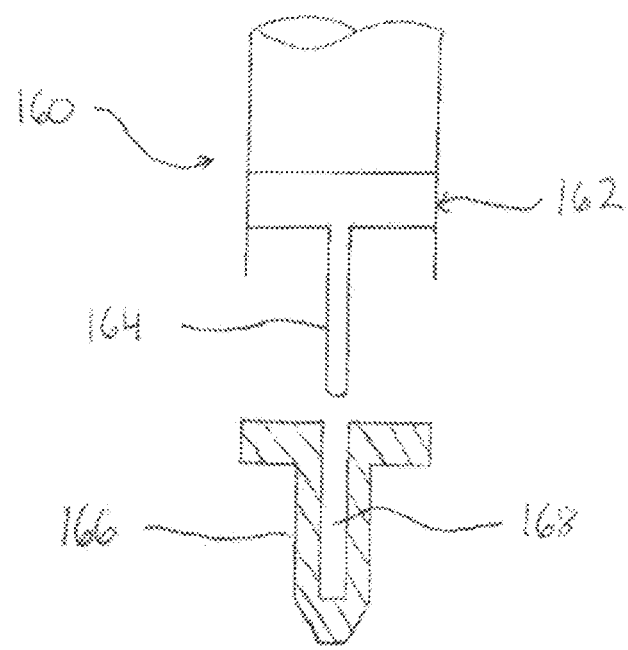
FIGS. 11A and 11B illustrate a physical positive feedback device.
Figure 11B:
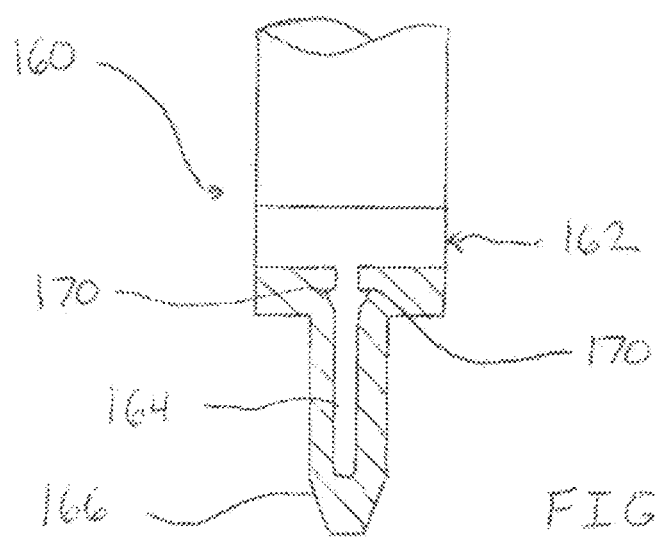

FIGS. 11A and 11B illustrate a feedback instrument 160 for performing such a physical positive feedback check. An end effector 162 includes a post 164 which emits ultrasonic energy. A thermoplastic fastener 166 is placed on the end effector 162 with the post 164 in a bore or receptacle 168 of the fastener 166. After emitting ultrasonic energy and welding the fastener to an implant or tissue, the surgeon may actuate a biasing prong or prongs 170 from the post 164 of the end effector while the post 164 is still in the fastener 166. In a stored configuration, the prongs 170 are positioned within the post 164. In a deployed configuration, the prongs 170 extend radially from the post 164 by the activation of a handle, switch, or button. The extended prongs 170 dig slightly into the material of the fastener 166 so that the surgeon may now pull or tug on the instrument 160 proximally to verify that the fastener 166 is securely welded in place. Additionally, the prongs 170 and/or post 164 may include a strain gauge or other force measuring device to measure and display to the surgeon how many pounds of pull strength is being put on the fastener.

Figure 12A:
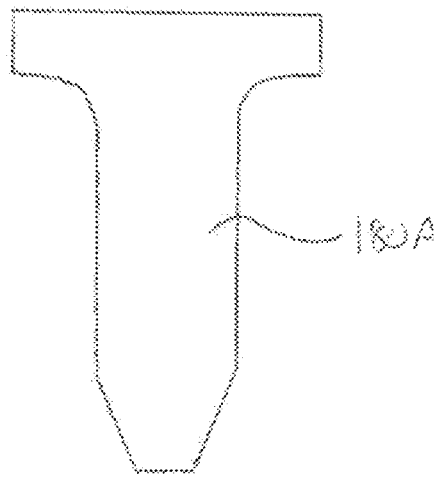
FIGS. 12A-12F show various embodiments of thermoplastic fasteners.
Figure 12B:
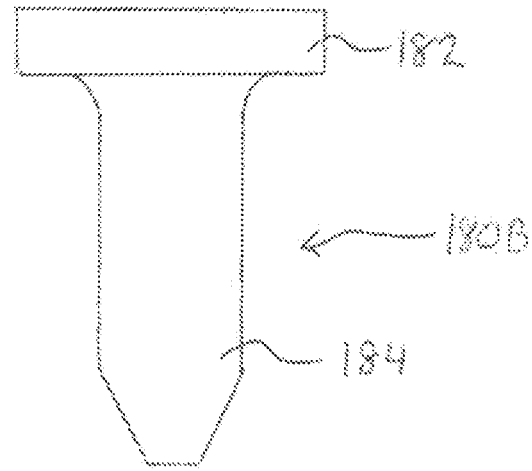
Figure 12C:
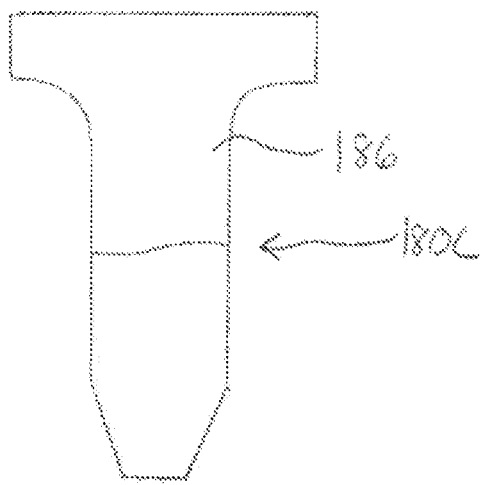
Figure 12D:
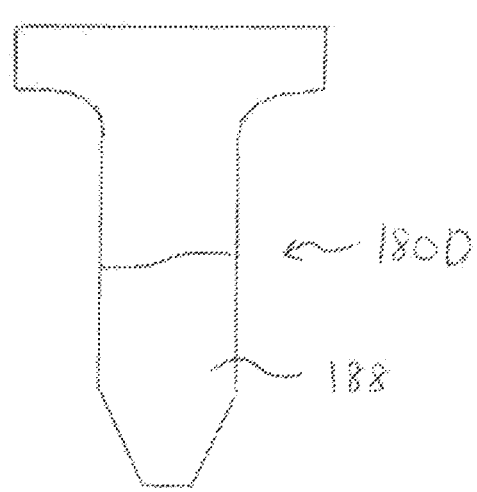
Figure 12E:
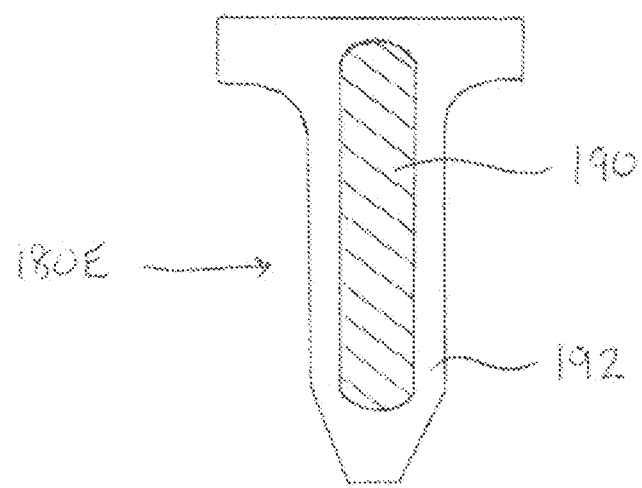
Figure 12F:
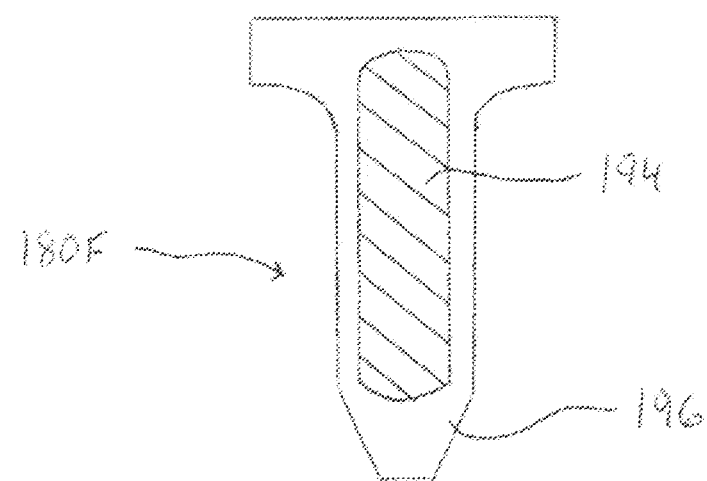

Some exemplary fasteners of the present invention are illustrated in FIGS. 12A-12F. The fastener 180A of FIG. 12A is made entirely of a thermoplastic material such as PEEK. In FIG. 12B, the fastener 180B includes one type of thermoplastic material in the lid 182 and a different type of thermoplastic material in the post 184. Each material may have different welding properties. FIG. 12C shows a fastener 180C with only a proximal portion 186 made of PEEK, while FIG. 12D illustrates a fastener 180D with only a distal portion 188 made of PEEK. In FIG. 12E, the fastener 180E includes a rigid metallic core 190 which is enclosed by a thermoplastic 192. The fastener 180F of FIG. 12F has a polymeric core 194 surrounded by PEEK 196. Although not illustrated in these examples, the fasteners may include a central bore for receiving the post of the end effector.

Figure 13A:
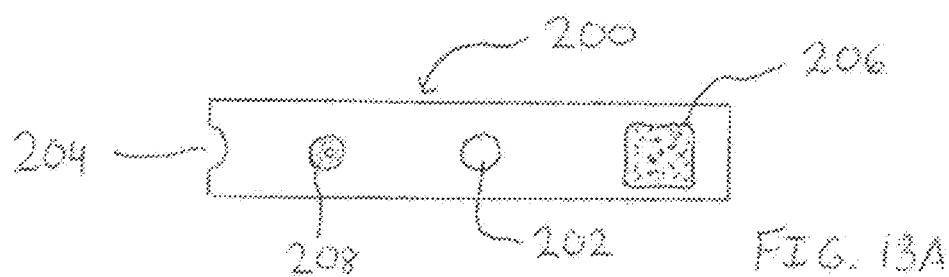
FIGS. 13A and 13B illustrate bonding regions of implants.
Figure 13B:
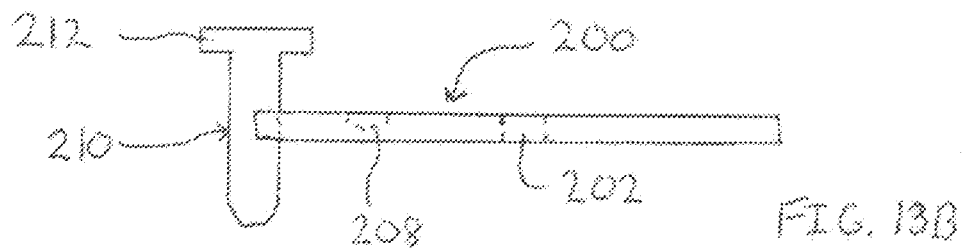

FIGS. 13A and 13B show a bone plate or rod 200 for use with the trauma welding system of the present invention. Plate or rod 200 may be free of holes or may include pre-drilled thru-holes 202 or edge-holes 204 for positioning fasteners therethrough. The holes may be formed by the manufacturer at the factory or by the surgeon in the operating room. The plate or rod 200 may include a roughened surface 206 in some areas or over the entire surface. The roughened areas 206 provide a bonding region for fasteners or other thermoplastic implants. Additionally, the plate 200 may include blind holes 208 for securing a fastener therein. The blind hole 208 is an indentation in the surface of the plate 200 which extends only partially into the plate 200. The thru-hole, roughened area, and blind hole are bonding regions. In FIG. 13B, a thermoplastic fastener 210 is positioned in an edge-hole 204 of the plate 200. The distal end of the fastener 210 may be seated in another implant or tissue, such as bone. Because the plate includes the edge-hole, the fastener may be first at least partially implanted, then the edge-hole of the plate may be positioned around the fastener. Once properly aligned, the plate 200 and fastener 210 may be welded together and the proximal end or head 212 of the fastener 210 may be contoured as desired.

Figures 14A, 14B, 14C, 14D:
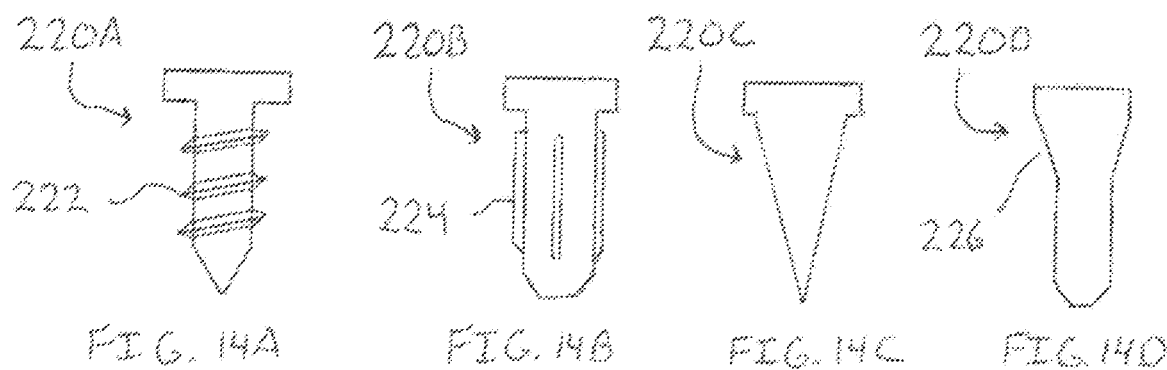
FIGS. 14A-14D show more embodiments of thermoplastic fasteners.

In addition to the fasteners described in FIGS. 12A-12F, other fastener configurations are illustrated FIGS. 14A-14D. In FIG. 14A, the fastener 220A includes a mechanical locking mechanism in addition to thermal bonding. The fastener 220A includes thermoplastic material and includes helical threads 222 disposed on the outer surface thereof. In FIG. 14B, the fastener 220B includes longitudinally extending edges 224. These longitudinal edges 224 may function as energy directors to focus the ultrasonic energy along the edges providing a secure bond to tissue or an implant. FIG. 14C illustrates a wedge shaped or Morse taper fastener 220C. The fastener 220D of FIG. 14D includes an angled shoulder 226 which may be seated against an implant or tissue and thermally bonded in place.

Figures 15A, 15B:
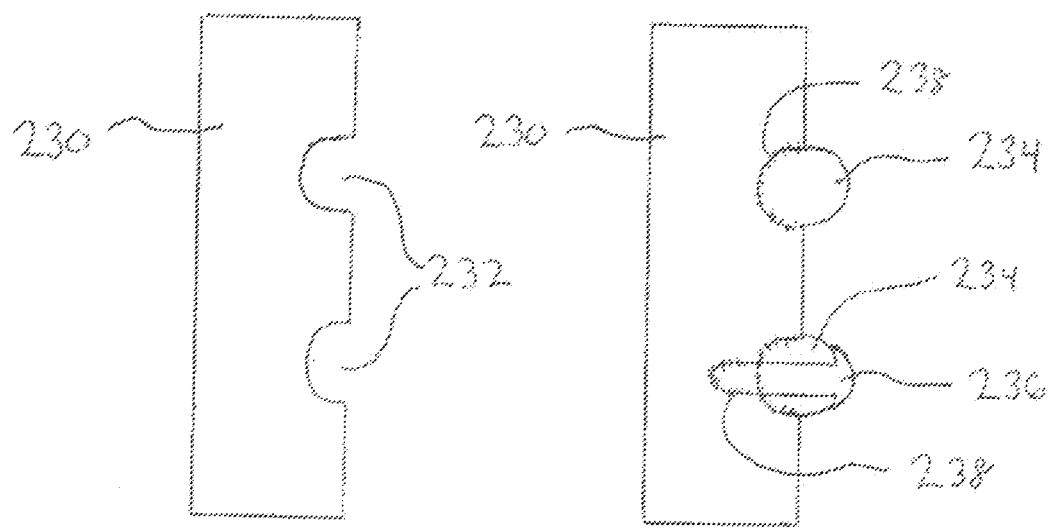
FIGS. 15A and 15B illustrate notched plates and rods for stabilizing bones.

The combination of thermoplastic material and ultrasonic energy of the present invention is advantageous for modifying and preparing implants while the implants are in the body. In FIG. 15A, a plate 230 may be positioned against bone to stabilize a fractured bone or damaged vertebrae. With the plate 230 in place, a notch or nest 232 may be cut using heat energy or other mechanical means such as a drill or saw. The notches 232 are dimensioned and configured to receive a rod 234 or fastener. Therefore, implanting and thermally bonding a rod in the notch 232 creates a desired geometric shape with the plate 230 and rod 234 extending generally perpendicular to each other. In this configuration, the assembly may be used to stabilize the spinal column or may function as a combination internal-external fracture bone stabilizer. In the latter case, a first plate may be positioned against the fractured bone, while an exterior plate may be bonded to one or more rods extending from the notches of the first plate. The first plate provides internal fixation, and the exterior plate provides external fixation. The rods bonded between the two plates function as pins passing through the skin and other soft tissue. To further secure a rod within the notch of the plate, a fastener 236 may be inserted as shown in FIG. 15B. The plate 230, rod 234, and fastener 236 may be thermally welded at several bonding regions 238.

Figure 16A:
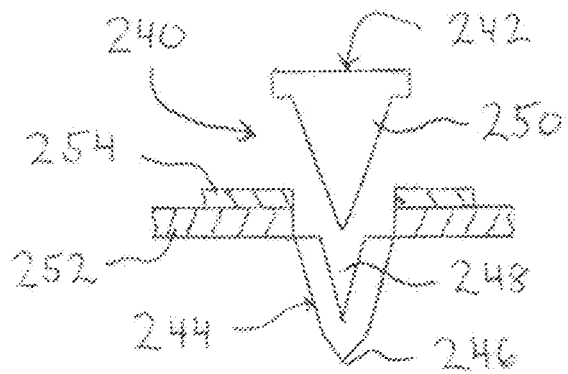
FIGS. 16A and 16B show a wedge-shaped expandable thermoplastic fastener.
Figure 16B:
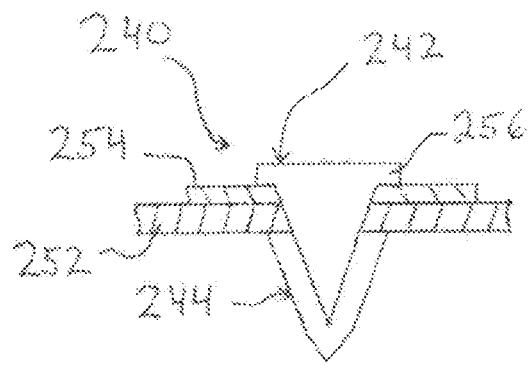

The thermoplastic fasteners of the present invention may also be expandable. FIGS. 16A and 16B illustrate one embodiment of a fastener 240 which includes a cap 242 and an expandable anchor 244. The anchor 244 is generally V-shaped or conical, convex shaped. The anchor 244 may include a tissue-piercing distal tip 246 to penetrate into and through tissue and implants, such as plates or rods. As seen in FIG. 16A, the anchor 244 includes a bore 248 that may taper down from the proximal end to the distal end. The bore 248 is dimensioned and configured to expand when receiving the post 250 of the cap 242. Therefore, the post 250 tapers from the proximal end or head down to the distal tip. The distal tip of the post 250 may also include a tissue-piercing end. In an exemplary method of use, the expandable anchor 244 is inserted through a layer of tissue 252. A plate or other implant 254 (or other tissue) is placed adjacent the tissue 252. The post 250 of the cap 242 is moved distally through the plate 254 and tissue 252 and into the bore 248 of the anchor 244 causing the anchor to expand outwardly or radially, as shown in FIG. 16B. With the head 256 of the cap 242 pressing the plate 254 against the tissue 252, the cap 242 is ultrasonically welded to the anchor 244. The anchor is prevented from being removed from the tissue because the expanded wall portions of the anchor contact the underside of the tissue.

Figure 17A:
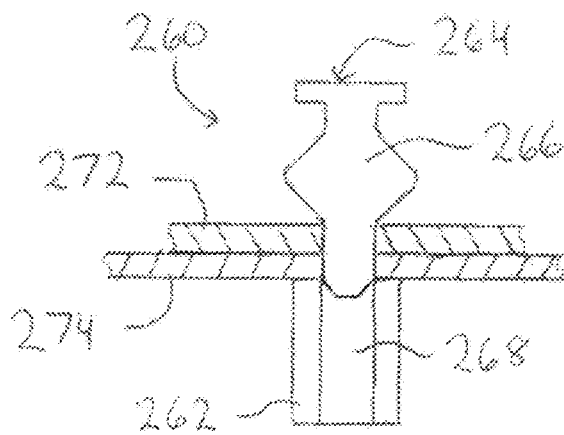
FIGS. 17A and 17B illustrate a bulge-shaped expandable fastener.
Figure 17B:
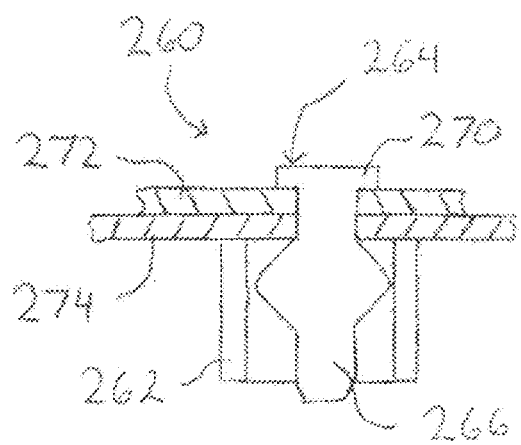

FIGS. 17A and 17B illustrate another expandable fastener 260 embodiment. The principle of insertion and expansion are similar to the fastener of FIGS. 16A and 16B. However, in this embodiment, the anchor 262 is generally cylindrical in shape. The anchor 262 has a cylindrical bore therein. The cap 264 includes a post 266 which is generally cylindrical and has a widened portion disposed between a proximal portion and a distal portion. The diameter of the distal portion of the post 266 is configured for initial insertion in the bore 268 of the expandable anchor 262. The diameter of the widened portion is configured such that it expands the walls of the anchor 262 radially outward as the cap 264 is moved distally into the anchor 262. In a seated configuration, the cap 264 is ultrasonically welded to the anchor 262 and the head 270 of the cap 264 holds a plate or tissue 272 against lower tissue 274. The expanded walls of the anchor contact the lower tissue preventing the fastener from being pulled out.

Figure 18A:
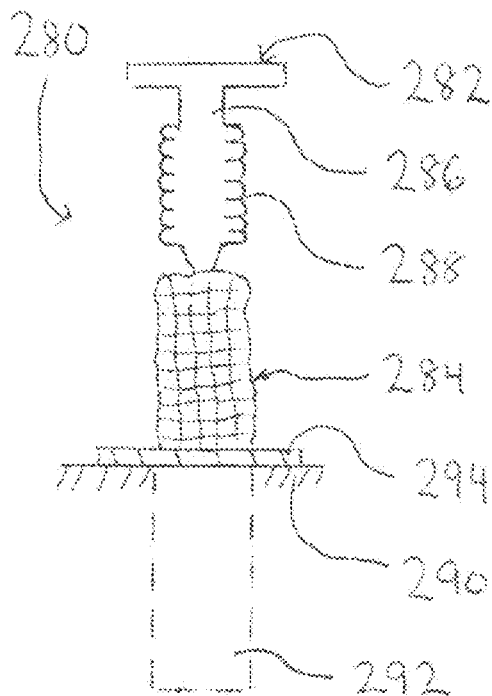
FIGS. 18A and 18B show a mesh expandable fastener.
Figure 18B:
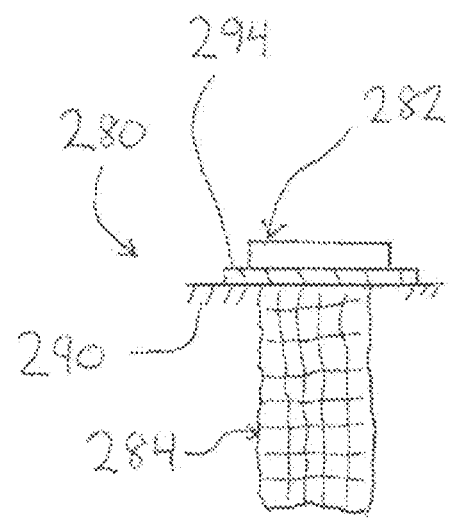

Referring to FIGS. 18A and 18B, the fastener 280 includes a cap 282 and an anchor 284 which is configured as a tubular mesh. The tubular mesh 284 has an unexpanded diameter and an expanded diameter. The post 286 of the cap 282 is dimensioned to fit, within the lumen of the tubular mesh 284 to expand the mesh to its expanded diameter. The post 286 may include ridges or ring-like structures 288 disposed thereon to aid in the expansion of the tubular mesh anchor 284. In an exemplary method of use, the anchor 284, in its unexpanded diameter, is positioned in tissue 290. A hole 292 may be drilled into the tissue 290 for receiving the anchor 284 if desired. A bone plate or other implant 294 is placed adjacent the bone 290. The cap 282 is moved through the plate 294 and tissue 290 and into the lumen of the mesh 284.

The mesh achieves its expanded diameter in at least one of two ways. First, the insertion of the post (with ridges) into the mesh causes the mesh to expand thereby preventing the anchor from pulling out of the tissue. Alternatively, the post with or without ridges may be inserted into the lumen of the mesh while the mesh maintains its unexpanded diameter. Ultrasonic energy and pressure from the welding horn may be applied to the cap causing it to swell thereby locking the anchor into the tissue. It is also contemplated that a combination of expansion methods may be used. That is, the post with ridges may be inserted into the lumen of the mesh causing the anchor to expand. Then, ultrasonic energy may be applied to the fastener to further expand the mesh and bond the cap to the anchor.

Figure 19A:
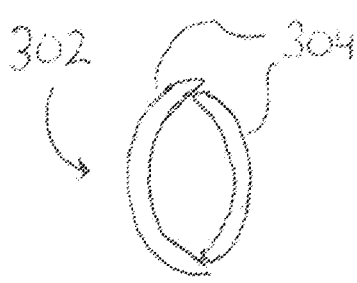
FIGS. 19A and 19B illustrate a tube-shaped expandable fastener.
Figure 19B:
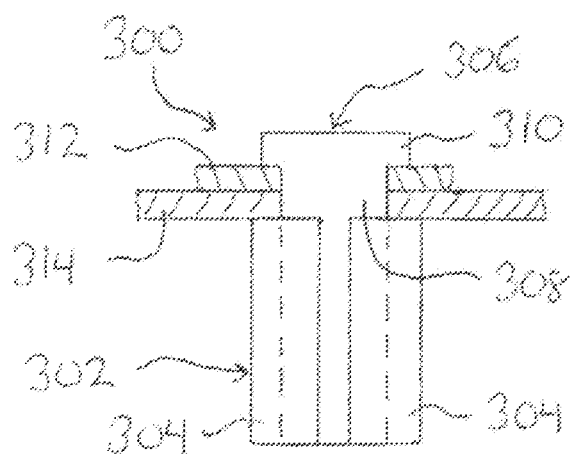

Another embodiment of an expandable fastener 300 is illustrated in FIGS. 19A and 19B. A top or bottom view of the anchor 302 is shown in FIG. 19A. The anchor 302 includes two or more arced members or longitudinal portions of a tube 304. When placed together as in FIG. 19A, the anchor 302 is in an unexpanded configuration. The cap 306 includes a post 308 and lid 310. To fasten a bone plate or other implant 312 to tissue 314, the anchor 302 in its unexpanded configuration is inserted into the tissue 314. The post 308, which may include a tissue-piercing point, is inserted through the plate and tissue. As the post 308 enters the anchor 302, the arced members 304 are moved outwardly or radially. This is possible because the inner bore diameter of the anchor 302 in its unexpanded configuration is smaller than the diameter of the post 308 of the cap 306. Once the cap 306 is pressed into the anchor 302, it is ultrasonically welded to the anchor 302. The anchor and fastener are prevented from being pulled out of the tissue because the proximal ends of the expanded arced members of the anchor contact the tissue. The lid of the cap holds the bone plate firmly against the tissue.

Figure 20A:
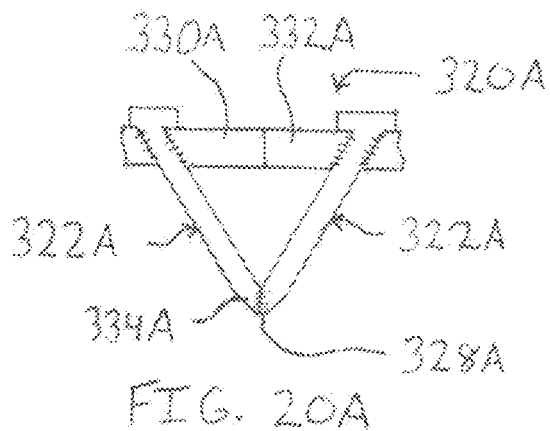
FIGS. 20A-20E show triangulation fasteners.

The trauma welding system of the present invention also provides fasteners configured as triangulation staples. Examples of these staples are illustrated in FIGS. 20A-20E. In FIG. 20A, the staple 320A includes first and second nails or braids 322A. The nails 322A include a long post and a head disposed on the proximal end of the post. The head may be slanted, angled, or pivotable to allow the head to seat flush against an implant or tissue. The distal end of the post includes a tissue-piercing tip 328A. The nails 322A may include a central bore configured for receiving an end effector. As shown, the fastener 320A includes two nails; however, it is contemplated that the triangulation staples of the present invention may include three or more nails. The staple 320A of FIG. 20A is shown holding two bone plates or other implants 330A and 332A against each other at their edges. The first nail 322A is inserted through the first plate 330A near the edge of the first plate. The first nail 322A is angled generally between 30 and 60 degrees with respect to vertical. A second nail 322A is inserted through the second plate 332A near the edge of the second plate. The second nail 322A is also angled such that the distal tips 328A of the first and second nails contact each other. Ultrasonic energy is applied to the nails 322A to bond the distal tips 328A together to form a bonding area 334A. The nails 322A may also be welded to the plates 330A and 332A where the nails passed through the plates. Additionally, the edges of the bone plates may be ultrasonically welded together. When implanted, the staple 320A securely holds the two plates 330A and 332A together and fastens the plates to tissue, such as bone.

Figure 20B:
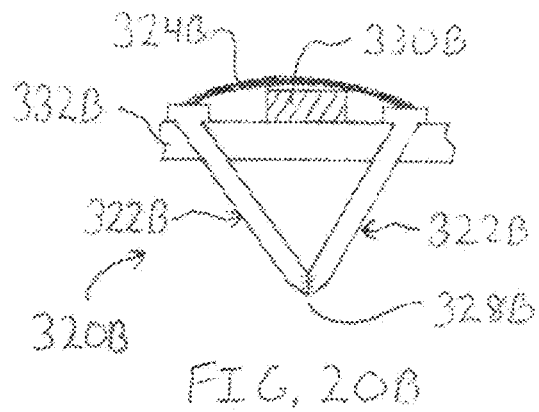

In FIG. 20B, the triangulation staple 320B includes two nails 322B with a suture or cable 324B connected with the heads of the nails. In an exemplary use of this staple configuration, an implant 330B is positioned adjacent another implant or tissue 332B. The first nail 322B of the staple is inserted into the tissue 332B on one side of the implant 330B. The second nail 322B is inserted into the tissue 332B on another side of the implant 330B. The cable 324B, spanning between the nails, contacts the implant 330B. As the nails 322B are driven further into the tissue 332B, the cable 324B tensions and presses the implant 330B against the tissue 332B. Also, with the nails firmly implanted in the tissue, the distal tips 328B of the nails 322B contact each other. Ultrasonic energy may be used to weld the distal tips 328D together to form a bonded region.

Figure 20C:
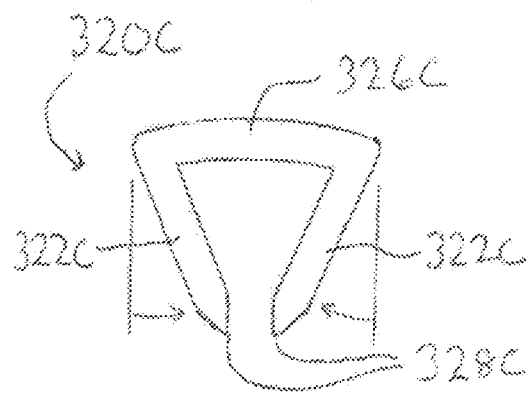

The triangulation staple 320C of FIG. 20C is a one-piece design. The first and second nails 322C are connected to each other by a cross member 326C attached at the proximal ends or the nails. The nails 322C may be rotatable or pivotable from their connection with the cross member 326C. The distal ends of the nails may include tissue-piercing tips 328C. In a pre-implantation configuration, the nails 322C extend generally perpendicular to the cross member 326C. In use, the staple 320C is inserted through tissue, an implant, or both. The staple is inserted with the nails 322C being generally perpendicular to the cross member. Once positioned, the nails 322C may be pivoted such that the distal tips of the nails contact each other. The rotation of the nails 322C may be performed by an instrument designed to angle the nails, for example by using the central bore therein. With the tips in contact, the nails 322C may be ultrasonically welded together to form a secure fixation of the implant and/or tissue.

Figure 20D:
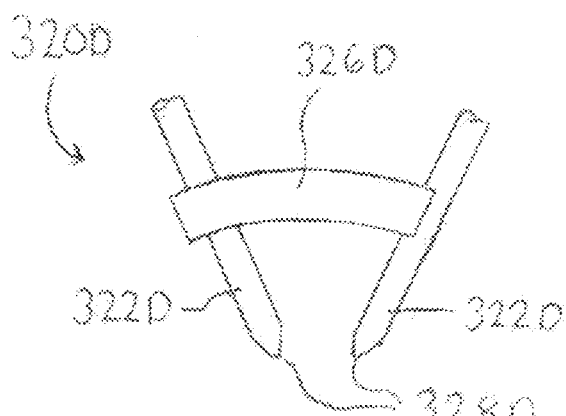
Figure 20E:
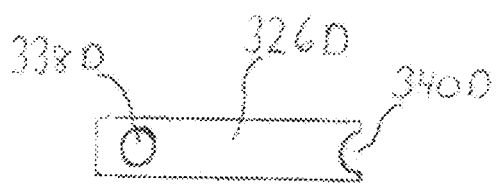

In FIGS. 20D and 20E the staple 320D includes a cross member 326D which has channels for allowing the nails 322D to slide therein. The channels have a central axis which intersect below the cross member 326D such that when the nails 322D are moved distally through the channels, the distal tips 328D of the nails connect each other, similar to the previously described embodiments. As seen in FIG. 21E, the cross member 326D includes one thru-channel 338D and one edge-channel 340D. This configuration allows the nails 322D to be inserted sequentially (not at the same time, if desired). In an exemplary method of use, the first nail 322D is partially positioned in the implant (or tissue) to be fastened. The first nail 322D is angled relative to vertical at an angle generally equal to angles of the channels of the cross member 326D. Then, the edge-hole 340D of the cross member 326D is positioned around the first nail 322D. The second nail 322D is inserted into the thru-hole 338D of the cross member 326D, and both nails 322D are fully inserted into the implant/tissue. The distal tips 328D of the nails 322D may be ultrasonically welded together, and the nails 322D may be ultrasonically welded to the cross member 326D.

Figure 21:
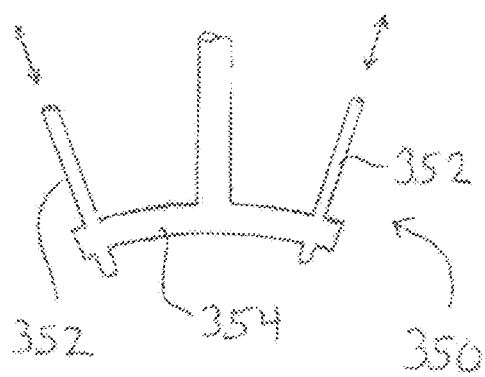
FIG. 21 is a welding horn for a triangulation fastener.

An exemplary staple welding horn 350 is shown in FIG. 21. The horn 350 includes two elongate horn shafts 352 disposed in channels in a horn base 354. The horn shafts 352 may be slideable within the channels. Both the horn shafts 352 and the horn base 354 may emit ultrasonic energy for welding the thermoplastic material, such as PEEK, of the above described staples. In use, the horn shafts 352 are retracted proximally. The horn 350 is placed over the staple such that the horn shafts 352 align with the central bore in the nails. It should be noted that the nails of the staples previously described may include longitudinally extending bores not only to receive the ultrasonic horn but also to receive an instrument for positioned the nails in implant and/or tissue. With the horn 350 properly aligned, the horn shafts 352 may be distally extended into the channels of the nails. Ultrasonic energy and a desired weld profile may be used to thermally bond the staple.

Figure 22A:
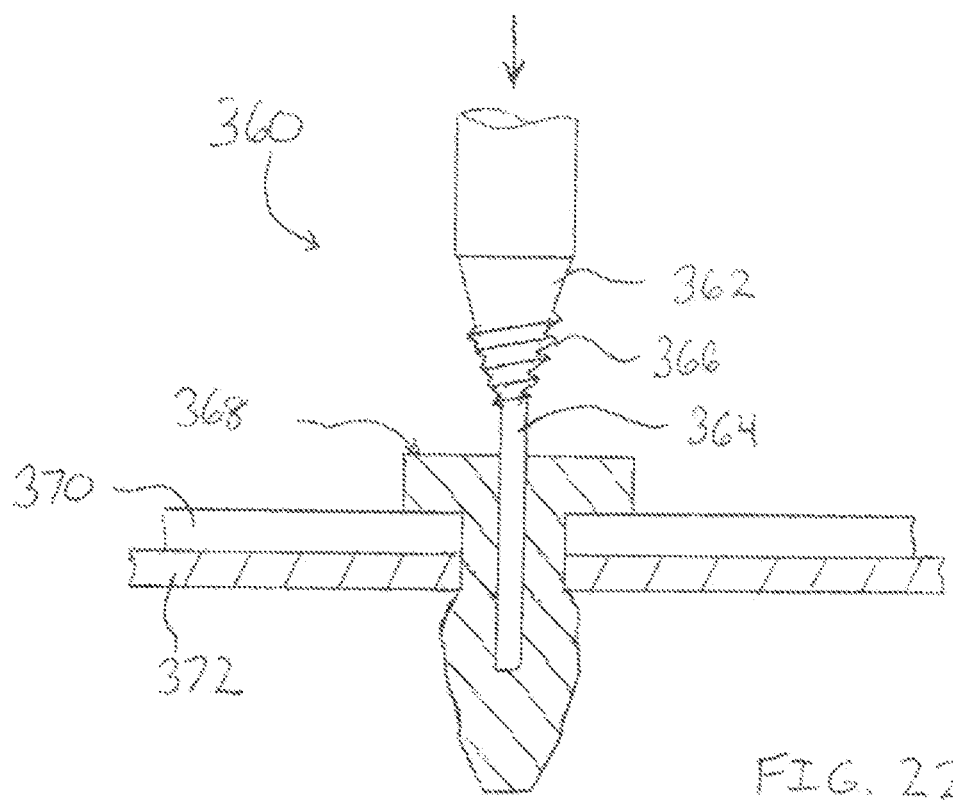
FIGS. 22A and 22B illustrate a thermoplastic implant removal device.
Figure 22B:
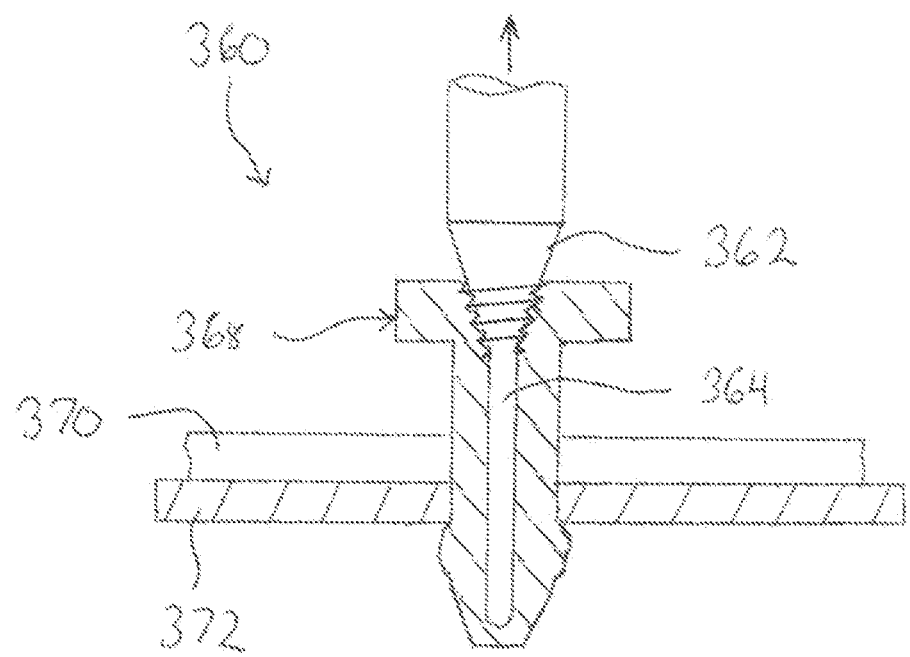

Referring now to FIGS. 22A and 22B, a thermoplastic removal instrument 360 is shown. The instrument 360 includes an ultrasonic welding horn shaft 362. The distal portion or the shaft 362 is generally conical and tapers inward toward the distal tip. An elongate pin 364 extends from the distal tip. The distal portion of the shaft 362 includes helical threads 366 disposed on the outer surface thereof. It is contemplated that besides having helical threads 366, the distal portion of the shaft may include any engagement means such as barbs, prongs, or other similar configurations. To remove a thermoplastic component, the elongate pin 364 of the instrument 360 is inserted into a channel of the component. The channel may already exist in the component or may need to be created with a drill and bit. With the pin 364 in the channel, the instrument 360 is moved further distally until the distal portion of the shaft 362 contacts the component. The distal portion is then threaded into the component with the helical threads 366. Ultrasonic energy may then be emitted from the pin 364 to soften the thermoplastic material of the component. As the material is softened, the instrument 360 may be pulled proximally, and the distal portion of the shaft 362 may begin to pull the component out. The softened thermoplastic material adjacent the pin 364 can be reshaped as the component is pulled from the implant/tissue.

In FIGS. 22A and 22B, a PEEK fastener 368 is holding a bone plate 370 to bone 372. The fastener 368 may be removed from the bone 372 with the method just described. In FIG. 22A, with the fastener 368 in place, the distal portion of the fastener 368 is thick thereby locking the fastener 368 in the bone 372. In FIG. 22B, as the fastener 368 is pulled proximally, the distal portion thins or narrows as it is pulled from the bone 372 and plate 370. Because the fastener 368 is only softened and not liquefied, the removal instrument 360 is able to remove substantially all, if not entirely all, of the thermoplastic material from the bone 372.

Figure 23A:
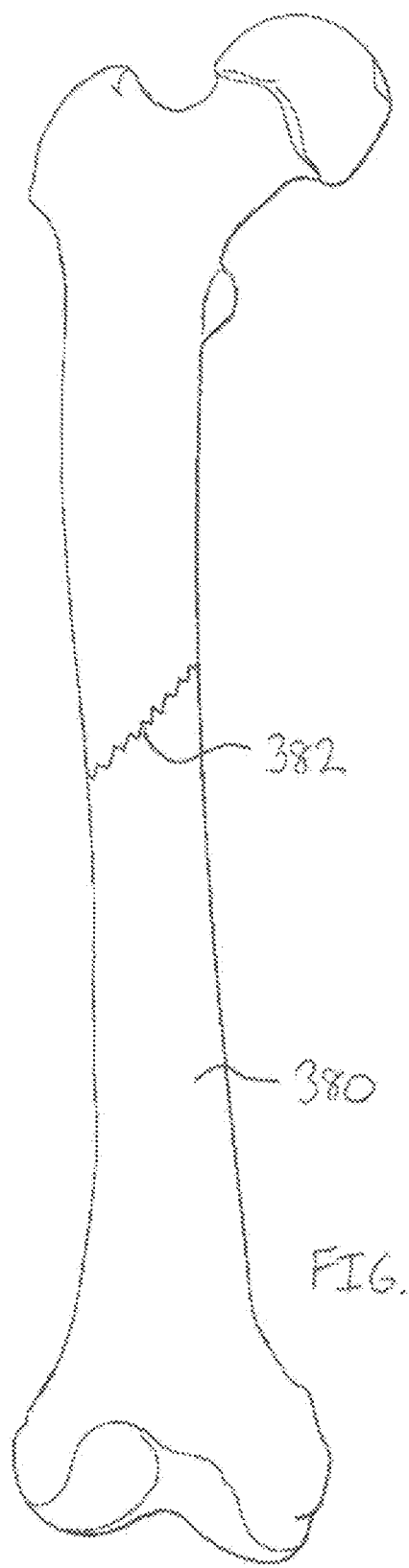
Figure 23B:
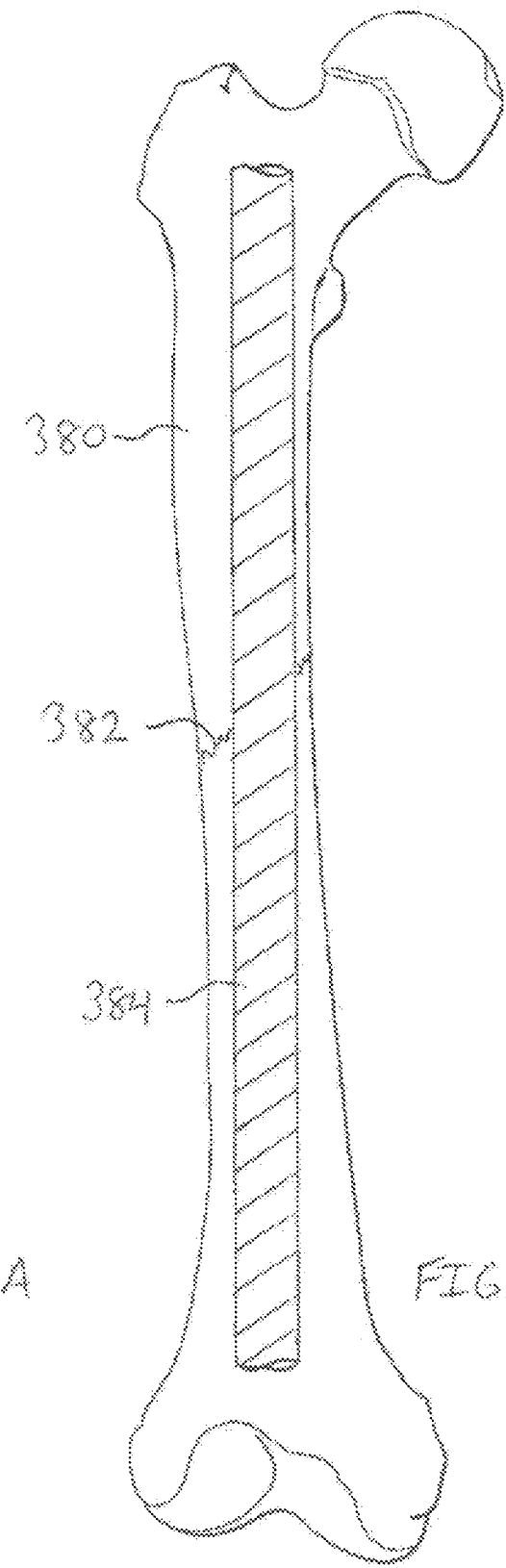

FIGS. 23A-23D illustrate a method of stabilizing a fracture bone with the devices of the present invention. In FIG. 23A a femur 380 is shown with a fracture 382. An intramedullary rod 384 may be placed within the medullary canal or the femur 380, as seen in FIG. 23B. The rod 384 may be made of thermoplastic material, such as PEEK. The rod 384 is positioned in the bone such that it spans the fracture on each side. In FIG. 23C, a plurality of channels are created in the femur 380. The channels are dimensioned to receive a fastener of the present invention. A first channel 386 is created in cortical bone of the femur 380. The first channel 386 creates a passage from the exterior of the femur to the IM rod 384. A second channel 388 is created in the cortical bone and slightly into the IM rod 384. The second channel 388 forms an indentation or nest in the rod 384. A third channel 390 is formed entirely through the femur 380 and IM rod 384. The third channel 390 is a thru-hole which extends through the cortex (both cortical sides) of the femur 380. A fourth channel 392 is created in cortical bone and partially into the IM rod 384. The fourth channel 392 forms a blind-hole in the rod 384. The channels may be formed by any means known to surgeons, such as by a drill and bit, a guidewire, a reamer, or other similar instrument. It is contemplated that any number of channels and any combination of channel types may be created in the bone and IM rod.

In FIG. 23D fasteners are positioned in the channels and ultrasonically welded in place. Before a first fastener 394 is placed in the first channel 386, the surface of the IM rod 384 exposed by the channel requires preparation for bonding. The surface may be roughened in situ using any suitable instrument. Alternatively, the surface may be roughened by the manufacture or the surgeon before implantation in the bone. With the bonding surface prepared, the first fastener 394 in placed in the first channel 386 such that the distal end of the fastener 394 contacts the bonding surface of the rod 384. An energy source, such as ultrasonic energy, may be applied to the fastener to thermally bond the first fastener 394 with the IM rod and femur. A second fastener 396 is placed in the second channel 388 with the distal end of the second fastener 396 positioned in the indentation in the rod 384. The second fastener 396 may then be ultrasonically welded to the rod and femur. A third fastener 398 is placed in the thru-hole of the third channel 390. The leading end or the third fastener 398 is configured for insertion through the channel, while the trailing end of the fastener may include a cap or head. The third fastener 398 is ultrasonically welded to the IM rod and femur. The leading end of the third fastener 398 may be contoured or flattened to form a leading end head. A fourth fastener 400 is placed in the fourth channel 392 and within the blind hole in the rod. The fourth fastener 400 is thermally welded, and the cap or head is contoured to conform to the outer surface of the femur. It is contemplated that the three-horn instrument of FIGS. 4A-4C may be used to create the bonding regions, to weld the fasteners, and to contour the thermoplastic implants.

Referring now to FIGS. 24A and 24B, the devices and methods of the present invention are used to repair an end portion of a bone 410 having a plurality of fractures 412. Like the repair of the fractured femur of FIGS. 23A-23D, a PEEK intramedullary rod 414 is placed in the medullary canal of the bone 410. A plurality of channels is created through the end portion of the bone 410 and into the IM rod 414. Any channel type previously described may be used in this method. A plurality of thermoplastic fasteners 416 are placed in the channels and are ultrasonically welded to the rod 414. Multiple (three or more) fasteners 416 may be welded to the end portion of the IM rod 414 without reducing the strength of the rod. Since the fasteners and rod are made of PEEK, the thermally bonded fasteners within the rod enhance the strength of the rod. Therefore, many fasteners may be bonded with the rod without losing structural support from the channels created in the rod.

Figure 25A:
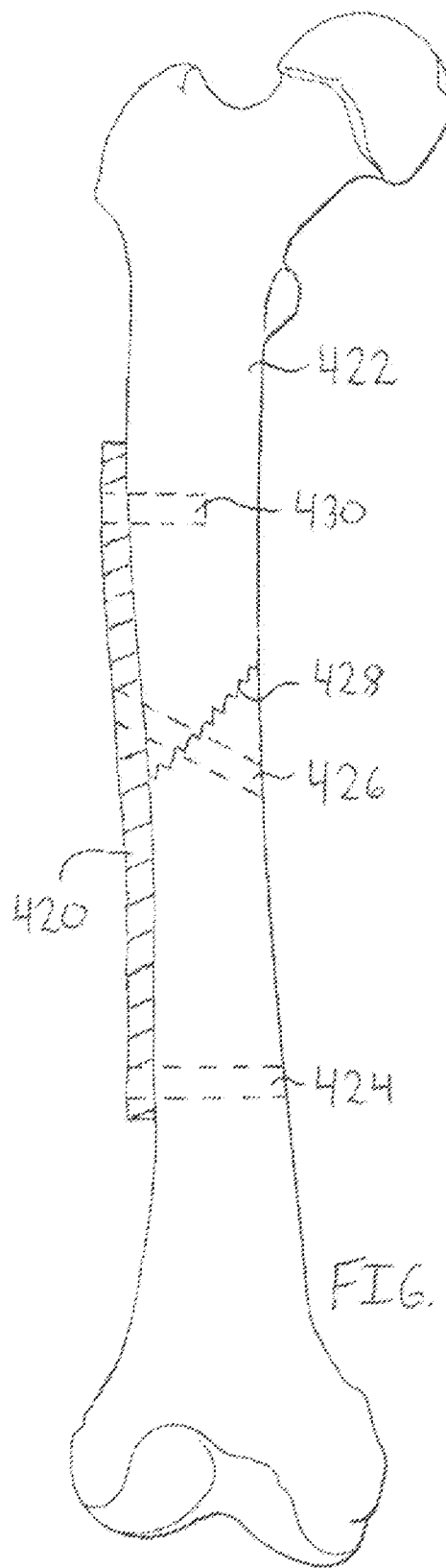
FIGS. 25A and 25B show the repair of a fractured bone with a thermoplastic plate.
Figure 25B:
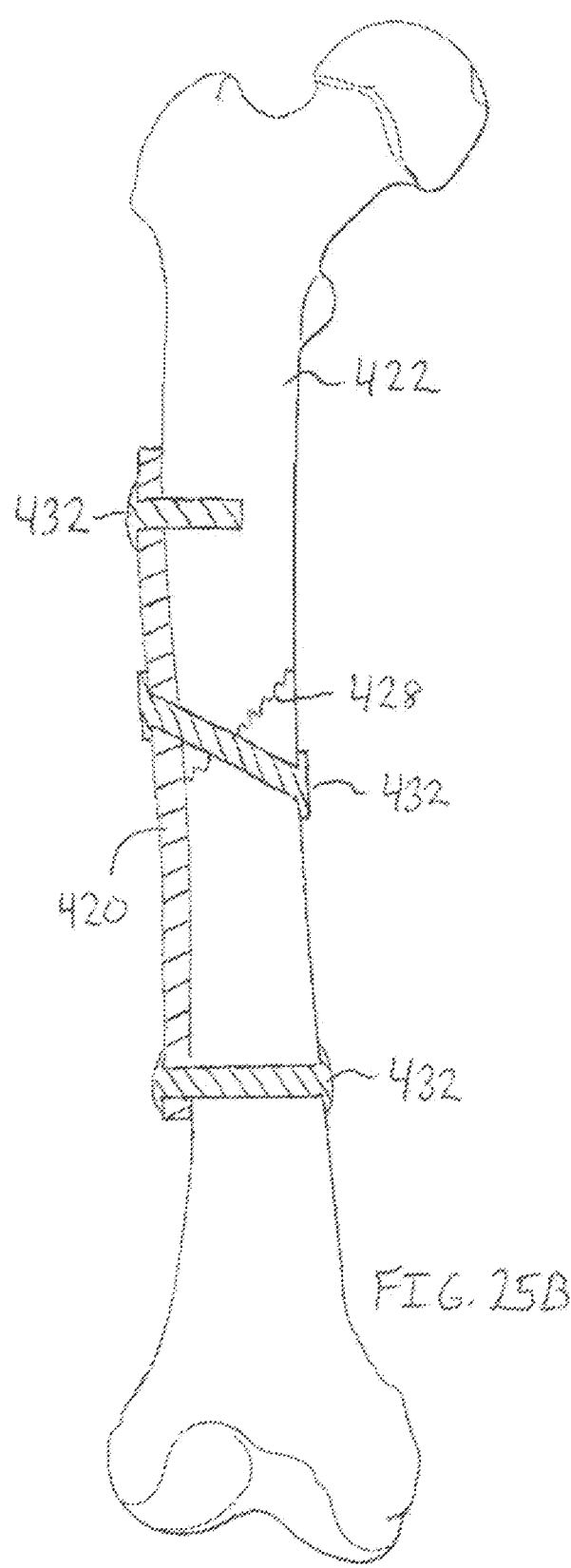

Another method and apparatus for repairing a fractured bone is illustrated in FIGS. 25A and 25B. Instead of an intramedullary rod being placed in the bone canal, a bone plate 420 is positioned against the fractured femur 422 on the exterior side of the bone. The bone plate 420 is made of thermoplastic material such as PEEK. A first channel 424 is created through the plate 420 and through the bone 422 to form a thru-hole. A second channel 426 is drilled through the bone plate 420, across the fracture 428, and through the bone 422. A third channel 430 is formed through the plate 420 and partially into the femur 422. Additional channels may be created as desired. In FIG. 25B, PEEK fasteners 432 are placed in the channels and ultrasonically welded to the femur 422 and bone plate 420. The fastener type and method of welding each fastener may be similar to previously described embodiments.

FIGS. 26A and 26B show a combination configuration for repairing a fractured bone. The combination includes an IM rod 440 positioned in the medullary canal of the bone 442 and a bone plate 444 positioned against the exterior surface of the bone 442. The rod and plate may be made of PEEK. In FIG. 26A, a plurality of channels 446 are created through the plate, bone, and/or rod. PEEK fasteners, shown in FIG. 26B, are positioned in the channels 446 and ultrasonically welded to the plate, bone, and rod. A first fastener 448 is welded to a bonding region 450 on the surface of the rod 440. A second fastener 452 is welded in an indentation in the rod 440. A third fastener 454 extends through the plate, bone, and rod. The third fastener 454 includes a mushroomed or contoured head on its distal end, and on the proximal end, no head is needed since the fastener bonds directly to the bone plate 444. A fourth fastener 456 is positioned in a blind hole in the rod 440. The fourth fastener 456 is also free of a proximal head or cap. As seen in FIG. 26B, the bone plate 444 is contoured to conform to the exterior surface of the femur 442. This may be performed with ultrasonic energy, resistive heating, or other suitable energy source.

Figure 27A:
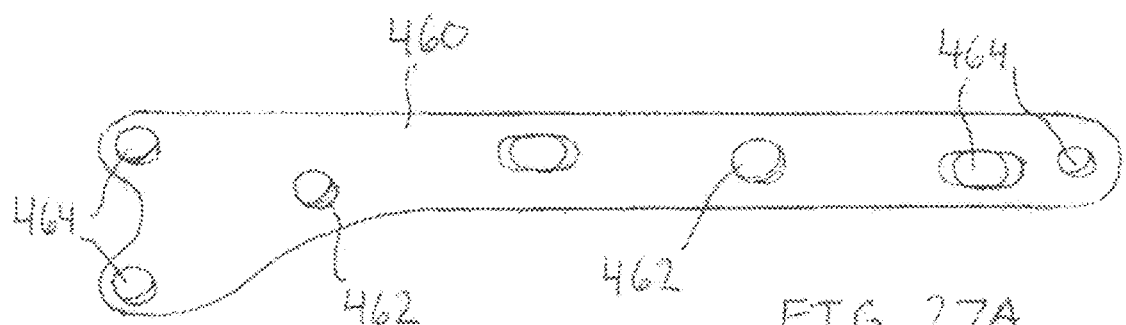
FIGS. 27A-27C show a bone plate of the present invention.
Figure 27B:
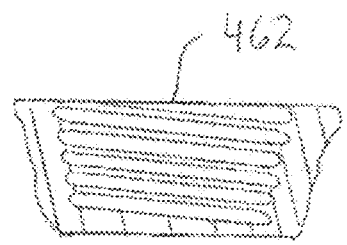
Figure 27C:
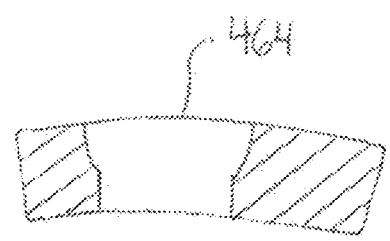

An exemplary bone plate 460 of the present invention is shown in FIGS. 27A-27C. Some previously described bone plates and IM rods included no pre-fabricated holes. Instead, the surgeon formed channels in the plates and rods to insert fasteners. In the embodiment of FIG. 27A, the bone plate 460 includes a plurality of openings. Some openings are threaded while others are free of treads. FIG. 27B is a cross sectional view of a threaded opening 462 of the plate 460. FIG. 27C is a cross sectional view of an unthreaded opening 464. The plate 460 is made of thermoplastic material such as PEEK.

Figures 28A, 28B, 28C, 28D:
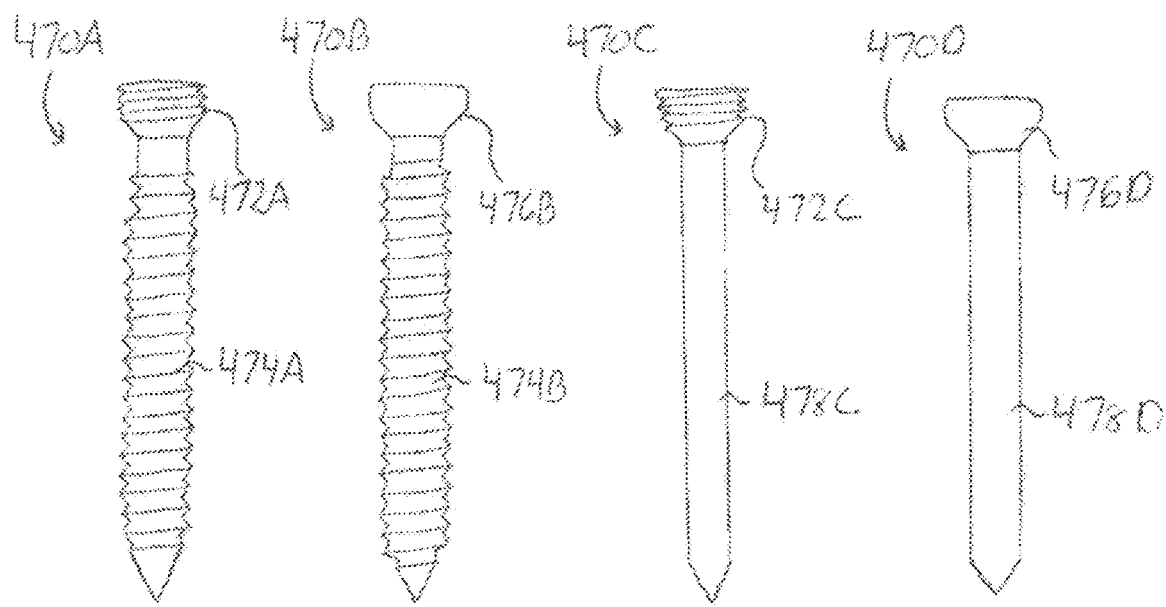
FIGS. 28A-28D illustrate exemplary fasteners for use with a bone plate or other implant.

Shown in FIGS. 28A-28D are exemplary fasteners for affixing the bone plate to a bone. The fasteners are made of PEEK and may include a central channel configured for receiving a welding horn. FIG. 28A shows a PEEK fastener 470A having a threaded head 472A and a threaded shaft 474A. The threaded head 472A is dimensioned to be threaded into one of the threaded openings 462 of the bone plate 460. The thread shaft 474A is configured for insertion in tissue. FIG. 28B shows a fastener 470B with a smooth, unthreaded head 476B and a threaded shaft 474B. The unthreaded head 476B is configured for insertion in one of the unthreaded openings 464 of the bone plate 460. FIG. 28C shows a fastener 470C having a threaded head 472C and smooth shaft 478C. FIG. 28D shows a fastener 470D with a smooth head 476D and smooth shaft 478D. In use, the bone plate is positioned on a fractured bone. Fasteners of FIGS. 28A-28D are positioned through the openings in the plate and into the bone. The fasteners are ultrasonically welded to the plate and bone. The smooth head or smooth shaft of a fastener is thermally bonded to the plate or tissue, while the threaded head or threaded shaft is mechanically secured and thermally bonded to the plate and/or tissue.

Figures 29, 30:
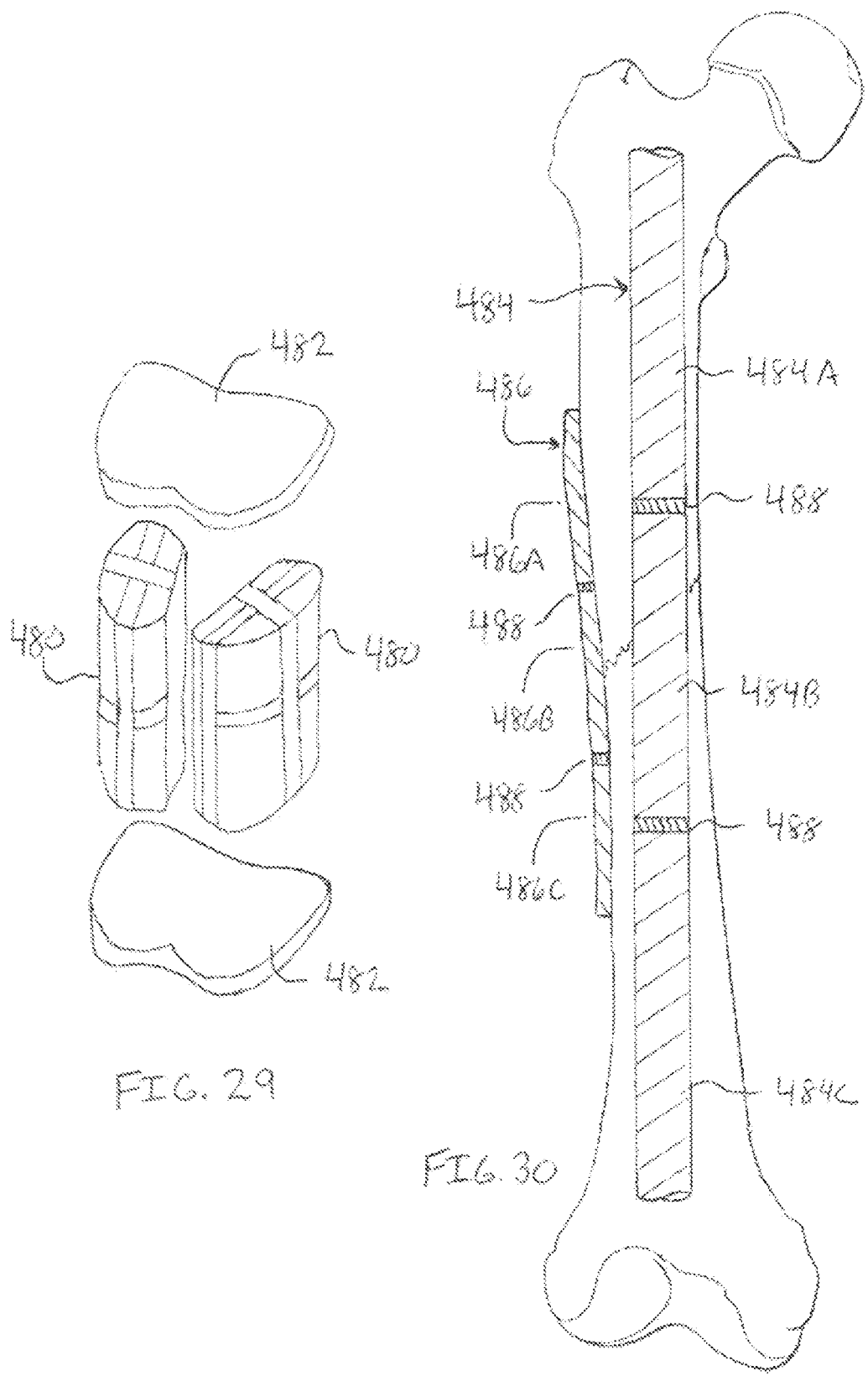
FIG. 29 shows modular assembly of a spinal implant.
FIG. 30 illustrates sequential welding of an intramedullary rod.

The trauma welding system also provides for the modular assembly of implants intracorporeally. In FIG. 29, spinal cages 480 include thermoplastic material which may be welded to vertebral body replacement components 482. The use of ultrasonic energy to weld the assembly together in the body prevents damage to surrounding tissue since the vibration energy creates just enough heat to soften and make tacky the thermoplastic material. FIG. 30 illustrates a modular IM rod 484 and a modular bone plate 486. The IM rod 484 includes a first portion 484A welded to a second portion 484B at a bonding region 488. The second portion 484B is welded to a third portion 484C at another bonding region 488. In this embodiment, the smaller portions of the rod may be implanted using minimally invasive techniques. Each portion may be welded to an adjacent portion intracorporeally. The bone plate 486, likewise, includes a plurality of modular portions 486A, 486B, 486C which may be thermally bonded together in the body. It is also contemplated that the small portions of the rod, plate, or other implant may be assembled by the surgeon in the operating room prior to implantation. This way, the implant manufacture can produce small portions of an implant allowing the surgeon to select the size and number of portions to assembly to create a custom tailored implant. It is contemplated that intracorporeally sequential welding applies to other types of implants as well, such as modular stents, modular acetabular component, modular spacers, and modular wedges.

Figure 31A:
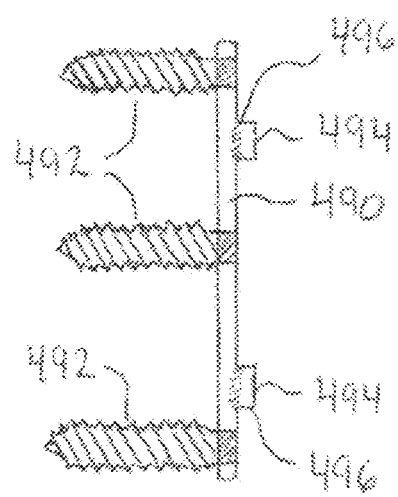
FIGS. 31A and 31B show the stabilization of the spine using thermoplastic implants.
Figure 31B:
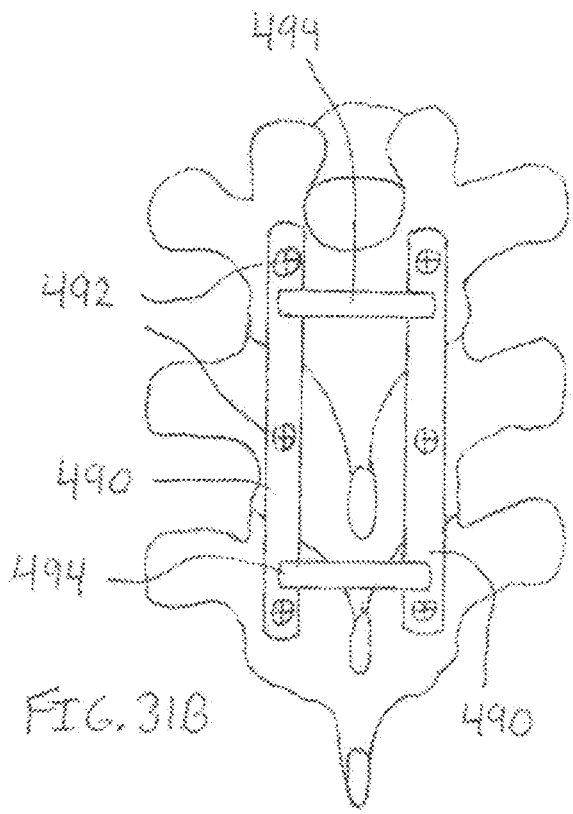

In a further embodiment of the present invention shown in FIGS. 31A and 31B, the trauma welding system may be used to stabilize joints of the spine such as intervertebral joints and facet joints. Stabilization of the spine is achieved by attaching rigid rods, plates, spacers, or wedges 490 between two or more vertebrae. Fasteners 492, such as pedicle screws, are inserted into the vertebrae, and plates/rods 490 are connected to the screws 492. The spinal rods, plates, fasteners, etc. may include thermoplastic material, such as PEEK. The implants may be biodegradable or biostable. In FIG. 3IB, PEEK pedicle screws 492 are inserted into vertebral bodies using the methods described herein. PEEK stabilizing plates 490 span the pedicle screws 492 and are ultrasonically bonded with the screws. Stabilizing cross bars 494 are thermally welded to the stabilizing plates at bonding regions 496. It is contemplated that any combination of fasteners, rods, plates, and wedges may be ultrasonically welded to stabilize joints of the spine.

Figure 32:
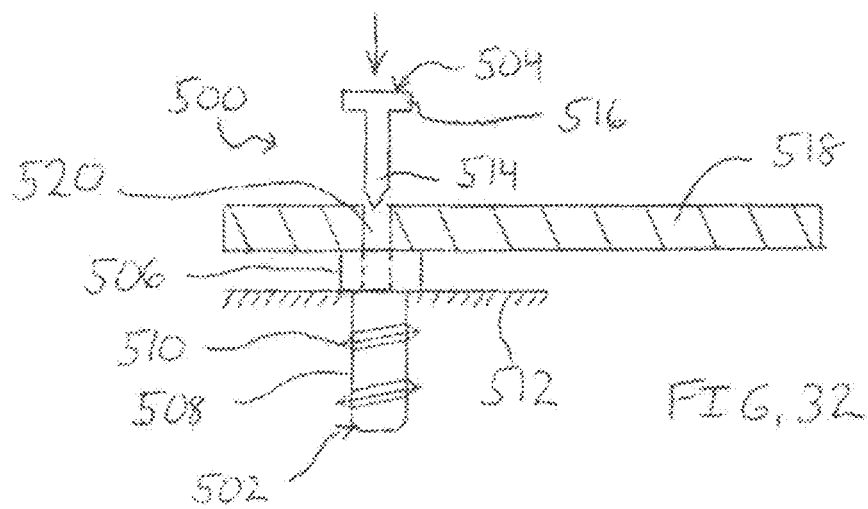
FIG. 32 illustrates an exemplary embodiment of a pedicle implant.

In FIG. 32, a spacing fastener 500 is shown. The fastener 500 includes an anchor 502 and a cap 504. The anchor 502 is generally a cylindrical shaft with a head 506 disposed on the proximal end of the shaft 508. The shaft 508 may include helical threads 510 for mechanical locking into tissue 512. The anchor 502 includes a bore extending along the central axis of the anchor. The fastener 500 further includes a cap 504 having a post 514 and a lid 516 attached to the proximal end of the post. The post 514 is dimensioned and configured for insertion into the bore of the anchor 502. Both the cap and anchor may be made of thermoplastic material such as PEEK. In an exemplary method of use, the anchor 502 is implanted in tissue 512 as shown in FIG. 32. The anchor 502 may be mechanically and/or thermally bonded in the tissue. A bone plate or rod 518 is placed over the head 506 of the anchor 502. A pre-drilled passageway 520 formed in the plate by the manufacturer is aligned with the bore of the anchor. Alternatively, a passageway 520 may be formed by the surgeon and aligned with the bore. The cap 504 is inserted through the passageway 520 of the plate 518 and into the bore of the anchor 502. The cap, plate, and anchor may be thermally bonded together with ultrasonic energy. In the implanted configuration, the head 506 of the anchor 502 acts as a spacer between the tissue 512 and plate 518. The spacing fastener 500 of FIG. 32 may be used as a pedicle screw separating a stabilizing plate from vertebral bodies.

In a further embodiment, the trauma welding system may be utilized to provide flexible stabilization of the spine, or any other joint or bone of the body. The soft tissue around and near a joint may become weakened over time, and the range of motion of the joint usually increases thereby allowing excessive tissue laxity. Also, instability of a joint may be caused by structural changes within the joint as a result of trauma, degeneration, aging, disease, or surgery. An unstable spinal joint may be rigidly stabilized as previously explained or may be dynamically stabilized to allow some range of motion of the spinal joints. Fasteners, screws, plates, rods, etc. made of PEEK may be implanted between two or more vertebrae. The plates and rods are configured and dimensioned to permit some flexing and/or bending. The amount of flexibility of these PEEK implants may be adjusted by the surgeon in the operating room using energy, such as ultrasound, resistive heating, etc. and by varying the weld parameters.

Figure 33:
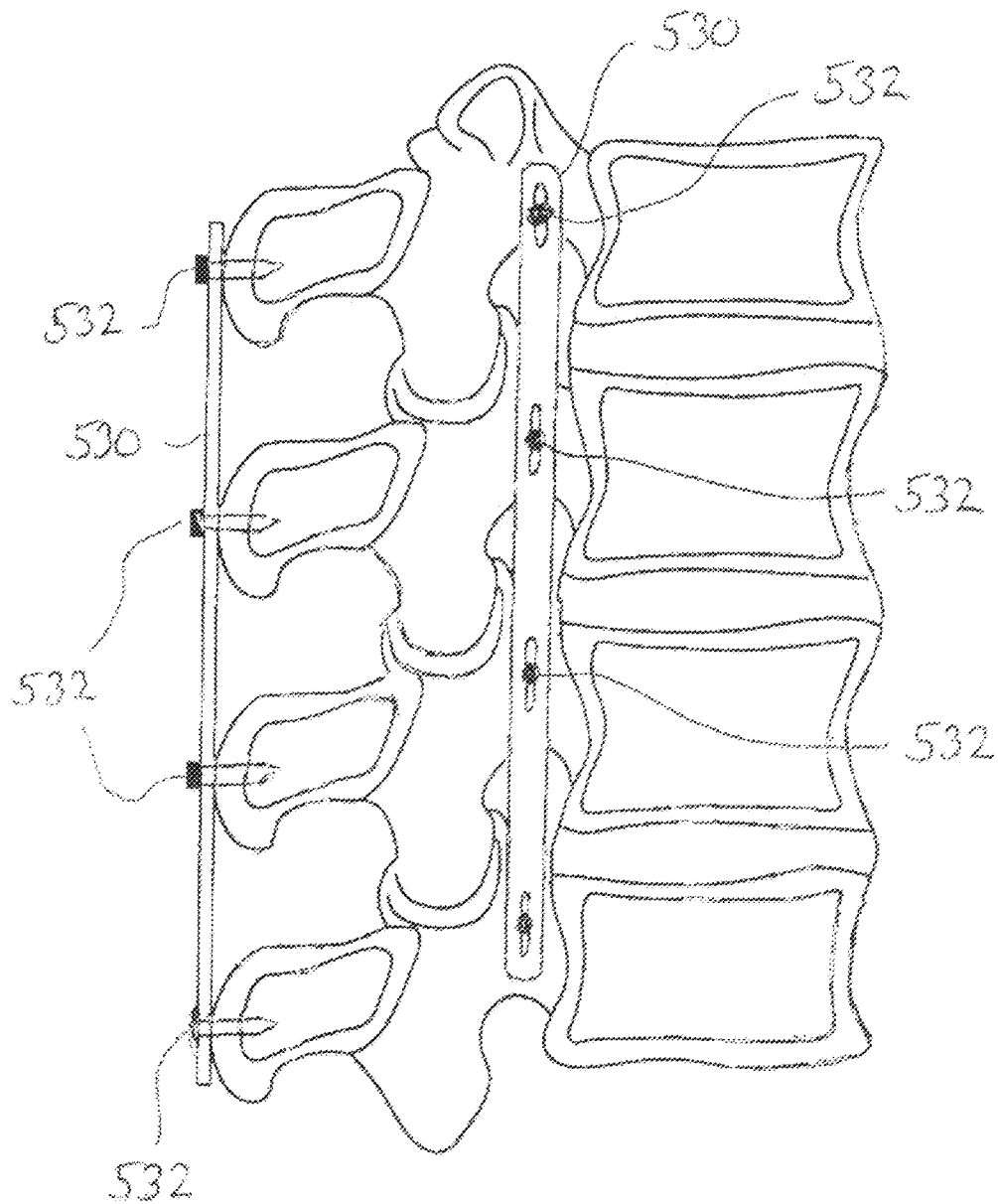
FIG. 33 shows stabilization of the spinal column with thermoplastic implants.

As seen in FIG. 33, a plate or rod 530 may be configured to lock with a fastener 532 in one direction, but would allow movement in another direction. For example, the plate 530 and fastener 532 permits superior and inferior motion of the spine but would prevent lateral motion. Also, the plate 530 and fastener 532 may permit motion in one plane and restrict motion in a different plane. The fasteners and plates of FIG. 33 may be made of PEEK and may be ultrasonically bonded to stabilize the spine.

FIGS. 34A and 34B illustrate another embodiment to stabilize a joint such as a joint of the spine. The swivellable pedicle screw assembly 540 may be used to connect a longitudinal bar 542 to a pedicle screw 544 thereby forming a spine stabilization device. The assembly 540 includes a body 546 having an upper end, a lower end, a hole 548 which is open at least towards the bottom and has an axis, and a through hole positioned perpendicular to the axis. The assembly 540 also has a collet chuck 550 mounted coaxially on the inside of the body 546 in such a way that it can slide along the axis. The collet chuck 550 has a through hole 552 which is flush with the through hole or the body 546, and a chamber which faces at least downwards and is defined by tongues spring-mounted against the cylinder axis. When the collet chuck 550 is inserted in the body, the through holes 552 align to allow insertion of the longitudinal bar 542. The head 554 of a pedicle screw 544 can be clicked into the chamber from below by spring-action. The assembly 540 allows for the pedicle screw 544 to be inclined within a certain range. The assembly may be made of thermoplastic material such as PEEK. Ultrasonic energy may be used to thermally bond the head 554 of the pedicle screw 544 within the chamber of the collet chuck 550 and to bond the longitudinal bar 542 with the pedicle screw 544.

It is contemplated that a simple ball and socket assembly may be used to stabilize the spine as well. The ball is the head of the pedicle screw as described above. The socket includes a chamber for receiving the ball. The socket may include an attachment means, such as a thru-hole or a thermal bonding region, for receiving and affixing a plate or rod. The ball, socket and plate/rod may be ultrasonically welded together to form a spine stabilizing configuration.

Figure 35A:
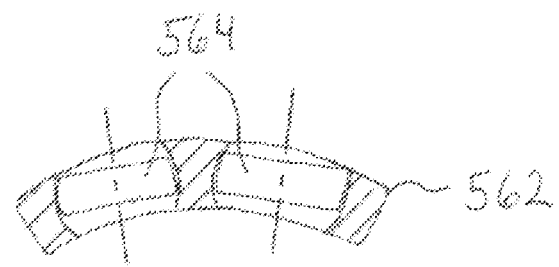
FIGS. 35A and 35B show a thermoplastic bone fixation assembly.
Figure 35B:
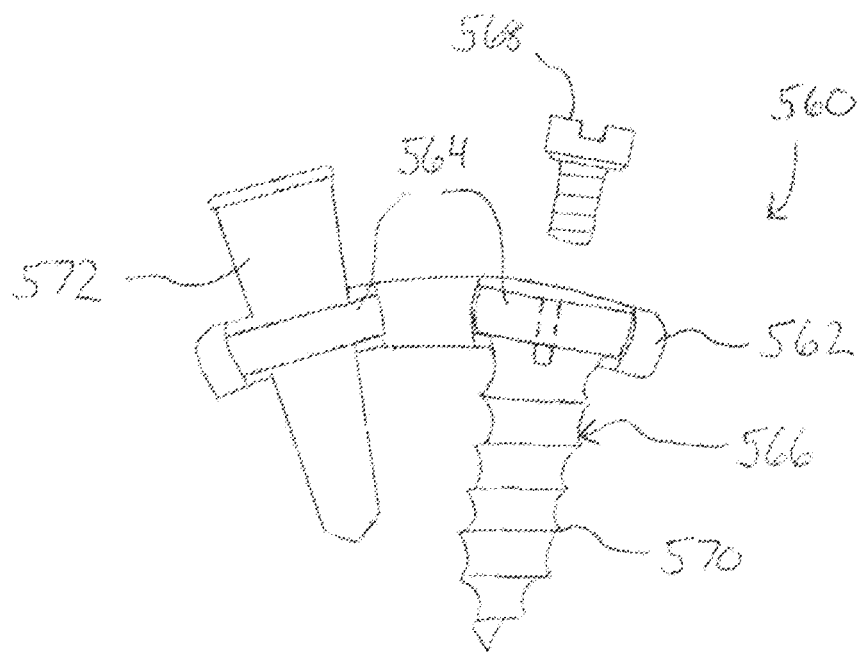

FIGS. 35A and 35B illustrate a bone fixation assembly 560 for securing a bone plate to bone. The assembly 560 includes the fixation device 562, a bushing 564, a fastening screw 566, and a locking screw 568. The bushing 564 is seated within a through hole in the fixation device 562 and can rotate within the through hole and has a sidewall with a bore. The sidewall has at least one slot for allowing outward expansion of the sidewall against the through hole to thereby lock the bushing 564 at a selected angle relative to the axis of the through hole. The fastening screw 566 has a threaded shaft 570 for insertion through the bore of the bushing 564 and threads into bone to secure the bushing 564 and fixation device 562 to bone. The head of the fastening screw 566 fits in the bushing and includes a radial wall and open end defining a recess. The radial side wall has at least one slit for allowing outward expansion of the radial wall thereby outwardly expanding the sidewall of the bushing 564. The locking screw 568 has a body that threads in the head of the fastening screw 566 to thereby outwardly expand the radial wall of the fastening screw 566. The assembly components may be made of PEEK. In an alternative embodiment, a fastening member 572, made of PEEK, replaces the fastening screw 566 and locking screw 568. In this embodiment, the fastening member 572 is inserted through the bore of the bushing 564 and into the bone. The fastening member 572 may be ultrasonically welded to the bushing 564 and the bushing 564 may be thermally bonded to the fixation device 562. The fastening member 572 is ultrasonically bonded to the bone using the welding methods described herein.

Figure 36A:
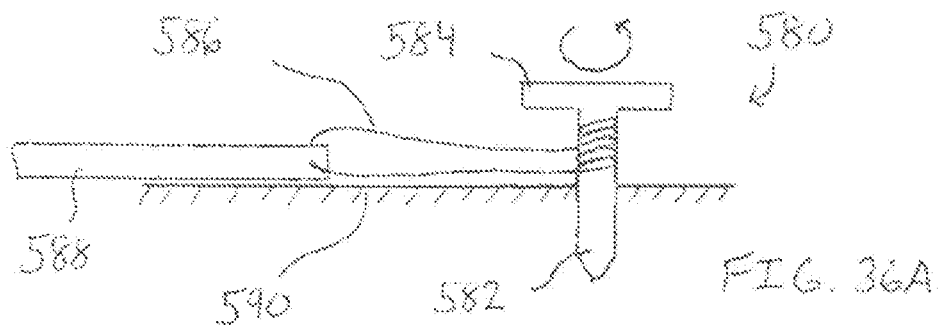
FIGS. 36A and 36B illustrate a thermoplastic suture tensioning device.
Figure 36B:
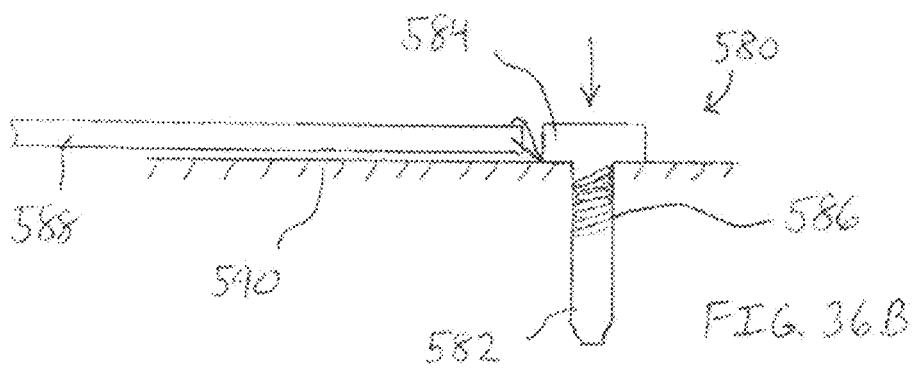

Referring now to FIGS. 36A and 36B, a cable tensioning fastener 580 is illustrated. The fastener 580 includes a post 582 and a cap 584 disposed on the proximal end of the post. The post 582 is configured for winding a suture or cable 586 thereon. The suture 586 may be attached to the post 582 by applying heat to PEEK material of the post, setting the suture into the softened PEEK, and allowing the PEEK to harden. Alternatively, a small channel may extend radially through the post. The suture 586 may be threaded through the channel. In a simple configuration, the suture 586 may be wrapped over itself on the post 582, like a spool of string. In an exemplary method of use as shown in FIGS. 36A and 36B, the suture or cable 586 is placed through or around tissue 588 such as a rotator cuff. The suture 586 is attached to the post 582 of the fastener 580 as previously described. The fastener 580 is then rotated to coil up the suture 586 on the post 582 and draw the rotator cuff 588 in close to the fastener 580. To secure the assembly, the fastener 580 is inserted into tissue such as bone 590. Ultrasonic energy is applied to the fastener 580 to bond the fastener to the tissue 590 and bond the suture 586 to the post 582 of the fastener 580. In this position, the rotator cuff is securely fastened to the bone.

Figure 37:
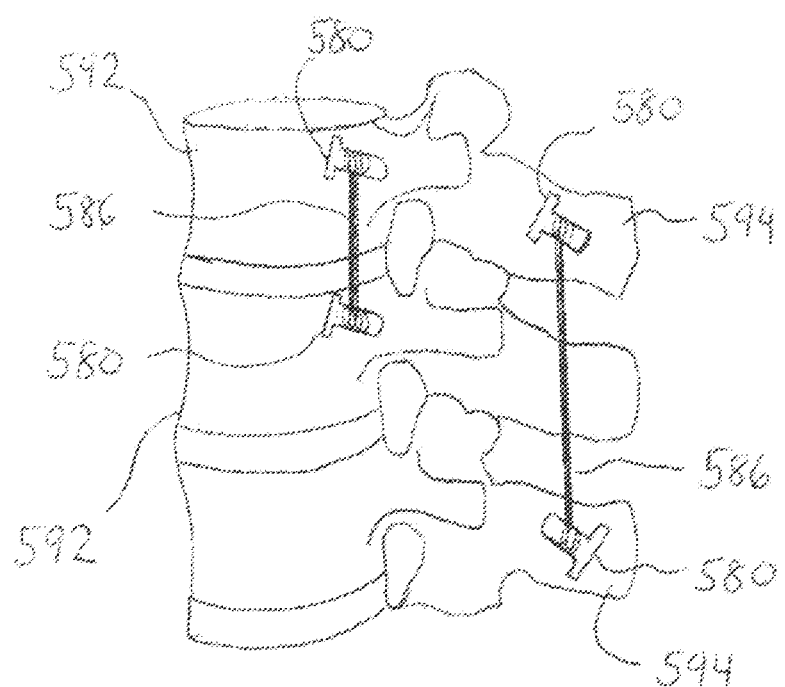
FIG. 37 shows the tensioning device of FIGS. 36A and 36B in use to stabilize the spine.

FIG. 37 illustrates another exemplary use of the cable tensioning fastener 580 of FIGS. 36A and 36B. A first tensioning fastener 580 is positioned in a vertebral body 592. A second fastener 580 is positioned in an adjacent vertebral body 592. A cable 586 spans between the posts of the first and second fasteners. One or both fasteners are rotated to tension the cable, and the fasteners are implanted in the vertebrae and ultrasonically welded in place. Third and fourth fasteners are implanted in spinous processes 594. A tensioned cable 586 is connected with the fasteners 580. The embodiment of FIG. 37 provides controlled stabilization of the spine by affixing flexible or non-flexible cables between vertebrae. Flexible cables provide dynamic stabilization, while non-flexible cables provide rigid stabilization.

Figure 38A:
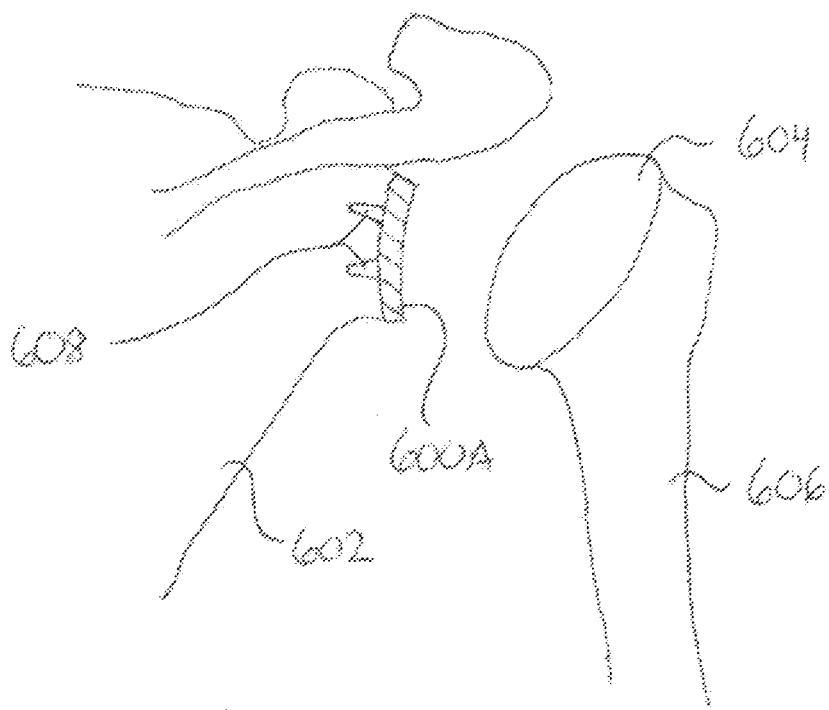
FIGS. 38A-38C illustrate a thermoplastic glenoid repair component.
Figures 38B, 38C:
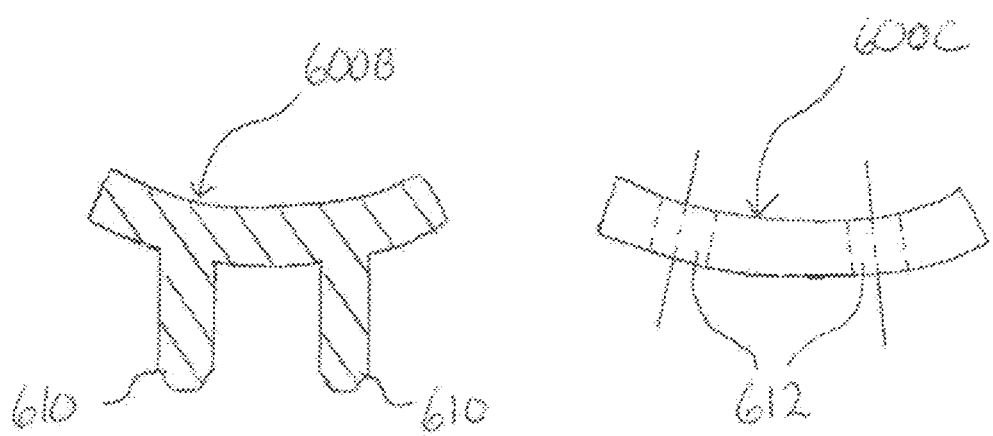

The present invention also provides a glenoid replacement component 600A, shown in FIG. 38A. The inner side is configured for placement on the scapula 602, and the outer side is configured for articulation of the head 604 of the humerus 606. Thermoplastic fasteners 608 secure the component 600 to bone. In FIG. 38B, a glenoid replacement component 600B is shown having prongs 610 extending from the inner side. The prongs 610 may be inserted into pre-drilled holes in the scapula and ultrasonically welded therein. FIG. 38C illustrates another embodiment of a glenoid replacement component 600C. The component 600C includes two thru-holes 612 extending from the outer to the inner side of the component. PEEK fasteners may be used to secure the replacement component to bone. The caps or heads of the fasteners may be contoured and flattened so as to not interfere with the head of the humerus.

Figure 39:
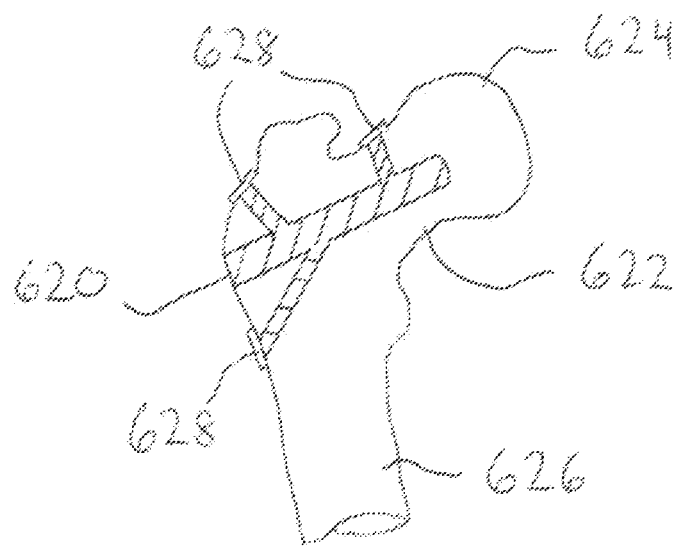
FIG. 39 shows a thermoplastic cross pin.
Figure 40:
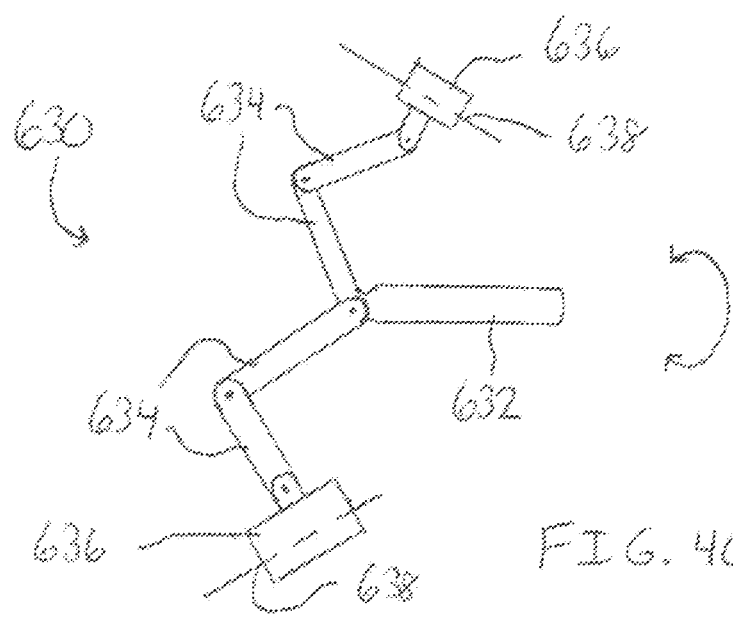
FIG. 40 illustrates a jig device for use with the cross pin of FIG. 39.

Referring now to FIG. 39, a thermoplastic cross pin 620 is illustrated. The pin 620 may be made of PEEK. The cross pin 620 is used to stabilize and strengthen the neck 622 and head 624 of the femur 626. To implant the pin, the pin 620 is positioned in a channel extending into the neck 622 and head 624. The pin 620 may be mechanically locked within the channel and/or may be thermally bonded within the channel. Thermoplastic fasteners 628 are placed through the conical bone of the femur 626 and into contact with a bonding region on the pin 620. As previously described, the bonding region may be a roughened surface, an indentation, a blind-hole, or a thru-hole. The fasteners 628 are then ultrasonically welded to the pin 620 and bone to secure the pin 620 within the femur 626. FIG. 40 illustrates a cross pin jig 630 to be used during implantation of the pin 620. The jig 630 includes a shaft 632 and a series of pivoting arms 634 connected with the shaft 632. At the end of the pivoting arms 634 is an insertion guide 636. The guide 636 has a passageway 638 configured for guiding a fastener. The arms 634 pivot in one plane with respect to the shaft 632 such that the passageway 638 of the insertion guide 636 is always aligned with the shaft 632. In use, the shaft 632 of the jig 630 is inserted into the drilled channel extending into the neck and head of the femur. The insertion guides 636 are positioned adjacent the surface of the bone. A drill and bit is placed in the guide 636 and a hole is created through the cortical bone terminating in the channel. A plurality of holes may be formed in the bone to receive a plurality of fasteners. Once the holes have been drilled, the jig 630 is removed and the cross pin 620 is inserted into the channel. Fasteners are then placed through the holes and into contact with the cross pin 620. Ultrasonic welding bonds the fasteners, cross pin, and bone together. In an alternative embodiment, the shaft of the jig has a diameter which slides into a central passageway of the cross pin. In this embodiment, the cross pin may be implant in the channel, then the jig may be placed in the cross pin.

Figure 41:
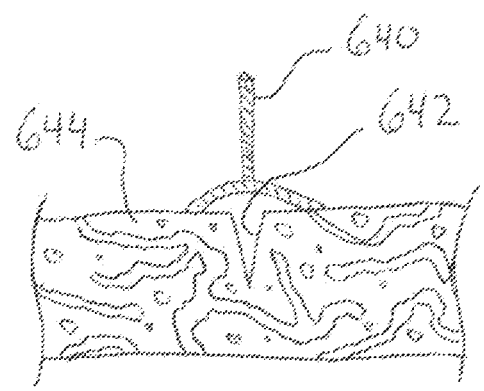
FIG. 41 shows cauterization of tissue using ultrasonic energy.
Figure 42:
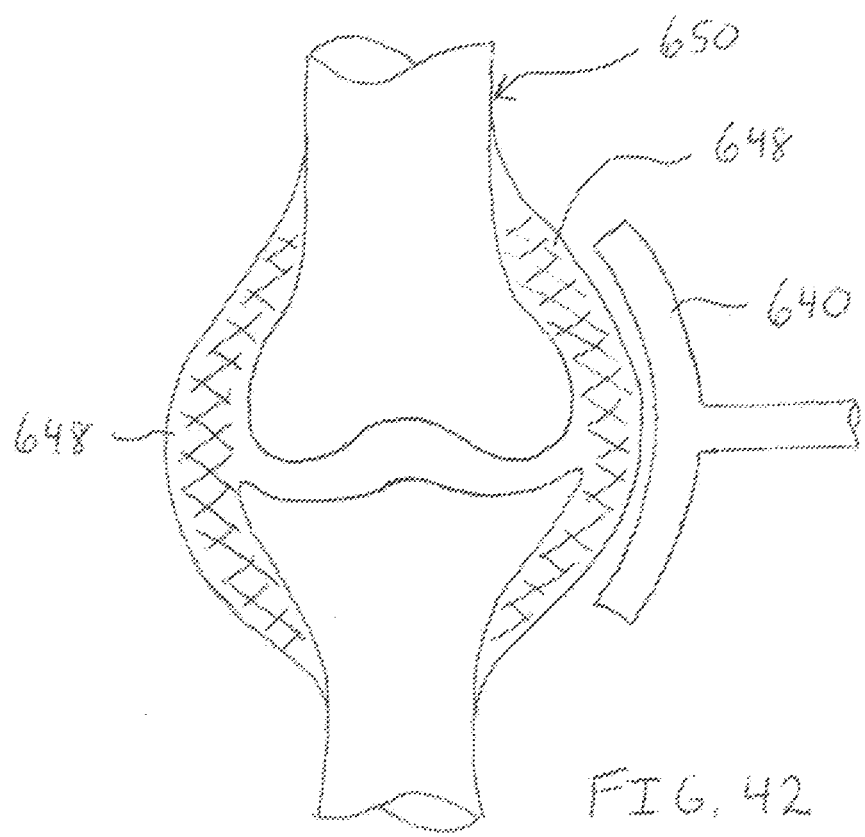
FIG. 42 illustrates cauterization of tissue using energy and gelatin.

In a related invention, FIG. 41 shows a tissue cauterization device 640. A cut or opening 642 is formed in soft tissue such as skin 644. To stop bleeding at the cut, ultrasonic energy may be applied to the tissue. An energy horn 640, similar to those previously described, may be placed in contact with bleeding tissue 644. Ultrasound energy emitted from the horn stops the flow of blood by hemostasis. In FIG. 42, ultrasound from an energy horn 640 is applied to gelatin 648 within a joint 650. The gelatin 648 binds to the tissue and stops bleeding. Gelatin, or other suitable substance, may also be used with the tissue cauterization device of FIG. 41.

Figure 43:
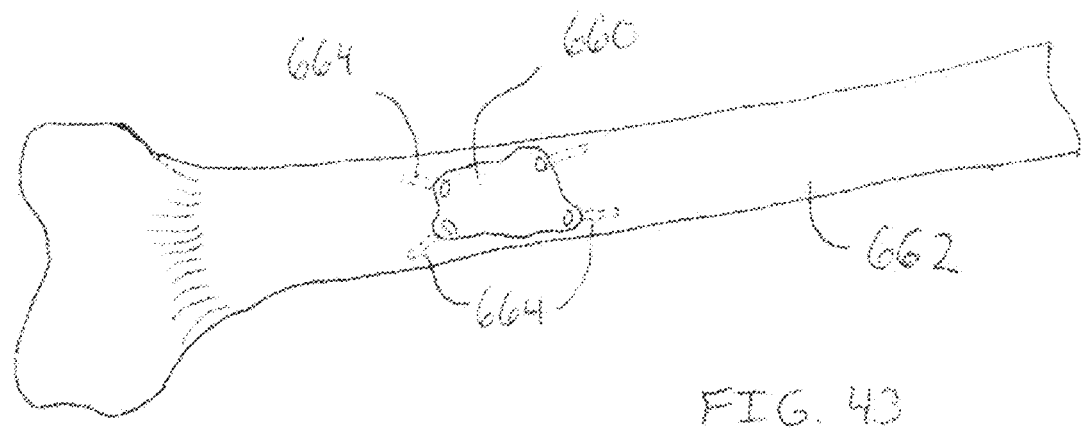
FIG. 43 shows the repair of tissue with a periosteal flap.

FIG. 43 illustrates a periosteal flap 660 used to repair a damaged bone 662. The flap 660 is fastened to the bone 662 using thermoplastic fasteners 664 and methods previously described. Tissue grafts may also secured intracorporeally using PEEK fasteners and ultrasonic energy.

It is also contemplated that metal may be ultrasonically welded to PEEK. For example, a fastener may be made of metal. By placing the metallic fastener on the end effector of the welding instrument, the fastener functions as an extension of the end effector. Therefore, applying pressure from an ultrasound-emitting metallic fastener to a PEEK implant drives the fastener into the implant and thereby secures the fastener to the implant. It is further contemplated that a thermoplastic fastener may be bonded with a metallic implant. Accordingly, the devices and methods described throughout may utilize metallic fasteners bonded to thermoplastic implants and thermoplastic fasteners bonded to metallic implants.

Figure 44A:
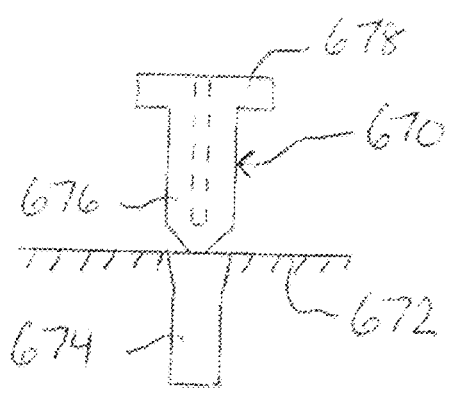
FIGS. 44A and 44B illustrate a method of bonding a thermoplastic fastener in bone.
Figure 44B:
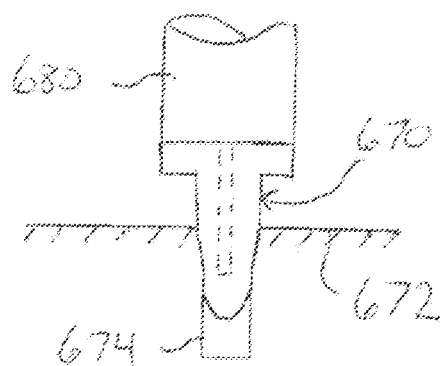

In a further embodiment of the present invention, a method for securing a thermoplastic fastener 670 into tissue 672 is provided. FIGS. 44A and 44B illustrate the method. In FIG. 44A, a channel 674 is drilled in tissue such as bone 672. The fastener 670 includes a post 676 and a lid 678, similar to other fasteners disclosed herein. The diameter of the post 676 is greater than the diameter of the channel 674 in the bone 672 such that the fastener 670 does not freely slide into the channel 674. In FIG. 44B, an end effector 680 is placed in and on the fastener 670. Ultrasonic energy is emitted from the end effector 680 to soften the thermoplastic material of the fastener 670. Simultaneously, downward pressure is applied to the end effector 680 and fastener 670 so that the softened material conforms to the smaller diameter of the channel 674. The fastener 670 is moved distally until it is fully seated in the bone 672. After energy is no longer emitted, the thermoplastic material re-hardens thereby securely bonding the fastener 670 to the bone 672.

In another application of the present invention, thermoplastic fasteners may be used to lock a drug delivery system to an implant or to tissue. For example, a reservoir, balloon, or bladder may be placed within the body and filled with a pharmaceutical substance, gene therapy, or cell therapy. Using PEEK or other thermoplastic, the reservoir may be sealed and stabilized in the body. The contents of the reservoir may leach out or elute out from pores or openings in the reservoir material. Alternatively, the thermoplastic may be biodegradable to allow the contents to escape from the reservoir and into the body. It is contemplated that other drug delivery systems may be used with the present invention. Also, the pharmaceutical agents may include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, bone growth inducing material, osteoinductive materials, apatite compositions with collagen, demineralized bone powder, or any agent previously listed. U.S. Provisional Patent Application No. 60/728,206 entitled "Drug Eluting Implant" discloses means for delivering therapeutic agents. The above-mentioned provisional application is incorporated by reference herein in its entirety.

The welding system of the present invention may further include the process of welding collagen similar to the way PEEK is bonded. Collagen fibers may be infused within a biodegradable polymer or gelatin to enhance welding properties. An energy source, such as ultrasonic energy, may be used to weld the collagen. As previously described the quality of weld depends upon the welding parameters of time, energy time, wattage, frequency, pulsation, pressure, etc. In an exemplary embodiment, collagen is placed in biodegradable polyglycolic acid. Once implanted, the polymer would biodegrade leaving the collagen fibers to heal surrounding tissue. Also, imbedded in the polymer may be cells, antibiotics, keratin, tissue inductive factors, or other pharmaceutical agents disclosed herein.

Alternatively, the collagen fibers may be packed very densely and may be desiccated. The fibers may be welded together or an interfacial material such as talc, glass, graphite, or protein may be added to harden the fibers to a gelatin. In an exemplary embodiment, collagen fibers may be combined with denatured porcine collagen cells. The two substances may be welded together to form a unitary implant. The implant may be fastened within the body for cell therapy, gene therapy, or for the delivery of pharmaceutical agents.

Another welding technique that may be utilized with the present invention is plasma welding. Generally, there are four states of matter in physics: solid, liquid, gas, and plasma. Plasma is a gas in which atoms have been ionized. Therefore, plasma has magnetic and electrical fields that move unpredictably, altering the environment. As the environment changes, so does the plasma. These ionized gases or plasma can be used to fuse bone or weld material within the body. Plasma welding may be controlled similar to the way thermal welding is controlled as previously described. A plasma stream may be used for polymeric welding, protein welding, or collagen welding. When welding intracorporeally, cold plasma welding may be used to prevent tissue necrosis. Cold plasma can weld tissue, polymers, metals, ceramics, and composites to each other and to one another. Cold plasma may also be used to debride wounds in surgery, to selectively kill bacteria, to roughen the surface of tissue to make it more receptive to pharmaceutical agents, or to prepare a surface of a bone for a joint replacement component. It can also be used to shrink tissue and polymers, ablate tissue, or smooth out wrinkles for plastic surgery either on the surface of the skin or under the skin. Cold plasma welding may be performed through a cannula in a straight line or curved/deflected to reach a target site within the body. The plasma energy may be altered by accelerating electrical charges or electromagnetic fields.

In a related invention, welding of thermoplastics, tissue, implants, etc. described herein may be performed utilizing suction or negative pressure. For example, suction may be applied to a bone to pull a cartilage graft or plate to the surface of the bone. A tube may be placed within the bone to create a negative pressure. This would temporarily hold the implant and contour it to the surface while an energy source is used to weld the graft to the bone with or without traditional or thermoplastic fasteners. Also, suction may be used to stabilize an implant during welding or while an adhesive is curing. Examples of biocompatible adhesives include mollusk adhesive, protein adhesive, fibrin adhesive, cyanoacrylates, or other known adhesives.

The present invention also may be used in other ways for the fixation or securing of tissue and/or implants during a surgical procedure. The use of the invention in such a procedure may assist in restoring at least partial tissue-function in a treated area. In this scenario, the fixation device may include a tissue-penetrating cap positionable in an anchor. Tissue may be fastened so that tissue-function is at least partially restored and the operation region is stabilized for enhanced healing.

The fixation devices of at this and other embodiments of the invention may be used in combination with fasteners in the prior art. Examples of fasteners, implants and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072;

5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; and Ser. No. 10/797,685. The above cited patents and patent applications are hereby incorporated by reference in their entirety.

Figure 45:
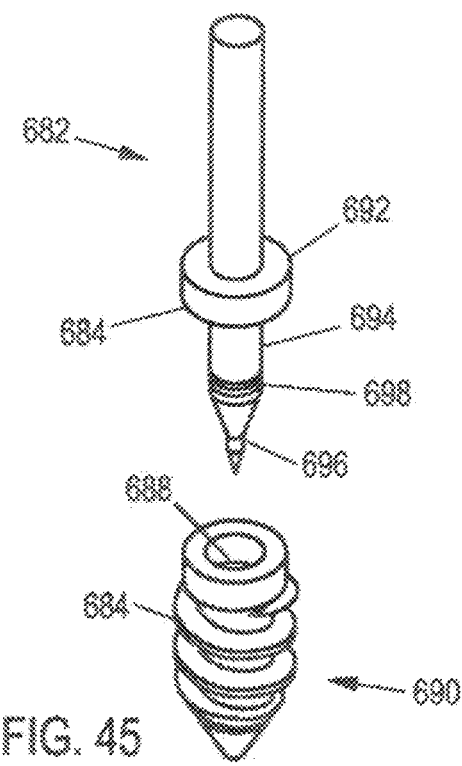
FIG. 45 illustrates a perspective view of one embodiment of a fixation device of the present invention.

FIG. 45 illustrates an exemplary embodiment of a fixation device 682 of the present invention, where the fixation device includes a cap 684 and an anchor 686. The anchor 686 is generally cylindrical in shape and includes a bore 688 disposed in a first end of the anchor 686. A second end of the anchor may be substantially conical although as explained in greater detail below the second end may have other shapes as well. The central longitudinal axis of the bore 688 may be congruent with a central longitudinal axis of the anchor 686. The bore 688 may extend only partially into or completely through the anchor 686. The anchor of FIG. 1 includes threads 690 in a helical pattern disposed on the exterior surface. The helical threads 690 are configured to allow the anchor 686 to be inserted in tissue similar to the way a screw is inserted into wood, with or without a pre-drilled hole.

The cap 684 of the fixation device 682 includes a lid 692 and a post 694. The post 694 is generally cylindrical in shape and is dimensioned to fit within the bore 688 of the anchor 686, while the lid 692 is generally disk shaped. The proximal end of the post 694 is connected with the underside of lid 692 to form a fastener configuration similar to a nail. The cap 684 may be cannulated, i.e. a channel may extend through the longitudinal axis of the cap. The channel may be dimensioned for the positioning of a guide wire, insertion tool, and/or energy source therein. The distal portion of the post 694 may be chamfered to form a pointed tip 696. The chamfered surfaces of the distal portion may extend from the distal opening of the channel to the outer surface of the post 694. The chamfered post tip 696 allows the cap 684 to penetrate through tissue without substantial tearing.

The post 694 of the cap 684 and bore 688 of the anchor 686 may further include one or more mechanical locks that may be used to help hold the cap 684 and anchor 686 together when desired. For example, a mechanical lock can be used to hold the cap tip 696, post 694, or other portions of the cap 684 within the anchor 686 when the device is being employed to secure tissue and/or an implant. Examples of mechanical locks may include one or more projection 698 disposed on the outer surface of the post 694. FIG. 45 illustrates one example of a projection where the cap post 694 has a circumferential ridge 698. One or more corresponding indentation(s) or grooves may likewise be provided in the surface of the anchor bore. Alternatively, one or more projections may be provided on the anchor bore, and the cap post may have one or more indentations or grooves.

Other mechanical locks may also be used with this and other embodiments of the invention. For example, a mechanical lock may utilize a mechanically, outwardly expanding post and/or a mechanically inwardly expanding anchor/bore; a hydrophilically, outwardly expanding post and/or a hydrophilically, inwardly expanding anchor/bore; helical threads on the post and corresponding threads in the bore; and biocompatible adhesive disposed in the bore of the anchor and/or on the post of the cap. Examples of adhesives may include cyanoacrylate adhesives, hydrogel adhesives, monomer and polymer adhesives, fibrin, polysaccharide, Indermil® or any other similar adhesive. Other exemplary mechanical locks discussed in greater detail herein may also be applied to many embodiments of the invention.

Alternatively, the cap 684 may be secured to the anchor 686 by thermal fastening. As previously explained, certain materials of the cap 684 and anchor 686 may have the characteristic of becoming melted, tacky, and/or flowable when energy such as heat is applied to the fixation device. The material may be resorbable by the body or non-resorbable. Such material may include polylactic acid (PLLA), polyglycolic acid (PGA), a co-polymer of PLLA and PGA, resins, polyetheretherketone (PEEK), polyethylene (PE), ultra-high-molecular-weight-polycarbonate (PC), acetal (Delrin), and other suitable polymers. The thermally bonding material may be dispersed within the cap and anchor and/or may be coated on the surface of the cap and anchor. Additionally, the cap and the anchor may be made entirely from the thermally bonding material.

In an exemplary embodiment, the fixation device is made of PEEK which is a suitable thermally bondable material. Also, an implant in which the fixation device fastens to tissue may include a thermally bondable material. For example, a plate, rod, spacer, wedge or other implants disclosed herein may be secured to tissue. An energy source, such as ultrasound or resistive heating, may be used to secure the cap to the anchor and to secure the implant to the fixation device. The energy source also may heat the implant which may include thermally deformable material, such as PEEK. The implant may also be deformable or conformable to adjacent tissue.

To bond the cap 684 and anchor 686 of the fixation device 682 together, an energy source may be applied to one of or both of the cap 684 and anchor 686. Suitable energy sources may include ultrasonic; RF; laser; heat transmitted through conduction, convection, or radiation; resistive heating; microwave; electromagnet; ultraviolet; infrared; electroshockwave; or other known energy sources. The cap 684 and anchor 686 may also be coupled by protein welding. Preferably, when the cap 684 and anchor 686 are designed to be thermally coupled, at least a portion of both the cap and anchor include, or are made of a thermally bondable polymer, such as those previously described. The use of energy to bond the cap 684 and anchor 686 which have similar polymeric material allows the melting of the material to occur consistently or uniformly throughout welded area of the fixation device 682. This helps reduce the risk of necrosis to the surrounding tissue and also is believed to provide better control of welding conditions. If the thermally bondable material is metal, magnetic pulse welding could used to bond the cap and anchor of the fixation device.

To apply an energy source to the fixation device 682, the energy producing instrument may include a projection, such as an arm, which is positionable within the cannulated cap 684 and anchor bore 688. In this configuration, energy may be emitted from the projection and into the cap 684 and anchor 686. Since the projection extends through the cannulated cap and anchor, the fixation device 682 is subjected to energy along its longitudinal length. Therefore, the material of the cap 684 and anchor 686 may be bonded in a consistent, even, and/or uniform manner.

It is also contemplated that the fixation device 682 may include energy focusing material. The energy focusing material may be particles or chips disposed within the material of the cap 684 and/or anchor 686. The energy focusing material also may be a sleeve or particles disposed in the channels of the cannulated cap 684 and anchor bore 688. The energy focusing material may also be dispersed in rings or discs disposed within the material of the device 682. The rings may be positioned generally perpendicular to the longitudinal axis of the device. Furthermore, the energy focusing material may be disposed in bars or rods positioned generally parallel to the long axis of the device. The energy focusing material may be metallic, ceramic, polymeric, composite, or other suitable material. For example, iron oxide may be used. The energy focusing material may help capture energy from an energy source and/or emit energy for bonding the cap and anchor to each other.

Figure 46:
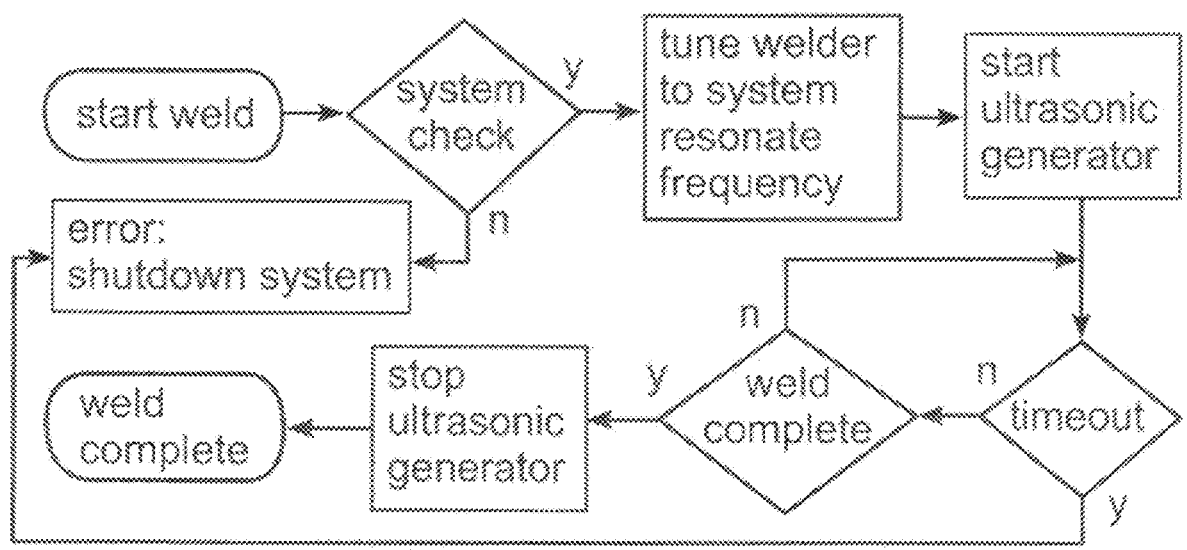
FIG. 46 illustrates an exemplary process for ultrasonic welding.

An exemplary process for ultrasonic welding is illustrated in FIG. 46. The welding process begins by either pushing the generator footswitch or using the control on the hand piece. Upon starting, the generator may first perform a system check. The software may also check for proper patient grounding, ground offset issues, as well as other vital circuits. If there are errors with the system or the grounding, the generator can give a visual or audible indication that an error has occurred, and the ultrasonic signal generator may be disabled to prevent inadvertent use.

If no errors are detected, the system may then sweep a frequency range, such as from about 38.5 kHz to about 43.5 kHz, to tune the circuit. Current measurements may be used to find the resonate frequency of the system, which in some embodiments may be close to 41 kHz. The ultrasonic signal is then sent to the hand piece where a resonator turns the waveform into linear movement.

Welding of the fixation device of the present invention could also be done using thermal energy. The process for thermal welding is similar to the one used for ultrasonic, except that it may not be necessary to tune the system. The energy signal sent to the weld can be either AC or DC. To allow for longer heater life, a pulse width modulated (PWM) signal could be used. The PWM signal allows for the energy to be rapidly switched on and off with a varying duty cycle proportional to the total system energy needed for the weld environment.

Another way to connect the cap and anchor of the fixation device may be through the combination of mechanical locking and welding. For example, the outer surface of the cap post 694 may include a circumferential ridge 698 and the interior surface of the anchor bore 688 may include a corresponding circumferential groove. Both the cap 684 and anchor 686 could include, or be made of, a biocompatible, thermally bonding polymer. The mechanical lock of the fastener could hold the cap 684 in the anchor 686 while an energy source, like an ultrasonic welder, is used to melt and bond the cap 684 and anchor 686 together. In this configuration, the mechanical lock may act as a temporary hold until the cap 684 and anchor 686 are permanently welded together. This configuration allows a surgeon to temporarily connect the cap 684 and anchor 686 and then inspect the assembly and tissue or implant to confirm it is in a desired position.

Alternatively, the fixation device 682 may include a more permanent mechanical lock in combination with thermal bonding. For example, the cap post 694 may include helical threads and the anchor bore 688 may include corresponding helical threads 690. In this configuration the cap post 694 may be screwed into the anchor 686 to securely connect the cap and anchor. The holding power of the cap and anchor may then be enhanced by thermally bonding the material of the cap and anchor together.

As previously described, the anchor 686 of the fixation device 682 may be screwed into a pre-drilled passageway in bone. The helical threads 690 disposed on the outer wall of the anchor allow the anchor to be screwed into and secured in the drilled passageway. Another way to implant the anchor 686 is by providing a self-penetrating or self-tapping helical thread configuration. In this configuration, the leading tip of the anchor 686 includes sharp edges, similar to the distal end of a drill bit, to allow the anchor to penetrate hard tissue as the anchor is being rotated. Such an anchor may include rigid threads and/or a rigid exterior wall on which the threads are disposed. The rigid exterior surface may include metal or ceramic material which functions as a shell. Within the rigid shell may be a polymer inner core including thermally bendable material. The benefits of this anchor design are that it is self-tapping requiring no pre-drilled passageway in bone and that the cap post and anchor may still be thermally bonded together.

Furthermore, the fixation device of the present invention may include therapeutic substances to promote healing. These substances could include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable polymer layer or layers.

The therapeutic agents may also be placed within one or more cavities disposed in a fixation device of the present invention. Different agents may be disposed in different cavities of the device to specifically tailor the implant for a particular patient. Dosages of the therapeutic agent may be the same or different within each of cavities as well. The cavities may include a cover which may release the agent in a controlled or timed manner. The cover may be biodegradable or bioerodible to allow the agent to release to surrounding tissue. Examples of suitable therapeutic agents include bone growth inducing material, bone morphogenic proteins, osteoinductive materials, apatite compositions with collagen, demineralized bone powder, or any agent previously listed. U.S. Provisional Patent Application No. 60/728,206 entitled "Drug Eluting Implant" discloses means for delivering therapeutic agents. The above-mentioned provisional application is incorporated by reference herein in its entirety.

Figure 47A:
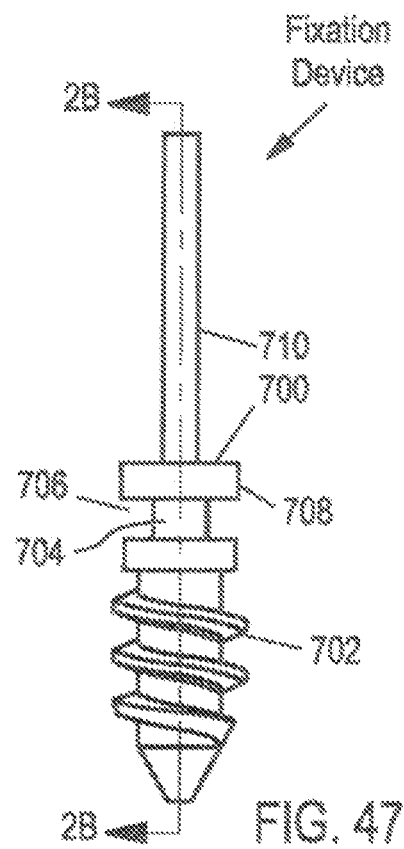
FIG. 47A shows a side view of the fixation device of FIG. 45 with a cap positioned in the anchor and an energy source deposited within the cap and anchor.

FIG. 47A shows a cap 700 inserted within an anchor 702. The post 704 of the cap 700 is positioned in the bore of the anchor 702. A gap 706 is shown between the bottom of the cap lid 708 and the trailing end or proximal end of the anchor. When the fixation device is in use, the tissue and/or implant to be fastened may be placed in the gap 706 to thereby squeeze the tissue between the lid 708 and anchor 702.

Figure 47B:
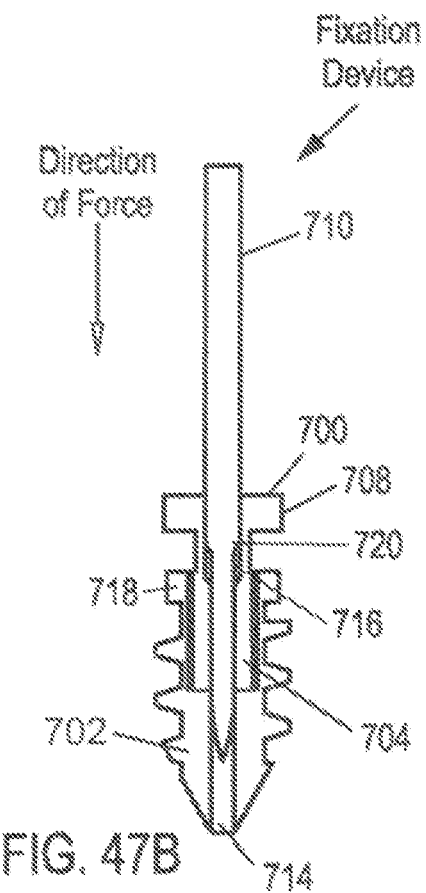
FIG. 47B is a cross-sectional view of FIG. 47A.

In FIG. 47B, the interior configurations of the cap 700, anchor 702, and heater 710 are illustrated. The anchor 702 includes a bore 712 and channel 714. The bore 712 is dimensioned to receive the post 704 of the cap 700. The channel 714 may be dimensioned to receive the distal portion of the heater 710. The channel 704 may also be dimensioned to receive a guide wire to assist in more precise placement of the anchor 702 in tissue and placement of the cap 700 within the bore 712 of the anchor 702. The cap 700 also may have a bore 716 and a channel. The cap bore 716 may be dimensioned to receive an intermediate portion of the heater 710, while the cap channel may be dimensioned to receive the distal portion of the heater 710 and/or a guide wire.

To lock the cap 700 and anchor 702 of FIG. 47B together, the cap post 704 is inserted into the anchor bore and a lock 718 is actuated to temporarily resist inadvertent separation of the cap 700 from the anchor 702. Preferably, the lock 718 prevents the cap 700 and anchor 702 from moving relative to each other. The heater 710 may be inserted through the cap bore 716, cap channel, anchor bore 712, and anchor channel 714. The heater 710 may include a curved or angled edge 720 a part of a transition between the intermediate portion and distal portion of the heater 710. The heater 710 may be inserted until the edge 720 contacts the cap bore 716. The portion of the cap bore 716 that contacts edge 720 may be curved, angled, or otherwise configured to have a surface that corresponds to the contact area of the edge 720. The cap angled edge may form the transition between the cap bore and cap channel. The contact between the cap and heater allows for the transmission of forces from the heater to the cap and to the anchor. The applied force helps create a snug fit between the cap post and anchor bore while the heater applies energy to the fixation device for thermal bonding.

Figure 48:
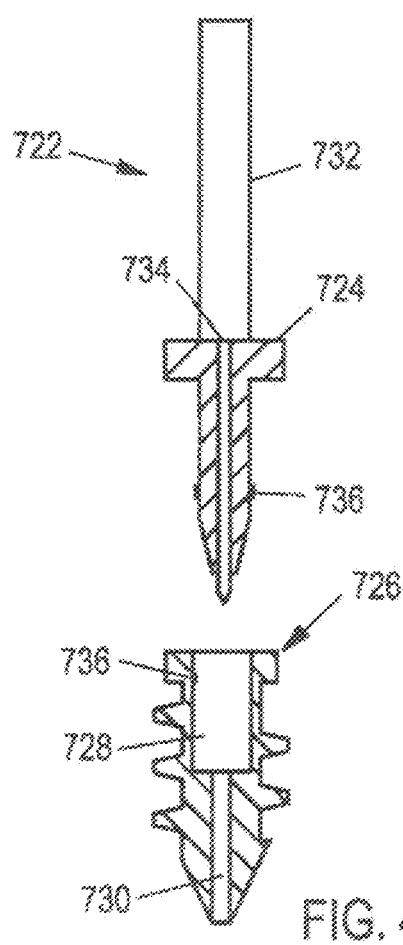
FIG. 48 illustrates the fixation device of FIG. 45 with a pusher means positioned against the cap.

FIG. 48 illustrates another embodiment of a fixation device 722. In this embodiment, the cap 724 includes a channel but does not include a bore. The anchor 726 includes both a bore 728 and a channel 730. As shown, the heater 732 has a cap-contacting surface 734 between its proximal portion and distal portion. In FIG. 47B, the force was applied from the heater 710 to the cap 700 through the angled edges of the heater and cap bore. However, in the embodiment illustrated in FIG. 48 forces applied to the heater 732 may be transferred to the top surface of the cap 724. While the force is applied, energy from the heater 732 may be released to thermally bond the cap 724 and anchor 726. The cap 724 and anchor 726 may also include one or more temporary or permanent locks 736 as previously described.

Figure 49:
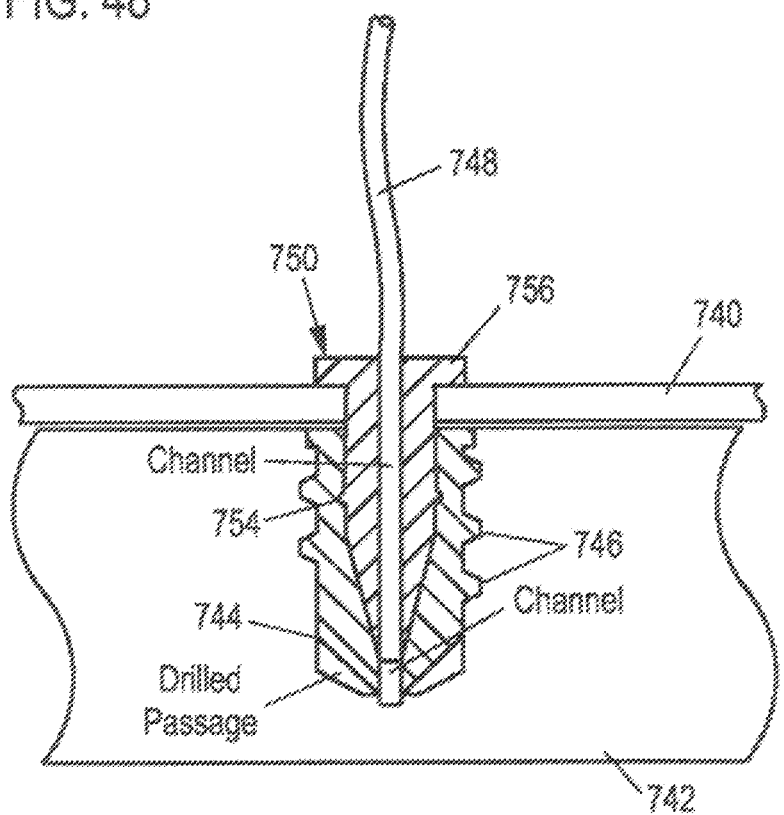
FIG. 49 shows the fixation device of FIG. 45 employed to fasten tissue.

Referring now to FIG. 49, another embodiment of a fixation device of the present invention is employed to secure a first tissue type or implant 740, such as a rotator cuff, to a second tissue type, such as bone 742. Alternatively, a plate 740, such as a bone plate, may be fastened to a fractured bone. Although a plate 740 is shown and described, other implants, such as a mesh, can be used. The anchor 744 is inserted into a drilled passageway in bone 742. In this embodiment, the anchor 744 includes external helical threads 746; therefore, the anchor 744 may be screwed into the bone passageway. It is contemplated that such an anchor 744 having helical threads 746 would also be configured to permit screwing of the anchor 744 into the drilled passageway. For example, a groove may be disposed on the bottom of the anchor bore. The groove may be configured to receive a tool, such as a flat-head type screw driver, for rotating the anchor into the bone; the bore itself may be configured to receive an Allen-type wrench; or the trailing end of the anchor may include a groove(s) to receive a fiat-head or Phillips-head type tool. In one alternative embodiment, there may be no structural feature of the anchor itself for insertion, but rather a tool may be inserted and mechanically expanded within the anchor bore to permit rotation of the anchor into tissue.

Insertion of the anchor 744 into the bone 742 may be further performed with a guide wire 748 or other similar surgical instrument. The wire 748 may be placed in the bone at the desired location for the fixation device. The passageway in the bone may be formed by moving a cannulated drill bit along the guide wire 748. Then the anchor 744 may be slideably disposed over the guide wire 748 in the anchor channel and inserted into the drilled passageway. The cap 750 is also slideably disposed over the guide wire 748 and is moved through the soft tissue, such as the rotator cuff, and into the anchor 744. The distal tip of the cap post 752 may be chamfered to permit the post to penetrate through the soft tissue without significantly damaging the tissue. The cap post 752 may be further aided during insertion through the soft tissue by the use of the distal tip of the guide wire 748 or the distal tip of an energy source, such as the one described in FIG. 48. The post 752 shown in FIG. 49 may include a chamfered leading tip having no blunt surface. A blunt-free tip and the use of a pointed guide wire or pointed energy source may allow the cap to more easily penetrate the soft tissue in stages. That is, first the guide wire 748 or energy source may be used to create a small hole in the soft tissue. Then, the blunt-free, chamfered tip of the post 752 may stretch or widen the hole to a larger diameter without significant tearing of or damage to the soft tissue.

With the cap 750 disposed in the soft tissue, the cap post 752 is inserted into the anchor bore. A mechanical lock 754 may be utilized to hold the cap 750 and anchor 744 together while an energy source is used to weld the cap and anchor together. In this final configuration, the soft tissue is sandwiched between, and preferably is held firmly against the bone by the underside of the cap lid 756.

Figure 50:
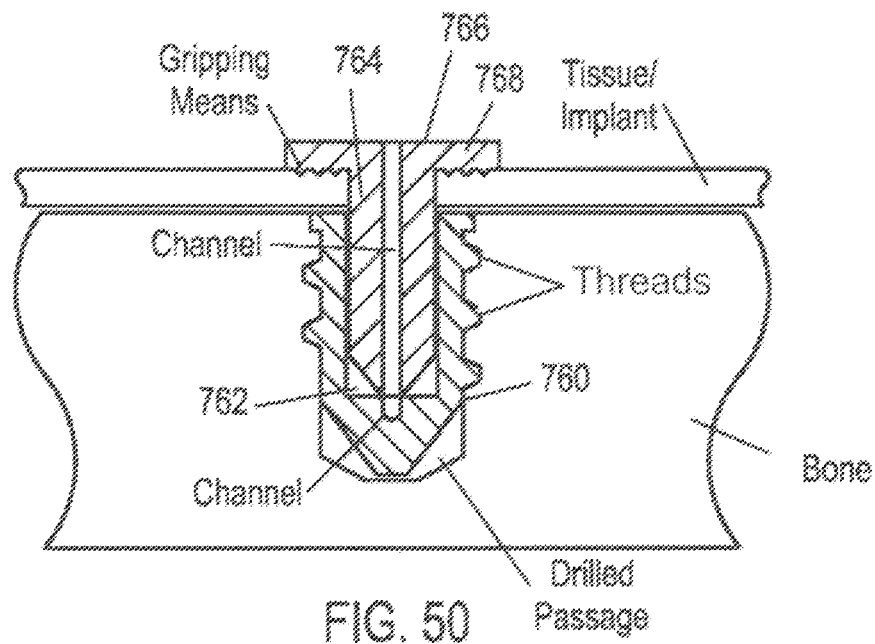
FIG. 50 is a cross-sectional view of another embodiment of a fixation device being free of a mechanical locking means.

FIG. 50 shows another exemplary embodiment or a fixation device. The anchor 760 is similar in construction to the anchor of FIG. 49. However, the anchor bore 762 and the cap post 764 do not have a mechanical lock. Instead, fastening of the cap and anchor is provided by thermal bonding only. Preferably, both the cap 766 and anchor 760 include, or are made of, the same or similar biocompatible polymer so that the two components of the fixation device may be easily welded together. With the cap post 764 being free of any mechanical lock, the cap 766 is able to be positioned anywhere within the bore 762 of the anchor 760. Therefore. if the tissue or implant to be fastened to the bone is thin, the cap 766 may be inserted fairly deeply into the anchor 760 and welded. If the tissue or implant is thick, the same length cap may still be used with the anchor; however, the cap post 764 is just not inserted as far into the anchor bore 762 prior to welding. Alternatively, a plurality of caps having differing length cap posts may also be provided so that the surgeon may select a cap of desired length according to the type of tissue or implant used in the treated area. If two or more caps of differing lengths are provided, the different sizes may be indicated on the caps, such as by molding a size or other indicator onto the cap lid 768.

One notable feature of the embodiment of FIG. 50 and other embodiments described herein is the lack of energy directors required for welding the cap to the anchor. Some prior art fasteners designed for thermal welding require projections disposed between the two parts of the fasteners. Often, these directors take the form of longitudinal ridges disposed on the outer surface of a male fastener section or disposed on the inner surface of a female fastener section. The purpose of the directors is to concentrate the energy thereon to weld the fastener sections together. As seen in FIG. 50, no directors are disposed between the cap and anchor. When an energy source, such as an ultrasonic welder, is placed in the cap 766, substantially all, and preferably the entire exterior surface of the cap that is in contact with the anchor bore may be welded to the anchor. This produces a uniform bond between the cap and anchor. Alternatively, because the cap is cannulated, the distal tip of the energy source may be positioned adjacent the contact location of the distal end of the cap post and the distal end of the anchor bore. This allows the energy source to weld the cap and anchor at that contact location.

As previously mentioned, the cap and anchor of the fixation device may be held together by a mechanical lock, by thermal bonding, or by a combination of mechanical locking and thermal bonding. The embodiment of FIG. 51 includes an example of a fixation device 770 having a permanent type of mechanical lock. With a permanent type of mechanical locking, thermal welding may not be necessary to hold the cap and anchor together because the mechanical lock may provide sufficient holding strength on its own. The anchor 772, as shown, is similar to the anchors previously described. However, in this embodiment, the anchor bore 774 includes helical threads 776 disposed in the wall of the bore 774. The bore threads 776 are configured to receive threads 778 disposed on the exterior surface of the cap post. The cap 780 is insertable within the anchor by screwing the cap post 778 into the anchor bore 774. In addition, to enhance the holding power of the fixation device, the cap 780 and anchor 772 may include a biocompatible polymer which bonds together with the application of energy, such as ultrasonic energy.

Figure 51:
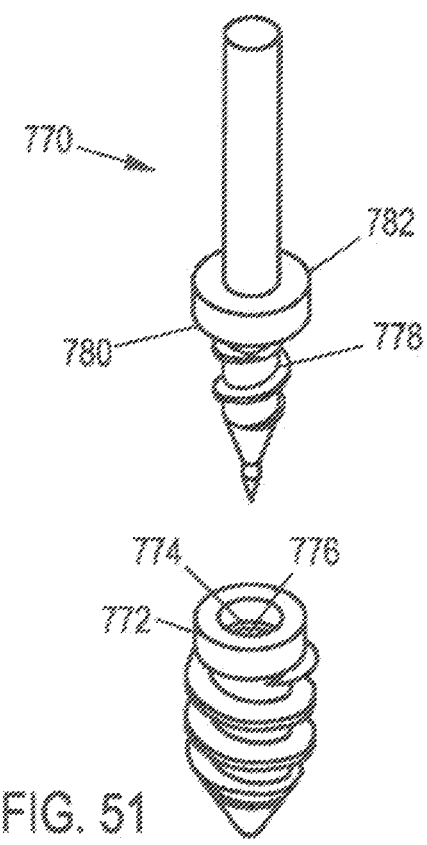
FIG. 51 shows yet another embodiment of a fixation device having a threaded cap.

It is also contemplated that a washer or spacer may be utilized with the fixation device of FIG. 51. The washer may be placed over the cap post 778 and positioned against the bottom side of the cap lid 782. Therefore, as the cap 780 is being screwed into the anchor 772, the washer prevents the spinning cap 782 lid from damaging the tissue. The washer would remain stationary relative to the tissue, while the cap lid 782 would spin against the washer. As illustrated in FIG. 50, the surface of the washer that contacts tissue or an implant may be configured with a plurality of projections that can help grip the tissue or implant material.

Figure 52:
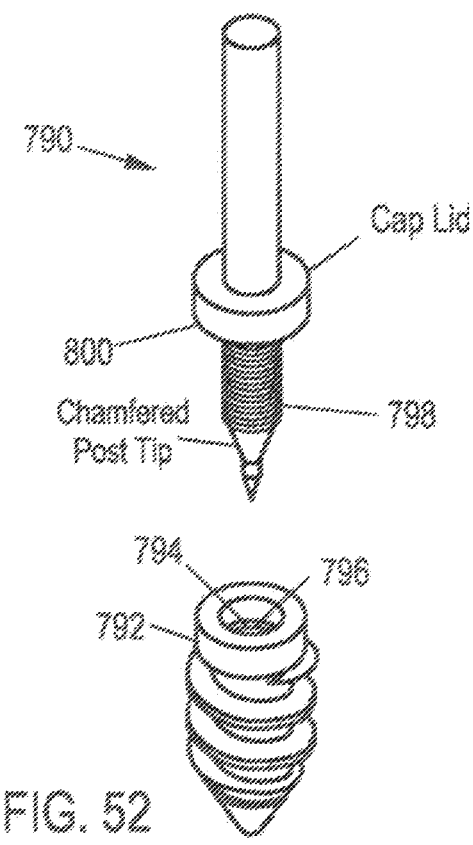
FIG. 52 illustrates a further embodiment of a fixation device having a plurality of post ribs.

Like the embodiment described above, the fixation device 790 of FIG. 52 includes a permanent type of mechanical locking. The anchor 792, as shown, is similar to the anchors previously described; however, the anchor bore 794 includes a plurality of circumferential grooves 796 disposed in the wall of the bore. The bore grooves 796 are configured to receive circumferential ribs 798 disposed on the exterior surface of the cap post. The cap 800 is insertable within the anchor 792 by pushing the cap post into the anchor bore 794. In addition, to enhance the holding power of the fixation device 790, the cap 800 and anchor 792 may include a biocompatible polymer which bonds together with the application of energy, such as ultrasonic energy. The configuration of the mechanical lock of this embodiment may be altered so that the cap post has a plurality of groves or indentations, which the anchor bore has a plurality of projections or ribs.

FIGS. 8 and 9 illustrate yet another embodiment of a fixation device 802 of the invention. The anchor 804 may include a material which is polymeric, hydrophilic, expandable, compressible, or combinations thereof. The anchor 804 may be made of such material or the material may be mixed within or coated on the anchor. For example, the anchor may include, or be made of, a hydrophilic material which expands when it comes in contact with liquid. The hydrophilic material may be desiccated body tissue, foam, or a polymer. A hydrophilic anchor 804 is shown in FIG. 8 in a normal, non-expanded configuration. Body fluid is absorbed by the anchor 804, and it swells to a larger diameter or greater size. The expansion of the anchor results in an interference fit between the anchor 804 and the bone, tissue or material 806 in which it is disposed, thereby providing frictional forces on the outer surface of the anchor to increase its gripping force. Projections 808 may be disposed on the outer surface of the anchor 804 to further increase the frictional forces that hold the expanded anchor in place.

Figure 53:
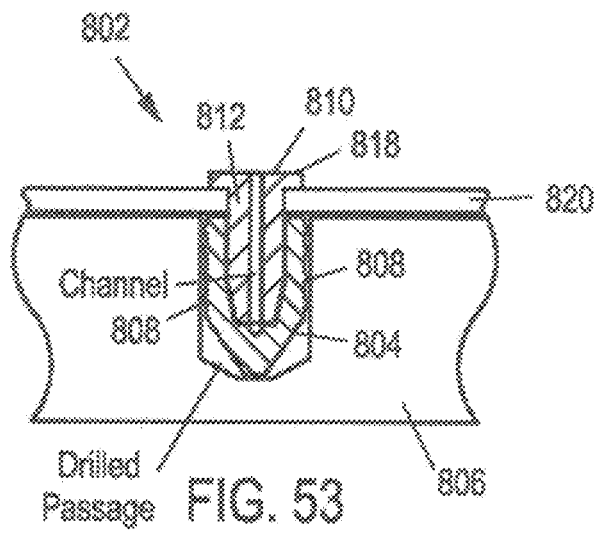
FIG. 53 is a cross-sectional view of another embodiment of a fixation device having an expandable anchor with radially extending projections.
Figure 54:
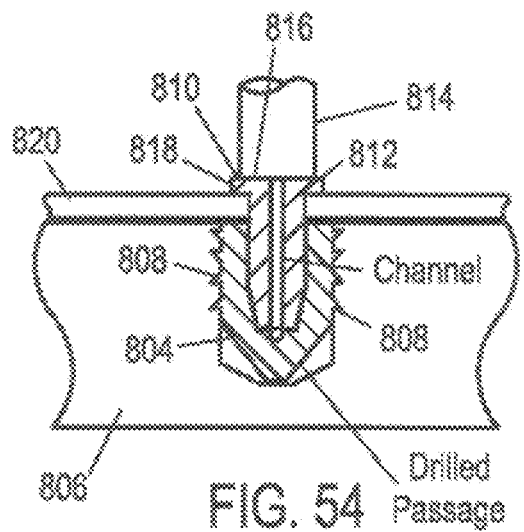
FIG. 54 illustrates the: fixation device of FIG. 53 in an expanded configuration.

In its initial, non-expanded configuration, the anchor 804 and projections 808 may fit within the bore of the anchor. In the expanded or swelled configuration, the projections 808 may be forced into the surrounding tissue to thereby help lock the anchor 804 to the tissue 806. The projections 808 may be small pointed nubs, angled ramps, raised ridges, spikes, circumferential rings, and similar configurations. The projections 808 illustrated in FIGS. 53 and 54 are angled ramps oriented in opposite directions so that the proximal ramps prevent the anchor from being pulled out of the tissue while the distal ramps prevent the anchor from being pushed further into the tissue.

In another example, the anchor 804 may include, or be made of, a compressible-expandable material, such as foam, gel, or a polymer. Prior to insertion of the anchor 804 into the drilled passageway in the tissue, the anchor and projections may be compressed into a smaller diameter or size. The compressed anchor 804 may be positioned in the tissue as shown in FIG. 53 and then allowed to expand to its normal, expanded configuration as seen in FIG. 54.

It should be noted that regardless of whether the anchor includes a hydrophilic material or a compressible-expandable material, the cap 810 may be secured to the anchor 804 by a mechanical lock, by thermal bonding, or by a combination of mechanical locking and thermal bonding. Also, the cap 810 may be secured to the anchor 804 by the expanding feature of the anchor 804. Not only may the anchor expand radially outward to increase overall diameter size, but it may also expand radially inward into the cap post 812 thereby enhancing the locking strength between the cap and anchor. This inward expansion of the anchor 804 against the cap 810 may be the sole means for fastening the cap 810 and anchor 804 or may be utilized in conjunction with mechanical locking or thermal bonding as described herein.

For example, an anchor 804 of the present invention may be made of a material which expands hydrophilically or inherently after compression and which can be thermally welded to a polymer in the cap. The expansion of the anchor 804 locks the anchor to tissue 806 and provides additional holding power of the cap 810 and anchor 804 in conjunction with a thermal weld. As another example, the anchor 804 could have a coating which expands hydrophilically or inherently after compression. The coating may be placed over a polymer material which may not expand but which may be thermally weldable to the cap 810. In this example, the anchor 804 may not expand inwardly against the cap 810; but instead a thermal weld, and if desired a mechanical lock, may be used to secure the cap and anchor.

As best seen in FIG. 54, an energy source is positioned through the cannulated cap 810 and anchor 804. Energy, such as ultrasound, heat, or RF, is transmitted to the fixation device to bond the cap and anchor. The energy source 814 shown in FIG. 54 includes a lid-contacting surface 816. Therefore, because the anchor 804 includes projections 808 to help prevent the anchor 804 from being pushed further into the tissue, a force can be applied to the cap lid 818 through the energy source to thereby firmly squeeze or pinch the tissue or implant 820 between the cap lid 818 and bone 806.

Figure 55:
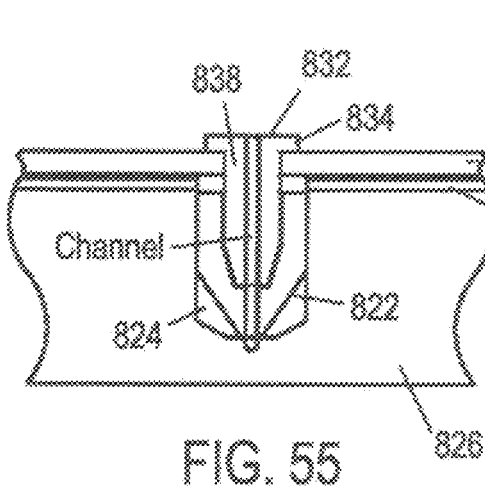
FIG. 55 shows yet another embodiment of a fixation device having an expandable anchor with a substantially smooth exterior, tissue-contacting surface.
Figure 56:
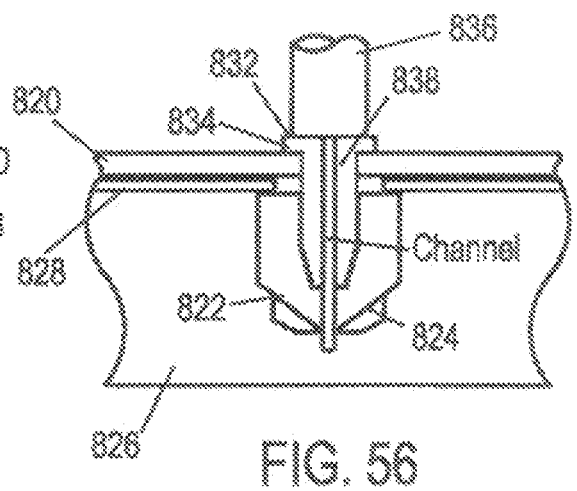
FIG. 56 illustrates the fixation device of FIG. 55 in an expanded configuration.

FIGS. 55 and 56 illustrate an exemplary embodiment of the fixation device having an expandable anchor 822 without projections disposed on the outer surface of the anchor. Instead, the anchor 822 has a substantially smooth exterior surface and a non-expanded diameter which is equal to or slightly less than the diameter of the drilled passageway 824 in the bone 826. As seen in FIG. 55, the anchor 822 in its non-expanded configuration is inserted into the bone 826 such that the trailing end or proximal end of the anchor 822 is positioned at or slightly distal to the bottom surface of the cortical bone 828. In this orientation, the anchor 822 can expand into the cancellous bone 826, and the trailing end of the expanded anchor 822 will be adjacent to the underside of the cortical bone 828. In FIG. 56, an overlap region 830 is shown where the expanded anchor 822 and cortical bone 828 overlap each other. With the anchor 822 expanded and orientated in this way, the anchor 822 is held firmly in the bone thereby preventing the anchor from being pulled out.

To secure the cap 832 to the lid 834, an energy source 836 may be positioned through the cannulated cap and anchor. Energy, such as ultrasound, heat, or RF, may be transmitted to the fixation device to bond the cap 832 and anchor 822 when the fixation device includes a thermally bondable material. Alternatively, or additionally, the exterior surface of the cap post 838 and the inside wall of the anchor bore may include a mechanical lock. Alternatively, or additionally, the anchor may expand inwardly to hold the cap relative to the anchor.

FIGS. 57A-57D illustrate an exemplary method of implanting the fixation device to secure tissue to bone. Shown in FIG. 57A, an anchor 840 is inserted into a drilled passage 842 in a bone, tissue, or implant 844. The anchor 840 includes helical threads 846 to form a mechanical lock between the anchor 840 and bone, tissue, or implant 844. To further stabilize the anchor 840, at least a portion of the anchor 840 may be expanded within the bone passage. The tissue 848 may be speared with a cap post 850 and an insertion instrument 852 which may be disposed in the cannulated cap. As previously described, the insertion instrument 852 or guide wire may have a pointed distal tip which helps create a small hole in the tissue. Because the cap post 850 includes a chamfered distal portion, the insertion of the cap post 850 through the tissue 848 stretches the small hole created by the insertion tool and presents undesired excessive tearing of the tissue 848.

Figure 57A:
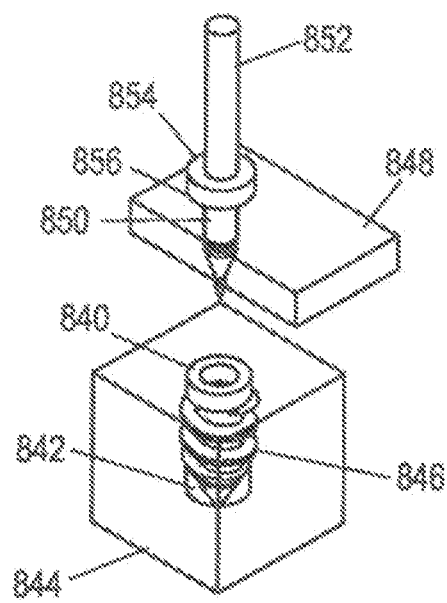
FIG. 57A-D arc perspective views illustrating the steps of deploying the fixation device of the present invention.
Figure 57B:
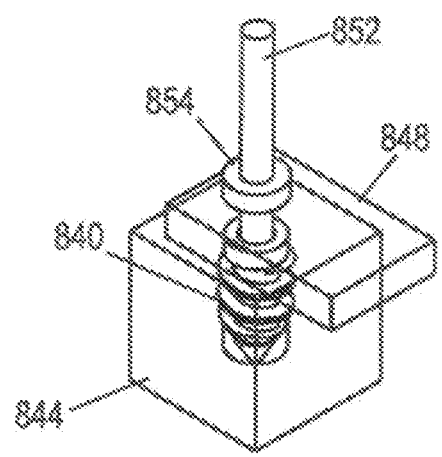

In FIG. 57B, the cannulated cap 854 and insertion instrument 852 are aligned with the anchor 840, and the cap post 850 is inserted into the anchor bore. The insertion tool 852 is pushed distally to squeeze the tissue 848 between the cap lid 856 and anchor/bone. The cap post 850 may be inserted partially into the anchor bore if thick tissue is being fastened, or the cap post 850 may be inserted further toward the bottom of the anchor bore when a thin piece of tissue 848 is being fastened. In the latter configuration, the anchor 810 may include a channel extending between the distal tip and the bottom of the bore to accommodate the pointed distal tip of the insertion instrument 852. Regardless of the depth of insertion of the cap 854 into the anchor 840, a mechanical lock may be engaged to temporarily or permanently secure the cap 854 to the anchor 840.

Precise depth placement of the cap in the anchor may be required for certain applications. For example, in rotator cuff repair, the typical thickness of a healthy rotator cuff is 5 to 10 mm. Therefore, to provide a secure fixation of the rotator cuff to the bone, a gap between the lid and anchor/bone may be about 2 to 3 mm. To obtain a consistent gap, the anchor depth adjustment on the insertion instrument could be manually set. The instrument could have gradations that correspond to the depth of the anchor's top surface into the bone. Also, the depth that the cap may be inserted may be controlled with the insertion tool by adjusting the spacing of the end effector and sheath covering the end effector. The sheath may be marked with indicia or have a window through which the cap can be seen. Furthermore, the cap itself may have a mechanical stop preventing the cap from progressing too deep into the anchor. The mechanical stop may be a stepped post shaft.

Moreover, the use of a mechanical lock, such as circumferential ribs and corresponding grooves may be strategically placed on the fixation device such that each locking or snapping of a rib in a groove represents a known distance the cap has traveled in the anchor. By knowing the distance the cap has been inserted in the anchor, the gap distance can be determined. The desired gap distance may also be preset into the energy source generator and controlled with closed loop feedback by a position sensor such as an LVDT. This could measure the amount the cap melts into the anchor by stopping the energy when the desired gap is achieved. Finally, for a mechanical locking cap, the cap insertion instrument may include markings denoting depth of insertion.

Figure 57C:
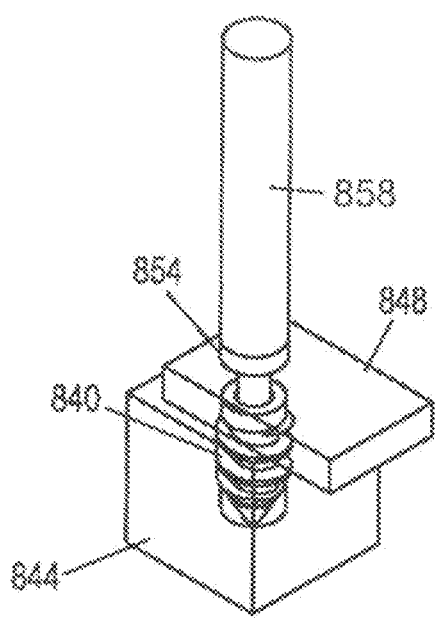
Figure 57D:
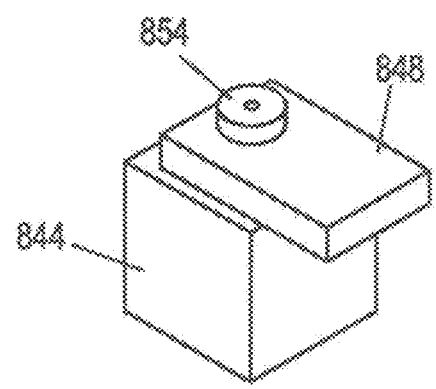

The cap insertion tool 852 is removed in FIG. 57C and an energy source 858 is inserted into the cannulated cap 854 and anchor 840. Energy is applied to the fixation device to thermally bond the cap and anchor together. Thermal bonding may be in addition to mechanical locking or may be the sole means for bonding the cap and anchor. FIG. 57D illustrates the fixation device completely implanted. The tissue 848 is held firmly relative to the bone 844. A portion of the tissue between the cap lid 856 and the anchor 840 and bone 844 is being compressed.

Figure 58:
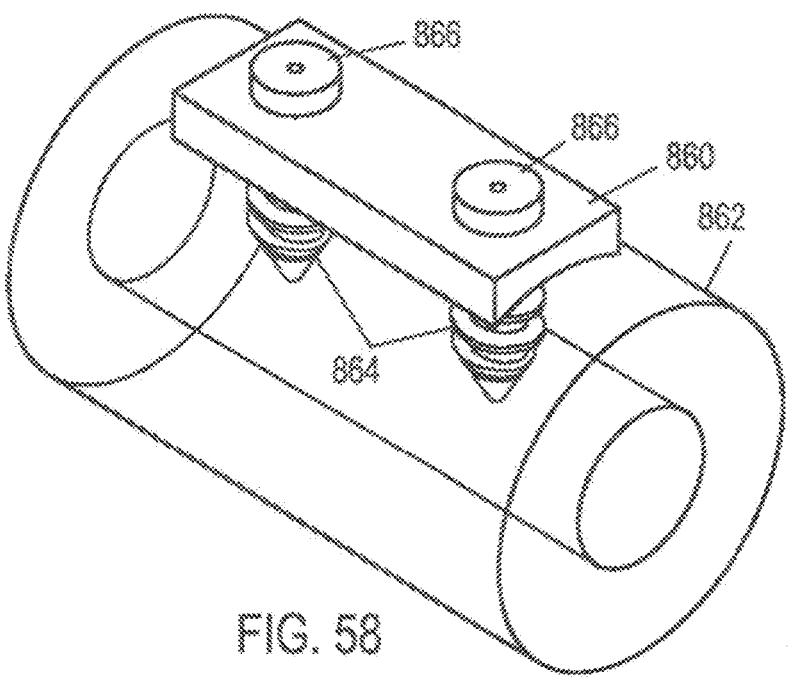
FIG. 58 illustrates a use of a fixation device to stabilize a fractured bone.

Referring now to FIG. 58, two types of fixation devices of the present invention are shown with a bone plate 860 to stabilize a fractured bone 862. White the following example depicting a use of the present invention involves only two devices and a plate, it is contemplated that two or more fixation devices may be employed. Also, instead of a bone plate 860, a tissue graft such as a bone graft may be secured to a bone. As shown in FIG. 58, two anchors 864 are inserted into the bone 862. A bone plate 860 is positioned adjacent the bone 862 with two holes in the plate aligning with the two anchors 864. A cap 866 is then inserted through the bone plate 860 and into the each of the anchors 864. The caps 866 may be secured to the anchors 864 by mechanical locks, by thermal bonding, by expansion, or by combinations thereof.

The design of the post of the cannulated cap permits the use of a bone plate 860 which does not require pre-formed fastening holes. Such a plate may be made from a polymeric material that is strong enough to stabilize the bone, yet can still be penetrated by the distal tip of the insertion tool and chamfered distal portion of the cap post. In this embodiment, the location of the drilled passageways in the bone for placement of the anchors does not need to be aligned with pre-existing holes in the plate, giving the physician greater discretion as to the placement of the fixation devices.

Figure 59:
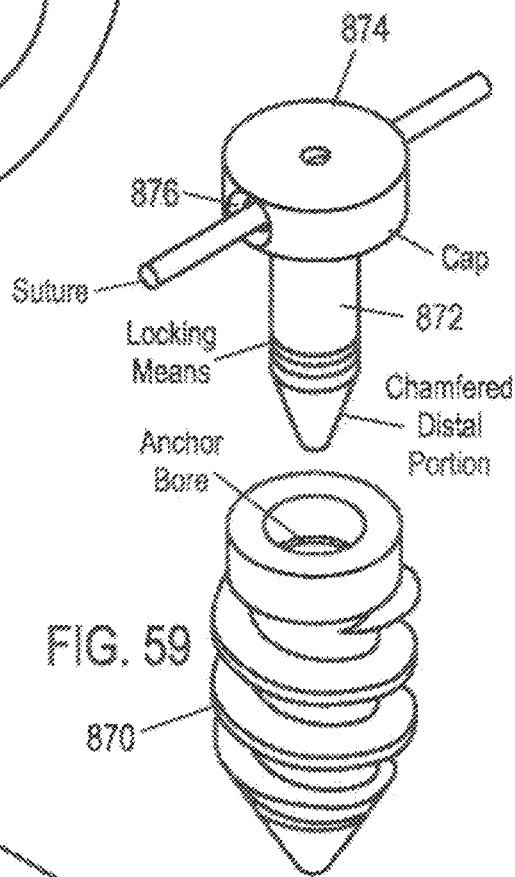
FIG. 59 shows another embodiment of a fixation device having a suture positioned therethrough.

Another embodiment of the present invention is illustrated in FIG. 59. The anchor 870 and cap post 872 of this embodiment may utilize any of the various structural features described herein. The anchor 870 and cap post 872 may be secured together mechanically, thermally, through expansion, or combinations thereof. The cap lid 874 includes a lumen 876 extending radially therethrough. The lumen 876 may be generally perpendicular to and extend through the longitudinal axis of the cap. The lumen 876 may be dimensioned to receive a portion of a suture, K-wire, cable, or similar fastening member. The suture when placed through the lumen of the lid provides for a secondary fixation of tissue and/or an implant. For example, the cap may be inserted into the anchor 870 to secure a bone plate to a bone. For additional reinforcement, a suture may be positioned through the lumen 876 of the lid, wrapped around the bone and plate, and secured.

Figure 60:
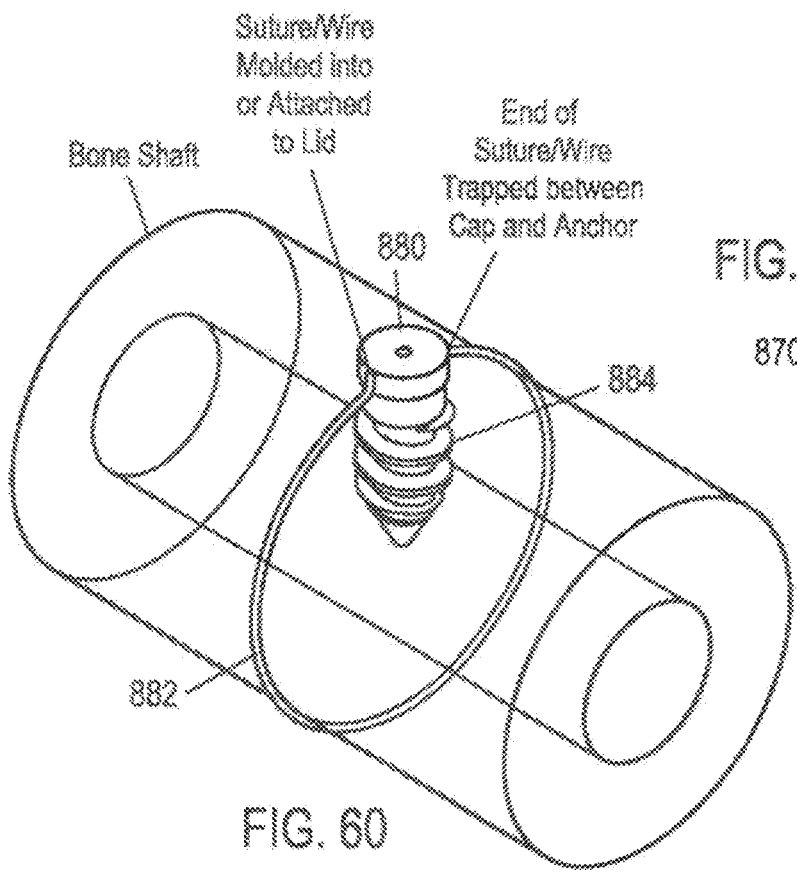
FIG. 60 is a perspective view illustrating an embodiment of the fixation device having an integrated suture therein.

FIG. 60 shows yet another embodiment of the fixation device of the present invention. Unlike a cap lid having a lumen for the passage of a suture as described above for FIG. 59, the cap lid 880 of FIG. 60 includes a suture or wire 882 molded into or attached to the lid 880. The suture 882 may be connected on a side surface or the top surface of the lid. The suture 882 extends from the lid 880 and is positionable about tissue and/or an implant. A portion of suture is also positionable between the underside of the lid 880 and the upper surface of the anchor 884. In this configuration, an anchor 884 may be inserted into tissue and the cap 880 is then positioned in the anchor bore but not yet welded to the anchor. A portion of the suture 882 may be sandwiched between the cap lid 880 and anchor 884, then the cap is secured to the anchor either mechanically, thermally, via expansion, or combinations thereof. As seen in FIG. 60, the suture 882 may extends from one side of the cap, can be looped around tissue or an implant, and may be returned generally to the opposite side of the cap 880 to be pinched and secured to the fixation device.

Figure 61:
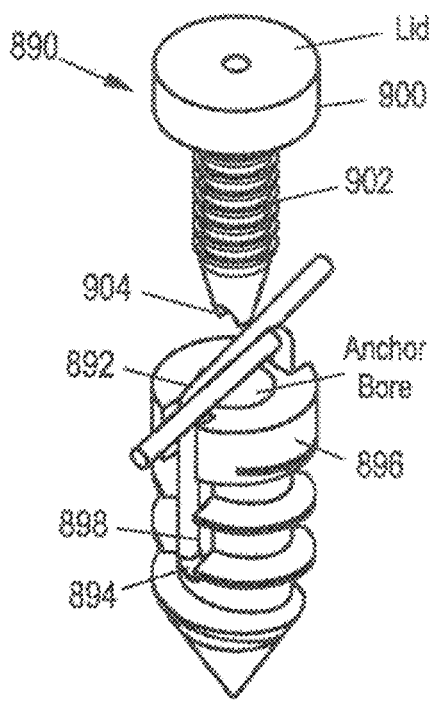
FIG. 61 shows yet another embodiment having a suture positioned in a channel and groove of the anchor.

FIG. 61 depicts another embodiment of a fixation device 890 with a suture 892. A lumen 894 extends radially through the anchor 896 at a location intermediate between the leading and trailing ends of the anchor. The lumen 894 may extend perpendicular to and through the central longitudinal axis of the anchor 896. A groove 898 disposed in the threads or outer surface of the anchor 896 runs generally parallel to the longitudinal axis of the anchor and extends from one end of the lumen 894 to the trailing or proximal end of the anchor 896. Another groove 898 disposed in the threads of the anchor also runs generally parallel to the long axis of the anchor but extends from the other end of the lumen 894 to the proximal end of the anchor 896. A suture 892 is positionable within the lumen 894 and grooves 898 of the anchor 896. The cap 900 of the fixation device 890 may be similar to the cap described in FIG. 52 which has a plurality of circumferential ridges disposed on the post. The anchor bore may have a plurality of corresponding circumferential grooves disposed in the wall of the bore. The cap post 902 has the additional feature of a cut-out or notch 904 located at the distal tip. The notch 904 is dimensioned to receive one or more sections of suture.

In use, a suture 892 is positioned through the radially extending lumen 894 and grooves 898 in the anchor 896. The anchor 896 is then inserted in tissue such that two sections of the suture 892 extend from the anchor/tissue. The suture sections are secured to or around tissue or an implant such that a portion of one or both suture segments is positioned over the proximal opening of the anchor bore. The cap 900 is aligned with the anchor bore, and the notch of the cap 904 is placed about one or both of the suture segments 892. The cap 900 is moved into the anchor bore while maintaining the suture segment(s) in the notch 904 of the post. When fully seated, the circumferential ridges of the post mate with the circumferential grooves of the anchor bore, and one or both suture segments are pinched/held between the cap post and the outer wall of the anchor bore.

Figure 62:
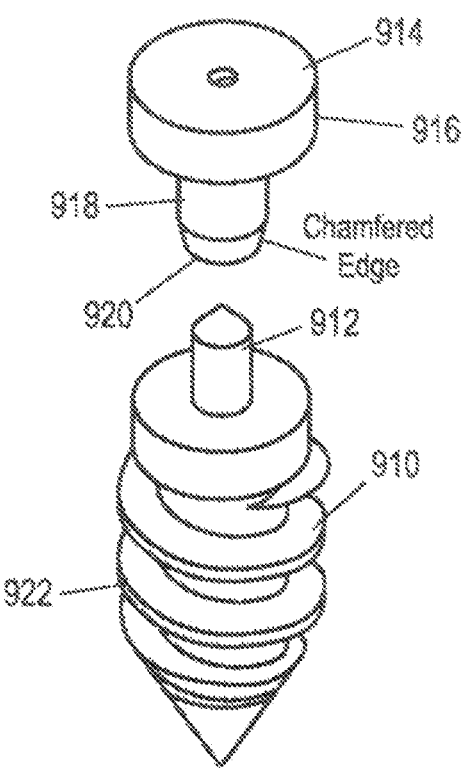
FIG. 62 illustrates a different embodiment of the fixation device in which the anchor has a post and the cap has a post bore.

In FIG. 62, another exemplary embodiment of the present invention is illustrated. The anchor 910 in this embodiment includes a post 912 extending from the proximal or trailing edge of the anchor. The post 912 may include a pointed proximal tip to permit the post to penetrate through and/or extend beyond tissue or an implant. Preferably, the proximal tip does not include a blunt end so that the tissue or implant is not necessarily worn or damaged. The cap 914 includes a lid 916 and post 918 like previous embodiments. However, in this embodiment, the post 918 includes a bore 920 which is configured to receive the anchor post 912. The cap post 918 may include a chamfered leading edge for easy penetration of the cap post through tissue or an implant. The cap 914 and anchor 910 may be cannulated to allow insertion of a guide wire or an energy source.

The fixation device of FIG. 62 may be used for the fixation of tissue or an implant as follows. The anchor 910 is inserted in tissue, such as bone, with the anchor post 912 extending from the bone. The anchor 910 may include external helical threads 922 which permit the anchor 910 to be screwed into the bone. Additionally, or alternatively, the anchor 910 may be held in the bone via expansion of the anchor. Tissue or an implant is aligned over the anchor and pressed over the anchor post 912. The cap 914 of the device holds the tissue to the bone by placing the cap post bore 920 over and about the anchor post 912. The cap 914 and anchor 910 may be secured to each other by mechanical means, thermal bonding, via expansion, or combinations thereof. It is further contemplated that implantation of the device may be performed over a guide wire positioned in the cannulated cap and anchor.

Figure 63A:
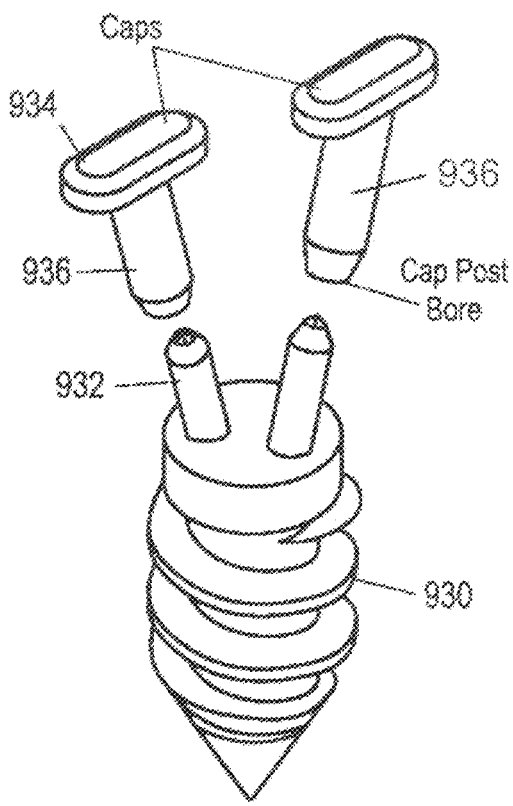
FIGS. 63A and 63B show a fixation device having a plurality of caps connectable to a plurality of anchor posts.
Figure 63B:
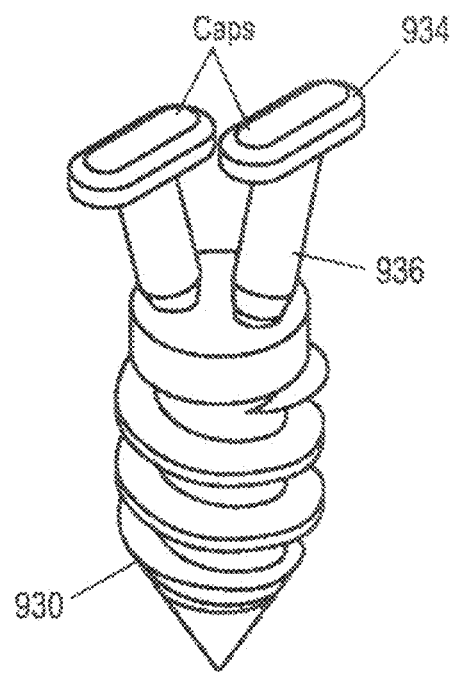

Referring to the embodiment shown in FIGS. 63A and 63B, the anchor 930 includes two posts 932. The anchor 930, if desired, may include two or more posts 932. The posts may be parallel to or at an angle to the longitudinal axis of the anchor. In FIG. 63A, the two posts 932 are angled away from each other. In this configuration the fixation device may provide an enhanced stabilization and fixation of tissue or an implant. The cap lid 934 may be designed to remain generally parallel to the top surface of the anchor 930, or they can remain perpendicular to the cap post 936 and be at an angle relative to the top surface of the anchor 930. The method of implanting the embodiment of FIGS. 63A-B is similar to the implantation of the fixation device of FIG. 62. However, multiple caps are inserted onto the multiple anchor posts by way of mechanical locks, thermal bonding, anchor expansion, or combinations thereof.

Figure 64A:
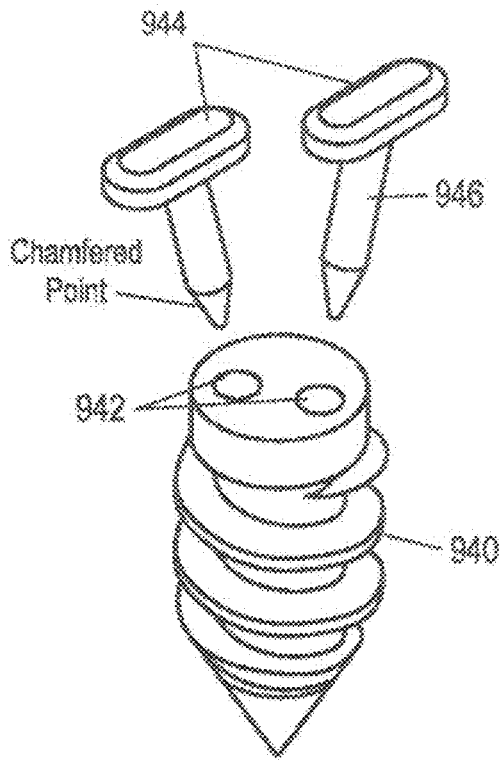
FIGS. 64A and 64B illustrate an embodiment having an anchor with a plurality of bores in which a plurality of cap posts is positionable.
Figure 64B:
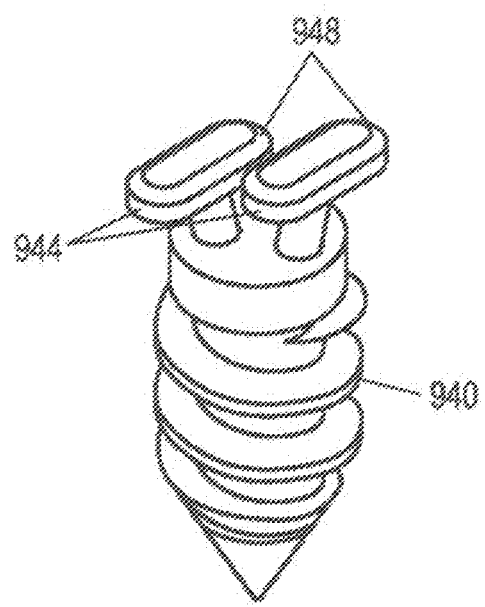

As shown in FIGS. 64A and 64B, another exemplary embodiment includes an anchor 940 having two bores 942. The anchor 940, if desired, may include two or more bores. The bores 942 may be parallel to, at an angle to, and/or offset from the longitudinal axis of the anchor 940. The cap 944 includes a post 946 connected with a lid 948. The cap post 946 is configured for insertion into one of the bores 942 of the anchor 940. The distal tip of the cap post is pointed for penetration through tissue or an implant. The cap lid 948 may be designed to remain generally parallel to the top surface of the anchor, or it can remain perpendicular to the cap post and be at an angle relative to the top surface of the anchor. The method or implanting the embodiment of FIGS. 64A-B is similar to the implantation of the fixation device of FIGS. 63A-B. However, multiple cap posts that penetrate the tissue or implant, are positioned in the anchor bores, and are secured to the anchor by way of mechanical locking, thermal bonding, anchor expansion, or combinations thereof.

Figure 65A:
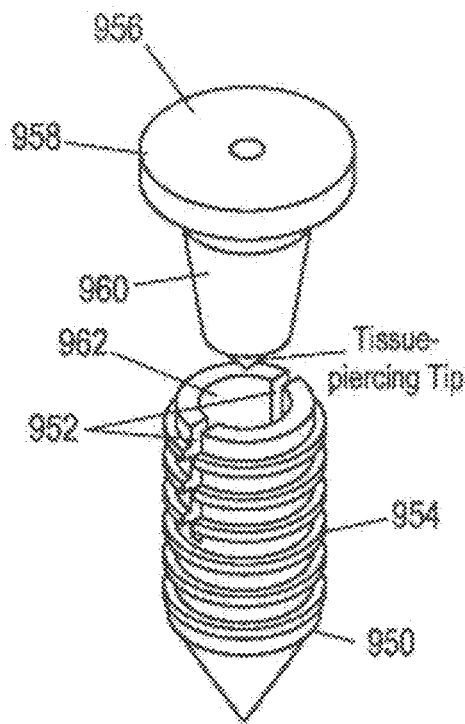
FIGS. 65A and 65B are perspective views of another embodiment of a fixation device having an anchor with friction ribs and slots.
Figure 65B:
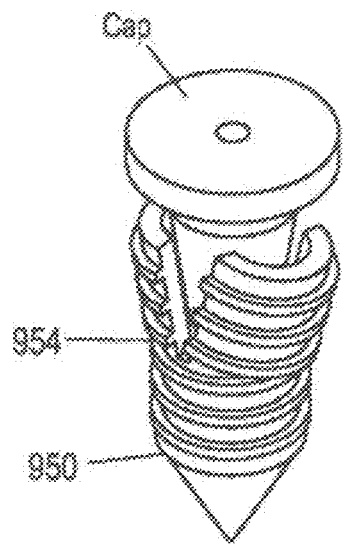

Referring to FIG. 65A, another exemplary fixation device is illustrated. The anchor 950 includes two slots 952 disposed in the wall of the anchor. The slots 952 extend from the trailing end of the anchor to an intermediate area between the trailing and leading ends of the anchor 950. The slots 952 extend completely through the anchor wall. The exterior surface of the anchor includes protrusions 954 that increase the frictional forces between the anchor and the engaging tissue. Any configuration or structure described herein may be used to increase the frictional forces. As illustrated in FIG. 65A-B, the protrusions 954 may comprise a plurality of circumferential ribs. The cap 956 of the fixation device includes a lid 958 and post 960. The cap post 960 is connected with the lid 958 and tapers in diameter as the post extends from the lid 960. The distal tip of the cap post 960 includes a chamfered point for piercing and stretching tissue.

In use, the anchor 950 is inserted in tissue such as bone or in an implant material. The anchor 950 may be inserted in a pre-drilled passageway in the bone or may be include a self-tapping tip and not require a pre-drilled hole. Tissue or an implant may be positioned over the anchor 950, and the cap 956 can be inserted into the anchor bore 962 through the tissue or implant. As seen in FIG. 65B, the cap post 960 is inserted into the bore of the anchor. Because the cap post 960 is tapered, as it is pushed into the anchor bore 962, portions of the anchor 950 are separated as the slots bias outward. In this configuration, the anchor is locked into the bone with the circumferential ribs and by the outwardly biased anchor portions. If movement of the anchor wall is restricted by bone, tissue, or an implant, then the resistive forces may instead be increased at insertion of the cap post 960 imparts outward pressure on the anchor walls. The cap and anchor may be bonded together by mechanically locking, thermal bonding, via expansion, or combinations thereof. The cap 956 and anchor 950 may be cannulated to receive a guide wire, insertion tool, and/or energy source.

Figure 66:
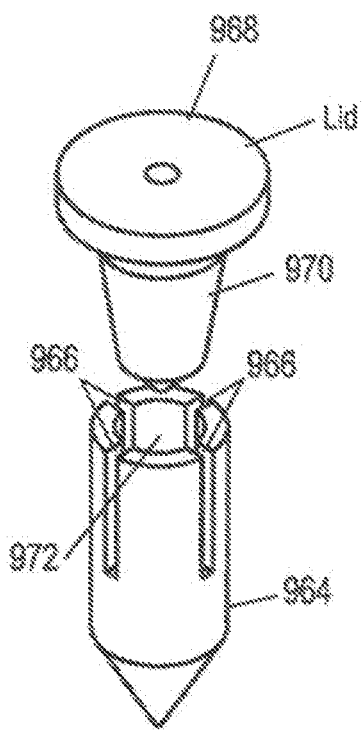
FIG. 66 shows a fixation device having an anchor with a substantially smooth outer surface and a plurality of slots disposed in the anchor wall.

In FIG. 66, an embodiment similar to FIGS. 65A-B is shown, except the exterior surface of the anchor 964 is substantially smooth. The anchor 964 also includes two or more slots 966 disposed in the anchor wall. It is contemplated that the anchor may include two, three, four, five, six, or more slots. In use, the anchor 964 is inserted in bone such that the trailing or proximal end of the anchor is positioned just under the bottom surface of cortical bone. The cap 968 is inserted through tissue or an implant. The tapered cap post 970 is moved distally into the anchor bore 972 forcing the anchor segments separated by the slots to outwardly bias. The biased anchor segments penetrate into the surrounding cancellous bone, and the proximal ends of the anchor segments overlap the cortical bone. In this configuration the anchor is prevented from being pulled out of the bone since the proximal ends of the anchor segments come in contact with the underside of the cortical bone. The cap and anchor may be bonded together by mechanical locking, thermal bonding, via expansion, or combinations thereof. The cap and anchor may be cannulated to receive a guide wire, insertion tool, and/or energy source.

Figure 67:
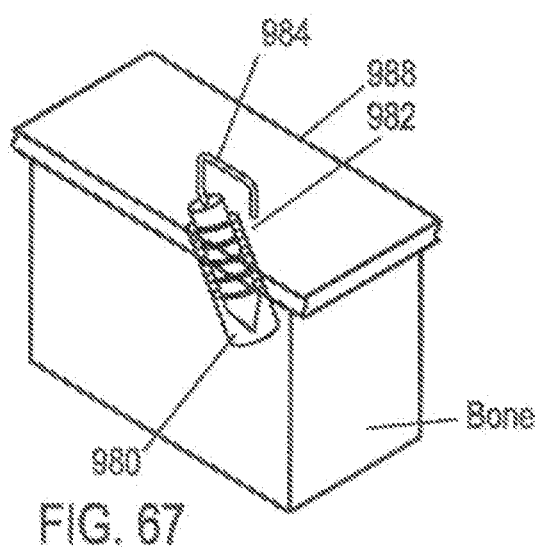
FIG. 67 is a perspective view of a triangulation fixation device.
Figure 68:
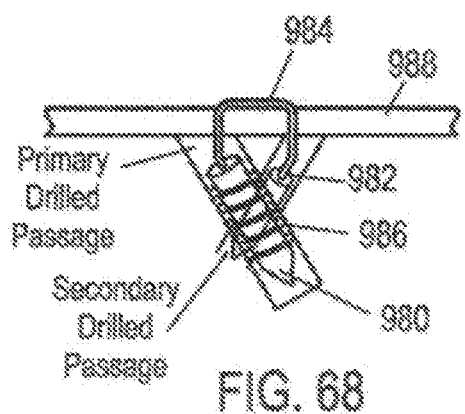
FIG. 68 is a side view of the triangulation device of FIG. 67.

Referring to FIGS. 67 and 68, a triangulation fixation device includes two anchors 980, 982 with a suture, cable, or band 984 attached to the anchors. A primary anchor 980 is generally cylindrical in shape and includes a channel extending therethrough at an angle to the central longitudinal axis of the anchor. The channel is configured for receiving a secondary anchor 982. The secondary anchor 982 includes a tissue-piercing and tissue-stretching leading tip. The anchors may be cannulated to allow insertion of a guide wire, insertion tool, and/or energy source. The band 984 is connected to both the primary and secondary anchors 980, 982. The band 984 may be pivotably or rotatably attached to the anchors so that the anchors can be inserted in tissue without the band being twisted or tangled.

To implant the triangulation fixation device, a primary passageway is drilled in tissue such as bone. The diameter, depth, and angle of the primary passageway are predetermined based on the configuration of the primary anchor 980. A secondary passageway is drilled in the bone which intersects the first passageway. The diameter, depth, and angle of the secondary passageway are predetermined based on the configuration of the primary and secondary anchors 980, 982. The primary anchor 980 is first inserted into the primary passageway. The primary anchor 980 may be secured within the passageway by helical threads 986, by expansion, or by other suitable means disclosed herein. The secondary anchor 982 is moved through tissue with the leading tip and positioned in the secondary passage. The secondary anchor 982 is inserted into the channel of the primary anchor 980 and fastened to the primary anchor 980 by a mechanical lock, thermal bonding, expansion, or combinations thereof. Locking the anchors together tensions the band interconnected between the anchors thereby fastening the tissue 988 to the bone.

Figure 69:
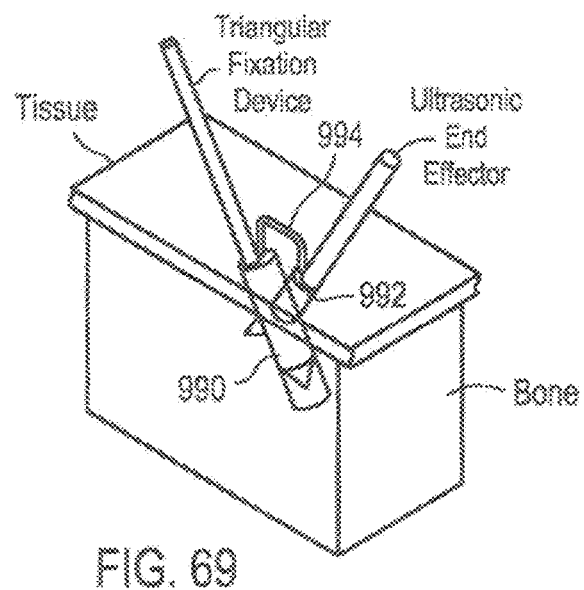
FIG. 69 is a perspective view of another embodiment of a triangulation fixation device.
Figure 70:
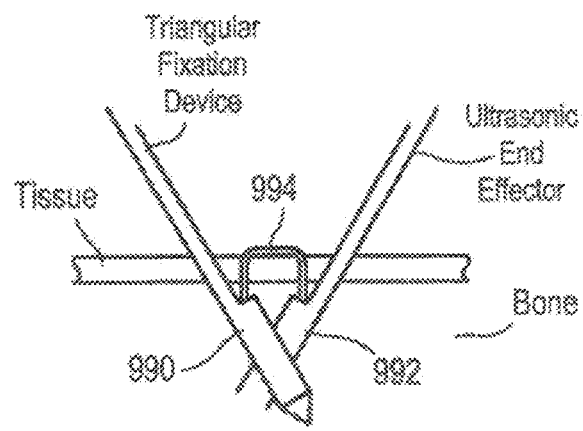
FIG. 70 is a side view of the triangulation device of FIG. 69.

Another embodiment of a triangulation fixation device is shown in FIGS. 69 and 70. This embodiment is similar to the one previously described except the anchors 990, 992 do not have threads disposed on their outer surfaces, i.e., the anchors have smooth sides. A suture, band, or other flexible material 994 is disposed between the primary and secondary anchors 990, 992. The suture 994 may be attached to the trailing end or the side of each anchor 990, 992. The primary anchor 990 is generally cylindrical in shape and includes a pocket or receptacle therein at an angle to the central longitudinal axis of the anchor. The pocket or receptacle is configured for receiving a distal portion of the secondary anchor 992. The secondary anchor includes a tissue-piercing and tissue-stretching leading tip. The chamfered leading portion of the secondary anchor may 992 also act as a conical energy director to assist in thermal bonding. The anchors may be cannulated to allow insertion of a guide wire, insertion tool, and/or energy source. The cannulas in the anchors may be congruent to the longitudinal axis of the anchors or offset from the long axis of the anchors so as to not interfere with the suture or band 994.

To implant the triangulation fixation device of FIGS. 69 and 70, a primary passageway is drilled in tissue such as bone. The diameter, depth, and angle of the primary passageway are predetermined based on the configuration of the primary anchor 990. A secondary passageway is drilled in the bone which intersects the first passageway. The diameter, depth, and angle of the secondary passageway are predetermined based on the configuration of the primary and secondary anchors 990, 992. The primary anchor 990 is inserted into the primary passageway, and then the secondary anchor 992 is moved through tissue with the leading tip and positioned in the secondary passage. Insertion of the anchors may be performed with a suitable insertion instrument. The secondary anchor 992 is inserted into the pocket or receptacle of the primary anchor and fastened to the primary anchor by a mechanical locking, thermal bonding, expansion, or combinations thereof. As shown, an ultrasonic end effector may be used to bond the anchors together. Locking the primary and secondary anchors together helps prevent the anchors from being pulled out of the bone.

The triangulation fixation devices described above included a primary anchor having a channel, pocket or receptacle in which the secondary anchor is positioned and secured. It is also contemplated that the anchors may be attached to each other by way of hooks, loops, latches, or similar mechanical means. For example, one anchor may have a hook on its distal end while the other anchor may have a hook or loop at its distal end. The anchors may be positioned in their respective drilled passageways in bone and are connected to each other with the hook/loop combination. In another example, the primary anchor may have a hook/loop at its midsection while the secondary anchor may have a hook/loop at its distal end. The primary and secondary anchors may be secured together by such a mechanical means.

The suture or band of the triangulation fixation device may be tensioned to provide fixation of tissue and/or an implant. An energy source may be used to shrink the suture or band to an appropriate tension or length. The energy source may be one previously described. Alternatively, or additionally, the band (or anchors) may include shape memory material, such as Nitinol®. As this material is heated with a thermal probe or with natural body heat, the device could flex or bend to self-tighten or lock in tissue.

Figure 71:
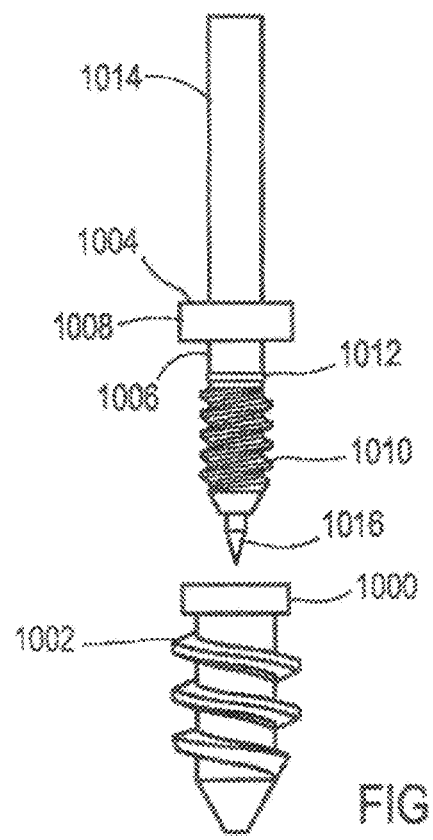
FIG. 71 is another exemplary embodiment of a fixation device having helical threads and a retaining ring disposed on the cap post.

Referring now to FIG. 71, another embodiment of a fixation device is illustrated. The anchor 1000 may have helical threads 1002 disposed on its outer surface for holding the anchor in tissue, such as bone. The cap 1004 includes a post 1006 attached to a lid 1008. Helical threads 1010 are disposed on the exterior surface of the cap post 1006. The threads on the cap post and anchor may be the same or different size. Also, the threads on the cap post and anchor may both be right-handed threads or may both be left-handed threads. Furthermore, the threads on one may be right-handed, while the threads on the other may be left-handed. The cap also includes a snap ring 1012 that allows the cap 1004 to be locked into the anchor 1000 preventing it from coming out after being screwed into the anchor bore. The snap ring 1012 on the cap post 1006 mates with a groove in the wall of the anchor bore. As shown in FIG. 71, the snap ring 1012 may be a circumferential ring that is tapered at its leading portion and has a shoulder at its trailing portion. The snap ring 1012 may extend partially around or entirely around the cap post 1006. The groove in the anchor bore may have a corresponding configuration to receive the snap ring. The tapered leading portion of the snap ring 1012 allows the ring to snap into the groove, and the shoulder prevents the ring (and cap) from being pulled out of the anchor.

The cap 1004 and anchor 1000 may be cannulated to receive a guide wire, an insertion instrument, and/or an energy source. As illustrated, an insertion tool is disposed in the cannulated cap. The insertion tool 1014 may include a piercing tip 1016 for penetration through tissue. The insertion tool 1014 may also include a mating means for temporarily connecting the tool and the cap. Examples of mating means between the insertion tool and cap may include a flat-shaped, square-shaped, rectangular-shaped, hexagonal-shaped, or octagonal-shaped projection and a corresponding socket.

Figure 72:
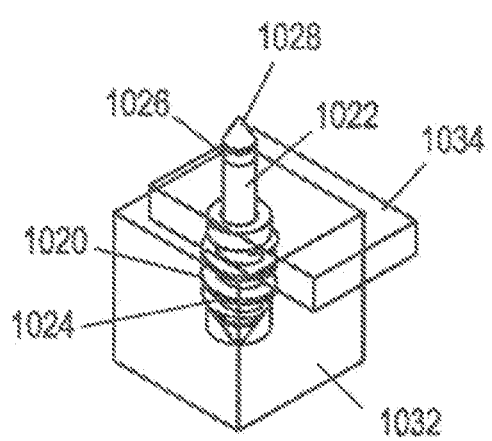
FIG. 72 is a perspective view of a further embodiment of a fixation device having an anchor post and a tissue piercing pin.

FIG. 72 illustrates another exemplary embodiment of a fixation device utilizing features of the invention. The device includes an anchor 1020 having a post 1022 connected with a body 1024. The anchor body 1024 may include means for securing the anchor body to the bone, such as helical threads, expansion, or other suitable means. The anchor post 1022 is generally cylindrical and has a bore extending therethrough, at least through the proximal end of the post. The anchor post 1022 may include a retaining ring or snap ring 1026 disposed on the outer surface of the anchor post. The retaining ring 1026 may be a circumferential projection or rib. The device further includes a tissue-piercing pin 1028 which may be insertable and removable from the anchor post bore. The pin 1028 may have a distal portion configured for insertion into the bore of the anchor post 1022. The proximal portion of the pin may be generally conical and have a point at the proximal tip. The tip and conical shape are designed to pierce and stretch tissue. The pin 1028 may be made of or include a metallic, composite, ceramic, or polymeric material. In FIG. 72, the pin 1028 shown is made of stainless steel. The device also includes a cap 1030 being generally disk shaped. The cap 1030 includes an orifice disposed therethrough which is dimensioned to receive the anchor post 1022. The orifice has a diameter which is equal to or slightly greater than the diameter of the anchor post. However, the orifice diameter is not greater than the diameter of the retaining ring on the anchor post.

Figure 73:
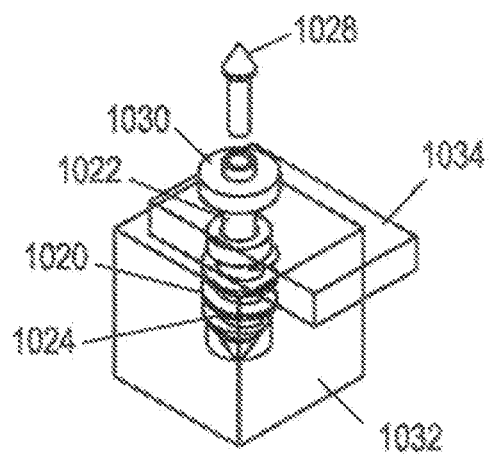
FIG. 73 illustrates the device of FIG. 72 in use

As illustrated in FIG. 73, the anchor is inserted in tissue 1032, such as bone. A passageway may be drilled in the bone and the anchor body inserted therein. Or, the anchor 1020 may be self-tapping and therefore not require a pre-drilled passageway. The anchor 1020 may be secured to the bone 1032 by mechanical means such as threads, expansion, or similar means. With the anchor post 1022 extending from the bone, the pin is placed in the anchor bore. Tissue 1034, such a rotator cuff, or an implant, such as a bone plate, may be positioned over the anchor above the pin. The tissue or implant 1034 is moved toward the bone such that the pointed and chamfered end of the pin pierces the tissue/implant and the anchor post penetrates through the tissue/implant. The pin may be removed from the anchor post bore by a magnetic instrument, graspers, claws, or other suitable surgical tool. The cap 1030 may be placed over the anchor post 1022. The cap 1030 is moved toward the anchor body thereby squeezing and fastening the tissue/implant 1034 toward the bone 1032. The cap 1030 may be held to the anchor post 1022 by the retaining or snap ring 1026. Alternatively, or additionally, the cap and anchor may be connected together by mechanical locking, by expansion, by thermal bonding, or combinations thereof. If thermal bonding between the cap and anchor is desired, an energy source, such as a resistive heater, ultrasonic staking instrument, or other suitable energy sources, may be used.

The fixation device of FIGS. 72 and 73 can be used with a guide wire or an insertion instrument as previously described with other fixation device embodiments. The anchor, cap, and/or pin may be cannulated to receive the wire or instrument. In this configuration, the fixation device may be placed with precision within tissue or an implant. Also, the fixation device of FIGS. 72 and 73 may be used with a suture. The suture may be used to fasten tissue and/or implant and then inserted through the cap and secured. The suture may be positioned between the cap and anchor to be secured. Furthermore, the suture may be molded into and extend from the cap and/or anchor. It is contemplated that the descriptions and features of the fixation devices and sutures of FIGS. 59-61 apply to the fixation device of FIGS. 72 and 73.

In a related invention, the fixation of tissue may be accomplished by heating collagen in tissue under defined pressure to create spot welds, i.e. tissue welding or protein welding. This fixation may be in addition to or separate from the previously described fixation devices. Heating of collagen in tissue may be done with an energy source such as ultrasonic energy, thermal energy, or other energy source previously mentioned. In addition, metallic particles, such as iron oxide, may be placed on the tissue to assist with heating.

In another related invention, laser tissue welding may be used in conjunction with or separate from the fixation devices. Laser tissue welding is a structureless method of wound closure that may be used on nerves, skin, muscles, ligaments, tendons, bone, and arterial anastomoses. After heating generated by laser exposure, a glue is formed between tissue edges that forms a weld upon cooling. With the use of laser welding, there may be no foreign body reaction and less scar formation. Laser welding when used with an artificial biomaterial made mostly of elastin and fibrin to weld tissue allows a broad surface area for welding. Also, the use of a pulsed diode laser may be used to maintain thermal confinement and therefore minimize excess heating.

In yet another related invention, tissue may be approximated or manipulated with an instrument utilizing suction or negative pressure. For example, a torn rotator cuff may require stretching or repositioning back to its anatomically correct position then may require fixation to bone using a fixation device described herein. The manipulation of the rotator cuff to its correct location may be achieved by placing the distal portion of an instrument against the rotator cuff, activating a vacuum or sucking force at the distal end of the instrument, and pulling the rotator cuff into position. The distal end of the instrument may include a suction port, a suction cup, a suction cup with a suction port therein, or other similar negative pressure means.

The fixation devices and above-mention related devices may be used in combination with each other. For example, a torn rotator cuff may need to be refastened to bone, or cartilage within a joint, such as the knee, may need to be repaired. The negative pressure instrument may be used to grab and move the cuff/cartilage into proper position. A fixation device may be implanted to temporarily or permanently secure the tissue to bone. Tissue or protein welding may be performed to provide a thorough bonding of the cuff/cartilage and bone.

Figure 74A:
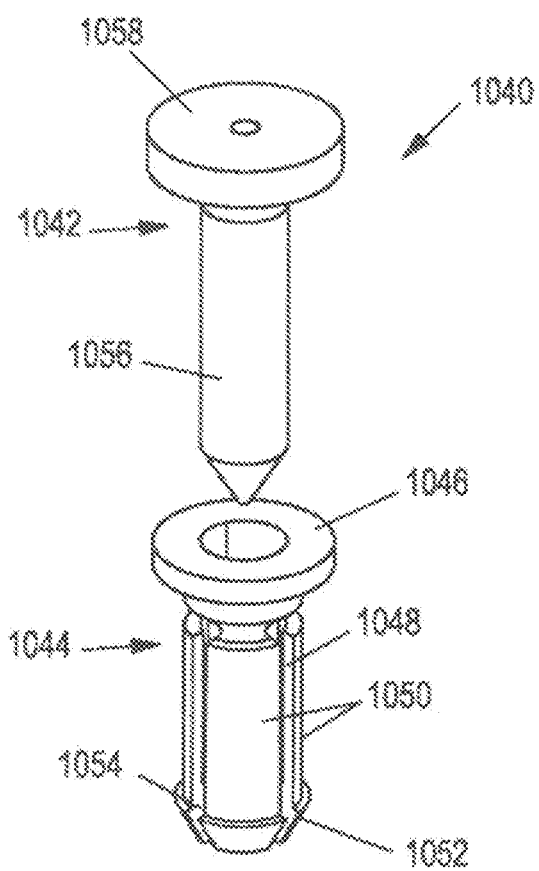
FIGS. 74A and 74B show an exemplary fastener having four biasing prongs.
Figure 74B:
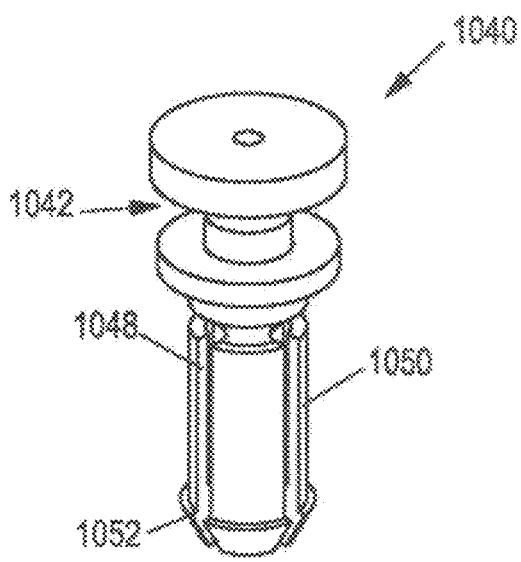

The present invention also may be used in additional types of intracorporeal welding devices and methods. Referring now to FIGS. 74A and 74B, a fastener 1040 includes a cap 1042 and anchor 1044. The fastener 1040 may be made of thermoplastic material. The anchor 1044 is generally tubular shaped with a circular flange 1046 attached to the proximal end. Four slots 1048 (two shown) are disposed longitudinally from the distal end of the anchor 1044. The four slots 1048 divide the anchor into four biasing prongs 1050. The prongs 1050 bias or hinge from generally the proximal end of the anchor 1044. Each biasing prong 1050 includes an outwardly projecting ridge 1052 and an inwardly projecting ridge 1054. The cap 1042 includes a post 1056 and a lid 1058 connected to the proximal end of the post 1056. Both the cap 1042 and anchor 1044 may include a tissue-piercing distal tip.

In use, the anchor 1044 may be placed in tissue, such as bone. Initially, the prongs 1050 of the anchor 1044 may not be biased outward during this step. Next, the cap post 1056 is inserted through an implant or tissue and positioned within a bore of the anchor 1044. When the cap post 1056 contacts the inwardly projection ridges 1054 of the prongs 1050, the prongs will be urged to move radially outward. The outwardly projecting ridges 1052 of the prongs 1050 are driven into surrounding tissue to thereby prevent the anchor from being pulled out of the bone. Once the cap is seated in its desired position, ultrasonic energy may be applied to the fastener 1040 to weld the anchor 1044 and cap 1042 together.

Figure 75A:
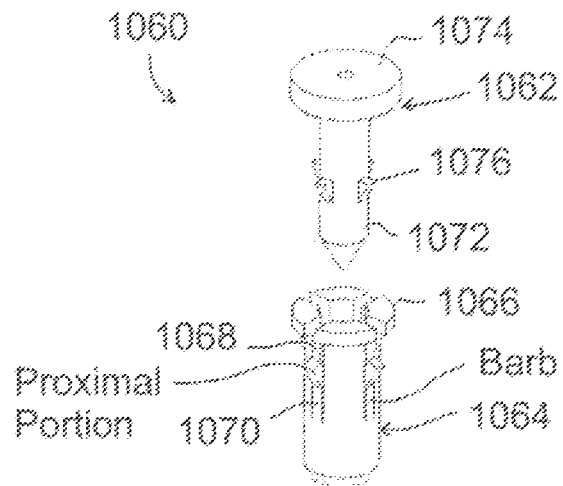
FIGS. 75A and 75B illustrate a fastener having lockable barbs.
Figure 75B:
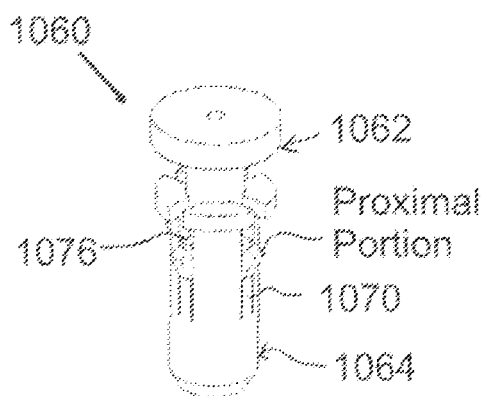

In FIGS. 75A and 75B, a fastener 1060 includes a cap 1062 and anchor 1064. The fastener 1060 may be made of thermoplastic material, such as PEEK or PLLA. The anchor 1064 is generally tubular shaped with circular flange 1066 attached to the proximal end. Four slots 1068 may be disposed longitudinally from the proximal end of the anchor 1064. Within each slot 1068 is a longitudinal barb 1070. The distal end of each barb 1070 is attached to the anchor 1064 while the proximal portion of the barb is free from attachment to the anchor and can be angled generally proximally and radially outward, i.e. between 30 and 60 degrees from the centerline of the anchor. The cap 1062 includes a post 1072 and a lid 1074 attached to the proximal end of the post. The post 1072 includes four wedge members 1076 attached to the exterior surface and spaced around the post 1072 such that each wedge member 1076 aligns with a slot 1068 in the anchor 1064. Each wedge member 1076 includes an angled face which is angled about the same as the proximal portions of the barbs 1070. Both the cap 1062 and anchor 1064 may include a tissue-piercing distal tip.

To implant the fastener of FIGS. 75A and 75B, the anchor 1064 may be inserted in tissue, such as bone. During insertion, the proximal portions of each barb 1070 which extend beyond the exterior surface of the anchor will flex or bend until they are forced radially inward a sufficient amount so that the anchor 1064 may fit within a passageway in the bone. The cap 1062 is then inserted through an implant or tissue and positioned in the bore of the anchor. The wedge members 1076 on the cap post 1072 may then slide into the slots 1068 of the anchor 1064. As the cap 1062 is seated, the wedge members 1076 of the cap force each longitudinal barb 1070 radially outward moving the proximal portion of each barb into surrounding tissue to secure the fastener in place. Ultrasonic energy may be applied to the fastener 1060 to secure the cap and anchor together.

Figure 76A:
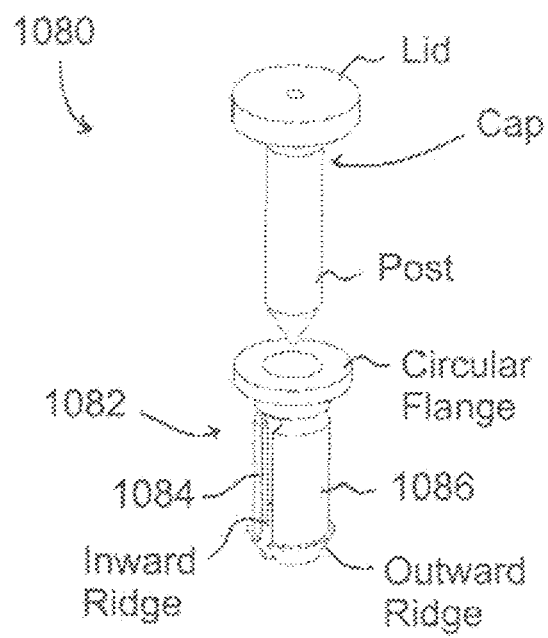
FIGS. 76A and 76B show an exemplary fastener having two biasing prongs.
Figure 76B:
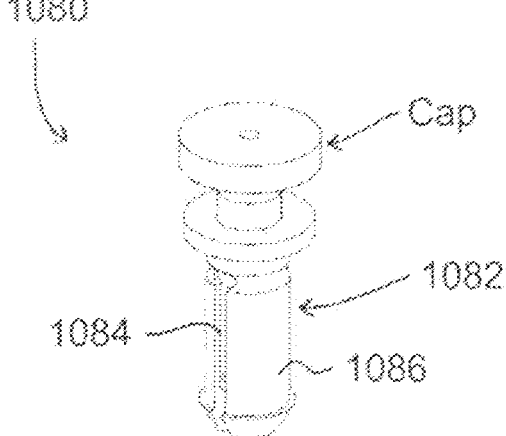

FIGS. 76A and 76B illustrate another embodiment of a fastener 1080 of the present invention. The fastener 1080 is similar to the fastener of FIGS. 74A and 74B except that the anchor 1082 includes two slots 1084 and two biasing prongs 1086. The method of implanting the fastener of FIGS. 76A and 76B is also similar to the method of inserting the fastener of FIGS. 74A and 74B.

Figure 77A:
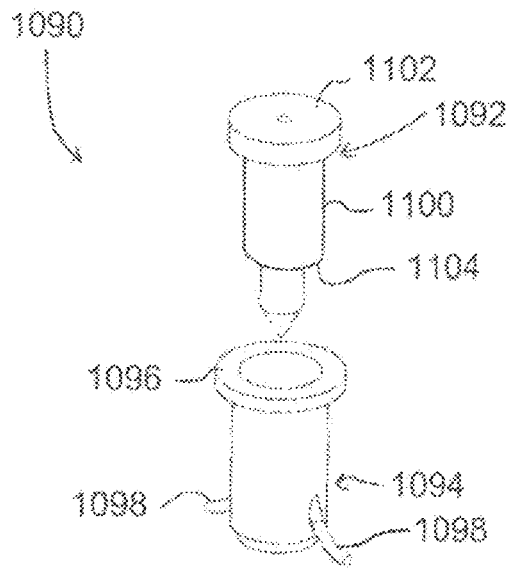
FIGS. 77A and 77B illustrate a fastener having slideable hooks.
Figure 77B:
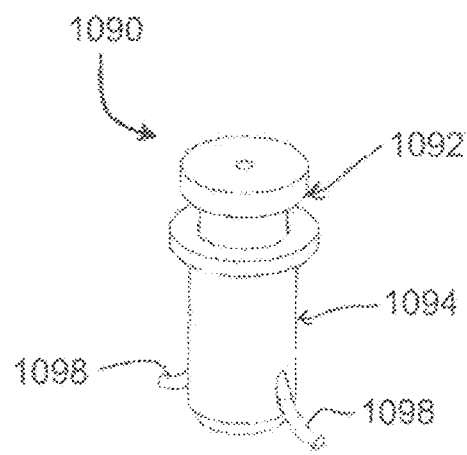

Referring now to FIGS. 77A and 77B, a fastener 1090 includes a cap 1092 and anchor 1094. The fastener 1090 may be made of thermoplastic material. The anchor 1094 is generally tubular shaped with a circular flange 1096 attached to the proximal end. Two slideable hooks 1098 may be disposed in the anchor 1094 and extend from the bore of the anchor and through channels in the anchor wall. The hooks 1098 are generally curved at least at the distal ends. The cap 1092 includes a post 1100 and a lid 1102 connected to the proximal end of the post. The post 1100 includes a shoulder 1104 formed by two different diameters of the post. The shoulder 1104 is configured for contact with the proximal ends of the hooks 1098 in the anchor 1094. Both the cap 1092 and anchor 1094 may include a tissue-piercing distal tip.

In use, the anchor 1094 may be placed in tissue, such as bone. The slideable hooks 1098 are substantially disposed in the anchor, i.e. little if any of the hook 1098 extends beyond the exterior wall of the anchor 1094 during insertion. Next, the cap post 1100 is inserted through an implant or tissue and positioned within the bore of the anchor 1094. When the shoulder 1104 of the post 1100 contacts the proximal ends of the hooks 1098, the hooks are moved distally and outwardly into surrounding tissue preventing the anchor 1094 from being pulled out of the bone. Once the cap 1092 is seated in its desired position, ultrasonic energy may be applied to the fastener to weld the anchor and cap together.

Figure 78A:
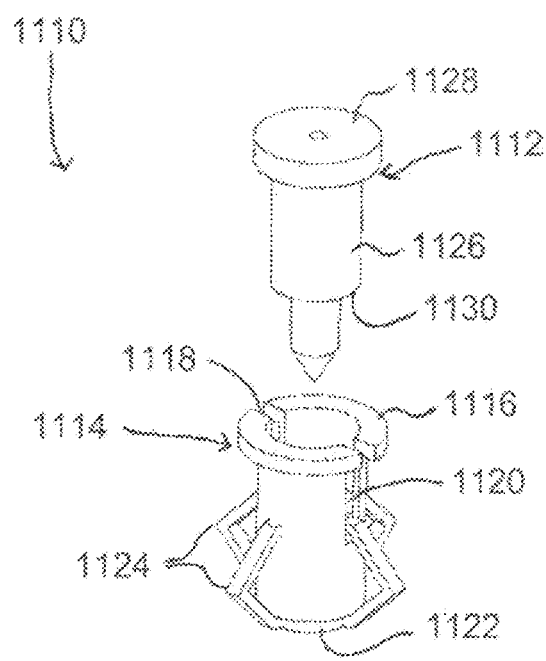
FIGS. 78A and 78B show an exemplary fastener having folding arms.
Figure 78B:
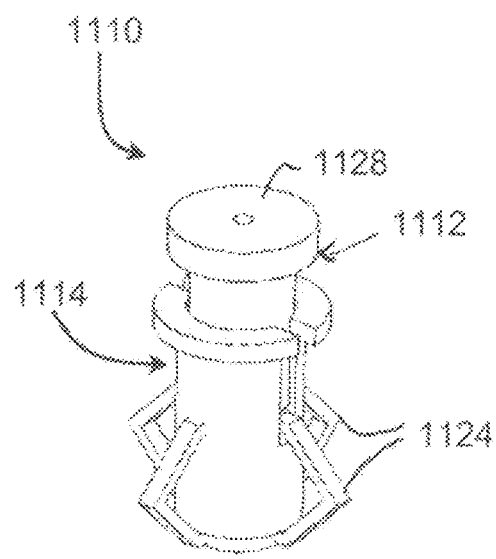

The fastener 1110 illustrated in FIGS. 78A and 78B also includes a cap 1112 and anchor 1114. The fastener 1110 may be made of thermoplastic material. The anchor 1114 is generally tubular shaped with a circular flange 1116 attached to the proximal end. Two or four slots 1118 may be disposed in the anchor wall and extend from the proximal end of the anchor. A folding member is disposed in the bore of the anchor and through the slots. The folding member includes a proximal ring 1120, a distal ring 1122, and two or four crimping arms 1124 corrected between the rings 1120, 1122. The folding member may be made of metal, thermoplastic, or other suitable material. The cap 1112 includes a post 1126 and a lid 1128 connected to the proximal end of the post. The cap post 1126 includes a shoulder 1130 formed by two different diameters of the cap post 1126. The shoulder 1130 is configured for contact with the proximal ring 1120 of the folding member. Both the cap 1112 and anchor 1114 may include a tissue-piercing distal tip.

The anchor 1114 may be placed in tissue, such as bone. During placement in bone, the crimping arms 1124 are substantially straight and the proximal ring 1120 of the folding member is located at the proximal end of the anchor bore. Next, the cap post 1126 is inserted through an implant or tissue and positioned within the bore of the anchor. When the post shoulder 1130 contacts the proximal ring 1120, the crimping arms fold 1124 or bend outwardly into surrounding tissue preventing the anchor from being pulled out of the bone. Once the cap 1112 is in its desired position, ultrasonic energy may be applied to the fastener to weld the anchor and cap together.

Figure 79A:
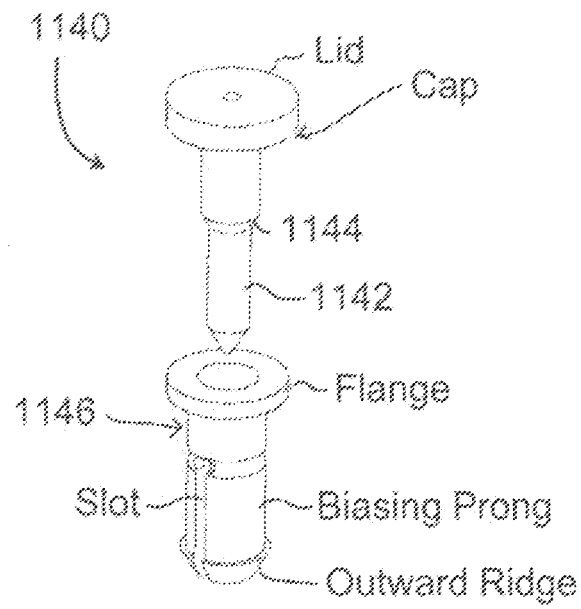
FIGS. 79A and 79B illustrate a fastener having biasing prongs and a tapered cap.
Figure 79B:
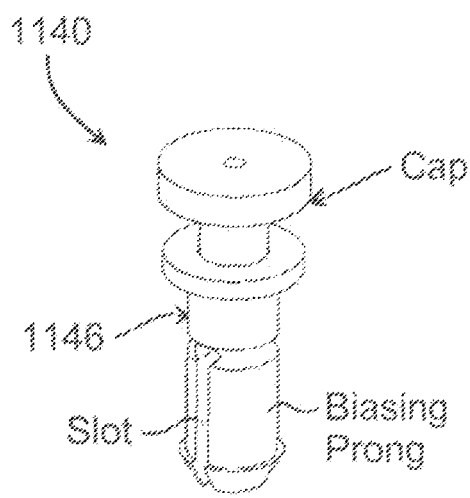

FIGS. 79A and 79B illustrate another embodiment of a fastener of the present invention. The fastener 1140 is similar to the fastener of FIGS. 76A and 76B except that the cap post 1142 includes a tapered portion 1144. The tapered position 1144 of the post 1142 is configured to be seated against a tapered ridge within the bore of the anchor 1146. The method of implanting the fastener 1140 of FIGS. 79A and 79B is also similar to the method of inserting the fastener of FIGS. 76A and 76B.

Figure 80A:
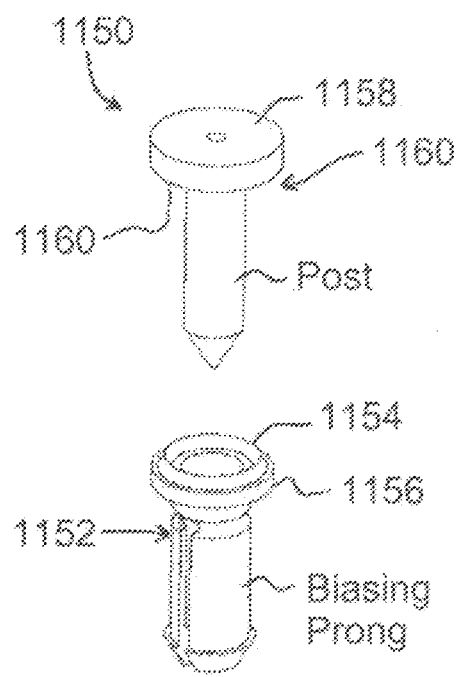
FIGS. 80A and 80B show an exemplary fastener having biasing prongs and a macrotexture welding region.
Figure 80B:
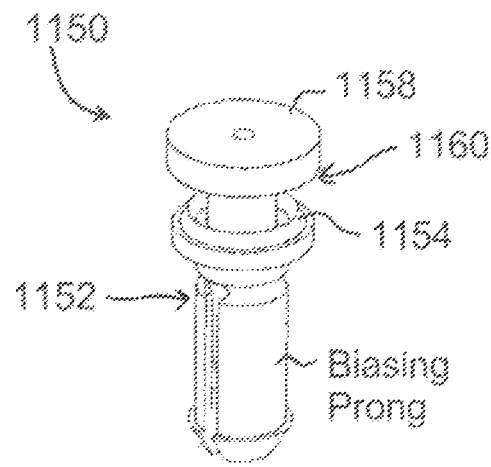

The fastener 1150 of FIGS. 80A and 80B is also similar to the fastener of FIGS. 76A and 76B. However, the circular flange 1156 of the anchor 1152 includes a circular rise 1154, and the underside of the cap lid 1158 includes a circular recess 1160 configured for receiving the circular rise 1154. The method of implantation is similar to methods previously described. During ultrasonic welding of the fastener 1150, however, the bonding between the cap 1160 and anchor 1152 is enhanced by the increased surface area provided by the circular rise 1154 and circular recess 1160.

Figure 81:
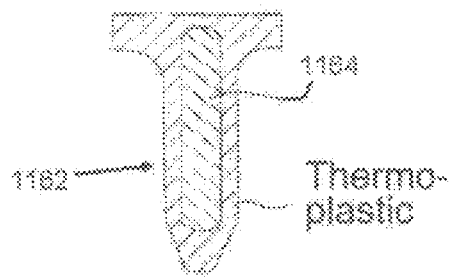
FIG. 81 is a cross sectional view of a fastener with a metallic core.
Figure 82:
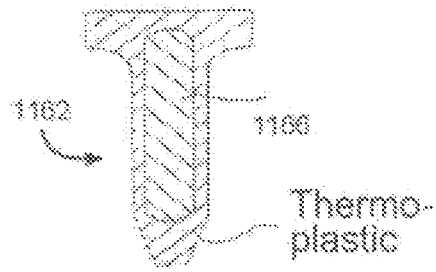
FIG. 82 is a cross sectional view of a fastener with a composite/polymer core.

FIGS. 81 and 82 illustrate another embodiment of the invention. In FIG. 81, the fastener 1162 includes a rigid metallic core 1164 which is enclosed by a thermoplastic. The fastener of FIG. 82 has a polymeric core 1166 surrounded by PEEK. Although not illustrated in these examples, the fasteners may include a central bore for receiving the post of an end effector.

Figure 83A:
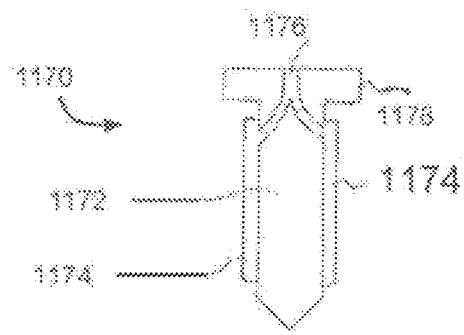
FIGS. 83A and 83B show a balloon fastener of the present invention.
Figure 83B:
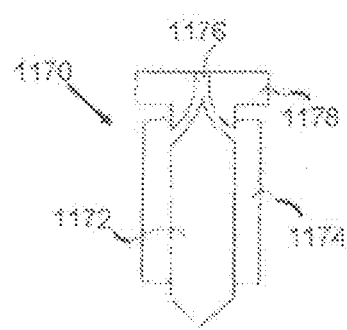

Referring now to FIGS. 83A and 83B, a balloon fastener 1170 is shown which includes an elongate body 1172 and one or more balloons 1174 disposed on the exterior surface of the body 1172. A passageway 1176 extends from the balloon(s) 1174 and through the fastener lid 1178. The passageway 1176 provides open communication between the interior of the balloon(s) and the exterior of the fastener 1170. The body 1172 may include a tissue-piercing tip. To implant the balloon fastener 1170, the balloon(s) may initially be in a deflated configuration and substantially positioned up against the exterior of the body. The fastener 1170 is positioned in tissue with the proximal surface of the lid exposed for access by the surgeon. Once placed in its desired position, the balloon(s) 1174 may be filled with air, gas, liquid, powder, etc. via the passageway 1176. The balloon(s) expand against adjacent tissue to thereby lock the fastener to the tissue. The passageway 1176 may be closed and sealed with ultrasonic energy and thermoplastic material.

Figure 84A:
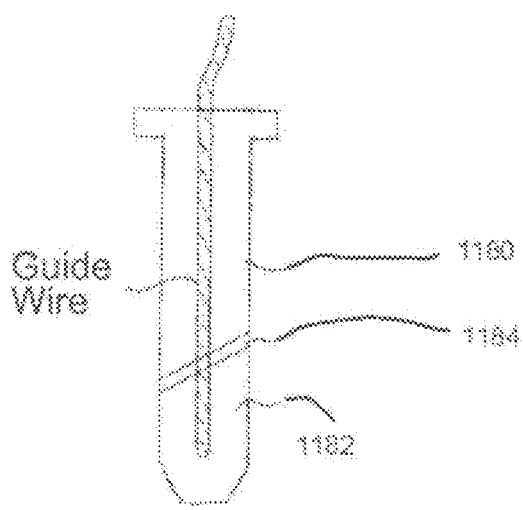
FIGS. 84A and 84B illustrate a living hinge fastener.
Figure 84B:
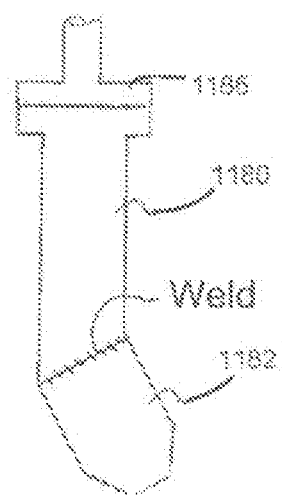

FIGS. 84A-B, 85A-B and 86A-B illustrate living hinge fasteners. In FIG. 84A, the fastener includes a main body 1180 and a toggling body 1182 connected to each other with a living hinge 1184. A guide wire is slideably disposed through the main body 1180 and toggling body 1182 to maintain the bodies in general alignment. As seen in FIG. 84B, with the guide wire removed, the living hinge 1184 normally biases the toggling body 1182 laterally from the main body 1180. When inserted in tissue, the toggling body 1182 moves into surrounding tissue to prevent the fastener from being pulled out. An end effector 1186 may be placed in engagement with the fastener to thermally bond the thermoplastic material of the main body and toggling body together.

Figure 85A:
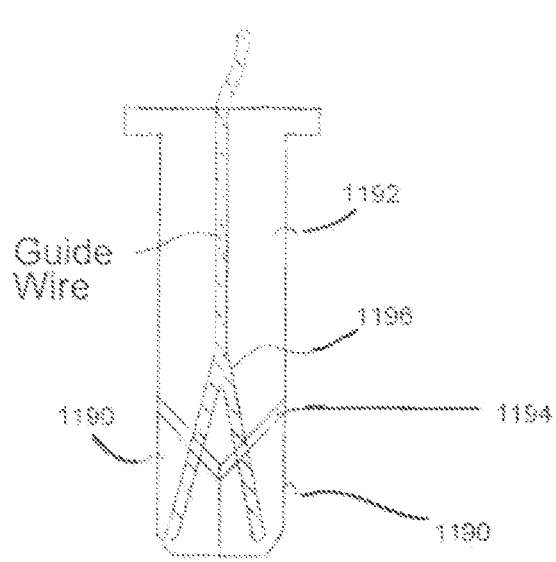
FIGS. 85A and 85B show a dual living hinge fastener.
Figure 85B:
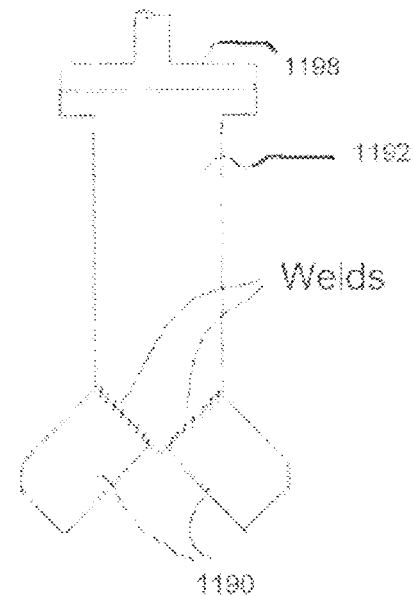

In FIG. 85A, the fastener includes two or more toggling bodies 1190 connected to the main body 1192 with two or more living hinges 1194. A single guidewire with a bifurcation 1196 or multiple guidewires may be used to hold the normally outwardly biased toggling bodies generally aligned with the main body 1192. FIG. 85B shows the guidewire removed and the toggling bodies 1190 extended. An end effector 1198 may be used to ultrasonically bond the main body 1192 to the toggling bodies 1190.

Figure 86A:
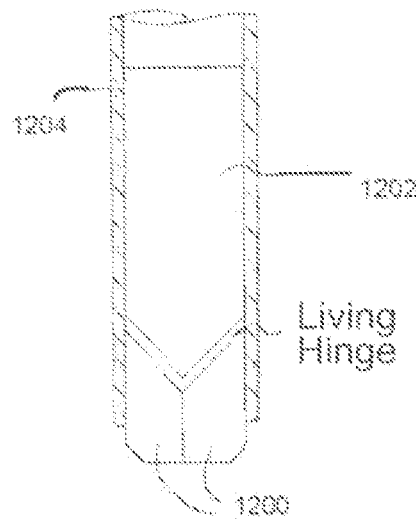
FIGS. 86A and 86B illustrate a dual living hinge fastener with a retaining sheath.
Figure 86B:
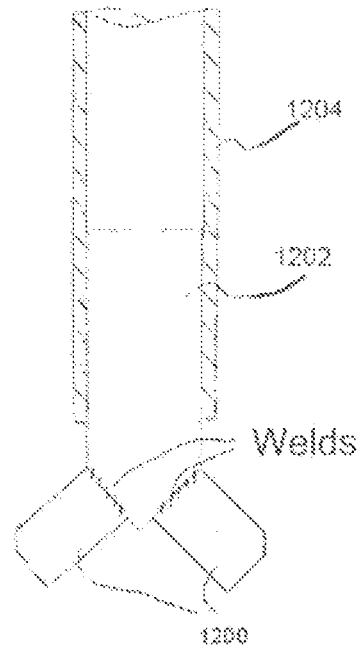

The living hinge fastener of FIGS. 86A and 86B is similar to the fastener of FIGS. 85A and 85B. However, instead of using a guidewire to maintain the toggling bodies 1200 generally aligned with the main body 1202, a sheath 1204 is disposed around the exterior surface of the fastener. To deploy the fastener of FIGS. 86A and 86B, the fastener within the sheath 1204 in placed in tissue. The sheath 1204 is removed and the toggling bodies 1200 normally extend outwardly into surrounding tissue. The toggling bodies 1200 may be ultrasonically welded to the main body 1202.

Figure 87:
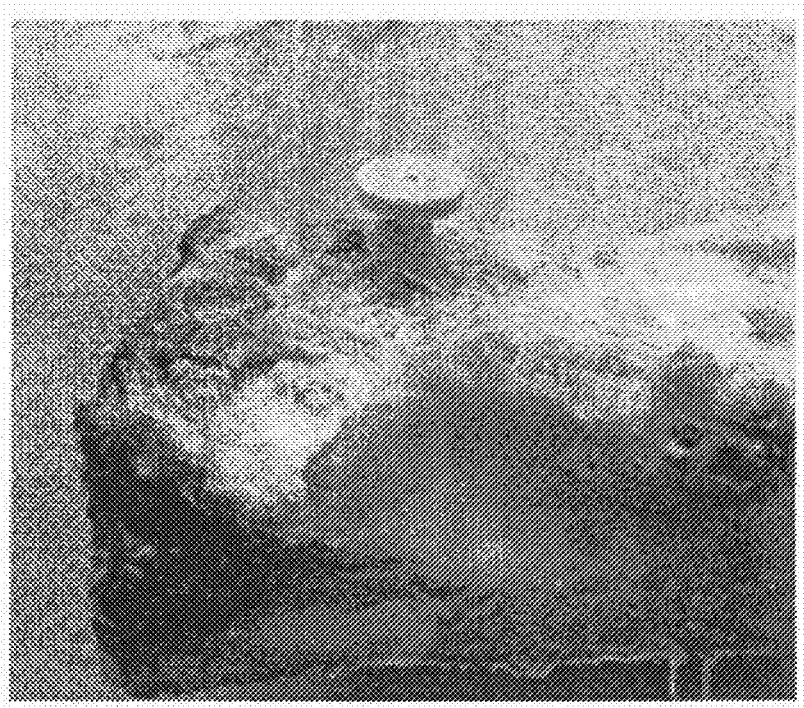
FIG. 87 is photograph of a thermoplastic fastener positioned in bone.
Figure 88:
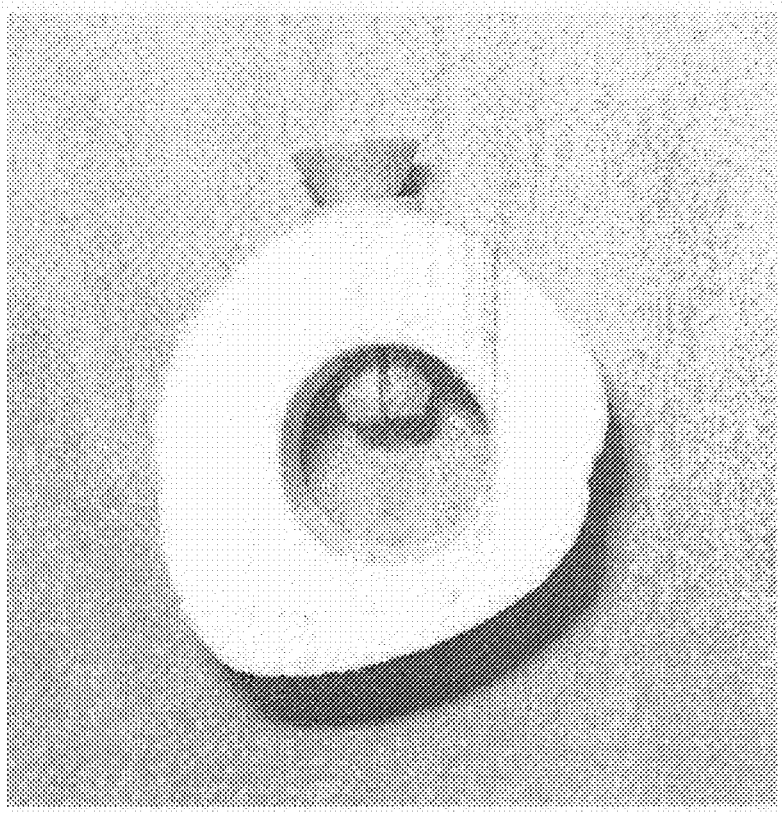
FIG. 88 is a photograph of a biasing prong fastener disposed in bone.

FIG. 87 is a photograph of a fastener of the present invention ultrasonically welded in bone. The fastener includes a post and lid connected to the post. A hole is drilled in the bone for insertion of the fastener. The diameter of the hole is less than the diameter of the post. The lid includes a small bore for an end effector. With the application of ultrasound and force, the fastener flows into the hole in the bone. In FIG. 88 a fastener includes an anchor and a cap. The anchor has slots which form a plurality of biasing prongs. With the cap inserted within the bore of the anchor, the prongs move radially outward and engage the bone thereby locking the fastener to the bone. The cap and anchor are ultrasonically welded together.

Figure 89:
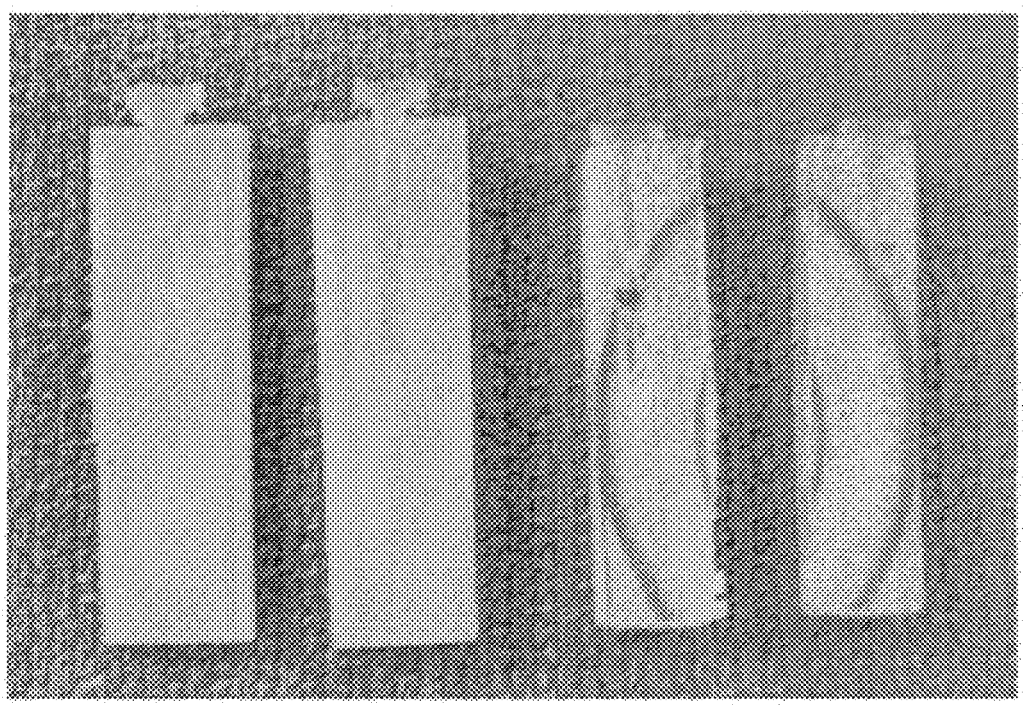
FIG. 89 is a photograph showing thermoplastic fasteners welded into simulated bone.
Figure 90:
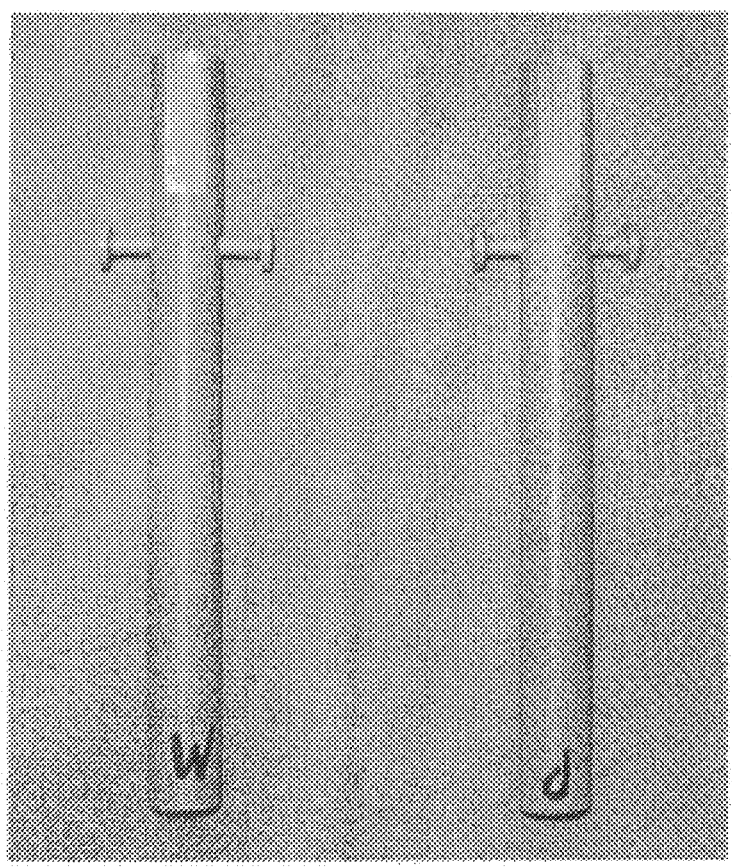
FIG. 90 is a photograph of metallic core fasteners disposed in a thermoplastic rod.
Figure 92B:

The photograph of FIG. 89 shows a cut away of thermoplastic fasteners bonded within channels. The diameter of the channels is less the diameter of the posts of the fasteners. With the application of ultrasonic energy and pressure the thermoplastic material flows into the channel, without the thermoplastic material liquefying. In FIG. 90 metallic core-thermoplastic fasteners are shown bonded to thermoplastic rods. The metallic cores can be seen in the x-ray image of FIG. 91. In FIGS. 92A and 92B, PEEK and PLLA fasteners are ultrasonically bonded in bone. The bone has been cut in half to show the posts of the fasteners disposed in channels of the bone.

Figures 93, 94:
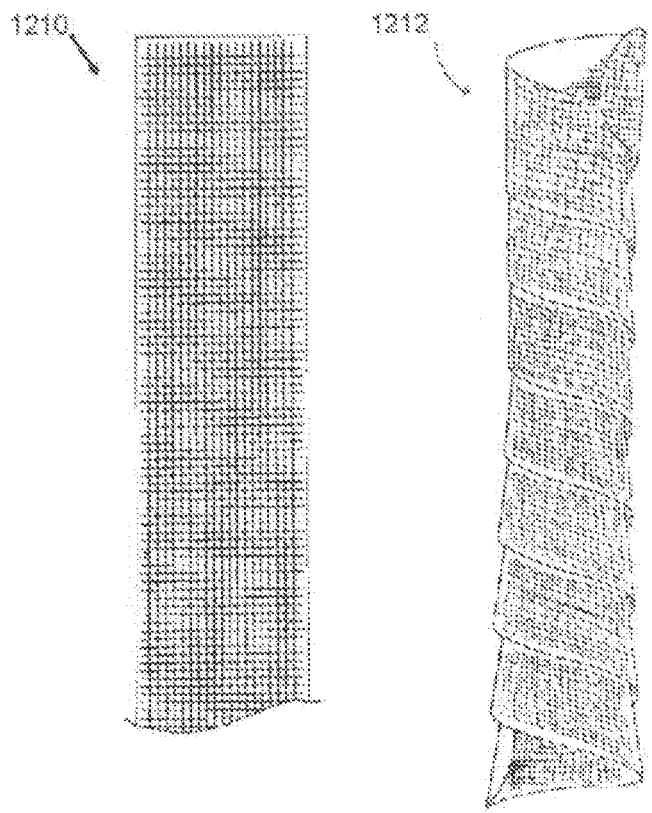
FIG. 93 shows a thermoplastic mesh sheet of the present invention.
FIG. 94 illustrates a helically wrapped mesh sheet.

Referring now to FIG. 93, a thermoplastic mesh sheet 1210 is shown. The sheet may include openings therethrough for the passage of body fluid. Alternatively, the sheet 1210 may be free from openings to function as an impermeable membrane. The sheet may include or may be made of thermoplastic material such as PEEK or PLLA. One or more layers of material may form the sheet. For example, an impermeable sheet may have a polymeric layer with no openings and, additionally, may include a mesh layer on one or both sides of the opening-free layer. A permeable sheet may include one, two, three, or more mesh layers.

Figure 95:
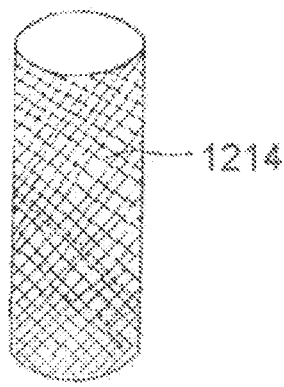
FIG. 95 shows a thermoplastic mesh cylinder.

In FIG. 94, a mesh sheet 1212 is helically wrapped to form a tube-like structure. The overlapping portions of the sheet 1212 may be ultrasonically welded together to form a unitary structure. The structure may be used as a prosthetic vessel, such as a blood vessel or any other body conduit. It may also be used for tissue repair by wrapping the structure around damaged tissue. FIG. 95 shows a cylindrical mesh sheet 1214. This configuration may also be used for tissue repair and/or tissue stabilization. For example, a fractured bone requires stabilization for proper healing. A mesh sheet may be positioned about the fractured portion of the bone. Ultrasonic energy may be used to bond the sheet to the bone. Additional energy may be used to shrink the sheet in diameter to apply a compressive force to the fractured bone.

Figure 96:
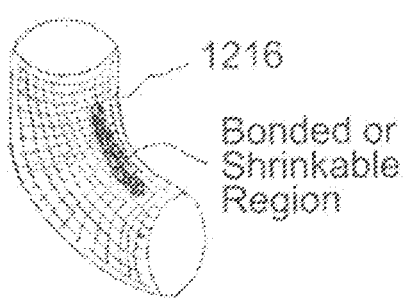
FIG. 96 illustrates a thermoplastic mesh cylinder thermally shaped into a curved mesh tube.

The cylindrical mesh sheet 1216 of FIG. 96 has been shaped using energy, such as ultrasound, resistive heating, etc. Shaping of the sheet 1216 allows the surgeon to form a tailored implant. It is contemplated that a non-cylindrical sheet may be shaped using energy as well. A flat sheet may be contoured to conform to the exterior surface of a body organ, such as the heart, stomach, the skin, a bifurcated vessel, and other body parts like the knee, elbow, or spine.

Figure 97:
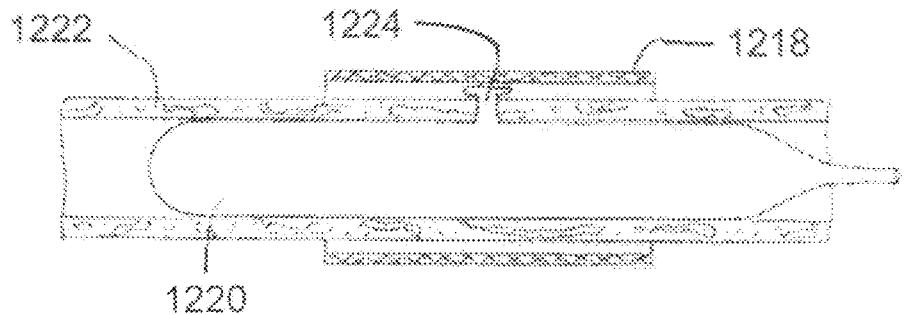
FIG. 97 shows a mesh cylinder positioned about an aneurysm of a vessel.

FIG. 97 illustrates a method of using a thermoplastic mesh sheet 1218 to repair a blood vessel 1222. An aneurysm 1224 has formed in the vessel wall. Instead of or in addition to treating the aneurysm with an embolic coil or other known device, a mesh sheet 1218 may be wrapped about the vessel 1222 over the aneurysm region. A balloon 1220 may be positioned within the vessel 1222 to provide structural rigidity to the vessel while ultrasonic energy is applied to the mesh sheet. The sheet may be bonded to the vessel and/or itself and shrunk in diameter to slightly compress the aneurysm. In this example, the mesh sheet 1218 may include an impermeable layer.

Figure 98:
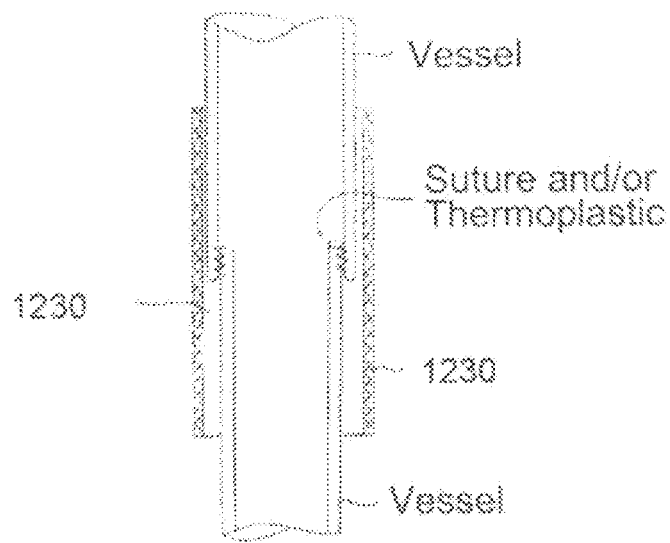
FIG. 98 illustrates a mesh cylinder disposed around an anastomosis surgery area.

FIG. 98 shows another use of a thermoplastic mesh sheet 1230. An anastomosis is shown joining two vessels. The vessels may be fastened together using known surgical techniques such a suturing. Alternatively, or in addition, a thermoplastic mesh sheet 1230 may be placed between overlapping portions of the vessel or at the ends of the vessels, and ultrasonic energy may be applied to the sheet to bond the vessels together. Furthermore, a permeable or impermeable mesh sheet 1230 may be used to wrap around the anastomosis region. The sheet may be ultrasonically bonded to the vessels and/or itself to create a fluid/blood tight seal at the surgery site.

Figure 99:
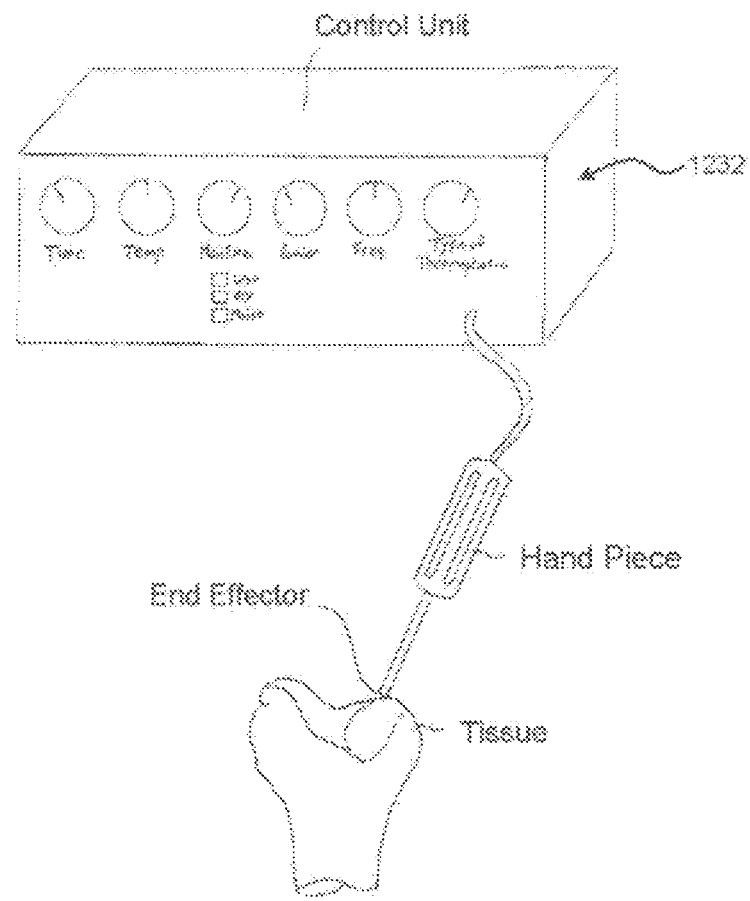
FIG. 99 shows an ultrasonic generator control unit and a handpiece positioned adjacent tissue.

FIG. 99 shows a welding control box 1232. A surgeon determines the optimum welding parameters and enters them into the control box prior to welding. An ultrasonic end effector is located on the distal end of the handpiece. Using different control settings, such as wattage, frequency, time, etc., the end effector may be used to flow thermoplastic material, clean tissue, and/or cut tissue (i.e. osteotomy).

Figure 100:
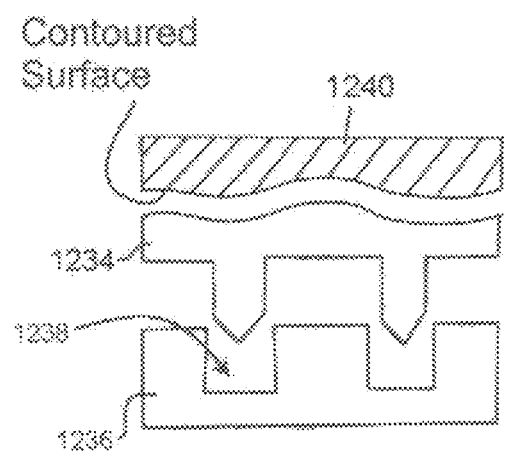
FIG. 100 illustrates modular implants for revision surgery.

Welding of polymeric material to other material such as metal or plastic may be useful in securing a tibial tray to a tibial plate in a knee replacement component. As shown in FIG. 100, a tibial bearing surface 1234 may be bonded to a metallic tibial component 1236. Instead of having a manufacturer produce multiple sizes of tibial replacement components, a single standard base 1236 may be made of metal and a bearing surface 1234 may be bonded to the base to form a custom component. The size, thickness, and configuration of the bearing component may be selected by a physician based on the patient's needs. The bearing component 1234 may be ultrasonically welded into or onto the base tibial component 1236. As shown in FIG. 100, the base component 1236 may have notches or channels 1238 in which the bearing component 1234 can move into by the application of an energy source 1240, such as heat. The bearing surface 1234 may be further contoured or sculpted by an energy source 1240, such as resistive heat, to create a customized surface tailored to meet the requirements of the patient.

Alternatively, the base component 1236 may be metal with a layer or areas of polymeric material disposed thereon/therein. In this configuration, instead of the bearing component 1234 being bonded directly to the metal, the bearing component 1234 may be bonded to the polymer on the metal base 1236. Also, to achieve the desired height of the tibial component, the surgeon may insert polymeric shims above and/or below the bearing component. The shims may be ultrasonically welded in place.

Additionally, polymeric components may be bonded to joint replacement components supplied by different manufacturers. It would be advantageous for a surgeon to be able to select individual joint replacement component that best fit the needs of the patient, regardless of manufacturer. Currently, joint replacement components are supplied as a set and can not be interchanged, mixed and matched. It is contemplated that the surgical welding systems of the present invention would allow surgeons to select one component from one manufacture, another component from another manufacturer, tailor one or both components, and implant the components as a customized set. For example, for a knee replacement system, a surgeon could use a tibial base plate from manufacturer A and a femoral component from manufacturer B. Using polymeric material and thermal welding, a bearing surface/polyethylene may be thermally bonded to the base plate 1236. The bearing surface 1234 may be contoured and shaped to receive the femoral component. One or more layers or inserts may be used to sequentially build up one or both of the components. This system gives the surgeon more options in selecting joint components and gives greater freedom in customizing the components.

Furthermore, welding of polymeric components may be performed in situ to repair or resurface a joint replacement component, such as a shoulder, hip, knee, ankle, or intervertebral disc. For example, the bearing surface 1234 of a knee component may become worn out over time causing the patient pain. Instead of removing the metallic component and implanting a new component which may be expensive and cause the patient additional pain and require longer rehabilitation, the existing bearing surface can be rebuilt, restored, replaced or reshaped using thermoplastics and thermal welding. In this revision joint replacement surgery, the existing worn out bearing surface may be prepared by removing all, some, or none of the polymeric surface. Then, a new polymeric component may be welded intracorporeally onto the old bearing or metallic component using ultrasound, radiofrequency, resistive heating, etc. The new bearing surface component may be selected based on the required thickness needed to restore the joint to its anatomically correct configuration. Contouring of the bearing surface may be performed intracorporeally or in the operating room prior to welding the new bearing component intracorporeally.

In addition to revision surgery, it is contemplated that ultrasonic energy and thermoplastics may be utilized with other procedures, such as revision arthroplasty, osteomous correction, fracture fixation, cementless fixation of an implant to tissue/bone, and bone graft fixation.

If needed, multiple layers of polymeric material may be added to the deteriorated joint component to build the joint up to the proper height (FIG. 101A-D). Rather than having an inventory of multiple inserts or components all varying in different thicknesses, standard inserts may be manufactured with a given thickness and welded together by the surgeon in the operating room to obtain the needed implant height. For example, inserts may be manufactured in 2 mm, 4 mm, and 8 mm thicknesses. A plurality of these inserts may be selectively bonded together to form a single insert. This may be done intracorporeally and/or within the operating room.

Figure 101A:
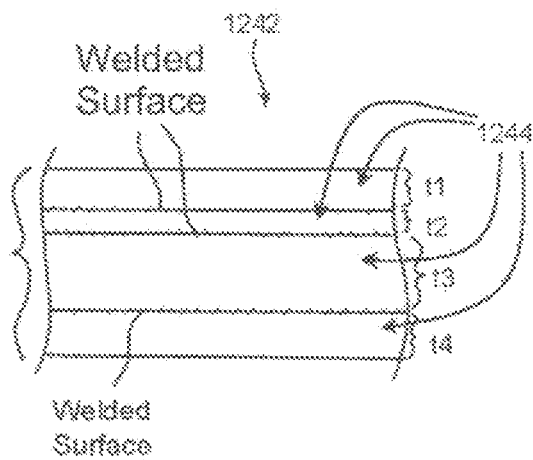
FIG. 101A shows a thermally welded layered implant.
Figure 101B:
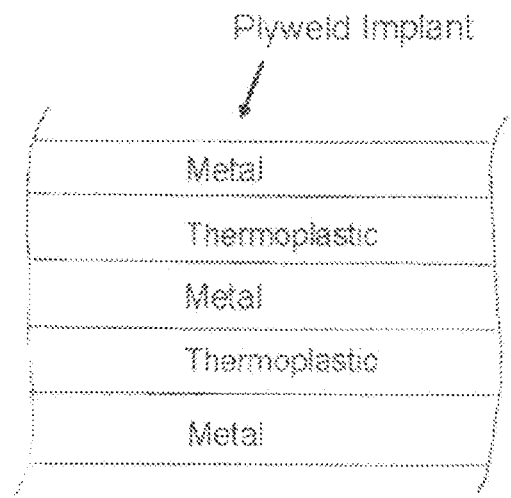
FIG. 101B illustrates a plyweld having metallic components welded together with thermoplastics.
Figure 101C:
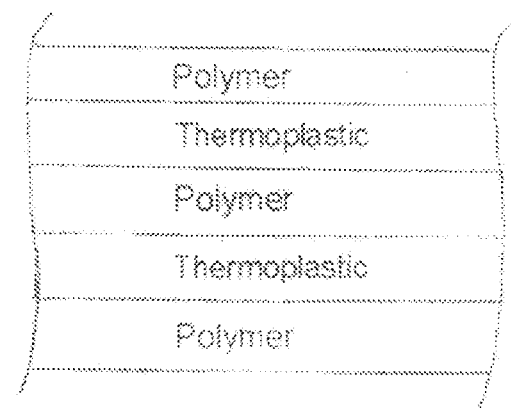
FIG. 101C shows a plyweld having polymeric components welded together with thermoplastics.
Figure 101D:
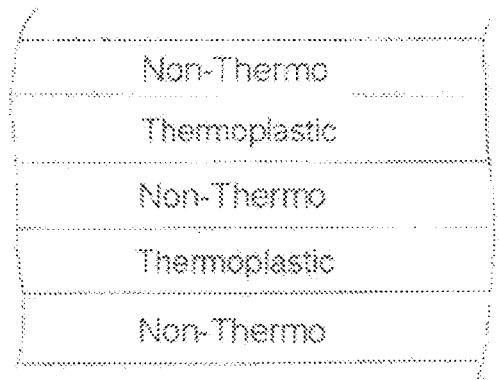
FIG. 101D illustrates a plyweld having various components welded together.

FIGS. 101A-101D illustrates an implant 1242, such as a joint replacement component, having a plurality of layers 1244 welded together to create a customized implant. All the added layers 1244 may be made of polymeric material such as PEEK, PLLA, or polyethylene. Alternatively, some of the layers may be made of a metallic or ceramic material (FIG. 101B). The layers may alternate between metallic/ceramic and polymeric material. In addition, the layers also may alternate between different polymeric or thermoplastic materials (FIG. 101C). Regardless of which material (polymer, metal, ceramic) each layer includes, the layers can be bonded to form a customized structure (see, e.g., FIG. 101D).

This structure is analogous to plywood where multiple layers of material are bonded together to form one unit instead, in the present invention, the "plyweld" is made of biocompatible layers of material which are thermally bonded together either by spot welding or full surface welding. Plyweld may be especially useful for minimally invasive surgery and nanotechnology applications where implants may be constructed intracorporeally to create a unitary structure. Such structures may be advantageous for cell therapy, gene therapy, drug delivery, bearing surface implants, and other suitable applications.

At least one of the layers of the plyweld structure may have an ingrowth surface. For example, a joint replacement component may have a bearing surface on one side and an ingrowth surface on the other side that, when implanted, is in contact with tissue. The ingrowth surface may be porous, honeycomb, biodegradable, biostable, or made from foam metal or foam titanium. The ingrowth surface may include a therapeutic substance, such as tantalum, HA, apatite, BMP, or other suitable agent.

In another embodiment of the present invention, joint replacement components can be made with a hardened bearing surface film bonded to a polymer. PEEK may be combined with a metallic or ceramic film to create the bearing surface. Joint replacement components generally employ metal on metal, such as cobalt chrome against cobalt chrome, or ceramic on ceramic. In the present invention, one or more bearing surfaces of a joint replacement component could be made out of PEEK which may have a nano-metallic or nano-ceramic film bonded to its articulating surface. For example, a diamond crystal or aluminum crystal may be bonded to the PEEK. The polymer may be a few microns to as much as 100 microns in thickness. For minimally invasive surgery, this embodiment is advantageous since the surgeon could introduce the implant bearing surface of smaller components into the body through a small incision. The components may be introduced through a cannula, under endoscopic guidance, or under magnetic guidance. Once inserted, the components may be welded together and attached to bone. It is contemplated that intracorporeally welding applies to other types of implants as well, such as modular stents, modular spinal cages, modular acetabular component, modular bone plates, modular IM rods, modular spacers, and modular wedges.

In addition to visualizing modular components during implantation, the components (joint replacement, spinal, intravascular) may be magnetically guided into and within the body. Magnetic particles, such as iron oxide or iron particles, may be placed within the polymeric components. A magnetometer or other known energy source may be used to identify the location and orientation of the modular components to aid in attaching the components to each other and to tissue. The iron particles may also enhance the thermal welding properties of the components. As previously discussed, metallic particles disposed within or on the surface of a thermoplastic material would aid in transferring energy, such as vibratory or heat energy, thereby creating an enhanced bonded interface.

Figure 102A:
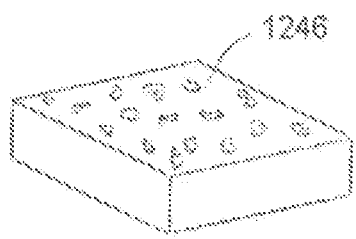
FIGS. 102A-102D illustrate various microtextures for use with welding.
Figure 102B:
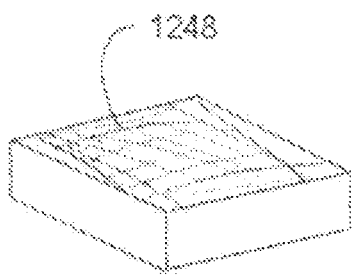
Figure 102C:
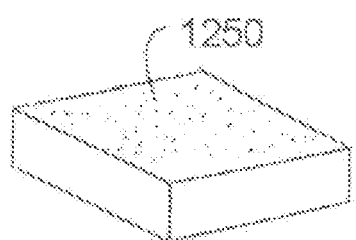
Figure 102D:
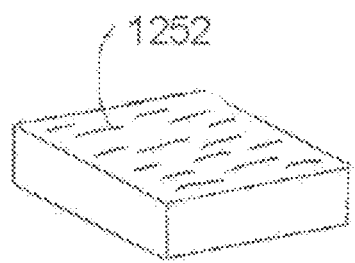

Whether welding different layers together to form a plyweld or ultrasonically welding to other implants together, the bonding region between two components may be enhanced with textured surface technology to increase the frictional characteristics of the components. A texture on the surface, usually opposite the energy director, increases weld strength, reduces flash and particulate matter, and reduces the total amount of energy required to weld the components. The components may include thermoplastic and/or metallic material. Two components made of similar material may be welded together using textured surfaces, or two components made from different materials may be bonded using textured surfaces. A microtextured surface may include small surface projections. For example, FIG. 102A shows an implant with pebbles 1246. In FIG. 102B, the implant includes a scratched or roughened surface 1248. FIG. 102C shows an implant with a grit blasted surface 1250, while FIG. 102D illustrates an implant with fiber-like materials 1252 disposed on the surface.

Figure 103A:
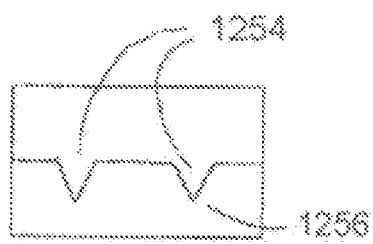
FIGS. 103A-103F show various macrotextures for use during welding.
Figure 103B:
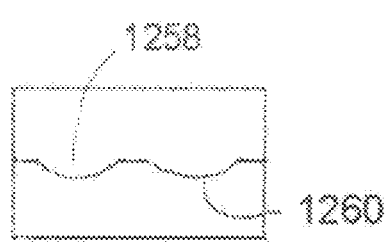
Figure 103C:
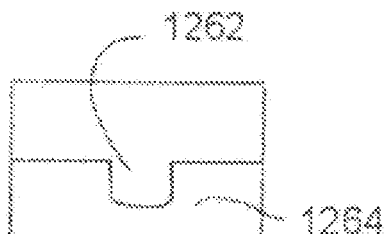
Figure 103D:
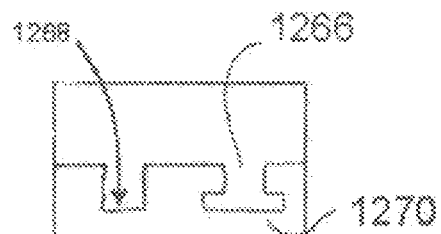

Thermally weldable implants may additionally, or alternatively, include a macrotextured surface. FIGS. 103A-103F illustrate various embodiments of macrotextured surfaces. In FIG. 103A, one implant includes V-shaped projections 1254 and the adjacent implant includes V-shaped grooves 1256. FIG. 103B shows convex bulges 1258 and concave indentations 1260. FIG. 103C illustrates a generally square projection 1262 and a square notch 1264. In FIG. 103D, the upper implant includes two square projections 1266. The lower implant includes one square notch 1268 and a T-shaped notch 1270. The square projection 1266 thermally welded into the T-shaped notch 1270 flows into the "T" to form a locking bond between the layers.

Figure 103E:
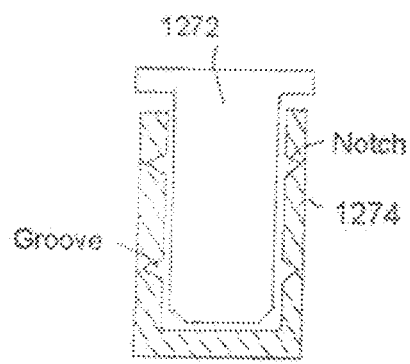
Figure 103F:
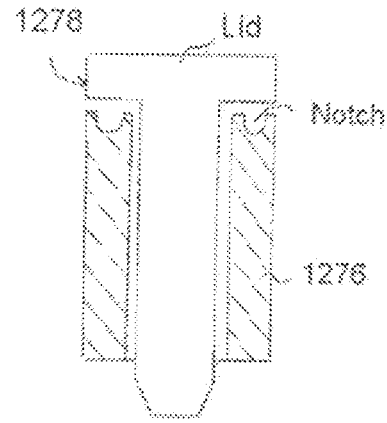

FIG. 103E illustrates a textured fastener. The cap 1272 may be made of thermoplastic material. The anchor 1274 may be made of thermoplastic material and/or metallic material. The anchor 1274 includes a macrotextured surface on the inside of the anchor bore. During ultrasonic welding, thermoplastic material of the cap 1272 flows into the grooves, notches or recesses of the macrotextured anchor. In FIG. 103F, the anchor 1276 includes a macrotextured surface at its proximal end or proximal surface. To this configuration, thermoplastic material of the cap lid 1278 flows into the notches, grooves, or recesses of the macrotextured anchor surface.

Figure 104:
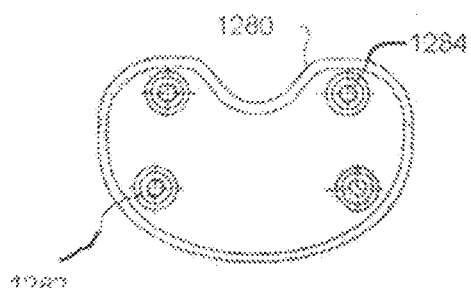
FIG. 104 illustrates a tibial tray component of the present invention.

In a related invention, FIG. 104 illustrates a tibial tray 1280 for implantation during knee replacement surgery. Typically, a tibial tray implant is fastened to the proximal end of the tibia with metal screws. Use of metal screws usually creates stress risers and can limit tissue ingrowth. Also, the tibial tray may subside slightly when secured with metal fasteners. To alleviate these common problems, thermoplastic fasteners 1282 utilizing features of the present invention may be used to implant tibial trays 1280. The tray of FIG. 104 includes a plurality of channels 1284 configured for receiving a thermoplastic fastener 1282. Any fastener disclosed herein or incorporated herein may be used to fasten the tibial tray. The tray may be made of metal. Alternatively, the tray may include both metallic and thermoplastic material. For example, the main body of the tray 1280 may be made of metal while the regions around the channels may be made of thermoplastic materials. In this embodiment, a thermoplastic fastener 1282 may be ultrasonically welded to bone and be bonded with the thermoplastic material of the tibial tray.

Figure 105:
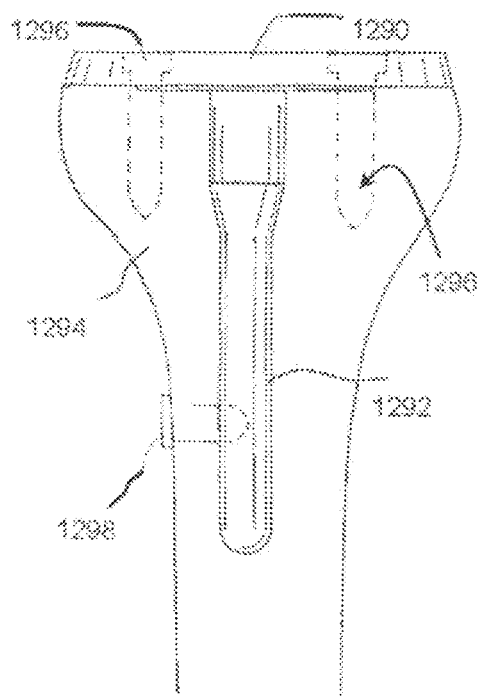
FIG. 105 shows a tibia implant secured with thermoplastic fasteners.

FIG. 105 shows a tibial tray 1290 which is similar to the tray of FIG. 104. However, the tray in this embodiment includes a stem 1292. The stem 292 may be made of metal, thermoplastic, or a combination thereof. The tibial tray 1290 is positioned on the proximal end of the tibia 1294 with the stem 1292 disposed in the medullary canal. Thermoplastic fasteners 1296 secure the tray to the tibia. Additional thermoplastic fasteners 1298 may be used to fasten the stem 1292 to the tibia 1294. The fasteners may include a core as described in FIGS. 81 and 82, although other fastener embodiments described herein may also be suitable.

Figures 106, 107:
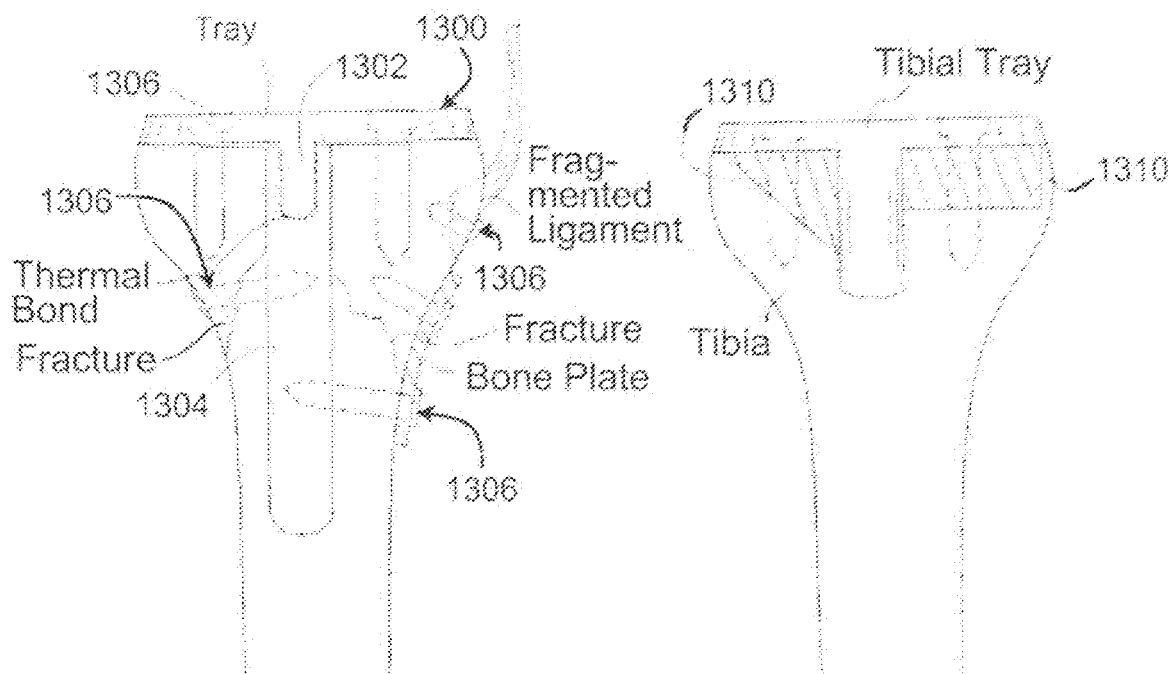
FIG. 106 illustrates the repair of the proximal end of the tibia.
FIG. 107 shows bone filler components and a tibia implant secured to bone.

In FIG. 106, a tibial tray 1300 includes a shortened stem 1302. As seen in the figure, the tibia is fractured in several locations. Thermoplastic components may be used to reconstruct the proximal end of the tibia. Initially, an intramedullary rod ("IM rod") 1304 may be positioned in the intramedullary canal of the tibia. The IM rod may be made of PEEK or other material suitable for welding to other components. Existing metallic IM rods require fasteners to be place through the cortical bone and into holes disposed in the rod. This configuration is prone to create stress risers. Therefore, using a weldable IM rod allows a surgeon to implant the rod within the bone and use thermoplastic pins or fasteners that can be welded to the rod. The pins may be placed anywhere along the length of the rod including the ends of the rod without the risk of creating stress risers. This PEEK rod and pin combination allows unicortical or bicortical fixation to lock the rod within the bone.

The tray 1300 is placed on the end of the tibia with the shortened stem 1302 inserted in to a notch in the IM rod 1304. The stem and rod may be ultrasonically bonded together. Thermoplastic fasteners 1306, with or without cores, may be used to fasten the tray to the bone and fasten the rod to the bone. Additional fasteners may be utilized to secure a fragmented ligament to its proper position as well as to secure a thermoplastic bone plate to the tibia.

Figure 108:
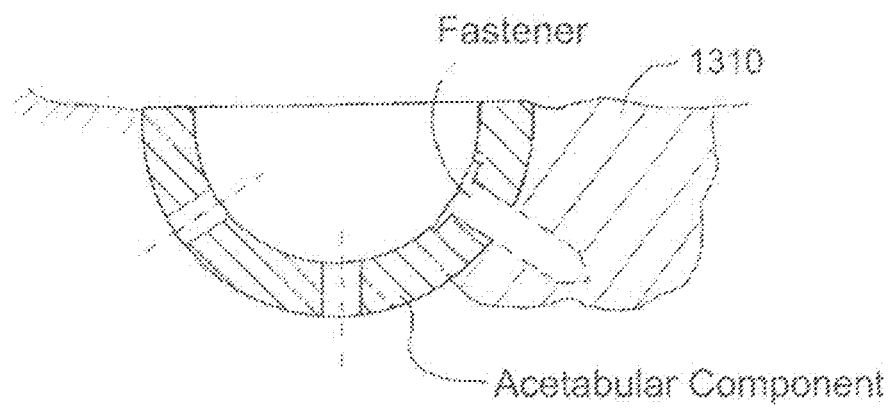
FIG. 108 illustrates a bone filler component and an acetabular implant fastened to bone.

In another embodiment of the invention, bone filler implants 1310 are shown in FIGS. 107 and 108. In FIG. 107, two bone voids exist at the proximal end of the tibia. To properly align and secure a tibial replacement component, two bone filler implants 1310 are positioned in the voids. The filler implants 1310 may be made of thermoplastic material and/or metal. Fasteners of the present invention are used to secure the tibial tray and bone filler implants to the tibia. Ultrasonic energy may be used to bond the fasteners to the tray, filler implants, and bone and to bond the filler implants to the tray and stem. FIG. 35 shows another example of bone filler implants. An acetabular component and a filler implant are thermally bonded to each other and are secured to bone with one or more thermoplastic fasteners.

Figures 109A, 109B:
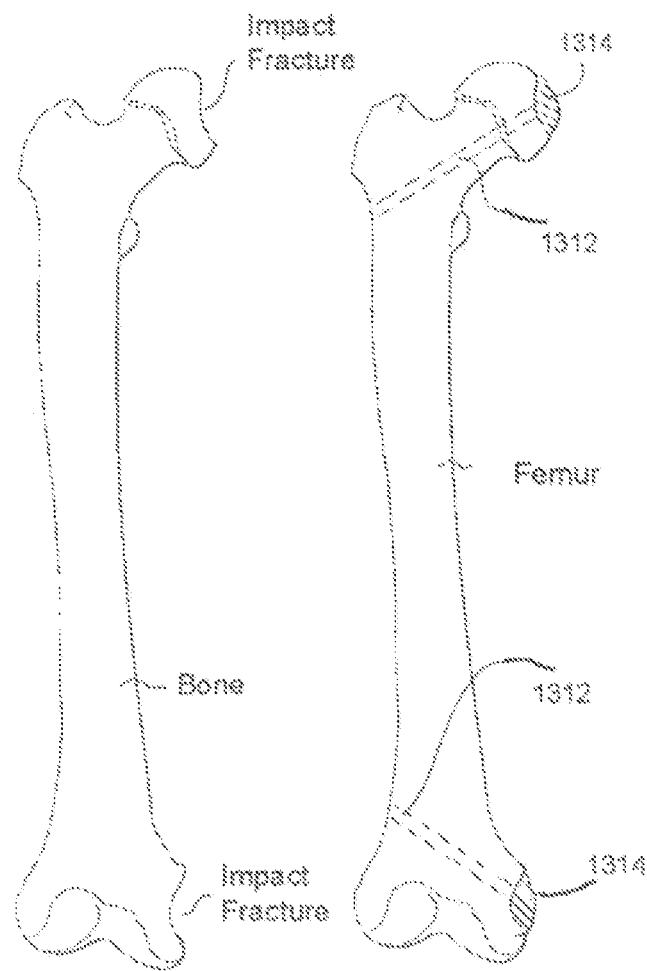
FIGS. 109A and 109B show impact fracture repair using thermoplastic and metallic components and ultrasonic energy.

Referring now to FIGS. 109A and 109B, the present invention may be used to repair an impact fracture. FIG. 109A shows a bone, specifically a Femur, with multiple impact fractures. To repair these fractures, a channel 1312 may be drilled through the bone and into the impact region. Using appropriate instruments inserted through the channel 1312, the impacted bone may be repositioned to its anatomically normal position. Then, using ultrasonic energy, flowable thermoplastic material 1314 is placed in the void of the impact region. The thermoplastic material 1314 bonds to the bone and provides structural support for the impact region.

Figures 110A, 110B:
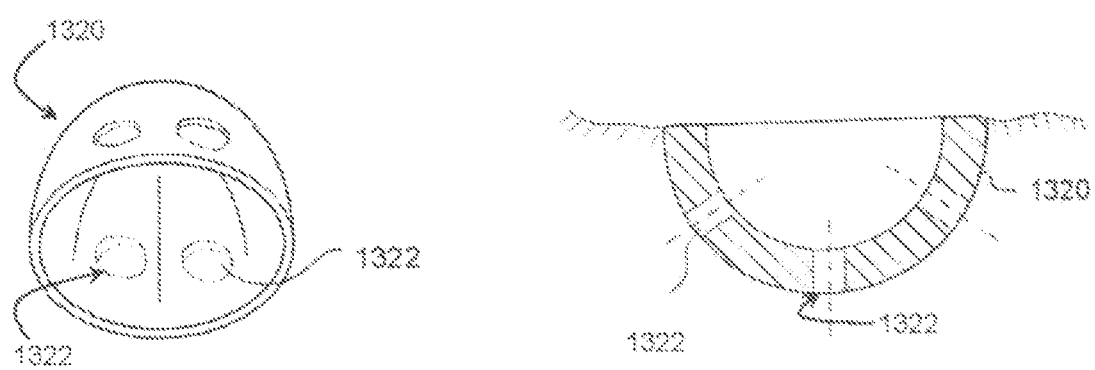
FIGS. 110A and 110B illustrate an acetabular implant of the present invention.

In a related invention, an acetabular implant 1320 is shown in FIGS. 110A and 110B. The implant 1320 is made of thermoplastic material, such as PEEK or PLLA. A plurality of holes 1322 extends through the walls of the implant and is configured for receiving a thermoplastic fastener. With the application of ultrasonic energy and pressure, the acetabular implant 1320 may be welded to bone, and the fasteners may be thermally bonded to the implant and bone.

In addition to using ultrasonic energy to flow thermoplastic material in the body, ultrasonic energy may also be used to weld metals and to melt solder intracorporeally. Other energy sources may be used as well, such as laser and cool plasma. Using intracorporeal metal welding and soldering, electrical and electronic components can be implanted and repaired in the body. For example, batteries from a pacemaker or other pump may be replaced; temperature, pH, or pressure sensors may be connected or reconnected; microprocessor or computer chips may be repaired; and entire circuit board may be implanted and electrically connected. These implanted electrical components may be encapsulated with thermoplastic material to protect surrounding tissue from damage, heat, shock, etc. and block body fluid from reaching the components. FIG. 111A shows a patient with a pacemaker 1330. Pacemakers usually have a limited service life and require replacement after a certain period of time. With the method and devices of the present invention, a pacemaker can be repaired or upgraded in situ. Electrical connections may be detached and reattached using ultrasonic energy and solder. A defibrillator made be implanted and connected to an existing pacemaker. In FIG. 111B, various electrical components 1332 may reside in an implant. These components include diodes, transistors, transformers, rectifiers, integrated circuits, resistors, capacitors, memory chips, etc. These components may be repaired or replaced intracorporeally and in situ.

Figure 113A:
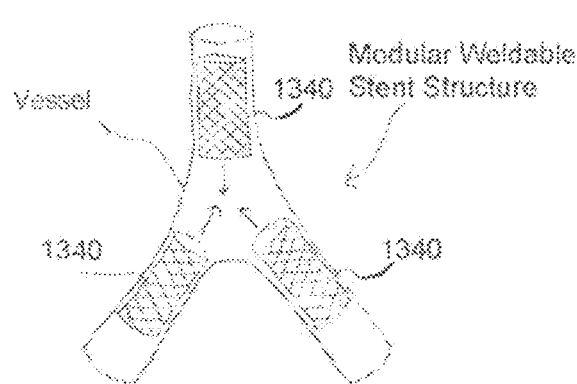
Figure 113B:
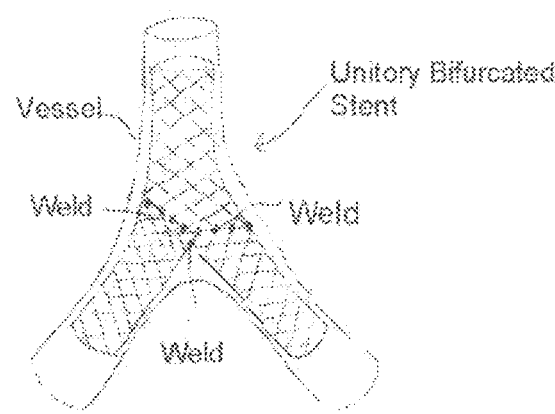

Metal to metal welding may also be performed intracorporeally using ultrasound, laser, and/or cold plasma. In FIGS. 112A and 112B, two stents 1334 positioned in a vessel 1336 are welded together to form one unitary stent 1338. Both stents 1334 are made of metal and are welded to each other in situ. In FIGS. 113A and 113B, multiple stems 1340 may be welded together to form a desired configuration either in the operating room or within the vessel. Where two vessels form a "T" or "Y" in the vasculature, a surgeon can thermally weld one stent 1340 to another stent 1340 in a "T" or "V" configuration. Also, a plurality of smaller stents may be built up within the body to form a larger stent. This method of welding tubular structures using metallic welding may also be applied to balloons and conduit tubing for medication pumps, diabetes insulin pumps, and pain pumps. Also, electrodes to an electrical stimulation unit may be welded to extend them or to seal them off.

Figure 114:
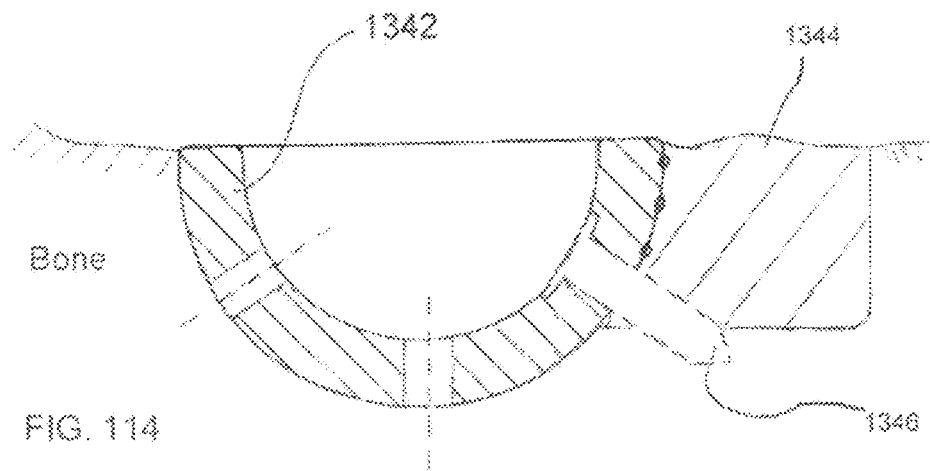

In another example of metal to metal intracorporeal welding, a metal implant may be bonded to a metallic bone filler implant. FIG. 114 shows a metallic acetabular component implant 1342 in bone. A metal filler implant 1344 is welded to the acetabular component 1342. Fasteners 1346 disclosed herein may be used to further secure the component and filler implant to bone.

The intracorporeal welding system of the present invention also may include shrinkable materials for use in surgery. Shrinkable materials provide a compressive force to tissue or implants when energy is applied. For example, a fastener may be implanted to secure an implant or tissue. The application of heat to the polymeric material of fastener causes the fastener to shorten or shrink thereby increasing the force provided by the fastener. The fastener may be positioned through two portions of a fractured bone then heated to shrink. The bone portions are compressed together for proper healing. In addition to fasteners, a suture, cerclage, wire, or cable may be made of shrinkable material. A cable may be placed through tissue or bone, positioned across a joint, or connected with an implant. When energy is applied to the cable, it shortens thereby creating a tension force and securing the object(s) to which is attached. A shrinkable cable positioned adjacent to or across a joint provides rigid and/or dynamic stabilization of the joint.

Figure 115A:
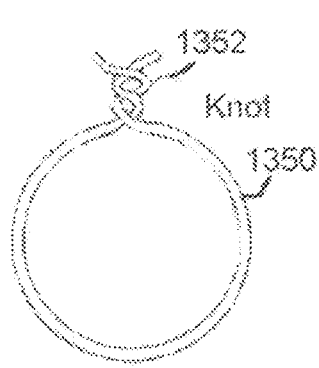
Figure 115B:
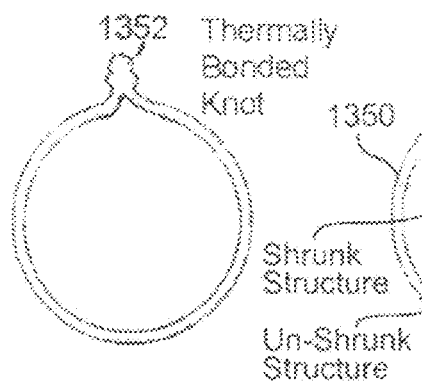
Figure 116:
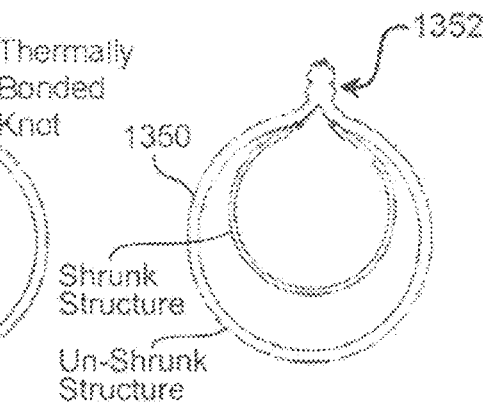
Figures 117A, 117B:
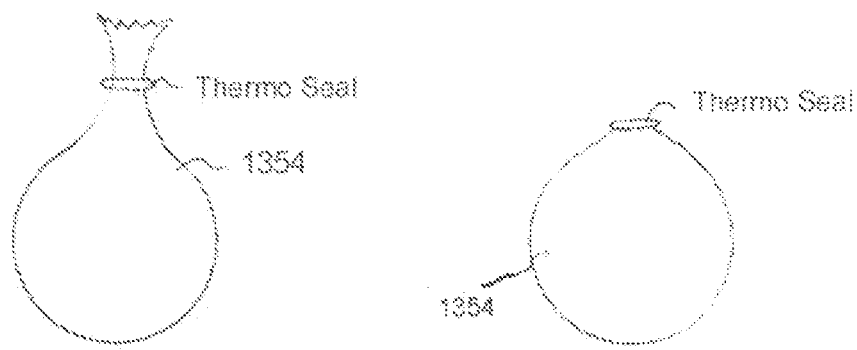

FIGS. 115A and 115B illustrate a thermally bondable suture. In FIG. 115A, the suture is knotted 1352. Frequently, however, knots creep and the suture loses tension. To solve this problem, ultrasonic energy may be applied to the thermoplastic material of the knot 1352. FIG. 115B shows the suture knot 1352 thermally bonded/melted to itself to prevent creep. In FIG. 116, the suture 1350 is reduced in length/diameter using ultrasonic energy. FIGS. 117A and 117B illustrate heat shrinkable implant pouches 1354. Implants placed in a pouch 1354 are sealed within. Applying energy to the pouch shrinks it to firmly hold the implant therein. Thermoplastic fasteners may be used to secure the pouch within the body.

Figure 118A:
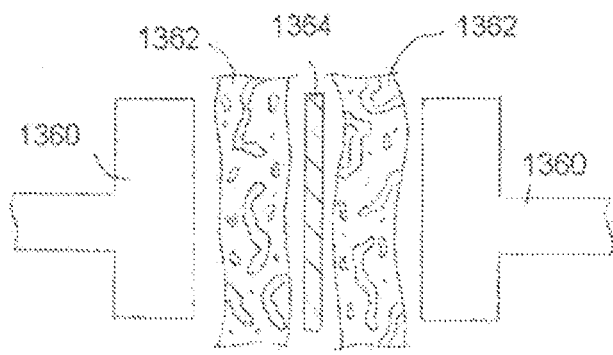
Figure 118B:
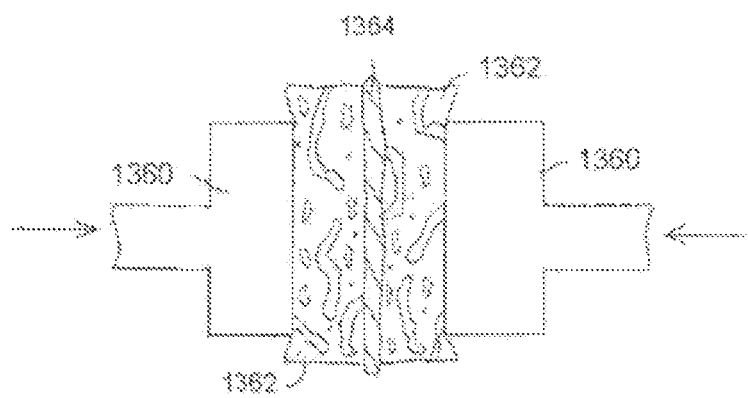

In another related invention, tissue may be bonded to tissue using thermoplastic material and ultrasonic energy. As shown in FIG. 118A, thermoplastic material, such as PEEK or PLLA may be positioned between two pieces of tissue. In FIG. 118B, an ultrasonic end effector and anvil 1360 is used to press the two pieces of tissue 1362 and the thermoplastic material 1364 together. The thermoplastic material 1364 bonds the tissue 1362. This method may be performed intracorporeally or in the operating room outside the body. The thermoplastic material 1364 may include a therapeutic agent such as proteins, cells, growth inducer, or similar substances. Other agents include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, hormones, cell therapy substances, gene therapy substances, bone growth inducing material, osteoinductive materials, apatite compositions with collagen, and demineralized bone powder. U.S. Provisional Patent Application No. 60/728,206 entitled "Drug Eluting Implant" discloses means for delivering therapeutic agents. The above-mentioned provisional application is incorporated by reference herein in its entirety.

Referring to FIG. 119A, a composite fastener 1370 is illustrated. The composite fastener 1370 includes a metallic core 1372 with helical threads 1374 disposed on the distal position of the core. A thermoplastic sleeve 1376 is positioned about and secured to the middle portion of the core. The composite fastener 1370 is shown in FIG. 119B implanted in a bone 1378. Initially, an IM rod 1380 may be positioned within the medullary canal or the bone. A channel is then drilled through the bone and IM rod. The composite fastener 1370 is inserted in the channel such that the threads of the fastener engage the cortex of the bone and the sleeve of the fastener engages the IM rod. Ultrasonic energy may be applied to the fastener to thermally bond the sleeve and IM rod. A bone plate may be positioned between the head of the fastener and the bone.

In many of the experiments, tests, and examples described below and elsewhere herein, ultrasound energy was used to weld thermoplastic material. The bond between implantable components may also be a chemical bond, covalent bond, ionic bond, or a bond using Vanderwall forces. It is contemplated that any energy source provided herein may be utilized.

Experiments and Testing

Testing of PEEK welding was performed with ultrasonic energy from an ultrasound generator and handpiece. The end effector that contacts the thermoplastic component was 0.180" in diameter, though other sizes may be used. During the welds, approximately 7-9 lbs of load was placed on the handpiece, which was delivered to the cap of the component during the weld. Settings of current=170 and time=3 second was initially used. The time corresponds to tenths of a second, so the weld time was 0.3 seconds. The current value is on a 0-255 scale.

Figure 121:

The majority of samples welded had a seat cap (fastener)/design as shown in FIG. 120. Seat caps 1380 that were tested were made from Acrylic, Nylon, UHMWPE and PEEK. In most cases the "anchor' in which the seat cap was welded into was a hole in a small block of the same material. However, with the Nylon samples, the anchor actually was threaded into a sawbone for welding and testing. To simulate "tissue" ⅛" thick neoprene was used as it could compress a little. To test the weld, a stainless steel wire or USP 5 suture was placed through the neoprene and force was applied to the wire to try and break the weld. FIG. 121 illustrates the apparatus used to test the welds.

The neoprene "tissue" stretched when tensioned and in some tests the neoprene failed prior to the cap and weld failing. In tests with Acrylic seats, the weld failed (rather than the neoprene "tissue" failing) at around 30 lbs. With the Nylon seats, the samples typically failed at loads of 30 lbs. UHMWPE samples did not weld well and the welds were easy to break by hand. In five PEEK seat tests, there were no weld failures, even at loads of 38 lbs where the "tissue" failed.

Figure 122:
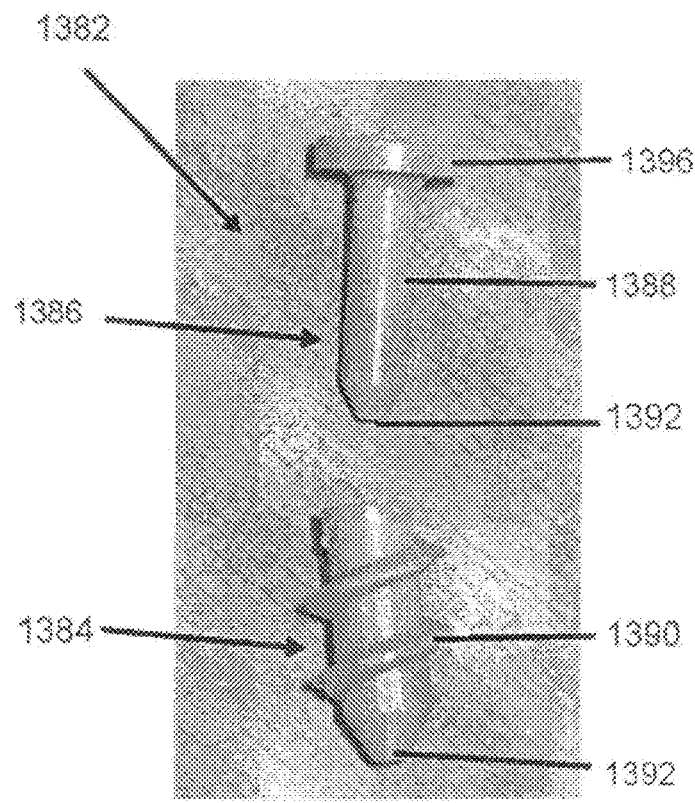
Figure 123:
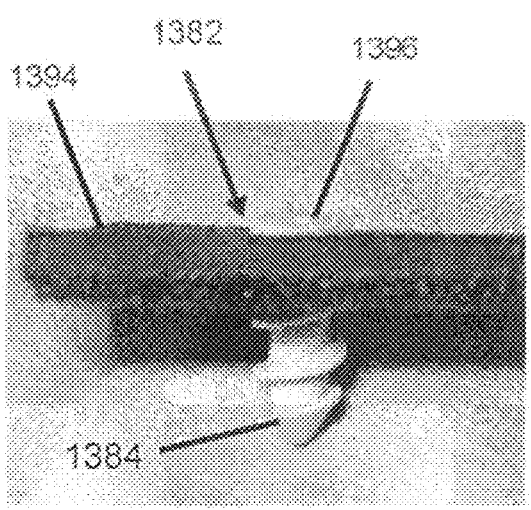

Referring to FIG. 122, a fastener 1382 includes an anchor 1384 and a cap/post nail 1386. The fastener 1382 includes a thermoplastic material such as PEEK. The anchor 1384 includes a bore configured to receive the post 1388 of the nail. The anchor 1384 also includes helical threads 1390 disposed on the outer surface thereon. Using the threads 1390, thermal welding, or both, the anchor 1384 is lockable within tissue. The distal portion of the post and the distal portion of the anchor include a tissue piercing point 1392. In FIG. 123, a piece of neoprene 1394 is used to simulate tissue. The neoprene is fastened between the cap 1396 and the anchor 1384. The post 1388 is thermally welded into the anchor bore using ultrasonic energy or other energy source.

Another test fastener 1400 is shown in FIG. 124. The fastener includes an anchor 1402 and a cap 1404. A distal portion of the anchor 1402 is configured for placement in tissue. The anchor 1402 may be mechanically locked in the tissue, thermally welded in the tissue, or a combination of both securing techniques. The anchor 1402 may have a pointed post 1406 which pierces the tissue requiring repair.

The disc shaped cap 1404 is then placed over the anchor post 1408, and energy, such as resistive heating or ultrasound, is emitted thereby staking the cap 1404 on the post 1408. The tip of the post may be contoured to a flattened configuration to reduce its profile. In FIG. 125, a strip of neoprene 1410, representing soft tissue, is held by the fastener 1400 of FIG. 124. During surgery, the distal portion of the fastener would be anchored in tissue. The cap 1404 is welded to the anchor post 1408, and the post is deformed to a flat configuration.

Testing was performed on components fastened using resistive heat. The simple prototypes were made from Acrylic and looked like the component in FIG. 120. The post was attached to the anchor and was 0.105" in diameter. The outer diameter of the cap and anchor was 0.236". For this test, a thin foil heater was attached to a handpiece and a board designed in-house. The board delivered a pulse width modulation signal and 10 watts of power. During a strength test the weld failed at about 30 lbs.

FIGS. 126 through 134 illustrate test samples of PEEK components. FIG. 126 shows PEEK fasteners 1412 that were ultrasonically welded to a PEEK rod placed inside the sawbone. The holes drilled through the sawbone and into the rod were drilled at the same time, as would be done in surgery. The small blind hole in the rod provides a flat surface for the fastener tip to weld against.

FIGS. 127 and 128 are of another PEEK rod with two different types of PEEK fasteners 1414 ultrasonically welded to the rod 1416. In FIG. 127, the fastener 1414 was designed to pass fully through the rod 1416. In this case, the fastener 1414 is stepped and welds to the rod at the mating of the hole entrance and the angled fastener surface. In FIG. 128, there is a blind hole and the tapered bottom of the fastener 1414 is welded at the bottom of the drilled hole.

FIGS. 129-131 show a PEEK plate 1418 secured to a sawbone 1420 with thread-in PEEK fasteners 1422. The two fasteners 1422 were threaded into the sawbone 1420 on opposite sides of a fracture 1424. The plate 1418 was secured as a cap 1426 was welded to the first fastener 1422, then the other was welded. The plate 1418 had slots pre-drilled through it, but it is possible that it could be drilled in surgery at the same time as the bone with the fastener passed through the newly drilled plate hole, provided that the welded cap 1426 is larger in diameter than the newly drilled hole.

FIG. 132 shows a small PEEK plate 1430 with fasteners 1432 ultrasonically welded to the hole openings. FIGS. 133 and 134 show 30 percent carbon reinforced PEEK fasteners 1434 welded to a rod 1436 of the same material.

In all of the cases, the welds were made with an ultrasonic handpiece and generator with a manual pressure applied by hand (in the 6 to 9 lb. range) with a weld time of 0.3 seconds. All of the welded specimens were tested by applying force with the hands. None of the welds failed. While the test specimens shown in FIGS. 126-134 were all made of medical grade PEEK, it is contemplated that other materials such as Acrylic, PMMA, polypropylene, polycarbonate, acetal, and polyphenylsulfone (RADEL) may also be used.

Further testing was performed with test samples made from virgin PEEK (non medical grade). FIG. 135 shows the test fastener 1438 and anchor 1440 used. The anchor 1440 in these samples was made so that it could be secured in a vise during welding and tensile testing. The samples were ultrasonically welded with an ultrasonic generator and handpiece. The weld time was 0.3 seconds, and pressure of about 7-8 lbs. was applied to the fastener by hand during welding.

FIG. 136 illustrates a fixture 1442 made for testing the samples. The top section mounts to the ultrasound generator and the bottom piece has a small hole in 0.040" thick aluminum so that the fastener post can pass through it. Samples were welded with this plate between the fastener 1444 and anchor 1446 sections as tissue would be. In the first set of testing, pull force was applied to the fastener in the direction of the post and anchor bore axis. The test was designed to preload the sample to 0.5 lbs, and then apply further force at a loading rate of 1.25 mm/s. The results are provided in Table 1, below.

TABLE 1

Tension Load Testing Results

| | |
|---|---|
| Number of samples: | 6 |
| Average Failure Load: | 46.0 lbs |
| Standard Deviation: | 18.1 lbs |
| Maximum Failure Load: | 75.5 lbs |
| Minimum Failure Load: | 20.3 lbs |

A second set of testing dealt with placing a shear load on the post in a direction perpendicular to the axis of the post and anchor bore. This load may be similar to what would be applied by tissue stretched over to be repaired. The preload and loading conditions for this test are identical to the prior test set. The orientation of the pull was the only difference. The results are provided in Table 2, below.

TABLE 2

Shear Load Testing Results

| | |
|---|---|
| Number of samples: | 5 |
| Average Failure Load: | 76.6 lbs |
| Standard Deviation: | 10.5 lbs |
| Maximum Failure Load: | 91.7 lbs |
| Minimum Failure Load: | 62.9 lbs |

In both tests, the PEEK prototypes had strength far exceeding the strength of a knotted USP 2 suture, which would be expected to be about 35 lbs.

Further results of PEEK and Acrylic testing are shown in FIGS. 137 and 138. As seen in FIG. 137, the mean failure tension load for PEEK ultrasonic weld samples was 46 lbs. while the mean failure shear load was about 76 lbs. In FIG. 138, the mean failure tension load for Acrylic heat stake samples was 29 lbs.

Exemplary Instruments

As previously discussed, a variety of energy emitting instruments may be used with the surgical welding system of the present invention. The instrument may produce energy such as resistive heating, radiofrequency, ultrasound (vibratory), microwave, laser, electromagnetic, electro shockwave therapy, plasma energy (hot or cold), and other suitable energy. FIGS. 139-142 illustrate an exemplary instrument 1450 and fastener 1452 of the present invention. The instrument 1450 shown is an ultrasonic handpiece with a sheath 1454 to cover and protect the end effector 1456 and hold the fastener. The sheath 1454 has a small counter bore at its tip to cover a portion of the cap 1458. There is also a bushing at a nodal point of the ultrasonic signal to prevent the end effector 1456 from contacting the sheath 1454. The tip of the end effector 1456 has a small post 1460 sticking out of the welding face which presses into a bore in the cap of the fastener. This can help align the fastener post into the anchor bore and keep the cap tight against the end effector face. After welding, the end effector 1456 easily pulls off.

The post 1460 on the end effector 1456 could be threaded or have a Morse taper to mate with the cap. Alternatively, the end effector 1456 may have a bore that the top of the cap mates into. The mating of the components could also be by threads or a Morse taper along with a straight post. Furthermore, the pin could be roughened on the outside surface for better adhesion.

Another exemplary instrument is illustrated in FIGS. 143A and 143B. A small cartridge heater 1462 may be used to deliver thermal energy. The heater 1462 may by a SUNROD ⅛ inch cartridge heater. To prevent heat build up of the outside shaft 1464, an air barrier may be formed between the heater and the shaft. In FIG. 143A, four set screws 1466 are used to create an air barrier, while in FIG. 248, a single set screw 1466 is used.

Referring to FIGS. 144A-144K, energy emitting instruments include various horn configurations. In FIG. 144A, the horn 1470 emits energy to the top surface of the implant as well as the central core. The horn 1472 of FIG. 144B is recessed to hold the thermoplastic implant 1474 during welding. In FIG. 144C, the horn 1476 is concave to provide a rounded surface to the implant 1478 after welding. The horn 1480 of FIG. 144D is concave and includes a central extension 1482 to deliver energy throughout the implant 1484. In FIG. 144E, the horn 1486 includes a spike 1488 within disposable within an implant 1490. The horn 1492 of FIG. 144F includes a threaded pin 1494 which is received by a bore in the implant 1496. In FIG. 144G, the horn 1498 includes dual spikes 1500. The distal portion of the horn 1502 of FIG. 144H is dimensioned to fit within the thermoplastic implant 1504. In FIG. 144I, a sleeve 1506 is disposed about the horn 1508 and implant 1510. The side-weld horn 1512 is shown in FIG. 144I. In FIG. 144K, a dual horn welder 1514 is used to simultaneously weld two fasteners 1516.

Exemplary Applications

The following examples further illustrate the diversity of the surgical welding system of the present invention. It is contemplated that the above description regarding welding parameters, thermoplastic material, and instruments may be used with the following examples. This list of examples is not all inclusive but rather shows some specific applications on how and where thermal welding may be utilized during manufacture and/or surgery.

FIGS. 145A and 145B illustrate one embodiment of the present invention. An anchor 1520, which may be made of PEEK or other suitable polymer, is placed into a predrilled passageway 1522 in bone 1524. An end effector 1526 is pressed against a surface of the anchor 1520 and ultrasonic energy is emitted from the effector. The energy softens the polymer thereby deforming the polymer and driving the anchor 1520 into the bone and locking the anchor within the bone. No initial mechanical lock is required. However, as previously discussed, the application of ultrasonic energy may be in lieu of or in addition to a mechanical locking means, such as threads.

In FIG. 146, a fractured bone has two sections 1530, 1532 which need to be rejoined and compressed for proper healing. The anchor 1534 is locked in the bone as previously described. A guidewire 1536 may be drilled from one bone section, through the fracture, into the other bone section, and to the anchor 1534. A cannulated drill 1538 may be used to create a bigger hole over the guidewire. After the channel is created, the drill can be removed.

Next, as shown in FIG. 147, a fastener 1540, which includes a cap 1542 and post 1544, is attached to the anchor 1534 to secure the tissue. The fastener 1540 may be slid through the drilled hole, over the guidewire 1536, across the fracture, and at least partially into the anchor. The post 1544 can then be welded into the anchor 1534 to close the fracture with the cap 1542 placing pressure against the outer surface of the bone to apply compressive force to the fracture. Further energy may be applied to the cap to deform or contour it to make it less obtrusive from the bone. Soft tissue and/or a bone plate may be positioned under the cap of the fastener.

In FIG. 148 a guide instrument 1546 is shown. The instrument properly aligns the drill and fastener 1540 into the anchor 1534. The instrument 1546 may be an aiming or alignment guide or some type of triangulation device. The instrument 1546 may be adjustable to fit various sized of bone/tissue or different angles of fastener insertion. FIG. 149 shows an anchor 1534 with multiple fasteners 1540 disposed therein.

In the embodiments described in FIGS. 145-149, the post 1544 of the fastener 1540 may be threaded. That is, when drilling the channel through the bone sections 1530, 1532 and across the fracture, the drill may be extended into or through the anchor 1534. A tap may be used to create helical threads within the channel in the anchor. Then, the threaded post of the fastener may be inserted in the channel and screwed into the anchor to thereby close the fracture. Energy may be used to further lock the fastener to the anchor. Alternatively, the post 1544 may extend completely through the anchor and extend out the opposite side of the anchor. In this configuration, a threaded nut may be placed on the distal end of the post. Furthermore, the distal end of the post may be thermally flattened or contoured. In another related embodiment, the cap 1542 of the fastener 1540 may be angled or may float or pivot on the proximal end of the post. This could allow the cap to lay flush against the tissue surface.

FIGS. 150A and 150B illustrate another application of the surgical welding system. Ultrasonic energy may be used to bond a metal/ceramic implant to a polymeric implant or a polymeric implant to another polymeric implant. A polymer implant 1550 is positioned against a metallic implant 1552. An extension or spike 1554 may extend from the polymer and be positioned through the metallic implant. Using ultrasonic energy, the extension is excited and formed by an ultrasonic horn 1556 or other energy source to soften and move over the metal thereby securing the two implants to each other.

Referring to FIGS. 151A and 151B, ultrasound energy may be used to move a first, polymeric material 1560, such as PEEK, into a second material 1562 that is more resistant to softening by an energy source. The second material 1562 may have a higher melting point, such as metal, ceramic, or a different thermoplastic material. Alternatively, the second material may be formed of a thermoset material. The polymer component may have energy directors that fit into a passage in the second material. The second material also may have undercuts or cavities 1564 for the polymer to move into and fill. As the PEEK is excited by the ultrasound energy, it moves into the voids of the second material. After the energy is removed, the polymer cools to mechanically lock the two dissimilar material components together.

In a further embodiment of the present invention shown in FIGS. 152-155, the surgical welding system may be used to repair and/or stabilize joints of the spine such as intervertebral joints and facet joints. Stabilization of the spine is usually achieved by attaching rigid rods 1570, plates 1572, spacers 1574, or wedges 1576 between two or more vertebrae. Fasteners 1578, such as screws, are inserted into the vertebrae, and the plate 1572 and/or rod 1570 is mechanically connected to the fastener 1578. The spinal rods, plates, fasteners, etc. may include thermoplastic material of the present invention, such as PEEK or PEAK. The implants may be biodegradable or biostable. For example, the fastener 1578 may be made of metal, and the rod 1570 or plate 1572 may be made of PEEK. The metal fasteners may be affixed to vertebrae, while polymeric rods may be welded to the fastener using ultrasonic energy. Alternatively, the fasteners 1578 may be made of PEEK, and the rods may be made of metal. The fasteners may be implanted in the vertebrae using energy, as previously disclosed. The rods/plates may be aligned with fasteners, and the polymeric material of the fasteners may be welded to the rods. Furthermore, both the fasteners 1578 and rods 1570 or plates 1572 may be made of PEEK. The fasteners are implanted in vertebrae by softening the PEEK with energy. The rods are attached to the fasteners also with energy, such as ultrasonic energy.

The fasteners and rods/plates also may include both PEEK and metal. For example, the fasteners may have a distal portion made of PEEK which thermally locks in bone by applying energy. The proximal portion of the fastener may include metal which may mechanically and/or thermally lock with a rod or plate. Alternatively, the distal portion of the fastener is metal, and the proximal portion is PEEK. Other embodiments of the invention using a composite of materials may also be used. Likewise, the rod and/or plate may also include both metal and thermoplastic material, such as PEEK. The rod and/or plate may be made mostly of metal; however, the plate may include PEEK where the fasteners attach to the rod/plate. It is contemplated that the fasteners, plates, and rods described herein may be made of PEEK, metal, ceramic, composite, or another polymeric material.

FIG. 155 shows a modular vertebral body replacement system 1580. The thermoplastics and energy of the present invention may be used to bond the components together intracorporeally. The CONSTRUX system in FIG. 155 is designed to be mechanically locked together during surgery. Using thermoplastics, the unit may be mechanically and thermally locked together using welding processes described herein.

Figure 156A:
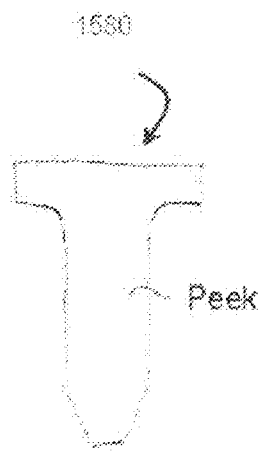
Figure 156B:
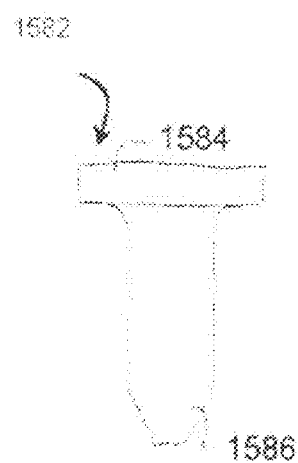
Figure 156C:
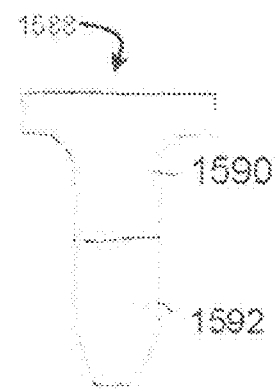
Figure 156D:
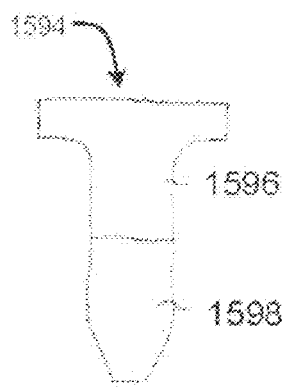
Figure 156E:
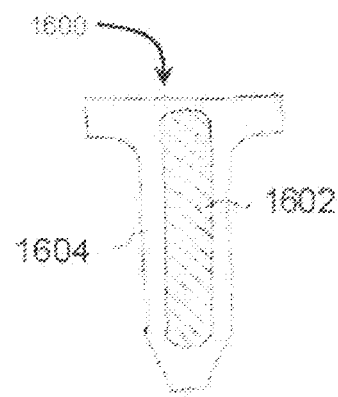
Figure 156F:
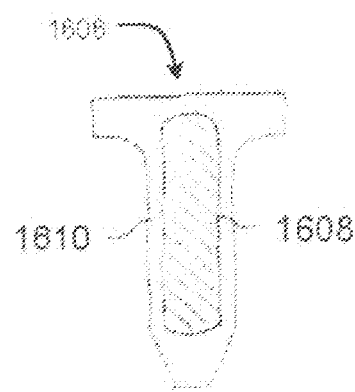

Additional exemplary fasteners are illustrated in FIGS. 156A-156F. The fastener 1580 of FIG. 156A is made entirely of a thermoplastic material such as PEEK. In FIG. 156B, the fastener 1582 includes two different thermoplastic materials 1584, 1586. Each material may have different welding properties. FIG. 156C shows a fastener 1588 with only a proximal portion 1590 made of PEEK, while FIG. 156D illustrates a fastener 1594 with only a distal portion 1598 made of PEEK. In FIG. 156E, the fastener 1600 includes a rigid metallic core 1602 which is enclosed by a thermoplastic 1602, such as PEEK. The fastener 1606 of FIG. 156F has a polymeric core 1608 surrounding by a thermoplastic 1610, such as PEEK.

Moreover, thermal energy used to soften and bond PEEK may also be used to contour and deform the fasteners, plates, and rods. Energy, such as resistive heating, may be applied to the plates and rods to shape them to a desired and anatomical configuration. Also, the fasteners, rods, and plates may be deformed using energy and positioned such that the combination produces compression or tension between two or more vertebrae.

In a further embodiment, the surgical welding system may be utilized to provide flexible stabilization of the spine, or any other joint or bone of the body, as suggested in FIGS. 152-154. The soft tissue around and near a joint may become weakened over time, and the range of motion of the joint usually increases thereby allowing excessive tissue laxity. Also, instability of a joint may be caused by structural changes within the joint as a result of trauma, degeneration, aging, disease, or surgery. An unstable spinal joint may be rigidly stabilized as previously explained or may be dynamically stabilized to allow some range of motion of the spinal joints. Fasteners, screws, plates, rods, etc. made of PEEK may be implanted between two or more vertebrae. The plates and rods are configured and dimensioned to permit some flexing and/or bending. The amount of flexibility of these PEEK implants may be adjusted by the surgeon in the operating room using energy, such as ultrasound, resistive heating, etc. and varying the weld parameters.

Additionally, as seen in FIG. 154, a plate 1572 or rod 1570 may be configured to lock with a fastener 1578 in one direction, but would allow movement in another direction. For example, the plate and fastener permits superior and inferior motion of the spine but would prevent lateral motion. Also, the plate and fastener may permit motion in one plane and restrict motion in a different plane. Other devices and methods for dynamic stabilization of the spine and other joints and bones are disclosed in U.S. patent application Ser. No. 11/258,795 entitled "Devices and Methods for Stabilizing Tissue and Implants" filed Oct. 26, 2005. The contents of the aforementioned patent application are incorporated herein by reference in its entirety.

In another embodiment, the welding system of the present invention may be used to thermally weld a spinal spacer or spinal cage to a bone. Currently, spinal cages are threaded into the spine or mechanically locked into the spine with barbs, threads, etc. In the present invention, the spinal cage may be made of PEEK and could lock into tissue by the application of ultrasonic energy and/or by the use of PEEK fasteners. The fasteners may extend from the cage to adjacent vertebrae. The fasteners may function as tension or compression bands to hold the cage in place. Additionally energy, such as resistive heating, may be use to contour the cage or spacer to a desired configuration such as to conform with the geometry of adjacent vertebrae. If multiple cages and/or spacers are required, the implants may be thermally welded together before implantation in the operating room, intracorporeally, or both.

In yet another embodiment of the present invention, the surgical welding system may be used to repair and stabilize a knee joint. For example, as seen in FIG. 157, a ligament (ACL), tendon, or bone graft 1612 may be fastened into position using thermoplastics and energy. Other polymers may be welded across the joint to provide rigid and/or dynamic stabilization. Also, a joint replacement component may be modified using thermoplastics and energy. In FIG. 158, one or more stabilizers 1614 may be bonded to the joint replacement component to provide stability between the tibial and femoral components 1616, 1618. It is contemplated that other joint replacement components, such as the hip, shoulder, elbow, ankle, etc. may include thermoplastic stabilizers. As seen in FIG. 158, the tray 1614 may be spot welded (or surface welded) to the tibial base component 1616.

Furthermore, PEEK fasteners and PEEK material may be used to stabilize or tether disc replacement components or other implants such as an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic, breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. As illustrated in FIG. 159, fasteners 1620 may be attached to or placed around the implant 1622 and secured to adjacent tissue preventing the implant from migrating. Other methods of tethering implants are disclosed in U.S. patent application Ser. No. 11/258,795, previously mentioned and incorporated by reference herein.

In another spinal application, a spinal implant may include a thermoplastic material to which a bearing surface coating may be applied. A nano-ceramic coating may be bonded to a spacer which is used to change positions of bones of a joint. The coating may be 3-5 microns thick or could be as thick as 50 microns. The coating may be alumina, Zirconia, or diamond type ceramic which is welded to the spacer using ultrasound energy, resistive heating, or other energy source. The spacer may be stabilized or tethered using PEEK fasteners as previously described. In one embodiment, the spacer is affixed to one vertebra with fasteners, and the other side of the spacer which includes the bearing surface coating is free to articulate against the adjacent vertebra. In addition to PEEK, other polymers such as polyurethane, polyethylene, polyester, or DELRIN may be used.

It is also contemplated that the welding system of the present invention may be used with other surgical applications. For example, cerclage wire may be made of PEEK. The wire could be used to secure a cervical plate for unicortical or bicortical fixation. Energy may be used to weld the wire and plate together. Energy may also be used to change the angle of fixation and to contour the plate. PEEK implants may be used to stabilize nucleus pulposus replacement components or to repair the annulus. PEEK implants may be used in a kyphoplasty. A balloon or mesh may be inserted into a spinal void. The mesh may be filled with fluid or graft material to expand the adjacent vertebral bodies. The mesh sack may then be sealed and anchored into position to prevent migration. The mesh, graft material, seal, and/or anchor may be made of PEEK and may be biodegradable material.

In a further application of the invention, the surgical welding system may be used with for intracranial and craniofacial surgery. Thermoplastic implants may be used to stabilize craniofacial plates. The plates may be contoured with energy to obtain the desired shape. PEEK fasteners may be implanted in tissue via mechanically, thermal welding, or both, and the plate may be attached to the fasteners via mechanical means, thermal welding, or a combination thereof. For face lifts, one or more PEEK fasteners and a suture or cable may be used to create a sling to reposition and tighten soft tissue such as skin. The fasteners may be secured to bone or other tissue. The suture may be positioned through the soft tissue using a magnetic suture passer and magnetic guidance thereby achieving a minimally invasive facial support. The fasteners and/or suture may be secured unicortically to the skull, mandible, maxilla, or other bones of the head. Also, PEEK may be used for sealing cerebrospinal fluid leaks. This may be performed with a thermoplastic and energy source, with or without vacuum/suction.

In another embodiment of the present invention, a fastener includes multiple portions made from a different polymeric material. For example, the fastener may have dual dermometry properties. (see, e.g., FIGS. 156A-156F). For instance, the cap may be made of one polymer while the post may be made of a different polymer. The two polymers may have different temperature transition regions. Therefore, one polymer would soften before the other polymer. Also, if using ultrasonic energy, the two polymers may soften at different frequencies, wattages, pressures, or other welding parameters. Alternatively, the post may be made of a polymer that softens with ultrasound, while the cap may be made of a polymer that softens with resistive heating. It is contemplated that any of the implants and devices disclosed herein may include multiple polymers having different welding parameters.

In addition to PEEK and the other polymers described herein, the implants, devices, and methods of the present invention may use keratin, a naturally occurring polymer. Keratin may be ultrasonically welded to itself, to other implants, or within tissue. This may be performed in the operating room or intracorporeally. Keratin may be bonded to collagen or to other known polymers. In an exemplary application, keratin may be used to fasten tissue to bone since keratin has BMP and tissue scaffold properties. It is contemplated that any of devices and methods disclosed herein may utilize keratin alone or in combination with PEEK, polylactic acid, or other polymer. Keratin may be used to make fasteners, disc replacements, joint replacement components, stents, cell scaffolds, drug reservoirs, etc. Also, joint bearing surfaces may include keratin with or without collagen or chondrocytes. The bearing surfaces may be fastened to a joint component using PEEK or PLA fasteners.

The surgical welding system also includes shrinkable materials for use in surgery. Shrinkable materials provide a compressive force to tissue or implants when energy is applied. For example, a fastener may be implanted to secure an implant or tissue. The application of heat to the polymeric material of fastener causes the fastener to shorten or shrink thereby enhancing the force provided by the fastener. The fastener may be positioned through two portions of a fractured bone then heated to shrink. The bone portions are compressed together for proper healing. In addition to fasteners, a suture, cerclage, wire, or cable may be made of shrinkable material. Cable may be placed through tissue or bone, positioned across a joint, or connected with an implant. When energy is applied to the cable, it shortens thereby creating a tension force and securing the object(s) to which is attached. A shrinkable cable positioned adjacent to or across a joint may provide rigid and/or dynamic stabilization of the joint. FIGS. 160A-160C illustrate configurations and uses of heat shrinkable implant pouches 1624. Implants 1626 may placed in a pouch are sealed within. Applying energy to the pouch 1624 shrinks it to firmly hold the implant 1626 therein. Thermoplastic fasteners may be used to secure the pouch within the body.

In a further embodiment of the present invention, thermoplastics and energy may be used to repair a hip joint. As shown in FIG. 161, bearing surface implants 1628 may be bonded to the acetabulum. Fasteners 1630 may also be used to secure the implants 1628. In FIG. 162, a prosthetic femoral head 1632 is attached to the femur with a fastener 1634. The head includes a thermoplastic material 1636 bonded to the surface to function as a bearing surface. The thermoplastic 1636 may articulate against acetabulum implants. FIG. 163 shows PEEK 1638 disposed on the surface of the femoral head. A bearing surface material 1640, such as nano-metal or nano-ceramic is welded to the PEEK. On the acetabulum, a bearing surface material is also welded to the bone with PEEK. With the replacement components implanted, the bearing surfaces articulate against each other.

It is contemplated the surgical welding system of the present invention may be used with and integrated with the methods and devices disclosed in U.S. Provisional Application No. 60/765,857 entitled "Surgical Fixation Device" filed on Feb. 7, 2006. In the '857 document, various thermoplastic fixation devices are disclosed. The fixation devices may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, multi-component, solid, hollow, polygon-shaped, pointed, self-introducing, and combinations thereof. Also, the devices may include, but are not limited to, metallic material, polymeric material, ceramic material, composite material, body tissue, synthetic tissue, hydrophilic material, expandable material, compressible material, heat bondable material, and combinations thereof.

The methods and devices disclosed in the '857 document may be used in conjunction with any surgical procedure of the body. The fastening and repair of tissue or an implant may be performed in connection with surgery of a joint, bone, muscle, ligament, tendon, cartilage, capsule, organ, skin, nerve, vessel, or other body parts. For example, tissue may be repaired during intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, flexor tendons, etc.

It is contemplated that the devices and methods of the present invention be applied using minimally invasive incisions and techniques to fasten muscles, tendons, ligaments, bones, nerves, and blood vessels. A small incision(s) may be made adjacent the damaged tissue area to be repaired, and a tube, delivery catheter, sheath, cannula or expandable cannula may be used to perform the methods of the present invention. U.S. Pat. No. 5,320,611 entitled "Expandable Cannula Having Longitudinal Wire and Method of Use" discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

U.S. Pat. Nos. 5,674,240; 5,961,499; and 6,338,730 also disclose cannulas for surgical and medical use expandable along their lengths. The cannula can be provided with a pointed end portion and can include wires having cores which are enclosed by jackets. The jackets are integrally formed as one piece with a sheath of the cannula. The cannula may be expanded by inserting members or by fluid pressure. An expandable chamber may be provided at the distal end of the cannula. The above mentioned patents are hereby incorporated by reference.

In addition to using a cannula with the present invention, an introducer may be utilized to position implants at a specific location within the body. U.S. Pat. No. 5,948,002 entitled "Apparatus and Method for Use in Positioning a Suture Anchor" discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fixation devices disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired; a damaged rotator cuff may be mended. The patent documents mentioned above are hereby incorporated by reference.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

It is further contemplated that the present invention may be used in conjunction with the devices and methods disclosed in U.S. Pat. No. 5,329,846 entitled "Tissue Press and System" and U.S. Pat. No. 5,269,785 entitled "Apparatus and Method for Tissue Removal." For example, an implant secured within the body using the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled "Surgical Devices Assembled Using Heat Bondable Materials." For example, the implants of the present invention may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the devices and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the implants and methods described and incorporated herein may be used to approximate the damaged portion of the vessel.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A method for stabilizing a bone, the method comprising:
    positioning an implant having an external bonding surface in the medullary canal of the bone;
    forming a passageway through the cortex of the bone;
    positioning an unthreaded fastener comprising a body and a leading end face in the passageway through the cortex of the bone such that bonding material at the leading end face of the fastener contacts the external bonding surface of the implant; and
    thermally bonding the bonding material at the leading end face of the fastener to the external bonding surface of the implant,
    wherein the body of the bonded fastener is external to the implant.

2. The method of claim 1 wherein the bone is fractured.

3. The method of claim 1 wherein ultrasonic energy is used to thermally bond the fastener to the external bonding surface of the implant.

4. The method of claim 1 further comprising preparing the external bonding surface of the implant prior to thermal bonding of the fastener.

5. The method of claim 1 further comprising at least one of positioning the implant, forming the passageway through the cortex of the bone, and positioning the fastener with a robotic mechanism.

6. The method of claim 1 further comprising thermally bonding the bonding material at the leading end face of the fastener to the external bonding surface of the implant with a robotic mechanism.

7. The method of claim 1 wherein the bonding material at the leading end face of the fastener and the external bonding surface of the implant comprise at least one of PEEK, PEAK, PLA, PGA, and copolymers thereof.

8. The method of claim 1 wherein the thermal bonding is monitored with at least one of a pressure sensor and a temperature sensor.

9. The method of claim 1 wherein the leading end face of the fastener comprises a notch configured to contact the external bonding surface of the implant.

10. A method for stabilizing a bone, the method comprising:
    positioning an anchoring implant in the medullary cavity of the bone, wherein the anchoring implant includes a polymer, wherein the polymeric portion of the anchoring implant is configured to comprise an external bonding surface comprising at least one of PEEK, PEAK, PLA, PGA, and copolymers thereof;
    forming a passageway extending through the cortex of the bone to the medullary cavity of the bone;
    positioning an unthreaded fastener in the passageway through the cortex of the bone, the fastener comprising a body and a distal end, wherein the distal end of the fastener includes a distal end face in direct contact against the external bonding surface of the anchoring implant; and
    thermally bonding the distal end face of the fastener to the external bonding surface of the anchoring implant while the body of the fastener is positioned in the passageway through the cortex of the bone external to the implant, and the distal end face of the fastener is in direct contact against the external bonding surface of the anchoring implant,
    wherein the thermal bonding is monitored with at least one of a pressure sensor and a temperature sensor.

11. The method of claim 10 wherein the bone is fractured.

12. The method of claim 11 wherein ultrasonic energy is used to thermally bond the distal end face of the fastener to the external bonding surface of the anchoring implant.

13. The method of claim 10 further comprising at least one of positioning the anchoring implant, forming the passageway through the cortex of the bone, positioning the fastener, and thermally bonding the distal end face of the fastener to the external bonding surface of the anchoring implant with a robotic mechanism.

14. The method of claim 13 wherein the distal end face of the fastener is at least partially comprised of the same material as comprises the external bonding surface of the anchoring implant.

15. A method for stabilizing a bone, the method comprising:
    positioning a rod in the medullary canal of the bone, wherein the rod is at least partially comprised of PEEK, wherein the PEEK portion of the rod is configured to comprise at least a bonding region on an external surface of the rod;
    forming a passageway through the cortex of the bone;
    positioning an unthreaded fastener in the passageway through the bone, the fastener comprising a body and a distal end, wherein the distal end of the fastener includes a distal end face at least partially comprised of PEEK, wherein the PEEK distal end face of the fastener is configured to have a bonding feature;
    contacting the distal end face of the fastener directly against the bonding region on the external surface of the rod; and
    thermally bonding the at least partial PEEK distal end face of the fastener to the PEEK bonding region on the external surface of the rod while the fastener is positioned in the passageway through the bone external to the implant, and the distal end face of the fastener is contacted directly against the bonding region on the external surface of the rod, wherein the thermal bonding is monitored with at least one of a pressure sensor and a temperature sensor.

16. The method of claim 15 wherein the bone is fractured.

17. The method of claim 15 further comprising preparing the bonding region on the external surface of the rod prior to thermal bonding of the fastener.

18. The method of claim 15 wherein ultrasonic energy is used to thermally bond the bonding feature on the distal end face of the fastener to the bonding region on the external surface of the rod.

19. The method of claim 15 further comprising at least one of positioning the rod, forming the passageway through the cortex of the bone, positioning the fastener, and thermally bonding the fastener to the bonding region on the external surface of the rod with a robotic mechanism.

20. The method of claim 15 wherein the distal end of the fastener comprises a notch configured to contact the bonding region on the external surface of the rod.

* * * * *